(12) United States Patent
Sabbadini

(10) Patent No.: US 7,901,682 B2
(45) Date of Patent: *Mar. 8, 2011

(54) COMPOSITIONS AND METHODS FOR THE TREATMENT AND PREVENTION OF CANCER, ANGIOGENESIS, AND INFLAMMATION

(75) Inventor: Roger A. Sabbadini, Lakeside, CA (US)

(73) Assignee: Lpath, Inc., San Diego, CA (US)

( * ) Notice: Subject to any disclaimer, the term of this patent is extended or adjusted under 35 U.S.C. 154(b) by 219 days.

This patent is subject to a terminal disclaimer.

(21) Appl. No.: 11/638,730

(22) Filed: Dec. 13, 2006

(65) Prior Publication Data

US 2007/0212348 A1 Sep. 13, 2007

Related U.S. Application Data

(63) Continuation of application No. 10/028,156, filed on Dec. 21, 2001, now Pat. No. 6,881,546.

(60) Provisional application No. 60/257,926, filed on Dec. 22, 2000.

(51) Int. Cl.
*A61K 39/395* (2006.01)
*G01N 33/53* (2006.01)

(52) U.S. Cl. ............... 424/141.1; 424/130.1; 424/138.1; 435/7.1

(58) Field of Classification Search ............... None
See application file for complete search history.

(56) References Cited

U.S. PATENT DOCUMENTS

| | | | |
|---|---|---|---|
| 4,150,949 A | 4/1979 | Smith | |
| 4,816,450 A | 3/1989 | Bell et al. | |
| 4,937,232 A | 6/1990 | Bell et al. | |
| 5,079,263 A | 1/1992 | Zeeck et al. | |
| 5,137,919 A | 8/1992 | Igarashi et al. | |
| 5,151,360 A | 9/1992 | Handa et al. | |
| 5,248,824 A | 9/1993 | Igrashi et al. | |
| 5,260,288 A | 11/1993 | Igarashi et al. | |
| 5,331,014 A | 7/1994 | Kimura et al. | |
| 5,369,030 A | 11/1994 | Hannun et al. | |
| 5,391,800 A | 2/1995 | Igrashi et al. | |
| 5,430,169 A | 7/1995 | Boumendiel et al. | |
| 5,444,087 A | 8/1995 | Patel et al. | |
| 5,585,476 A | 12/1996 | MacLennan et al. | |
| 5,627,171 A | 5/1997 | Park et al. | |
| 5,663,404 A | 9/1997 | Igarashi et al. | |
| 5,677,288 A | 10/1997 | Marangos | |
| 5,677,337 A | 10/1997 | Wei et al. | |
| 5,851,782 A | 12/1998 | Hannun et al. | |
| 5,877,167 A | 3/1999 | Igarashi et al. | |
| 5,919,687 A | 7/1999 | Chatterjee | |
| 5,929,039 A | 7/1999 | Woodcock et al. | |
| 5,989,803 A | 11/1999 | Tabas et al. | |
| 6,051,598 A | 4/2000 | Shayman et al. | |
| 6,057,126 A | 5/2000 | Munroe et al. | |
| 6,130,067 A | 10/2000 | Tsui | |
| 6,140,060 A | 10/2000 | Chun et al. | |
| 6,187,562 B1 | 2/2001 | Duckworth et al. | |
| 6,210,976 B1 | 4/2001 | Sabbadini | |
| 6,284,798 B1 | 9/2001 | Amtmann et al. | |
| 6,306,911 B1 | 10/2001 | Wachter et al. | |
| 6,323,201 B1 | 11/2001 | Carson et al. | |
| 6,352,844 B1 | 3/2002 | Maurer et al. | |
| 6,423,527 B1 | 7/2002 | Saba et al. | |
| 6,534,322 B1 | 3/2003 | Sabbadini | |
| 6,534,323 B1 | 3/2003 | Sabbadini | |
| 6,610,835 B1 | 8/2003 | Liotta et al. | |
| 6,613,322 B2* | 9/2003 | Tabas et al. | 424/94.6 |
| 6,649,362 B2 | 11/2003 | Gamble et al. | |
| 6,858,383 B2 | 2/2005 | Sabbadini | |
| 6,881,546 B2* | 4/2005 | Sabbadini | 435/7.1 |
| 7,169,390 B2* | 1/2007 | Sabbadini | 424/155.1 |
| 2001/0041688 A1 | 11/2001 | Waeber et al. | |
| 2002/0150582 A1 | 10/2002 | Friedrichs et al. | |
| 2003/0125533 A1 | 7/2003 | Kossida et al. | |
| 2003/0219782 A1 | 11/2003 | Saba et al. | |

FOREIGN PATENT DOCUMENTS

| | | |
|---|---|---|
| EP | 0173648 A2 * | 3/1986 |
| EP | 0173663 | 3/1986 |
| JP | 09-110722 | 4/1987 |
| JP | 2000-293181 A | 10/2000 |
| WO | WO 97/44019 | 11/1997 |
| WO | WO 98/03529 | 1/1998 |
| WO | WO 98/28445 | 7/1998 |
| WO | WO 98/40349 | 9/1998 |
| WO | WO 98/57179 | 12/1998 |
| WO | WO 99/07855 | 2/1999 |
| WO | WO 99/12890 | 3/1999 |
| WO | WO 99/16888 | 4/1999 |
| WO | WO 99/33972 | 7/1999 |
| WO | WO 99/38983 | 8/1999 |
| WO | WO 99/41265 | 8/1999 |
| WO | WO 99/41266 | 8/1999 |
| WO | WO 99/46277 | 9/1999 |
| WO | WO 99/61581 | 12/1999 |
| WO | WO 00/00593 | 1/2000 |

(Continued)

OTHER PUBLICATIONS

Granziero, Krajewski, Farness, Yuan, Courtney, Jackson, Peterson, and Vitiello. Adoptive immunotherapy prevents prostate cancer in a transgenic animal model. European Journal of Immunology, 1999. vol. 29, pp. 1127-1138.*

(Continued)

*Primary Examiner* — Anne M. Gussow
(74) *Attorney, Agent, or Firm* — BioTechnology Law Group; Daniel M. Chambers

(57) ABSTRACT

Methods and compositions are disclosed that are useful for the prevention and/or treatment of cancer, angiogenesis, and inflammation. The beneficial effects of the compositions and methods are achieved through the use of pharmaceutical compositions that include agents that bind sphingolipids or sphingolipid metabolites. In one embodiment the agent is an antibody or antibody derivative. In some embodiments, the agent is a receptor of a sphingolipid or a sphingolipid metabolite. Also disclosed are methods for identifying and isolating therapeutic agents.

7 Claims, 6 Drawing Sheets

FOREIGN PATENT DOCUMENTS

| | | |
|---|---|---|
| WO | WO 00/21919 | 4/2000 |
| WO | WO 00/40262 | 7/2000 |
| WO | WO 00/52173 | 9/2000 |
| WO | WO 00/56135 | 9/2000 |
| WO | WO 00/58448 | 10/2000 |
| WO | WO 00/58491 | 10/2000 |
| WO | WO 00/59517 | 10/2000 |
| WO | WO 00/70028 | 11/2000 |
| WO | WO 00/72833 | 12/2000 |
| WO | WO 01/04108 | 1/2001 |
| WO | WO 01/04139 | 1/2001 |
| WO | WO 01/07418 | 2/2001 |
| WO | WO 01/31029 | 5/2001 |
| WO | WO 01/38295 | 5/2001 |
| WO | WO 01/55410 | 8/2001 |
| WO | WO 01/57057 | 8/2001 |
| WO | WO 01/60990 | 8/2001 |
| WO | WO 01/71045 | 9/2001 |
| WO | WO 01/72701 | 10/2001 |
| WO | WO 01/80903 | 11/2001 |
| WO | WO 01/85953 | 11/2001 |

OTHER PUBLICATIONS

Byers. What can randomized control trials tell us about nutrition and cancer prevention? CA Cancer Journal, 1999. vol. 49, pp. 353-361.*

Wright, Shin, and Morrison. Genetically engineered antibodies: progress and prospects. Critical Reviews in Immunology, 1992. vol. 12, pp. 125-168.*

MSNBC News Services. Mixed results on new cancer drug. Nov. 9, 2000.*

Gura. Systems for identifying new drugs are often faulty. Science, 1997. vol. 278, pp. 1041-1042.*

Sabbadini. Targeting sphingosine-1-phosphate for cancer therapy. British Journal of Cancer, 2006. vol. 95, pp. 1131-1135.*

Forni, Lollini, Musiani, and Colombo. Immunoprevention of cancer: is the time ripe? Cancer Research, 2000. vol. 60, pp. 2571-2575.*

De Gruijl and Curiel. Cancer vaccine strategies get bigger and better. Nature Medicine, 1999. vol. 5, pp. 1124-1125.*

Chatterjee, Foon, and Kohler. Idiotypic antibody immunotherapy of cancer. Cancer Immunology Immunotherapy, 1994. vol. 38, pp. 75-82.*

Bodey, Bodey, Siegel, and Kaiser. Failure of cancer vaccines: the significant limitations of this approach to immunotherapy. Anticancer Research, 2000. vol. 20, pp. 2665-2676.*

Abe et al., "Structural and stereochemical studies of potent inhibitors and glucosylceramide synthase and tumor cell growth," *J. Lipid Res.* 36(3):611-621 (1995).

Abe et al., "Glycosphingolipid depletion in Fabry disease lymphoblasts with potent inhibitors of glucosylceramide synthase," *Kidney Int.* 57(2):446-454 (2000).

Abe et al., "Use of Sulfobutyl Ether-Cyclodextrin as a Vehicle for D-threo-1-Phenyl-2-decanoylamino-3-morpholinopropanol-Related Glucosylceramide Synthase Inhibitors," *Anal. Biochem.* 287(2):344-347 (2000).

Ambati, "Age-related macular degeneration: etiology, pathogenesis, and therapeutic strategies," *Surv. Ophthalmol.* 48(3):257-293 (2003) (Abstract Only).

An et al., "Identification of cDNAs encoding two G protein-coupled receptors for lysosphingolipids," *FEBS Letts.* 417(3):279-282 (1997).

An et al., "Characterization of a Novel Subtype of Human G Protein-coupled Receptor for Lysophosphotatidic Acid," *J. Biol. Chem.* 273(14):7906-7910 (1998).

An et al., "Sphingosine 1-phosphate-induced cell proliferation, survival, and related signaling events mediated by G protein-coupled receptors Edg3 and Edg5," *J. Biol. Chem.* 275(1):288-296 (2000).

Ancellin et al., "Extracelluar export of sphingosine kinase-1 enzyme: Sphingosine 1 phosphate generation and the induction of angiogenic vascular maturation," *J. Biol. Chem.* 277(8):6667-6675 (2001).

Andrieu-Abadie et al., "L-carnitine prevents doxorubicin-induced apoptosis of cardiac myocytes: role of inhibition of ceramide generation," *FASEB J.* 13(12):1501-1510 (1999).

Arenz et al., "Synthese des ersten selektiven irreverilben Inhibitors der neutralen Sphingomyelinase," *Angew Chem.* 112:1498-1500 (2000) (GERMAN); "Synthesis of the First Selective Irreversible Inhibitor of Neutral Sphingomyelinase," *Angew. Chem. Int. Ed.* 39(8):1440-1442 (2000) (English Equivalent).

Arenz et al., "Manumycin A and its Analogues Are Irreversible Inhibitors of Neutral Sphingomyelinase," *Chem. Biochem.* 2(2):141-143 (2001).

Arenz et al., "Synthesis and Biochemical Investigation of Scyphostatin Analogues as Inhibitors of Neutral Sphingomyelinase," *Bioorg. Medicinal Chem.* 9(11):2901-2904 (2001).

Arenz et al., "Synthesis of the First Selective Irreversible Inhibitor of Neutral Sphingomyelinase," *Eur. J. Org. Chem.* 2001(1):137-140 (2001).

Ariga et al., "Role of Sphingolipid-mediated cell death in neurodegenerative diseases," *J. Lip. Res.* 39(1):1-16 (1998).

Bajjalieh at al., "Ceramide Kinase," *Methods Enzymol.* 311:207-215 (1999).

Barbone et al., "Robotic Assay of Sphingomyelinase Activity for High Throughput Screening," *Meth. Enzymol.* 311:168-176 (1999).

Bawab et al., "Molecular Clonging and Characterization of a Human Mitochondrial Ceramidase," *J. Biol. Chem.* 275(28):21508-21513 (2000).

Bernardo et al., "Purification and Characterization of Magnesium-dependent Neutral Sphingomyelinase from Bovine Brain," *J. Biol. Chem.* 275(11):7641-7647 (2000).

Betto et al., "Sphingosylphosphocholine modulates the ryanodine receptor/calcium-release channel of cardiac sarcoplasmic reticulum memberances," *Biochem. J.* 322(1):327-333 (1997).

Bielawska et al., "(1S,2R)-D-erhthro-2-(N-My- ristoylamino) -1-phenyl-1-propanol as an Inhibitor of Ceramidase," *J. Biol. Chem.* 271(21):12646-12654 (1996).

Cain et al., "Therapeutic Strategies to Reduce TNF-a Mediated Cardiac Contractile Depression Following Ischemia and Reperfusion," *J. Mol. Cell. Cardiol.* 31(5):931-947 (1999).

Boudker et al., "Detection and Characterization of Ceramide-1-phosphate Phosphatase Activity in Rat Liver Plasma Membrane," *J. Biol. Chem.* 268(29):22150-22155 (1993).

Brady et al., "The metabolism of sphingomyelin. II. Evidence of an enzymatic deficiency in Niemann-Pick disease," *Proc. Natl. Acad. Sci. USA* 55(2):366-369 (1966).

Brindley et al., "Analysis of Ceramide 1-phosphate and Sphingosine-1-phosphate Phosphatase Activities," *Methods Enzymol.* 311:233-244 (1999).

Brownlee, "Intracellular signalling: sphingosine-1 -phosphate branches out," *Current Biol.* 11(13):R535-R538 (2001).

Burton et al., "Human antibodies from combinatorial libraries," *Adv. Immunol.* 57:191-280 (1994).

Cain et al., "Therapeutic Strategies to Reduce TNF-a Mediated Cardiac Contractile Depression Following Ischemia and Reperfusion," *J. Mol. Celt Cardiol.* 31(5):931-947 (1999).

Caligan et al., "A High-Performance Liquid Chromatographic Method to Measure Sphingosine 1-Phosphate and Related Compounds from Sphingosine Kinase Assays and Other Biological Samples," *Anal. Biochem.* 281(1):36-44 (2000).

Chan et al., "Ceramide Path in Human Lung Cell Death," *Am. J. Respir. Cell Mol. Biol.* 22(4):460-468 (2000).

Chan et al., "Purification and Characterization of Neutral Sphingomyelinase from Helicobacter pylori," *Biochemistry* 39(16):4838-4845 (2000).

Chatterjee, "Sphingolipids in Atherosclerosis and Vascular Biology," *Arterioscler. Throm. Vasc. Biol.* 18(10):1523-1533 (1998).

Chatterjee, "Neutral Sphingomyelinase," *Adv. Lip. Res.* 26:25-48 (1993).

Chatterjee, "Neutral Sphingomyelinase: past, present, and future," *Chem. Phys. Lipids* 102(1):79-96 (1999).

Chatterjee et al., "Molecular Cloning, Characterization, and Expression of a Novel Human Neutral Sphingomyelinase," *J. Biol. Chem.* 274(52):37407-37412 (1999).

Chau et al., "Synthesis of Simple Aryl Neutral Sphingomyelinase Inhibitors," *Am. Chem. Soc.* (2001) (Abstract Only).

Chun, "Lysophospholipid receptors: implications for neural signaling," *Crit. Rev. Neuro.* 13(2):151-168 (1999).

Chun et al., "A Growing Family of Receptor Genes for Lysophosphatidic Acid (LPA) and other Lysophospholipids (LPs)," *Cell Biochem. Biophys.* 30(2):213-242 (1999).

Cordis et al:, "HPTLC analysis of sphingomyelein, ceramide and sphingosine in ischemic/reperfused rat heart," *J. Pharm. Biomed. Anal.* 16(7):1189-1193 (1998).

Cuvlilier et al., "Suppression of ceramide-mediated programmed cell death by sphingosine-1-phosphate," *Nature* 381(6585):800-803 (1996).

Dickson et al., "Serine Palmitoyltransferase," *Methods Enzymol.* 311:3-9 (1999).

Edsall et al., "N, N-Dimethylsphingosine is a potent competitive inhibitor of sphingosine kinase but not of protein kinase C: modulation of cellular levels of sphingosine 1-phosphate and ceramide," *Biochem.* 37(37):12892-12898 (1998).

Edson et al., "The Aminoglycosides," *Mayo Clin. Proc.* 74(5):519-528 (1999).

Eichler et al., "Peptide, peptidomimetic, and organic synthetic combinatorial libraries," *Med. Res. Rev.* 15(6):481-496 (1995).

Fensome et al., "A Neutral Magnesium-dependent Sphingomyelinase Isoform Associated with Intracellular Membranes and Reversibly Inhibited by Reactive Oxygen Species," *J. Biol. Chem.* 275(2):1128-1136 (2000).

Fujii et al., "Mg2+ binding and catalytic function of sphingomyelinase from *Bacillus cereus*," *J. Biochem* (Tokyo) 124(6):1178-1187 (1998).

Fukushima et al., "A single receptor encoded by *vzg-1llp$_{A1}$/edg-2* couples to G proteins and mediates multiple cellular responses to lysophosphatidic acid," *Proc. Natl. Acad. Sci. USA* 95(11):6151-6156 (1998).

Furneisen et al., "Enzymological properties of the LPP1-encoded lipid phosphatase from *Saccharomyces cerevisiae*" *Biochim. Biophys. Acta* 1484(1):71-82 (2000).

Garcia-Ruiz, "Human placenta sphingomyelinase, an exogenous acidic pH-optimum sphingomyelinase, induces oxidative stress, glutathione depletion, and apoptosis in rat hepatocytes," *Hepatology* 32(1):56-65 (2000).

Gates et al., "Serum amyloid p component: its role in platelet activation stimulated by sphingomyelinase d purified from the venom of the brown recluse spider (*Loxosceles reclusa*)," *Toxicon.* 28(11):1303-1315 (1990).

Gatt et al., "Niemann Pick disease: presence of the magnesium-dependent sphingomyelinase in brain of the infantile form of the disease," *J. Neurochem.* 31(2):547-550 (1978).

Gavrilenko et al., "Nucleotide sequence of phospholipase C and sphingomyelinase genes from *Bacillus cereus* BKM-B164," *Bioorg. Khim.* 19(1):133-138 (1993).

Geeraert et al., "Conversion of dihydroceramide into ceramide: involvement of a desaturase," *Biochem. J.* 327(125):125-132 (1997).

Ghosh et al., "Effects of gentamicin on sphingomyelinase activity in cultured human renal proximal tubular cells," *J. Biol. Chem.* 262(26):12550-12556 (1987).

Ghosh et al., "Identification, partial purification, and localization of a neutral sphingomyelinase in rabbit skeletal muscle: Neutral sphingomyelinase in skeletal muscle," *Mol. Cell. Biochem.* 189(1-2):161-168 (1998).

Gilmore et al., "A *Bacillus cereus* cytolytic determinant, cereolysin AB, which comprises the phospholipase C and sphingomyelinase genes: a nucleotide sequence and genetic linkage," *J. Bacterial.* 171(2):744-753 (1989).

Glickman et al., "Molecular Cloning, Tissue-Specific Expression, and Chromosomal Localization of a Novel Nerve Growth Factor-Regulated G-Protein-Coupled Receptor, nrg-1," *Mol. Cel. Neurosci.* 14(2):141-152 (1999).

Goetzl et al., "Diversity of cellular receptors and functions for the lysophospholipid growth factors lysophosphatidic acid and sphingosine 1-phosphate," *Faseb J.* 12(15)1589-1598 (1998).

Goetzl et al., "Eicosanoids and Other Bioactive Lipids in Cancer, Inflammation, and Radiation Injury, 4. 38: A Subfamily of G Protein-Coupled Cellular Receptors for Lysophospholipids and Lysosphingolipids, Introduction: The Biochemistry and Biology of Lipid Phosphoric Acids," *Adv. Exp. Med. Biol.* 469:259-264 (1999).

Gonda, et al., "The novel sphingosine 1-phosphate receptor AGR16 is coupled via pertussis toxin-sensitive and -insensitive G-proteins to multiple signalling pathways," *Biochem. J.* 337(Part 1):67-75 (1999).

Gonzalez-Zorn et al., "The smcL gene of *Listeria ivanovii* encodes a sphingomyelinase C that mediates bacterial escape from the phagocytic vacuole," *Mol. Microbial.* 33(3):510-523 (1999).

Graler et al., "EDG6, a Novel G-Protein-Coupled Receptor Related to Receptors for Bioactive Lysophospholipids, Is Specifically Expressed in Lymphoid Tissue," *Genomics* 53(2):164-169 (1998).

Gunther, "Myocardial contractility after infarction and carnitine palmitoyltransferase I inhibition in rats," *Eur. J. Pharma.* 406(1):123-126 (2000).

Hakogi et al., "Stereocontrolled synthesis of a sphingomyelin methylene analogue as a sphingomyelinase inhibitor," *Org. Lett.* 2(17):2627-2629 (2000).

Hanada et al., "Specificity of Inhibitors of Seine Palmitoyltransferase (SPT), a Key Enzyme in Sphingolipid Biosynthesis in Intact Cells: A novel evaluation system using an SPT-defective mammalian cell mutant," *Biochem. Pharmacol.* 59(10):1211-1216 (2000).

Hannun et al., "Functions of Sphingolipids and Sphingolipid Breakdown Products in Cellular Regulation," *Science* 243(4890):500-507 (1989).

Hannun et al.., "The Sphingomyelin Cycle: A Prototypic Sphingolipid Signaling Pathway," *Adv. Lipid Res.* 25:27-41. (1993).

Hannun, "Functions of Ceramide in Coordinating Cellular Responses to Stress," *Science* 274(5294):1855-1859 (1996).

Hannun at al, "Ceramide in the eukaryotic stress response," *Trends Cell Biol.* 10(2):73-80 (2000).

He et al., "A Fluorescence-Based High-Performance Liquid Chromatography Assay to Determine Acid Ceramidase Activity," *Anal. Biochem.* 274(2):264-269 (1999).

Heringdorf et al., "Stimulation of intracellular sphingosine-1 -phosphate production by G-protein-coupled sphingosine-1 -phosphate receptors," *Eur. J. Pharmacol.* 414(2-3):145-154 (2001).

Hernandez et al., "Rapid Activation of Neutral Sphingomyelinase by Hypoxia-Reoxygenation of Cardiac Myocytes," *Circ. Res.* 86(2):198-204 (2000).

Hetland et al., "Phospholipase C from *Bacillus cereus* has sphingomyelinase activity," *Scand. J. Clin. Lab. Invest.* 42(1):57-61 (1982).

Higuchi et al., "Acidic sphingomyelinase-generated ceramide is needed but not sufficient for TNF-induced apoptosis and nuclear factor-kappa B activation," *J. Immunol.* 157(1):297-304 (1996).

Hinkovska-Glacheva et al., "Activation of a Plasma Membrane-Associated Neutral Sphingomyelinase and Concomitant Ceramide Accumulation During IgG-Dependent Phagocytosis in Human Polymorphonuclear Leukocytes," *Blood* 91(12):4761-4769 (1998).

Hise et al., "Fatty Acyl Chain Composition in the Determination of Renal Membrane Order," *J. Clin. Invest.* 77(3):768-773 (1986).

Hla et al., "An Abundant Transcript Induced in Differentiating Human Endothelial Cells Encodes a Polypeptide with Structural Similarities to G-Protein-coupled Receptors," *J. Biol. Chem.* 265(16):9308-9313 (1990).

Hofmann et al., "Cloning and characterization of the mammalian brain-specific, $Mg^{2+}$-dependent neutral sphingomyelinase," *Proc. Natl. Acad. Sci. USA* 97(11):5895-5900 (2000).

Hofstadler et al., "Multiplexed Screening of Neutral Mass-Tagged RNA Targets against Ligand Libraries with Electrospray Ionization FTICR MS: a Paradigm for High-Throughput Affinity Screening," *Anal. Chem.* 71(16):3436-3440 (1999).

Holopainen et al., "Sphingomyelinase Activity. Associated with Human Plasma Low Density Lipoprotein," *J Biol. Chem.* 275(22):16484-16489 (2000).

Horn et al., "Sphingofungins E and F: Novel Serinepalmitoyl Trans-Ferase Inhibitors From *Paecilomyces variotii*," *J. Antibiot.* (Tokyo) 45(10):1692-1696 (1992).

Hoye et al., "Synthesis (and Alternative Proof of Configuration) of the Scyphostatin C(1')-C(20') Trienoyl Fragment," *Organic Letts.* 2(10):1481-1483 (2000).

Hudson, "Recombinant antibody fragments," *Curr. Op. Biotechnol.* 9(4):395-402 (1999).

Humpf et al., "Acylation of naturally occurring and synthetic 1-deoxysphinganines by ceramide synthase. Formation of N-palmitoyl-aminopentol produces a toxic metabolite of hydrolyzed fumonisin, AP1, and a new category of ceramide synthase inhibitor," *J. Biol. Chem.* 273(30):19060-19064 (1998).

Huwiler et al., "Physiology and pathophysiology of sphingolipid metabolism and signling," *Biochim. Biophys. Acta* 1485(2-3):63-99 (2000).

Igarashi, "Functional Roles of Sphingosine, Sphingosine 1-Phosphate, and Methylsphingosines: In Regard to Membrane Sphingolipid Signaling Pathways," *J. Biochem.* 122(6):1080-1087 (1997).

Ikezawa et al., "Studies on Sphingomyelinase of *Bacillus cereus*. 1. Purification and Properties," *Biochim. Biophys. Acta* 528(2):247-256 (1978).

Im et al., "Characterization of a novel sphingosine 1-phosphate receptor, Edg-8," *J. Biol. Chem.* 275(19):14281-14286 (2000).

Im et al., "Molecular Cloning and Characterization of a Lysophosphatidic Acid Receptor, Edg-7, Expressed in Prostate," *Mol. Pharmacol.* 57(4):753-759 (2000).

Izuhara et al., "Studies toward the Total Synthesis of Scyphostatin: First Entry to the Highly Functionalized Cyclohexenone Segment," *Organic Lett.* 3(11):1653-1656 (2001).

Jimbo et al., "Development of a New Inhibitor of Glucosylceramide Synthase," *J. Biochem.* 127(3):485-491 (2000).

Johansen et al., "*Bacillus cereus* strain SE-1: nucleotide sequence of the sphingomyelinase C gene," *Nucl. Acids Res.* 16(21)10370 (1998).

Jonghe et al., "Structure-Activity Relationship of Short-Chain Sphingoid Bases As Inhibitors of Sphingosine Kinase", *Bioorg. Medicinal Chem. Lett.* 9(21):3175-3180 (1999).

Kajstura et al., "Apoptotic and Necrotic Myocyte Cell Deaths Are Independent Contributing Variables of Infarct Size in Rats," *Lab. Invest.* 74(1):86-107 (1996).

Kanfer et al., "The Metabolism of Sphingomyelin. I. Purification and properties of a sphingomyelin-cleaving enzyme from rat liver tissue," *J. Biol. Chem.* 241(5):1081-1084 (1966).

Katircioglu et al., "Myocardial preservation in acute coronary artery occlusion with coronary sinus retroperfusion and carnitine," *J. Cardiovasc. Surg.* (Torino) 41(1):45-50 (1999).

Kay et al., "Identification of enzyme inhibitors from phage-displayed combinatorial peptide libraries," *Comb. Chem. High Throughput Screen* 4(7):535-543 (2001).

Kester, "Sphingolipid Metabolites and the Cellular Phenotype," *Trends Glycosci. Glycotechnol.* 9(50):447-460 (1997).

Kihara et al,, "Direct Measurement of Changes in Intercellular Calcium Transients During Hypoxia, Ischemia, and Reperfusion of the Intact Mammalian Heart," *Circ. Res.* 65(4):1029-1044 (1989).

Kimura et al., "Two Novel Xenopus Homologs of Mammalian $LP_{A1}$/EDG-2 Function as Lysophosphatidic Acid Receptors in *Xenopus oocytes* and Mammalian Cells," *J. Biol. Chem.* 276(18):15208-15215 (2001).

Kita et al., "Reverse hydrolysis reaction of a recombinant alkaline ceramidase of *Pseudomonas aeruginosa*," *Biochim. Biophys. Acta* 1485(2-3):111-120 (2000).

Kohama et al., "Molecular cloning and functional characterization of murine sphingosine kinase," *J. Biol. Chem.* 273(37):23722-23728 (1998).

Kolesnick et al., "Characterization of a Ceramide Kinase Activity from Human Leukemia (HL-60) Cells: Separation From Diacylglycerol Kinase Activity," *J. Biol. Chem.* 265(31):18803-18808 (1990).

Kolesnick, "The thereapeutic potential of modulating the ceramide/sphingomyelin pathway," *J. Clin. Inv.* 110(1):3-8 (2002).

Krown et al., "Tumor necrosis factor alpha-induced apoptosis in cardiac myocytes. Involvement of the sphingolipid signaling cascade in cardiac cell death," *J. Clin. Invest.* 98(12):2854-2865 (1996).

Kubota et al., "Accumulation of ceramide in ischemic human brain of an acute case of cerebral occlusion," *Japan J. Exp. Med.* 59(2):59-64 (1989).

Kubota et al., "Sphingomyelin changes in rat cerebral cortex during focal ischemia," *Neurol. Res.* 18(4):337-341 (1996).

Lanterman et al., "Characterization of sphingosine kinase (SK) activity in *Saccharomyces cerevisiae* and isolation of SK-deficient mutants," *Biochem. J.* 332(Part 2):525-531 (1998).

Lee et al., "Effect of Ischemia on Calcium-Dependent Fluorescence Transients in Rabbit Hearts Containing Indo 1. Correlation with Monophasic Action Potentials and Contraction," *Circ.* 78(4):1047-1059 (1988).

Lee et al., "Cell-cycle-dependent changes in ceramide levels preceding retinoblastoma protein dephosphorylation in G2/M," *Biochem. J.* 334(Part 2):457-461 (1998).

Lee et at, "Improved Inhibitors of Glucosylceramide Synthase," *J. Bio. Chem.* 274(21):14662-14669 (1999).

Lee et al., "Sphingosine 1-Phosphate Induces Angiogenesis: Its Angiogenic Action and Signaling Mechanism in Human Umbilical Endothelial Cells," *Biochem. Biophys. Res. Commun.* 264(3):743-750 (1999).

Lee et al., "Lysophosphatidic acid and sphingosine 1-phosphate stimulate endothelial cell wound healing," *Am. J. Physiol. Cell Physiol.* 278(3):C612-C618 (2000).

Levade, et al., "Sphingomyelinases and Niemann-Pick disease," *J. Clin. Chem. Clin. Biochem.* 24(4):205-220 (1986).

Li et al., "The Human Acid Ceramidase Genes (ASAH): Structure, Chromosomal Location, Mutation Analysis, and Expression," *Genomics* 62(2):223-231 (1999).

Liliom at al, "Sphingosylphosphocholine is a naturally occurring lipid mediator in blood plasma: a possible role in regulating cardiac function via sphingolipid receptors," *Biochem. J.* 355(Part 1):189-197(2001).

Lin et al., "Identification of neutral and acidic sphingomyelinases in *Helicobacter pylori*," *FEBS Lett.* 423(2):249-253 (1998).

Linn et al., "Regulation of de nova sphingolipid biosynthesis and the toxic consequences of its disruption," *Biochem. Soc.* 29(Part 6):831-835 (2001).

Lister et al., "Interaction of sphingomyelinase with sphingomyelin analogs modified at the G1 and C-3 positions of the sphingosine backbone," *Biochim. Biophys. Acta* 1256(1):25-30 (1995).

Little at al, "Surface display of antibodies," *Biotechn. Adv.* 12(3):539-555 (1994).

Liu et al., "Inhibition of the neutral magnesium-dependent sphingomyelinase by glutathione," *J. Biol. Chem.* 272(26):16281-16287 (1997).

Liu et al., "Purification and Characterization of a Membrane Bound Neutral pH Optimum Magnesium-dependent and Phosphatidylserine-stimulated Sphingomyelinase from Rat Brain," *J. Biol. Chem.* 273(51):34472-34479 (1998).

Liu et al., "Glutathione regulation of neutral sphingomyelinase in tumor necrosis factor-alpha-induced cell death," *J. Biol. Chem.* 273(18):11313-11320 (1998).

Liu at al, "Advances in the signal transduction of ceramide and related sphingolipids," *Crit. Rev. Clin. Lab. Sci.* 36(6):511-573 (1999).

Liu et al., "Molecular Cloning and Functional Characterization of a Novel Mammalian Sphingosine Kinase Type 2 Isoform," *J. Biol. Chem.* 275(26):19513-19520 (2000).

Liu et al., "Sphingomyelinase Assay Using Radiolabeled Substrate," *Meth. Enzymol.* 311:164-167 (2000).

Lochhead at al, "Fluorinated anesthetic exposure "activates" the renal cortical sphingomyelinase cascade," *Kidney Int.* 54(2):373-381 (1998).

Luberto et al., "Sphingomyelin synthase, a potential regulator of intracellular levels of ceramide and diacylglycerol during SV40 transformation. Does sphingomyelin synthase account for the putative phosphatidylcholine-specific phopholipase C?," *J. Biol. Chem.* 273(23):14550-14559 (1998).

Luberto at al, "Sphingolipid Metabolism in the Regulation of Bioactive Molecules," *Lipids* 34(Supp. 1):S5-S11 (1999).

Lynch at al, "Life on the edg," *Trends Pharmacol. Sci.* 20(12):473-475 (1999).

Magnelli et al., "BCL-2 Overexpression Abolishes Early Calcium Waving Preceding Apoptosis in NIH-3T3 Murine," *Biochem. Biophys. Res. Comm.* 204(1):84-90 (1994).

Mandala et al., "Inhibition of Serine Palmitoyl-Transferase Activity by Lipoxamycin," *J. Antibiot.* (Tokyo) 47(3):376-379 (1994).

Mandala et al., "The Discovery of Australifungin, a novel Inhibitor of Sphinganine N-Acyltransferase from *Sporormiella australis*. Producing Organism, Fermentation, Isolation, and Biological Activity," *J. Antibiot.* (Tokyo) 48(5):349-356 (1995).

Mandala et al., "Khafrefungin, a novel inhibitor of sphingolipid synthesis," *J. Biol. Chem.* 272(51):32709-32714 (1997).

Mandala et al., "Viridiofungins, Novel Inhibitors of Sphingolipid Synthesis," *J. Antibiot.* (Tokyo) 50(4):339-343 (1997).

Mandala et al., "Sphingoid base 1-phosphate phosphatase: a key regulator of sphingolipid metabolism and stress response," *Proc. Natl. Acad. Sci. USA* 95(1):150-155 (1998).

Mandala et al., "Isolation and Characterization of Novel Inhibitors of Sphingolipid Synthesis: Australifungin, Viridiofungins, Rustmicin, and Khafrefungin," *Methods Enzymol.* 311:335-348 (1999).

Mandala et al., "Molecular cloning and characterization of a lipid phosphohydrolase that degrades sphingosine-1-phosphate and induces cell death," *Proc. Natl. Acad. Sci. USA* 97(14):7859-7864 (2000).

Mandala et al., "Sphingosine-1-Phosphate Phosphatases," *Prostaglandins & Other Lipid Mediators* 64(1-4):143-156 (2001).

Mao et al., "Molecular cloning and characterization of SCaMPER, a Sphingolipid Ca2+ release-mediating protein from endoplasmic reticulum," *Proc. Natl. Acad. Sci. USA* 93(5):1993-1996 (1996).

Mao et al., "Cloning of an Alkaline Ceramidase from *Saccharomyces cerevisiae*: An Enzyme with Reverse (CoA-Independent) Ceramide Synthase Activity," *J. Biol. Chem.* 275(10):6876-6884 (2000).

Mao et al., "Cloning and Characterization of a *Saccharomyces cerevisiae* Alkaliine Ceramidase with Specificity for Dihydroceramide," *J. Biol. Chem.* 275(40):31369-31378 (2000).

Mao et al., "Cloning and Characterization of a Novel Human Alkaline Ceramidase: A Mammalian Enzyme That Hydrolyzes Phytoceramide," *J. Biol. Chem.* 276(28):26577-26588 (2001).

Marks et al., "Methods for Studying Glucosylceramide Synthase," *Methods Enzymol.* 311:50-59 (1999).

Martin et al., "Neutral Magnesium-Dependent Sphingomyelinase from Liver Plasma Membrane: Purification and Inhibition by Ubiquinol," *J. Bioenerg. Biomember.* 33(2):143-153 (2001).

Meacci et al., "Receptor-mediated activation of phospholipase D by sphingosine 1-phosphate in skeletal muscle C2C12 cells: A role for protein kinase C," *FEBS Lett.* 457(2):184-188 (1999).

Meldrum, "Tumor necrosis factor in the heart" *Am. J. Physiol.* 274(3):R577-R595 (1998).

Melendez et al., "Human sphingosine kinase: molecular cloning, functional characterization and tissue distribution," *Gene* 251(1):19-26 (2000).

Meroni et al., "Effect of N-Acetylsphingosine (C2) and the Ceramidase Inhibitor (1S,2R)-D-erythro-2-(n-myristoylamino)-1 phenyl-1-propanol on the Regulation of Sertoli Cell Function," *J. Androl.* 20(5):619-625 (1999).

Merrill et al., "Activities of serine palmitoyltransferase (3-ketosphinganine synthase) in microsomes from different rat tissues," *J. Lipid Res.* 26(5):617-622 (1993).

Michel et al., "Characterization of Ceramide Synthesis. A Dihydroceramide Desaturase Introduces the 4,5-*Trans*-Double Bond of Sphingosine at the Level of Dihydroceramide," *J. Biol. Chem.* 272(36):22432-22437 (1997).

Milstien et at, "Targeting sphingosine-1-phosphate: A novel avenue for cancer therapeutics," *Cancer Cell.* 9(3):148-150 (2006)(Abstract Only).

Mingeot-Leclercq et al., "Aminoglycosides: activity and resistance," *Antimicrob. Agents Chemother.* 43(4):727-737 (1999).

Mingeot-Leclercq et al., "Aminoglycosides: nephrotoxicity," *Antimicrob. Agents Chemother.* 43(5):1003-1012 (1999).

Mitsutake et al., "Purification, Characterization, Molecular Cloning, and Subcellular Distribution of Neutral Ceramidase of Rat Kidney," *J. Biol. Chem.* 276(28):26249-26259 (2001).

Miyake, "Serine palmitoyltransferase is the primary target of a sphingosine-like immunosuppressant, ISP-1/myriocin," *Biochem. Biophys. Res. Commun.* 211(2):396-403 (1995).

Mohan et al., "Evidence that Neutral Sphingomyelinase of Cultured Murine Neuroblastoma Cells is Oriented Externally on the Plasma Membrane," *Biochem. Biophys. Acta* 777(2):339-342 (1984).

Mohler et al., "Soluble Tumor Necrosis Factor (TNF) Receptors Are Effective Therapeutic Agents in Lethal Endotoxemia and Function Simultaneously as Both TNF Carries and TNF Antagonists," *J. Immunol.* 151(3):1548-1561 (1993).

Nakajima et al., "Expression and characterization of Edg-1 receptors in rat cardiomyocytes: Calcium deregulation in response to sphingosine 1-phosphate," *Eur. J. Biochem.* 267(18):5679-5686 (2000).

Nakajima et al., *Biophysical J.* 78:319 A (2000).

Napoli et al., "Ischaemic preconditioning of rat myocardium: effects on postischaemic coronary endothelium hypermaebility and microcirculatory damage," *J. Clin. Bas. Cardiol.* 1(1):37-42 (1998).

Nikolova-Karakashian et al., "Ceramidases," *Meth. Enzymol.* 311:194-201 (1999).

Ohta et al., "A possible role of sphingosine in induction of apoptosis by tumor necrosis factor-a in human neutrophils," *FEBS Lett.* 355(3):267-270 (1994).

Ohta et al., "Induction of apoptosis by sphingosine in human leukemic HL-60 cells: a possible endogenous modulator of apoptotic DNA fragmentation occurring during phorbol ester-induced differentiation," *Cancer Res.* 55(3):691-697 (1995).

Okamoto et al., "EDG1 Is a Functional Sphingosine-1-phosphate Receptor That Is Linked via a $G_{i/o}$ to Multiple Signaling Pathways, Including Phospholipase C Activation, $Ca^{2+}$ Mobilization, Ras-Mitogen-activated Protein Kinase Activation, and Adenylate Cyclase Inhibition," *J. Biol. Chem.* 273(42):27104-27110 (1998).

Okamoto et al., "EDG3 Is a Functional Receptor Specific for Sphingosine 1-Phosphate and Sphingosylphosphorylcholine with Signaling Characteristics Distinct from EDG1 and AGR16," *Biochem. Biophys. Res. Commun.* 260(1):203-208 (1999).

Okazaki et al., "Characteristics and partial purification of a novel cytosolic, magnesium-independent, neutral sphingomyelinase activated in the early signal transduction of 1 alpha,25-dihydroxyvitamin D3-induced HL-60 cell differentiation," *J. Biol. Chem.* 269(6):4070-4077 (1994).

Okino et al., "Molecular Cloning, Sequencing, and Expression of the Gene Encoding Alkaline Ceramidase from *Pseudomonas aeruginosa*: Cloning of A Ceramidase Homologue from mycobacterium Tuberculosis," *J. Biol. Chem.* 274(51):36616-36622 (1999).

Olivera et al., "Sphingosine-1-phosphate as second messenger in cell proliferation induced by PDGF and FCS mitogens," *Nature* 365(6446):557-560 (1993).

Olivera et al., "Assaying Sphingosine Kinase Activity," *Methods Enzymol.* 311:215-223 (1999).

Olshefski et al., "Glucosylceramide Synthase Inhibition Enhances Vincristine-Induced Cytotoxicity," *Int, J. Cancer* 93(1):131-138 (2001).

Oral et al., "Sphingosine mediates the immediate negative inotropic effects of tumor necrosis factor-alpha in the adult mammalian cardiac myocyte," *J. Biol. Chem.* 272(8):4836-4842 (1997).

Parrill et al., "Identification of Edg1 Receptor Residues That Recognize Sphingosine 1-Phosphate," *J. Biol. Chem.* 275(50):39379-39384 (2000).

Pitson et al., "Human sphingosine kinase: purification, molecular cloning and characterization of the native and recombinant enzymes," *Biochem J.* 350(Part 2):429-441 (2000).

Pitson et al., "Expression of a catalytically inactive sphingosine kinase mutant blocks agonist-induced sphingosine kinase activation. A dominant-negative sphingosine kinase," *J. Biol. Chem.* 275(43):33945-33950 (2000).

Presta et al., "Humanization of an Anti-Vascular Endothelial Growth Factor Monoclonal Antibody for the Therapy of Solid Tumors and Other Disorders," *Canc. Res.* 57(20):4593-4599 (1997).

Raag et al., "Single-chain Fvs," *FASEB J.* 9(1):73-80 (1995).

Rani et al., "Cell Cycle Arrest Induced by an Inhibitor of Glucosylceramide Synthase," *J. Biol. Chem.* 270(6):2859-2867 (1995).

Riley et al., "Alteration of tissue and serum sphinganine to sphingosine ratio: an early biomarker of exposure to fumonisin-containing feeds in pigs," *Toxicol. Appl. Pharmacol.* 118(1):105-112 (1993).

Riley et al., "Fermentation, partial purification, and use of serine palmitoyltransferase inhibitors from Isaria (= Cordyceps) sinclairii," *Meth. Enzymol.* 311:348-361 (1999).

Romiti et al., "Characterization of sphingomyelinase activity released by thrombin-stimulated platelets," *Mol. Cell. Biochem.* 205(1-2):75-81 (2000).

Runcie at al, "A Short and Efficient Route to Novel Scyphostatin Analogues," *Organic Lett.* 3(21):3237-3239 (2001).

Sabbadini et al., "Sphingosine is endogenous to cardiac and skeletal muscle," *Biochem. Biophys. Res. Comm*193(2):752-758 (1993).

Sabbadini et al., "The Mirf trial: predicting the incidence and severity of CAD using serum sphingolipids," *Circ.* 102(18):ll699 (2000).

Saint-Joanis et al., "Gene cloning shows the alpha-toxin of *Clostridium perfringens* to contain both sphingomyelinase and lecithinase activities," *Mol. Gen. Genet.* 219(3):453-60 (1989).

Saito et al., "Absolute Configuration of Scyphostatin," *Organic Letts* 2(4):505-506 (2000).

Sakai et al., "A devise for recording left ventricular contraction and electrocardiogram in nonworking isolated perfused rat heart," *Jpn J. Pharmacol.* 28(2):223-229 (1978).

Sawada et al., "Ordering of ceramide formation, caspase activation, and Bax/Bcl-2 expression during etoposide-induced apoptosis in C6 glioma cells," *Cell Death Differentiation* 7(9):761-7672 (2000).

Sato, "A new role of lipid receptors in vascular and cardiac morphogenesis," *J. Clin. Invest.* 106(8):939-940 (2000).

Sawai et al., "Function of the Cloned Putative Neutral Sphingomyelinase as Lyso-platelet Activating FactorPhospholipase C," *J. Biol. Chem.* 274(53):38131-38139 (1999).

Sawai et al., "Identification of ISC1 (YER019w) as Inositol Phosphosphingolipid Phospholipase C *Saccharomyces cerevisiae*," *J. Biol. Chem.* 275(50):39793-39798 (2000).

Schissel et al., "$Zn^{2+}$-stimulated Sphingomyelinase Is Secreted by Many Cell Types and Is a Product of the Acid Sphingomyelinase Gene," *J. Biol. Chem.* 271(31):18431-18436 (1996).

Sergeyev et al., "Lipid Spectrum of the Myocardium of White Rats Exposed to Hypoxic Hypoxia," *Kosm. Biol. Aviakosm. Med. (Russian)* 15(6):71-74 (1981).

Shayman et al., "Glucosylceramide Synthase: Assay and Properties," *Methods Enzymol.* 311:42-49 (1999).

Shayman et al., "Inhibitors of Glucosylceramide Synthase," *Methods Enzymol.* 311:373-387 (1999).

Shinghal et al., "Ceramide 1-Phosphate Phosphatase Activity in Brain," *J. Neurochem.* 61(6):2279-2285 (1993).

Siehler et al., "Sphingosine 1-Phosphate Activates Nuclear Factor-kappa B through Edg Receptors: Activation Through Edg-3 and Edg-5, but not Edg-1, in Human Embryonic Kidney 293 Cells," *J. Biol. Chem.* 276(52):48733-48739 (2001).

Siess et al., "Lysophosphatidic Acid and Sphingosine 1-Phosphate: Two Lipid Villains Provoking Cardiovascular Diseases?" *IUBMB Life* 49(3):161-171 (2000).

Smith et al., "Hypoxia, calcium fluxes, and inotropic state: Studies in cultured heart cells," *Am. Heart J.* 103(4 Part 2):716-723 (1982).

Smith et al., "Purified Fumonisin $B_1$ Decreases Cardiovascular Function but does not Alter Pulmonary Capillary Permeability in Swine," *Toxicol. Sci.* 56(1):240-249 (2000).

Spence, "Sphingomyelinases," *Adv. Lipid Res.* 26:3-23 (1993).

Spence et al., "A new Zn2+-stimulated sphingomyelinase in fetal bovine serum," *J. Biol. Chem.* 264(10):5358-5363 (1989).

Spiegel et al., "Sphingolipid metabolism and cell growth regulation," *FASEB J.* 10(12):1388-1397 (1996).

Spiegel et al., "Review: Roles of Sphingosine-1-phosphate in Cell Growth, Differentiation, and Death," *Biochemistry (Mosc).* 63(1):69-83 (1998).

Spiegel et al., "Functions of a new family of sphingosine-1-phosphate receptors," *Biochim. Biophys. Acta* 1484(2-3):107-116 (2000).

Sucheck et al., "Combinatorial synthesis of aminoglycoside libraries," *Curr. Opin. Drug Disc. Develop.* 4(4):462-470 (2001).

Sugita at al, "Ceramidase and ceramide synthesis in human kidney and cerebellum. Description of a new alkaline ceramidase," *Biochim. Biophys. Acta* 398(1):125-131 (1975).

Sugiyama et al., "Sphingosine 1-phosphate induces sinus tachycardia and coronary vasoconstriction in the canine heart," *Cardiovasc. Res.* 46(1):119-125 (2000).

Sumnicht et al., "Lipid Composition of Transverse Tubular Membranes from Normal and Dystrophic Skeletal Muscle," *Arch. Biochem. Biophys.* 215(2):628-637. (1982).

Szulc et al., "A facile regioselective synthesis of sphingosine 1-phosphate and ceramide 1-phosphate," *Tetrahedron Lett.* 41(41):7821-7824 (2000).

Tamura et al., "Mass Production of Sphingomyelinase of *Bacillus cereus* by a Protein-Hyperproducing Strain, *Bacillus brevis* 47, and Its Purification," *J. Biochem.* (Tokyo) 112(4):488-491 (1992).

Tanaka et al., "Structural Elucidation of Scyphostatin, an Inhibitor of Membrane-Bound Neutral Sphingomyelinase," *J. Am. Chem. Soc.* 199(33):7871-7872 (1997).

Tani et al., "Purification and Characterization of a Neutral Ceramidase from Mouse Liver: A single Protein Catalyzes the Reversible Reaction in Which Ceramide is Both Hydrolyzed and Synthesized," *J. Biol. Chem.* 275(5):3462-3468 (2000).

Tazabekova et al., "Synthesis of sphingomyelin phosphonate analogues and preparation of an affinity sorbent for the sphingomyelinase purification," *Bioorg. Khim.* 13(5):648-653 (1987).

Tomita et al.., "Secondary structure of sphingomyelinase from *Bacillus cereus*," *J. Biochem.* (Tokyo) 108(5):811-815 (1990).

Torley et al., "A turbidometric assay for phospholipase C and sphingomyelinase," *Anal. Biochem.* 222(2):461-464 (1994).

Tosaka et al., "Sphingosine 1-phosphate contracts canine basilar arteries in vitro and in vivo: possible role in pathogenesis of cerebral vasospasm," *Stroke* 32(12):2913-2919 (2001).

Triola et al., "Synthesis of a Cyclopropene Analogue of Ceramide, a Potent Inhibitor of Dihydroceramide Desaturase," *Angew. Chem. Int. Ed.* 40(10):1960-1962 (2001).

Tsunoda et al., "Early Fumonisin B1 Toxicity in Relation to Disrupted Sphingolipid Metabolism in Male BALB/c Mice," *J. Biochem. Mol. Toxicol.* 12(5):281-289 (1998).

Uchida et al., "Alutenusin, a Specific Neutral Sphingomyelinase Inhibitor, Produced by Penicillium sp. FO-7436," *J. Antibiot.* (Tokyo) 52(6):572-574 (1999).

Urdal, "The Biochemistry of Tumor Associated Gangliotriosylceramide and the Use of This Glycolipid as a Target for Antibody Dependent, Avidin Mediated Drug Killing of Tumor Cells," *Dissertation Abstracts Int.* 41(11B):4062-4063 (1980).

Usta et al., "Structural Requirements of Ceramide and Sphingosine Based Inhibitors of Mitochondrial Ceramidase," *Biochemistry* 40(32):9657-9668 (2000).

Van Brocklyn et al., "Sphingosine 1-phosphate-induced cell rounding and neurite retraction are mediated by the G protein-coupled receptor H218," *J. Biol. Chem.* 274(8):4626-4632 (1999).

Van Veldhoven et al., "Sphingosine-Phosphate Lyase," *Adv. Lipid Res.* 26:69-98 (1993).

Van Veldhoven, "Shingosine-l-phosphate Lyase," *Methods Enzymol.* 311:244-254 (1999).

Van Veldhoven et al., "Human sphingosine-1-phosphate lyase: cDNA cloning, functional expression studies and mapping to chromosome 10q22(1)," *Biochim. Biophys. Acta* 1487(2-3)128-134 (2000).

Visentin et al., "Validation of an anti-sphingosine-1-phosphate antibody as a potential therapeutic in reducing growth, invasion, and angiogenesis in multiple tumor lineages," *Cancer Cell.* 9(3):225-238 (2006).

Vivekananda et al., "Sphingomyelin metabolites inhibit sphingomyelin synthase and CTP:phosphocholine cytidylyltransferase," *Am. J. Physiol. Lung Cell. Mol. Physiol.* 228(1):L98-L107 (2001).

Walev et al., "Selective killing of human monocytes and cytokine release provoked by sphingomyelinase (beta-toxin) of *Staphylococcus aureus*," *Infect. Immun.* 64(8):2974-2979 (1996).

Wang et al., "A Single Amino Acid Determines Lysophospholipid Specificity of the S1 P1 (EDG1) and LPA1 (EDG2) Phospholipid Growth Factor Receptors," *J. Biol. Chem.* 276(52):49213-49220 (2001).

Wang et al., "Fumonisins and other inhibitors of de novo sphingolipid biosynthesis," *Adv. Lipid Res.* 26:215-234 (1993).

Webster's Dictionary, p. 1135 (1990).

Winter et al., "Making antibodies by phage display technology," *Annu. Rev. Immunol.* 12:433-455 (1994).

Xia et al., "Tumor necrosis factor-alpha induces adhesion molecule expression through the sphingosine kinase pathway," *Proc. Natl. Acad. Sci.* (USA) 95(24):14196-14201 (1988).

Xia et al., "High density lipoproteins (HDL) interrupt the sphingosine kinase signaling pathway. A possible mechanism for protection against atherosclerosis by HDL," *J. Biol. Chem.* 274(46):33143-33147 (1999).

Xu et al., "Involvement of de novo ceramide biosynthesis in tumor necrosis factor-alpha/cycloheximide-induced cerebral endothelial cell death," *J. Biol. Chem.* 273(26):16521-16526 (1998).

Xu et al., "Sphingosylphosphorylcholine is a ligand for ovarian cancer G-protein-coupled receptor 1," *Nat. Cell Biol.* 2(5):261-267 (2000).

Yada et al., "Purification and biochemical characterization of membrane-bound epidermal ceramidases from guinea pig skin," *J. Biol. Chem.* 270(21):12677-12684 (1995).

Yamada et al., "Nucleotide sequence and expression in *Escherichia coli* of the gene coding for sphingomyelinase of *Bacillus cereus*," *Eur. J. Biochem.* 175(2):213-220 (1988).

Yamaji et al., "Lysenin, a novel sphingomyelin-specific binding protein," *J. Biol. Chem.* 273(9):5300-5306 (1998).

Yamanaka et al., "Acid Sphingomyelinase of Human Brain: Purification to Homogeneity," *J. Neurochem*, 38(6):1753-1764 (1982).

Yamazaki et al., "Edg-6 as a Putative Sphingosine 1-Phosphate Receptor Coupling to Ca2+ Signaling Pathway," *Biochem. Biophys. Res. Commun*. 268(2):583-589 (2000).

Yatomi et al., "Sphiongosine-l-Phosphate: A Platelet-Activating Sphingolipid Released from Agonist Stimulated Human Platelets," *Blood* 86(1):193-202 (1995).

Yatomi et al., "Sphingosine 1-phosphate, a bioactive sphingolipid abundantly stored in platelets, is a normal constituent of human plasma and serum," *J. Biochem.* 121(5):969-973 (1997).

Yatomi et al., "Sphingosine 1-phosphate induces platelet activation through an extracellular action and shares a platelet surface receptor with lysophosphatidic acid," *J. Biol. Chem.* 272(8):5291-5297 (1997).

Yellon et al., "Ischaemic preconditioning limits infarct size in the rat heart," *Cardiovasc. Res.* 26(10):983-987 (1992).

Yoshimura et al., "Inhibition of Neutral Sphingomyelinase Activation and Ceramide Formation by Glutathione in Hypoxic PC12 Cell Death," *J. Neurochem.* 73(2):675-683 (1999) .

Yu et al., "Picotal role for acidic sphingomyelinase in cerebral ischemia-induced ceramide and cytokine production, and neuronal apoptosis," *J. Mol. Neurosci.* 15(2):85-97 (2000).

Zager et al., "Decreased expression of mitochondrial-derived $H_2O_2$ and hydroxyl radical in cytoresistant proximal tubules," *Kidney Int.* 52(4):942-952 (1997).

Zechner et al., "MKK6 inhibits myocardial cell apoptosis via a p38 MAP kinase-dependent pathway," *J. Biol. Chem.* 273(14):8232-8239 (1998).

Zelinski et al., "Phosphatidylcholine biosynthesis in isolated hamster heart," *J. Biol. Chem.* 255(23):11423-11428 (1980).

Zhang et al., "Comparative analysis of three murine G-protein coupled receptors activated by sphingosine-1-phosphate," *Gene* 227(1):89-99 (1999).

Zhang et al., "Human Acid Ceramidase Gene: Novel Mutations in Farber Disease," *Mol. Genet. Metab.* 70(4):301-309 (2000).

Zhou et al., "Identification of the First Mammalian Sphingosine Phosphate Lyase Gene and its Functional Expression in Yeast," *Biochem. Biophys. Res. Comm.* 242(3):502-507 (1998).

Zweerink et al., "Characterization of a Novel, Potent, and Specific Inhibitor of Serine Palmitoyltransferase," *J. Biol. Chem.* 267(35):25032-25038 (1992).

\* cited by examiner

SEQUENCE LISTING

<160> NUMBER OF SEQ ID NOS: 7

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccaggattca tcatatgtta aaag                                              24

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atcagtgggt gcatcagtag c                                                 21

<210> SEQ ID NO 3
<211> LENGTH: 333
<212> TYPE: DNA
<213> ORGANISM: Rattus sp.

<400> SEQUENCE: 3
atgttaaaag tgagcagggt ctcaagtgaa ggtttaatat cactttctat cactgaggca       60
cctgatctta agatcaggga tcctaagata gagaaactct accttccagt tttttattta      120
aatgcacaca tctacttaaa tgcactcagt actctcctga actctcattg tggcgagaac      180
tgttttcatg gttatgaaca attacagaat gccacttttc cagtttggag aaatatattc      240
atttatataa acagggtcag gaacaccaag aggcaaggag gaggggtgg tgtgagtggg       300 aaaggtgaga tgaagcagtg cttcctctct taa                                   333

<210> SEQ ID NO 4
<211> LENGTH: 333
<212> TYPE: DNA
<213> ORGANISM: Homo sapiens

<400> SEQUENCE: 4
atgttaaaag tgagcagggt ctcaagtgaa ggtttaatat cactttctat cactgaggca       60
cctgatctta agatcaggga tcctaagata gagaaactct accttccagt tttttattta      120
aatgcacaca tctacttaaa tgcactcagt actctcctga actctcattg tggcgagaac      180
tgttttcatg gttatgaaca attacagaat gccacttttc cagtttggag aaatatattc      240
atttatataa acagggtcag gaacatcaag aggcaaggag gaggggtgg tgtgagtggg       300 aaaggtgaga tgaagcagtg cttcctctct taa                                   333

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic

```
            primer

<400> SEQUENCE: 5
ttatggcaac cacgcacgcg cagg                                            24

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agaccgtcac ttgcagagga c                                               21

<210> SEQ ID NO 7
<211> LENGTH: 1146
<212> TYPE: DNA
<213> ORGANISM: Rattus sp.

<400> SEQUENCE: 7
atggcaacca cgcacgcgca ggggcacccg ccagtcttgg ggaatgatac tctccgggaa      60
cattatgatt acgtggggaa gctggcaggc aggctgcggg atccccctga gggtagcacc     120
ctcatcacca ccatcctctt cttggtcacc tgtagcttca tcgtcttgga gaacctgatg     180
gttttgattg ccatctggaa aaacaataaa tttcataacc gcatgtactt tttcatcggc     240
aacttggctc tctgcgacct gctggccggc atagcctaca aggtcaacat tctgatgtcc     300
ggtaggaaga cgttcagcct gtctccaaca gtgtggttcc tcaggagggg cagtatgttc     360
gtagccctgg gcgcatccac atgcagctta ttggccattg ccattgagcg gcacctgacc     420
atgatcaaga tgaggccgta cgacgccaac aagaagcacc gcgtgttcct tctgattggg     480
atgtgctggc taattgcctt ctcgctgggt gccctgccca tcctgggctg aactgcctg     540 gagaactttc ccgactgctc taccatcttg cccctctact ccaagaaata cattgccttt     600
ctcatcagca tcttcacagc cattctggtg accatcgtca tcttgtacgc gcgcatctac     660
ttcctggtca gtccagcag ccgcagggtg gccaaccaca actccgagag atccatggcc     720
cttctgcgga ccgtagtgat cgtggtgagc gtgttcatcg cctgttggtc ccccctttc     780 atcctcttcc tcatcgatgt ggcctgcagg gcgaaggagt gctccatcct cttcaagagt     840
cagtggttca tcatgctggc tgtcctcaac tcggccatga accctgtcat ctacacgctg     900
gccagcaaag agatgcggcg tgctttcttc cggttggtgt gcggctgtct ggtcaagggc     960
aaggggaccc aggcctcccc gatgcagcct gctcttgacc cgagcagaag taaatcaagc    1020
tccagtaaca acagcagcag ccactctcca aaggtcaagg aagacctgcc ccatgtggct    1080
acctcttcct gcgtcactga caaaacgagg tcgcttcaga atgggtcct ctgcaagtga     1140 cggtct                                                              1146
```

COMPOSITIONS AND METHODS FOR THE TREATMENT AND PREVENTION OF CANCER, ANGIOGENESIS, AND INFLAMMATION

RELATED APPLICATIONS

This application is a continuation of U.S. application Ser. No. 10/028,156, filed Dec. 21, 2001, now U.S. Pat. No. 6,881, 546, which claims priority to U.S. provisional patent application Ser. No. 60/257,926 entitled "Compositions and Methods for the Treatment and Prevention of Cardiac and Myocardial Disorders" by Sabbadini, Roger A., filed Dec. 22, 2000, each of which is hereby incorporated by reference it its entirety, including all Tables, Figures, and Claims.

This application is related to U.S. patent applications Ser. No. 10/029,372 (now abandoned), Ser. No. 10/028,520 (now abandoned), and U.S. application Ser. No. 10/029,401 (now issued as U.S. Pat. No. 6,858,383), each entitled "Compositions and Methods for the Treatment and Prevention of Cardiovascular Diseases and Disorders, and for Identifying Agents Therapeutic Therefor" by Sabbadini, Roger A., and filed Dec. 21, 2001, each of which is hereby incorporated by reference in its entirety, including all Tables, Figures, and Claims.

FIELD OF THE INVENTION

The invention relates generally to the area of treatment and/or prevention of cardiovascular and cerebrovascular diseases, disorders and physical trauma. The beneficial effect of the invention is achieved through the use of pharmaceutical compositions that contain. agents that interfere with the production and/or biological activities of sphingolipids and their metabolites. The invention is also drawn to methods for isolating, formulating and using pharmaceutical compositions, and kits and medical devices comprising such compositions.

BACKGROUND OF THE INVENTION

The following description includes information that may be useful in understanding the present invention. It is not an admission that any of the information provided herein, or any publication specifically or implicitly referenced herein, is prior art, or even particularly relevant, to the presently claimed invention.

Cardiovascular Diseases and Disorders

Ischemic heart disease is the leading cause of death in the U.S. Each year approximately 1.5 million people suffer heart attacks (myocardial infarctions), of which ⅓ (i.e. about 500, 000) are fatal. In addition, about 6.75 million Americans suffer from angina pectoris, the most common manifestation of cardiac ischemia. Angina pectoris is a painful feeling of pressure in the chest that results from ischemic heart disease. In total, there are 13.5 million patients living with ischemic heart disease in the U.S. Americans in the high-risk categories for this disease include persons having one or more indicators/risk factors therefor, including but not limited to hypertension, high levels of serum cholesterol and a family history of heart disease. Many people have at least one of these indicator/risk factors; for example, there are 50 million Americans diagnosed with hypertension alone.

"Ischemia" is a condition associated with an inadequate flow of oxygenated blood to a part of the body, typically caused by the constriction or blockage of the blood vessels supplying it. Ischemia occurs any time that blood flow to a tissue is reduced below a critical level. This reduction in blood flow can result from: (i) the blockage of a vessel by an embolus (blood clot); (ii) the blockage of a vessel due to atherosclerosis; (iii) the breakage of a blood vessel (a bleeding stroke); (iv) the blockage of a blood vessel due to acute vasoconstriction; (v) a myocardial infarction (when the heart stops, the flow of blood to organs is reduced and ischemia results); (vi) trauma; (vii) surgery, during which blood flow to a tissue or organ needs to be reduced or stopped to achieve the aims of surgery (e.g., angioplasty, heart and lung/heart transplants); (viii) exposure to certain agents, e.g., dobutamine or adenosine (Lagerqvist et al., Br. Heart J. 68:282-285, 1992) or (ix) anti-neoplastic and other chemotherapeutic agents, such as doxorubicin, that are cardiotoxic.

Even if the flow rate (volume/time) of blood is adequate, ischemia may nonetheless occur due to hypoxia. "Hypoxia" refers to conditions in which the oxygen content of blood is insufficient to satisfy normal cellular oxygen requirements. Hypoxic blood is, by definition, distinct from normoxic blood, i.e., blood in which the oxygen content is sufficient to satisfy normal cellular oxygen requirements. Such conditions include but are not limited to forms of heart failure that adversely affect cardiac pumping such as hypertension, arrhythmias, septic shock, trauma, cardiomyopathies and congestive heart disease.

Myocardial ischemic disorders occur when cardiac blood flow is restricted (ischemia) and/or when oxygen supply to the heart muscle is compromised (hypoxia) such that the heart's demand for oxygen is not met by the supply. Coronary artery disease (CAD) arising from arteriosclerosis, particularly atherosclerosis, is the most common cause of ischemia, and has symptoms such as stable or unstable angina pectoris. CAD can lead to acute myocardial infarctions (AMI) and sudden cardiac death. The spectrum of ischemic conditions which result in heart failure is referred to as Acute Coronary Syndrome (ACS). Reperfusion injury is often a consequence of ischemia, in particular when anti-coagulants, thrombolytic agents, or anti-anginal medications are used or when the cardiac vasculature is surgically opened by angioplasty or by coronary artery grafting.

Cardiotoxic agents are those materials which would cause a loss of cardiac function, including negative inotropy, arthyTHmias, heart failure, and cell death (both apoptotic and necrotic).

Presently, treatments for acute myocardial infarction and other cardiac diseases include but are not limited to mechanical devices and associated procedures therewith (e.g., coronary angioplasty; Grines et al., N. Engl. J. Med. 3298:673-679, 1993); thrombolytic agents such as streptokinase, tPA, and derivatives thereof. Adjuvants to these therapies include beta-blockers, aspirin and heparin, and glycoprotein (GP) IIb/IIIa inhibitors (Antman et al., Circ. 99:2720-2732, 1999). GP IIb/IIIa inhibitors decrease platelet aggregation and thrombus formation (for a review, see Topol, Lancet 353:227-231, 1999). Examples include but are not limited to monoclonal antibodies (e.g., abciximab), cyclic peptides (e.g., eptifibatide), and nonpeptide peptidomimetics (e.g., tirofibian, lamifiban, xemilofiban, sibrafiban, and lefradafiban).

Preventive treatments include but are not limited to those that reduce a patient's cholesterol levels by, e.g., diet management and pharmacological intervention. Statins are one type of agent that have been used to reduce cholesterol levels. Statins are believed to act by inhibiting the activity of HMG-CoA reductase, which in turn increases the hepatic production of cholesterol receptors (Nickenig et al., Circ. 100:2131-2134, 1999). The hepatic cholesterol receptors bind cholesterol and remove it from blood. Such agents include but are not limited to lovastatin, simvastatin, pravastatin, fluvastatin (Lennernas, Clin. Pharmackinet. 32:403-425, 1997). These and other statins slows the progression of coronary artery disease, and may induce regression of atherosclerotic lesions in patients. It is not known, however, whether other reductases are inhibited by such agents, and what side effects might occur as a result.

Cerebrovascular Diseases and Disorders

Patients experiencing cerebral ischemia often suffer from disabilities ranging from transient neurological deficit to irreversible damage (stroke) or death. Cerebral ischemia, i.e., reduction or cessation of blood flow to the central nervous system, can be characterized as either global or focal.

Focal cerebral ischemia refers to cessation or reduction of blood flow within the cerebral vasculature resulting from a partial or complete occlusion in the intracranial or extracranial cerebral arteries. Such occlusion typically results in stroke, a syndrome characterized by the acute onset of a neurological deficit that persists for at least 24 hours, reflecting focal involvement of the central nervous system and is the result of a disturbance of the cerebral circulation. Other causes of focal cerebral ischemia include vasospasm due to subarachnoid hemorrhage or iatrogenic intervention.

Global cerebral ischemia refers to reduction of blood flow within the cerebral vasculature resulting from systemic circulatory failure. The failure of the circulatory system to maintain adequate cellular perfusion leads to a in reduction of oxygen and nutrients to tissues. Thus, global cerebral ischemia results from severe depression of cardiac performance. The most frequent cause is acute myocardial infarction with loss of substantial muscle mass. Pump failure can also result from acute myocarditis or from depression of myocardial contractility following cardiac arrest or prolonged cardiopulmonary bypass. Mechanical abnormalities, such as severe valvular stenosis, massive aortic or mitral regurgitation, acutely acquired ventricular septal defects, can also reduce cardiac output. Additional causes include cardiac arrhythmia, such as ventricular fibrillation, and any cardiac disease described herein. Further causes include interventional procedures, such as carotid angioplasty, stenting or endarterectomy, which might otherwise result in focal cerebral ischemia, and also cardiac procedures which may result in global cerebral ischemia, such as cardiac catheterization, electrophysiologic studies, and angioplasty.

Those skilled in the art are easily able to identify patients having a stroke or at risk of having a stroke, cerebral ischemia, head trauma, or epilepsy. For example, patients who are at risk of having a stroke include, but are not limited to, patients having hypertension or undergoing major surgery.

Traditionally, emergent management of acute ischemic stroke consists of mainly general supportive care, e.g. hydration, monitoring neurological status, blood pressure control, and/or anti-platelet or anti-coagulation therapy. Heparin has been administered to stroke patients with limited and inconsistent effectiveness. In some circumstances, the ischemia resolves itself over a period of time due to the fact that some thrombi get absorbed into the circulation, or fragment and travel distally over a period of a few days. In 1996, the Food and Drug Administration approved the use of tissue plasminogen activator (t-PA) or Activase®, for treating acute stroke. However, treatment with systemic t-PA is associated with increased risk of intracerebral hemorrhage and other hemorrhagic complications. Aside from the administration of thrombolytic agents and heparin, there are no therapeutic options currently on the market for patients suffering from occlusion focal cerebral ischemia. Vasospasm may be partially responsive to vasodilating agents. The newly developing field of neurovascular surgery, which involves placing minimally invasive devices within the carotid arteries to physically remove the offending lesion may provide a therapeutic option for these patients in the future, although this kind of manipulation may lead to vasospasm itself.

Documents

U.S. Pat. No. 6,210,976 B1 and published PCT patent application WO98/57179 (PCT/US98/10486), both entitled "Methods for Early Detection of Heart Disease", hereby incorporated by reference, relate to the use of blood levels of certain sphingolipids for screening for early ischemic events before symptoms are presented in persons with high risk for heart disease, or in a triage setting for patients with acute coronary syndrome.

PCT Application PCT/US01/12706, published as WO 01/80903, entitled "Detection and Treatment of Atherosclerosis Based on Plasma Sphingomyelin Concentration", relates to enzymatic methods to measure plasma and tissue sphingomyelin concentrations, and that human plasma sphingomyelin levels are positively correlated with atherosclerosis and coronary heart disease.

U.S. Pat. No. 5,929,039, entitled "Method for Treating Cardiac Dysfunction and Pharmaceutical Compositions Useful Therefor", relates to disclose methods for the prophylaxis or treatment of cardiac arrhythmia using an agent capable of blocking or inhibiting the effect or release of inositol(1,4,5) trisphosphate in cardiac tissue. The agent may be an aminoglycoside, including gentamicin.

U.S. Pat. No. 5,677,288, entitled "Use of Aminoglycosides to Protect Against Excitotoxic Neuron Damage", relates to the use of an aminoglycoside, which may be gentamicin, that suppresses the flow of calcium ions into neurons through N-type calcium channels. The method relates to reducing excitotoxic damage to neurons, which can occur as a result of stroke, cerebral ischemia/hypoxia, or other events or conditions.

Published U.S. Patent Application 20010041688, entitled "Methods and Compositions for the Regulation of Vasoconstriction", relates to modulation of sphingosine kinase and sphingosine-1-phosphate phosphatase activity and EDG receptor signaling for the treatment of conditions relating to vasoconstriction and vasoconstriction, including migraine, stroke, subarachnoid hemorrhage and vasospasm.

Ancellin et al., "Extracelluar export of sphingosine kinase-1 enzyme: Sphingosine 1 phosphate generation and the induction of angiogenic vascular maturation", JBC Papers in Press. Published on Dec. 10, 2001 as manuscript M102841200 relates to events related to angiogenesis that are mediated by a sphingosine kinase.

SUMMARY OF THE INVENTION

The invention is drawn to compositions and methods for treating or preventing cardiovascular, cardiac, myocardial and other diseases, disorders or physical trauma, and/or cerebrovascular diseases and disorders, in which therapeutic agents are administered to a patient that alters the activity or concentration of an undesirable, toxic and/or cardiotoxic sphingolipids, or metabolites thereof. The therapeutic methods and compositions of the invention are said to be "sphingolipid-based" in order to indicate that they act by changing the absolute, relative and/or available concentration and/or activities of certain undesirable, toxic or cardiotoxic sphingolipids. The invention is also drawn to chemical libraries and screening assays that are used to identify novel sphingolipid-based therapeutics.

The compositions of the invention are used in methods of sphingolipid-based cardiovascular and cardiac therapy. "Cardiac therapy" refers to the prevention and/or treatment of myocardial diseases, disorders or physical trauma. Conditions of particular interest include but not limited to myocardial ischemia; acute myocardial infarction (AMI); coronary artery disease (CAD); acute coronary syndrome (ACS); cardiac cell and tissue damage that may occur during or as a consequence of pericutaneous revascularization (coronary angioplasty) with or without stenting; coronary bypass grafting (CABG) or other surgical or medical procedures or therapies that may cause ischemic or ischemic/reperfusion damage in humans; and cardiovascular trauma.

"Cardiovascular therapy" encompasses cardiac therapy as well as the prevention and/or treatment of other diseases associated with the cardiovascular system, such as heart disease. The term "heart disease" encompasses any type of disease, disorder, trauma or surgical treatment that involves the heart or myocardial tissue. Of particular interest are heart diseases that relate to hypoxia and/or ischemia of myocardial tissue and/or heart failure. One type of heart disease that can result from ischemia is reperfusion injury, such as can occur when anti-coagulants, thrombolytic agents, or anti-anginal medications are used in therapy, or when the cardiac vasculature is surgically opened by angioplasty or by coronary artery grafting. Another type of heart disease to which the invention is directed is coronary artery disease (CAD), which can arise from arteriosclerosis, particularly atherosclerosis, a common cause of ischemia. CAD has symptoms such as stable or unstable angina pectoris, and can lead to acute myocardial infarctions (AMI) and sudden cardiac death. The term "heart failure" encompasses acute myocardial infarction, myocarditis, a cardiomyopathy, congestive heart failure, septic shock, cardiac trauma and idopathic heart failure. The spectrum of ischemic conditions which result in heart failure is referred to as Acute Coronary Syndrome (ACS).

"Cerebrovascular therapy" refers to therapy directed to the prevention and/or treatment of diseases and disorders associated with cerebral ischemia and/or hypoxia. Of particular interest is cerebral ischemia and/or hypoxia resulting from global ischemia resulting from a heart disease, including without limitation heart failure.

"Toxic sphingolipids" are those sphingolipids that can cause or enhance the necrosis and/or apoptosis of cells, including, in some instances, particular cell types that are found in specific tissues or organs. "Cardiotoxic sphingolipids" are toxic sphingolipids that directly or indirectly cause or enhance cardiac arrythmias, the negative inotropy (loss of contractile function) of the heart and the necrosis and/or apoptosis of cells found in or associated with the heart, including but not limited to cardiomyocytes, cardiac neurons and the like. "Undesirable sphingolipids" include toxic and cardiotoxic sphingolipids, as well as metabolites, particularly metabolic precursors, of toxic and cardiotoxic sphingolipids. Undesirable, cardiotoxic and/or toxic sphingolipids of particular interest include but are not limited to ceramide (CER), sphingosine-1-phosphate (S-1-P) and sphingosine (SPH; D(+)-erythro-2-amino-4-trans-octadecene-1, 3-diol, or sphinganine).

The term "metabolites" refers to compounds from which sphingolipids are made, as well as those that result from the degradation of sphingolipids; that is compounds that are involved in the sphingolipid metabolic pathways (FIGS. 1 and 2). Metabolites include metabolic precursors and metabolic products. The term "metabolic precursors" refers to compounds from which sphingolipids are made. Metabolic precursors of particular interest include but are not limited to SPC, sphingomyelin, dihydrosphingosine, dihydroceramide, and 3-ketosphiganine. The term "metabolic products" refers to compounds that result from the degradation of sphingolipids, such as phosphorylcholine (a.k.a. phosphocholine, choline phosphate), fatty acids, including free fatty acids, and hexadecanal (a.k.a. palmitaldehyde).

As used herein, the term "therapeutic" encompasses the full spectrum of treatments for a disease or disorder. A "therapeutic" agent of the invention may act in a manner that is prophylactic or preventive, including those that incorporate procedures designed to target individuals that can be identified as being at risk (pharmacogenetics); or in a manner that is ameliorative or curative in nature; or may act to slow the rate or extent of the progression of a disease or disorder; or may act to minimize the time required, the occurrence or extent of any discomfort or pain, or physical limitations associated with recuperation from a disease, disorder or physical trauma; or may be used as an adjuvant to other therapies and treatments. The term "cardiotherapeutic agent" refers to an agent that is therapeutic to diseases and diseases caused by or associated with cardiac and myocardial diseases and disorders.

Without wishing to be bound by any particular theory, it is believed that the level of undesirable sphingolipids such as SPH or S-1-P, and/or one or more of their metabolites, cause or contribute to the development of cardiac and myocardial diseases and disorders. Because sphingolipids are also involved in fibrogenesis and wound healing of liver tissue (Davaille et al., J. Biol. Chem. 275:34268-34633, 2000; Ikeda et al., Am J. Physiol. Gastrointest. Liver Physiol 279:G304-G310, 2000), healing of wounded vasculatures (Lee et al., Am. J. Physiol. Cell Physiol. 278:C612-C618, 2000), and other disease states or disorders, or events associated with such diseases or disorders, such as cancer, angiogenesis and inflammation (Pyne et al., Biochem. J. 349:385-402, 2000), the compositions and methods of the present disclosure may be applied to treat these diseases and disorders as well as cardiac and myocardial diseases and disorders.

One form of sphingolipid-based therapy involves manipulating the metabolic pathways of sphingolipids in order to decrease the actual, relative and/or available in vivo concentrations of undesirable, toxic and/or cardiotoxic sphingolipids. The invention provides compositions and methods for treating or preventing cardiac and myocardial diseases, disorders or physical trauma, in which therapeutic agents are administered to a patient that alters the activity or concentration of an enzyme, wherein the enzyme catalyzes a reaction that produces or degrades undesirable, toxic and/or cardiotoxic sphingolipids, or metabolites thereof. An "enzyme" is a protein or polypeptide that catalyzes (causes, accelerates or enhances) a chemical reaction. The term "metabolism" is used to describe the biological construction or destruction of a compound. Metabolism comprises the synthesis (constructive metabolism, a.k.a. anabolism) of compounds and the degradation (destructive metabolism, a.k.a. catabolism) thereof. Enzymes of particular interest, and preferred modulating agents thereof (inhibitors/activators or stimulators/blocking agents), are described in the Detailed Description (see also Examples 7 through 10).

In one version of this form of sphingolipid-based therapy, metabolic steps that involve the production of sphingolipids are inhibited or blocked. Therapeutic agents and methods are used to decrease the amount or activity of enzymes that catalyze chemical reactions that degrade undesirable sphingolipids and/or metabolic precursors thereof. Thus, net sphingolipid catabolism is increased.

In another version of this form of sphingolipid-based therapy, metabolic steps that involve the destruction of sphingolipids are activated or stimulated. Therapeutic agents and methods are used to increase the amount or activity of enzymes that catalyze chemical reactions that degrade undesirable sphingolipids and/or metabolic precursors thereof. Thus, net sphingolipid anabolism is decreased.

One form of sphingolipid-based therapy involves the use of agents that bind undesirable, toxic and/or cardiotoxic sphingolipids, or metabolites thereof. Such sphingolipid-binding agents include but are not limited to proteins and polypeptide derivatives thereof that bind undesirable, toxic and/or cardiotoxic sphingolipids or metabolites thereof. Such a protein and polypeptide may, by way of non-limiting example, be a non-catalytic derivative of an enzyme involved in the sphingolipid metabolic pathways, a derivative of proteins that participate in the sphingomyelin signaling pathway, a derivative of a receptor that binds an undesirable, toxic and/or cardiotoxic sphingolipid, an antibody or antibody derivative that is directed to (specifically binds) an undesirable, toxic and/or cardiotoxic sphingolipid. Such derivatives are preferably water soluble. (Sphingolipid-binding agents are described in the Detailed Description of the Invention; see also Examples 6 and 14).

One form of sphingolipid-based therapy involves the use of agents that bind sphingolipid receptors that initiate and stimulate the sphingomyelin signaling pathway. This pathway ultimately results in increased ceramide production. An increased level of ceramide would, in turn, be expected to result in elevated concentrations of undesirable sphingolipids such as, e.g., S-1-P and SPH. Thus, inhibiting or blocking such receptors decreases, or at least prevents an increase due to the sphingomyelin signaling pathway, the intracellular production of ceramide and metabolites thereof (see the Detailed Description and Example 9). Another form of sphingolipid-based therapy involves the use of molecular genetics to generate therapeutic agents (see the Detailed Description and Example 18).

In one version of this form of sphingolipid-based therapy, the therapeutic agent is a protein (including, without limitation, polypeptides, oligopeptides, and peptidomimetics). A "protein" is a molecule having a sequence of amino acids that are linked to each other in a linear molecule by peptide bonds. The term protein refers to a polypeptide that is isolated from a natural source, or produced from an isolated cDNA using recombinant DNA technology; and has a sequence of amino acids having a length of at least about 200 amino acids. As used herein, the term "polypeptide" includes proteins, fusion proteins, oligopeptides and polypeptide derivatives, with the exception that peptidomimetics are considered to be small molecules herein. An "oligopeptide" is a polypeptide having a short amino acid sequence (i.e., 2 to about 200 amino acids). An oligopeptide is generally prepared by chemical synthesis. Although oligopeptides and protein fragments may be otherwise prepared, it is possible to use recombinant DNA technology and/or in vitro biochemical manipulations. For example, a nucleic acid encoding an amino acid sequence may be prepared and used as a template for in vitro transcription/translation reactions.

A "protein fragment" is a proteolytic fragment of a larger polypeptide, which may be a protein or a fusion protein. A proteolytic fragment may be prepared by in vivo or in vitro proteolytic cleavage of a larger polypeptide, and is generally too large to be prepared by chemical synthesis. Preferably, proteolytic fragments have amino acid sequences having a length from about 10 to about 5,000 amino acids; more preferably about 200 to 1000 amino acids; most preferably 200 to about 1,000 amino acids.

A therapeutic protein may be a dominant negative mutant of an enzyme that catalyzes a reaction that results in the production of an undesirable, toxic and/or cardiotoxic sphingolipid or a metabolite thereof, of a receptor for such a sphingolipid, or of a protein that participates in the sphingomyelin signaling pathway. A "dominant negative mutant protein" is one that, when expressed, (1) does not itself provide the activity of the wildtype protein and (ii) inhibits the action of the wildtype form of the protein. The therapeutic protein may be an enzyme, produced by recombinant DNA technology or any other appropriate method, that catalyzes a reaction that results in the degradation of a undesirable, toxic and/or cardiotoxic sphingolipid, or a metabolite thereof; and such an enzyme may be one that has been altered via molecular genetics to have improved desirable properties such as enhanced catalytic activity, tighter substrate binding, etc.

In another version of this form of sphingolipid-based therapy, the therapeutic agent is a nucleic acid (including, without limitation, DNA, RNA, and oligonucleotides). A therapeutic nucleic acid may have a sequence that is antisense to a nucleotide sequence found within an mRNA that encodes an enzyme that catalyzes a reaction. that results in the production of a undesirable, toxic and/or cardiotoxic sphingolipid, or a metabolite thereof, or a receptor thereof. Such nucleic molecules include antisense oligonucleotides. Such antisense nucleic acids bind to a specific target mRNA due to their complementary sequences, and prevent the mRNA from being processed or translated, or enhance or cause the degradation of the mRNA. A therapeutic nucleic acid may be a gene therapy construct that comprises and expresses, over-expresses or constitutively expresses (i) nucleic acids that are antisense to those that encode an enzyme that catalyzes a reaction that results in the production of a undesirable, toxic and/or cardiotoxic sphingolipid or a metabolite thereof; (ii) therapeutic proteins, such as enzyme that degrades a sphingolipid, or a dominant negative mutant that inhibits such an enzyme, or a sphingolipid-binding protein.

Any composition and method of the invention that may be used in sphingolipid-based therapy may be used in combination with any other compositions and methods for sphingolipid-based therapy, as well as in conjunction with therapeutic agents and compositions that are not sphingolipid-based. Useful adjuvant treatments for the sphingolipid-based treatments of the invention modulate the sphingomyelin signaling pathway and/or inhibit cytokines (see the Detailed Description and Example 14). An "adjuvant" is any agent that is added to a composition or therapeutic regimen to aid the therapeutic effect of the active agent(s) thereof.

An agent for sphingolipid-based therapy is formulated in a pharmaceutical composition. The pharmaceutical compositions of the invention may be formulated for rapid cardiac delivery. By "rapid cardiac delivery" it is meant that the therapeutic agent reaches a therapeutically effective concentration in the blood, serum, or specified tissue within about 30 to 60 minutes, preferably within about 15 to 20 minutes, more preferably within about 5 to 10 minutes, and most preferably within about 5 seconds to about 5 minutes, after its administration. The pharmaceutical compositions are used to treat cardiac, myocardial and other diseases, disorders or physical trauma.

Pharmaceutical and pharmaceutical compositions comprising one or more therapeutic agents of the invention are incorporated into kits and medical devices for such treatments. Medical devices are used to administer the pharmaceutical compositions of the invention to a patient in need thereof, and kits that include such devices. Such devices and kits may be designed for the routine administration, including self-administration, of the pharmaceutical compositions of the invention. Such devices and kits may also be designed for emergency use, i.e., in ambulances or emergency rooms, or during surgery, or in activities where injury is possible but where full medical attention may not be immediately forthcoming (i.e., hiking and camping, or combat situations). The invention thus provides cardiac and myocardial therapies based on the role of sphingolipids in cardiac and myocardial diseases, disorders and physical trauma.

The invention also provides screening assays, including high-throughput screening (HTS) assays, that are useful for identifying novel sphingolipid-based therapeutics. Chemical libraries are screened using these assays, preferably in a high throughput manner, to identify lead compounds and therapeutic agents.

In a related aspect, the invention provides a method of identifying molecules that specifically bind to, and/or otherwise interfere with the action of a sphingolipid target. A "sphingolipid target" is any molecule or moiety that is desired to obtain novel compounds that bind thereto or otherwise inhibit the activity thereof. Sphingolipid targets of the inventions include, but are not limited to, sphingolipids per se; sphingolipid receptors; and molecules involved in sphingolipid metabolism, including but not limited to enzymes that act on sphingolipids and sphingolipid metabolites.

In another embodiment, sphingolipids that are cardiotoxic at relatively high concentrations are used to precondition hearts. Preconditioning hearts with short cycles of ischemia and reperfusion is known to have a cardioprotective effect in rodents (Yellon et al., Cardiovasc Res 26:983-987, 1992; Napoli et al., J Clin Bas Cardiol 1:3742, 1998). In the preconditioning methods of the invention, sphingolipids that are cardiotoxic are administered in small doses. In the methods of the invention, sphingolipids, including but not limited to ceramide, sphingosine and sphingosine-1-phosphate given in low, intermittent doses may protect cardiac tissue from ischemia.

The invention provides benefits not previously obtainable in cardiovascular, cardiac and myocardial treatments. By way of non-limiting example, the consequences of acute cardiac or myocardial events may result from the end result of a cascade of molecular events that evolve rapidly after symptoms become apparent. Treatments that address early events in the cascade may not be able to "catch up" with such events, i.e., may not achieve an effective level until after some undesirable molecules that lead to cardiac or myocardial damage have been produced. Sphingolipid-based therapies act on undesirable events and molecules that occur or are present at the later stages of these cascades, they can act before such undesirable events occur or undesirable molecules are produced, and thus can prevent the occurrence of such events and/or production of such compounds to a greater degree than can be realized by therapies that act earlier in the cascade. Sphingolipid-based therapies addresses events that lead directly (rather than indirectly) to myocardial ischemia and other cardiac disorders, and undesirable side-effects of indirect treatments are thus reduced, minimized or eliminated. Sphingolipid-based therapies provide for preventative treatments that achieve an effective state relatively quickly and non-intrusive as compared to other preventative measures, e.g., changes in diet or surgery.

The summary of the invention described above is not limiting and other features and advantages of the invention will be apparent from the following detailed description of the preferred embodiments, as well as from the claims.

ABBREVIATIONS

Figure 1:
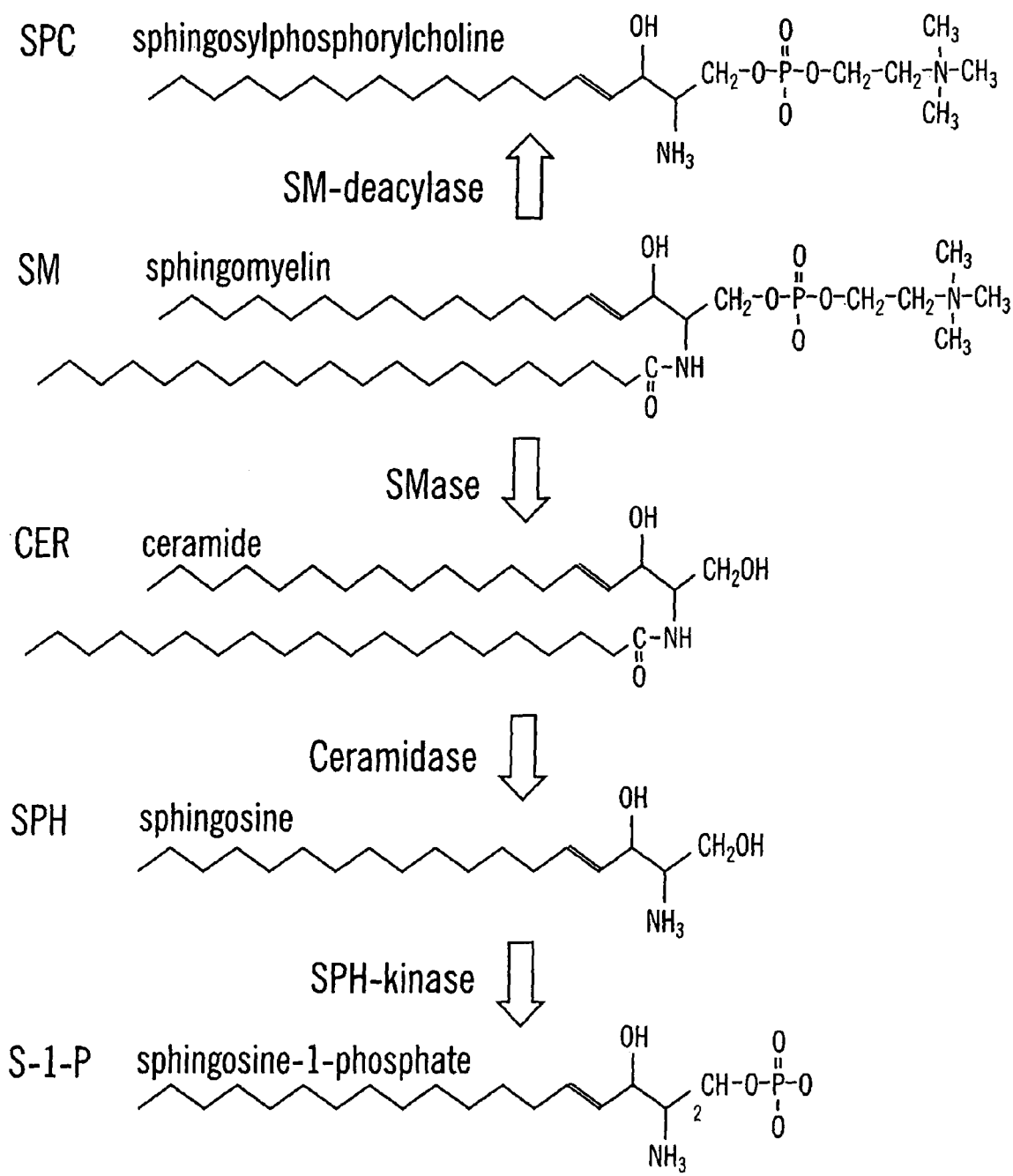
FIG. 1 shows a set of biochemical reactions that are a central part of the sphingolipid metabolic pathways.

Unless otherwise indicated, the following abbreviations are used herein.
Sphingolipids

| HSPH | Dihydrosphingosine |
| --- | --- |
| ER | Ceramide (N-acylsphingosine) |
| PC | Sphingosylphosphorylcholine |
| PH | Sphingosine |
| -1-P | Sphingosine-1-phosphate (a.k.a. S1P or SPP) |
| M | Sphingomyelin |

Enzymes

| CER kinase | ceramide kinase |
| --- | --- |
| SMase | Sphingomyelinase |
| SM-deacylase | Sphingomyelin deacylase |
| SPH kinase | Sphingosine kinase |
| S-1-P Lyase | Sphingosine-1-phosphate lyase |
| S-1-P Phosphatase | Sphingosine-1-phosphate lyase phosphatase |

DETAILED DESCRIPTION OF THE INVENTION

The present invention provides methods and compositions useful for the treatment of cardiovascular and cerebrovascular diseases and disorders, as well as other disease states that relate to sphingolipids and sphingolipid metabolites. The methods and compositions act by interfering with the metabolism of various sphingolipids and/or their metabolites; by binding sphingolipids, thereby reducing their effective concentration; by modulating the sphingomyelin signaling pathway; via modalities based on molecular genetics (including but not limited to the use of dominant negative proteins, antisense, gene therapy, and the like). All the above modalities of cardiovascular therapy may be used alone, in combination with each other, and/or in combination with other methods and compositions useful for cardiovascular therapy (including but not limited to those that interfere with the action of certain cytokines). The therapeutic methods and compositions of the invention are said to be "sphingolipid-based" in order to indicate that these therapies act by changing the relative, absolute or available concentration(s) of certain undesirable, toxic or cardiotoxic sphingolipids. Therapeutic administration of exogenous sphingolipids may have therapeutic benefit if give in a preconditioning regimen (i.e., low doses given intermittently).

Applicants believe, without wishing to be bound by any particular theory, that the level of undesirable sphingolipids such as CER, SPH or S-1-P, and/or one or more of their metabolites, may be directly responsible for cardiac dysfunction, during or immediately after cardiac ischemia such as during reperfusion injury. For example, sphingosine has negative inotropic effects on the heart (Oral H, Dorn G W, Mann D L. Sphingosine mediates the immediate negative inotropic effects of tumor necrosis factor-a in the adult mammalian cardiac myocyte. J. Biol. Chem. 1997; 272:4836-4842; Krown K, Yasui K, Brooker M, et al. TNFα receptor expression in rat cardiac myocytes: TNFα inhibition of L-type $Ca^{2+}$ current and $Ca^{2+}$ transients. FEBS Letters 1995; 376:24-30; Smith G W, Constable P D, Eppley R M, Tumbleson M E, Gumprecht L A, Haschek-Hock W M. Purified fumonisin B1 decreases cardiovascular function but does not alter pulmonary capillary permeability in swine. Toxicological Sciences 2000; 56:240-249, blocks Na/Ca exchangers Condrescu M, Reeves J P. Inhibition of sodium-calcium exchange by ceramide and sphingosine. J. Biol. Chem. 2001; 276:4046-4054, and the L-type calcium channel in heart cells Krown K, Yasui K, Brooker M, et al. TNFα receptor expression in rat cardiac myocytes: TNFα inhibition of L-type $Ca^{2+}$ current and $Ca^{2+}$ transients. FEBS Letters 1995; 376:24-30, and modulates the ryanodine receptor McDonough P M, Yasui K, Betto R, et al. Control of cardiac $Ca^{2+}$ levels: inhibitory actions of sphingosine on $Ca^{2+}$ transients and L-channel conductance. Circ. Res. 1994; 75:981-989, all of which can cause calcium deregulation that is observed when cardiac cells are treated with sphingosine (McDonough P M, Yasui K, Betto R, et al. Control of cardiac $Ca^{2+}$ levels: inhibitory actions of sphingosine on $Ca^{2+}$ transients and L-channel conductance. Circ. Res. 1994; 75:981-989; Krown K, Yasui K, Brooker M, et al. TNFα receptor expression in rat cardiac myocytes: TNFα inhibition of L-type $Ca^{2+}$ current and $Ca^{2+}$ transients. FEBS Letters 1995; 376:24-30). In addition, SPH inhibits the Na/H exchanger (Lowe J H N, Huang C-L, Ives H E. Sphingosine differentially inhibits activation of the Na+/H+ exchange by phorbol esters and growth factors. J. Biol. Chem. 1990; 265:7188-7194), that is responsible for pH regulation. Sphingosine has also been shown to produce cell death in heart cells Krown K A, Page M T, Nguyen C, et al. TNFα-induced apoptosis in cardiac myocytes: Involvement of the sphingolipid signalling cascade in cardiac cell death. J. Clin. Invest. 1996; 98:2854-2865; Zechner D, Craig R, Hanford D, McDonough P M, Sabbadini R A, Glembotski C C. MKK6 inhibits myocardial cell apoptosis via a p38 MAP kinase-dependent pathway. J. Biol. Chem. 1998; 273:8232-8239), and can also produce free radica damage during reperfusion Hernandez O, Discher, D., Bishorpric, N., Webster, K. Rapid Activation of Neutral Sphingomyelinase by Hypoxia-Reoxygenation of Cardiac Myocytes. Circ. Res 2000:198-204. Sphingosine-1-phosphate has been shown to produce cell death Zechner D, Craig R, Hanford D, McDonough P M, Sabbadini R A, Glembotski C C. MKK6 inhibits myocardial cell apoptosis via a p38 MAP kinase-dependent pathway. J. Biol. Chem. 1998; 273:8232-8239, and promote arrythmias and coronary vasoconstriction Sugiyama A, Yatomi Y, Ozaki Y, Hashimoto K. Sphingosine 1-phosphate induces sinus tachycardia and coronary vasoconstriction in the canine heart. Cardiovasc. Res. 2000; 46: 119-125; MacDonnell K, Severson D, Giles W. Depression of excitability by sphingosine 1-phosphate in rat ventricular myocytes. Am. J. Physiol. 1998;44:H2291-H2299; and Liliom K, Sun G, Bunemanns M, et al. Sphingosylphosphocholine is a naturally occurring lipid mediator in blood plasma: a possible role in regulating cardiac function via sphingolipid receptors. Biochem J. 2001; 355:189-197).

Because sphingolipids such as S-1-P are involved in fibrogenesis and wound healing of liver tissue (Davaille et al., J. Biol. Chem. 275:34268-34633, 2000; Ikeda et al., Am J. Physiol. Gastrointest. Liver Physiol 279:G304-G310, 2000), healing of wounded vasculatures (Lee et al., Am. J. Physiol. Cell Physiol. 278:C612-C618, 2000), and other disease states, or events associated with such diseases, such as cancer, angiogenesis and inflammation (Pyne et al., Biochem. J. 349: 385-402, 2000), the compositions and methods of the disclosure may be applied to treat these diseases as well as cardiac diseases. For example, S-1-P may be used therapeutically as a promoter of cardiac angiogenesis. The ability of S-1-P to stimulate angiogenesis in cell culture and in non-cardiac tissue has been reported (Lee et al., Sphingosine 1-Phosphate induces angiogenesis: its angiogenic action and signaling mechanism in human umbilical endothelial cells. Biochem Biophys Res Commun 1999; 264:743-325; Lee et al., Am J Physiol Cell Physiol 278:C612-C618, 2000). Recent evidence suggests that exogenously administered S-1-P crosses the blood-brain barrier and promotes cerebral vasoconstriction (Tosaka et al., Stroke 32: 2913-2919. 2001). This suggests that sphingolipids derived from cardiac or other non-cerebral sources could contribute to stroke. Consequently, interfering with sphingolipid production and/or action may be beneficial in mitigating stroke, particularly in stroke caused by peripherical vascular disease, atherosclerosis and cardiac disorders. s.For example, SIP may be used therapeutically as a promoter of cardiac angiogenesis. The ability of SIP to stimulate angiogenesis in cell culture and in non-cardiac tissue has been reported [Lee, 1999 #[1508]. Recent evidence suggests that exogenously administered SIP crosses the blood-brain barrier and promotes cerebral vasoconstriction (Tosaka et al., Stroke 32: 2913-2919. 2001). This suggests that sphingolipids derived from cardiac or other non-cerebral sources could contribute to stroke. Consequently, interfering with sphingolipid production and/or action may be beneficial in mitigating stroke, particularly in stroke caused by peripherical vascular disease, atherosclerosis and cardiac disorders.

It has been suggested that an early event in the course of cardiac ischemia (i.e., lack of blood supply to the heart) is an excess production by the heart muscle of the naturally occurring compound sphingosine, and that other metabolites, particularly sphingosine-1-phosphate (S-1-P), are also produced either by the heart tissue itself or by components of blood as a consequence of cardiac sphingolipid production and subsequent conversion in the blood. The present invention provides methods and the compositions thereof to inhibit and/or activate sphingolipid production and/or metabolism. More specifically, the present invention provides methods and the compositions that may block production of SPH, S-1-P and other metabolites by inhibiting and/or activating metabolic enzymes and/or sphingolipid receptors involving in the sphingolipid metabolic pathways. Since either hypoxia per se and/or cardiac-derived TNFα and/or other cytokines may trigger the sphingomyelin signal transduction cascade in the heart to increase the production of SPH, S-1-P and other metabolites, the present invention also provides methods and compositions to block cytokine release and/or its action.

The present invention thus provides methods and compositions thereof to reduce blood and tissue levels of key sphingolipids, e.g., SPH and S-1-P. Such methods and compositions include, but are not limited to, monoclonal and/or polyclonal antibodies directed to sphingolipids, which may be used, for example, to bind and thus lower the effective concentration of, undesirable sphingolipids in whole blood. The present invention also provides methods and the compositions thereof to indirectly reduce the absolute or effective (available) blood and tissue levels of key sphingolipids, e.g. SPH and S-1-P, including but not limited to methods and compositions for inhibiting and/or activating enzymes involving in the sphingolipid metabolic pathways; for the use of soluble fragments containing the sphingolipid binding domain of enzymes involved in sphingolipid metabolism, or the binding domain of sphingolipid binding proteins, to bind and reduce the effective concentration of undesirable sphingolipids; for the use of negative dominant (a.k.a. "transdominant") mutants of sphingolipid receptors and enzymes involved in sphingolipid metabolism; for genetic therapy to provide or alter a function of a sphingolipid enzyme or receptor; and for the use of antisense oligonucleotides or transcripts against mRNAs of the sphingolipid metabolic enzymes, and/or sphingolipid receptors, to reduce or eliminate the genetic expression of these enzymes. For a review of sphingolipid metabolism, see Liu et al., Crit Rev. Clin. Lab. Sci. 36:511-573, 1999.

The present invention also provides compositions for inhibiting the action or expression of cytokines, interferons, chemokines and the like, that may modulate events that occur during the sphingomyelin signaling pathway. This pathway, which it has been suggested is activated during cardiac ischemia/hypoxia (Bielawska et al., Am. J. Pathol. 151:1257-1263, 1997; Meldrum, Am. J. Physiol. 274:R577-R595, 1998; and Cain et al., J. Mol. Cell. Cardiol. 31:931-947, 1999), and which is stimulated by cytokines, interferons, chemokines and the like, ultimately results in increased ceramide production. An increased level of ceramide would, in turn, be expected to result in elevated concentrations of undesirable sphingolipids such as, e.g., S-1-P and SPH. For reviews of the sphingomyelin signaling pathway, see Hannun et al., Adv. Lipid Res. 25:27-41, 1993; Liu et al., Crit. Rev. Clin. Lab. Sci. 36:511-573, 1999; Igarashi, J. Biochem. 122: 1080-1087, 1997; Oral et al., J. Biol. Chem. 272:4836-4842, 1997; and Spiegel et al., Biochemistry (Moscow) 63.69-83, 1998.

Sphingolipids

The therapeutic methods and compositions of the invention are said to be "sphingolipid-based" in order to indicate that these therapies can change the relative, absolute or available concentration(s) of certain undesirable, toxic or cardiotoxic sphingolipids. "Toxic sphingolipids" are those that can, under certain circumstances, disturb the normal function of cells such as ones that cause or enhance the necrosis and/or apoptosis of cells, including, in some instances, particular cell types that are found in specific tissues or organs. "Cardiotoxic sphingolipids" are toxic sphingolipids that directly or indirectly cause a negative inotropic state or cause or enhance the necrosis and/or apoptosis of cells found in or associated with the heart, including but not limited to cardiomyocytes, cardiac neurons and the like, and/or can cause loss of cardiac function due to the negative inotropic, arrhythmic coronary vasoconstriction/spasm effects of the sphingolipids and/or their metabolites. "Undesirable sphingolipids" include toxic and cardiotoxic sphingolipids, as well as metabolites, particularly metabolic precursors, of toxic and cardiotoxic sphingolipids. Undesirable sphingolipids of particular interest include but are not limited to ceramide (CER), sphingosine-1-phosphate (S-1-P), and sphingosine (SPH).

Figure 2:
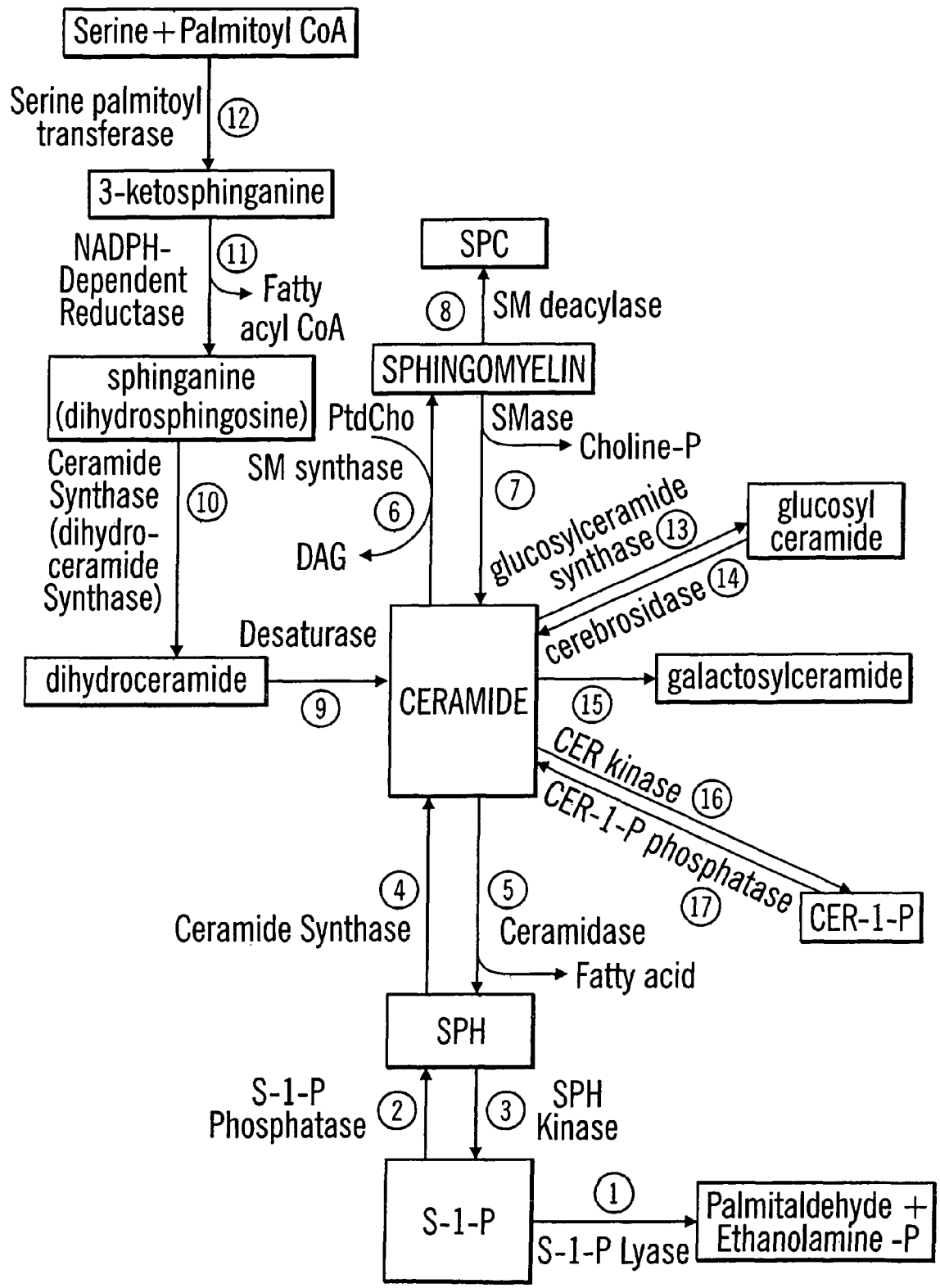
FIG. 2 is a more expansive view of sphingolipid metabolism and includes the biochemical reactions and enzymes shown in FIG. 1. Abbreviations: DAG, diacylglycerol); Ptd-Cho, phosphatidylcholine.

Sphingolipids are a unique class of lipids that were named, due to their initially mysterious nature, after the Sphinx. Sphingolipids were initially characterized as primary structural components of cell membranes, but recent studies indicate that sphingolipids also serve as cellular signaling and regulatory molecules (Hannun et al., Adv. Lipid Res. 25:2741, 1993; Speigel et al., FASEB J. 10:1388-1397, 1996; Igarashi, J. Biochem 122:1080-1087, 1997). The metabolic pathways for sphingolipids are shown in FIGS. 1 and 2.

One group of sphingolipids of particular interest is the set of sphingolipids involved in the sphingomyelin signal transduction pathway (Hannun et al., Adv. Lipid Res. 25:27-41, 1993; Liu et al., Crit. Rev. Clin. Lab. Sci. 36:511-573, 1999). In this regard, ceramide, sphingosine and sphingosine-1-phosphate have been most widely studied (Hannun et al., Science 243:500-507, 1989). Sphingolipid signaling molecules are derived from sphingomyelin and include but are not limited to sphingosine [(SPH; D(+)-erythro-2-amino-4-trans-octadecene-1,3-diol or sphingenine)], sphingosine-1-phosphate (S-1-P), ceramide (CER), as well as sphingosylphosphorylcholine (SPC) (see FIG. 1).

Ceramide and sphingomyelin (SPH) are intracellular second messengers activated by the sphingomyelin signal transduction cascade that occurs in response to inflammatory cytokines such as TNFα, γIFN, and IL-1□, and in response to ischemia/reperfusion (Bielawska et al., Am. J. Pathol. 151: 1257-1263, 1997; Zager et al., Kidney Int. 54:60-70, 1997). Accumulations of ceramide in ischemia of human and rat brains, and in renal ischemia have been alleged to occur (Kubota et al., Japan J. Exp. Med. 59:59-64, 1989; Kubota et al., Neuro. Res. 18:337-341, 1996; and Zager et al., Kidney Int. 54:60-70, 1997). Further, SIP causes cerebral vasoconstriction (Tosaka et al., Stroke 32: 2913-2919, 2001). Taken together, it is reasoned that either brain-derived or non-brain derived sphingolipids may contribute to stroke and that interfering with sphingolipid production and/or action may mitigate stroke.

Hernandez et al. (Circ. Res. 86:198-204, 2000) is stated to show that one of the earliest responses of cardiac myocytes to hypoxia and reoxygenation is the activation of neutral sphingomyelinase and the accumulation of ceramide. SPH has been allegedly implicated as mediating an early signaling event in apoptotic cell death in a variety of cell types (Ohta et al., FEBS Letters 355:267-270, 1994; Ohta et al., Cancer Res. 55:691-697, 1995; Cuvlilier et al., Nature 381:800-803, 1996). It is postulated that the cardiotoxic effects of hypoxia may result in part from sphingolipid production and/or from the inappropriate production of other metabolites (e.g. protons, calcium, certain free radicals) or signaling molecules (e.g. MAP kinases, caspases) that adversely affect cardiac function.

S-1-P is stored in platelets and is a normal constituent of human plasma and serum (Yatomi et al., J. Biochem. 121: 969-973, 1997). Sugiyama et al. (Cardiovascular Res. 46:119-125, 2000) is stated to demonstrate that S-1-P is a coronary vasoconstrictor and has other biological effects on canine hearts. Siess et al. have proposed a role for S-1-P in artherosclerosis (IUBMB Life 49:161-171, 2000). This has been supported by other data, including evidence that the protective effect of HDL is due to blocking SIP production (Xia et al., PNAS 95:14196-14201, 1988; Xia et al., J Biol Chem 274:33143-33147, 1999).

Treatment of neonatal and adult cardiac cells in culture with physiologically relevant levels of SPH and its immediate metabolite, S-1-P, has been related to the activation of cardiomyocyte cell death by apoptosis, a form of programmed cell death that may contribute to the size of the size of myocardial infarct (Krown et al., J. Clin. Invest. 98:2854-2865, 1996; Zechner et al., J. Biol. Chem. 273:8232-8239, 1998; Kajstura et al., Lab. Invest. 74:86-107, 1996).

Cordis et al. (J. Pharm. and Biomed. Analysis 16:1189-1193, 1998) states that levels of sphingosine are reduced in ischemia/reperfused rat hearts. In contrast, however, Bielawska et al., Am. J. Pathol. 151:1257-1263, 1997) is stated to present evidence that the levels of the immediate metabolic precursor of SPH, ceramide, are increased in rat neonatal cardiomyocytes perfused under ischemic conditions.

Sphingomyelin, the metabolic precursor of ceramide, has been stated to be increased in experimental animals subjected to hypoxia (Sergeev et al., Kosm. Biol. Aviakosm. Med. (Russian) 15:71-74, 1981). Other studies have been stated to show that internal membranes of muscle cells contain high amounts of SPH and sphingomyelin (Sumnicht et al., Arch. Biochem. Biophys. 215:628-637, 1982; Sabbadini et al., Biochem. Biophys. Res. Comm. 193752-758, 1993). Treatment of experimental animals with fumonisinB fungal toxins result in increase serum levels of SPH and DHSPH (SIP was not measured) with coincident negative inotropic effects on the heart (Smithe et al., Toxicological Sciences 56:240-249, 2000).

Modulation of the Metabolism of Sphingolipids for Therapeutic Benefit

One way to control the amount of undesirable sphingolipids in a patient is to alter the activity of an enzyme that catalyzes a reaction that is part of sphingolipid metabolism (see FIGS. 1 and 2). Specifically, to lower the amount of undesirable sphingolipids, one can inhibit or block enzymes involved in sphingolipid anabolism (constructive metabolism, i.e., reactions that lead to the production of undesirable sphingolipids). Additionally or alternatively, one can stimulate or activate enzymes involved in sphingolipid catabolism (destructive metabolism, i.e., reactions that lead to the breakdown of undesirable sphingolipids). For further details, see Examples 7-10.

There are several enzymes involved in the sphingolipid metabolic pathway that can be inhibited in order to reduce the amount of undesirable sphingolipids. As is explained herein, due to their deleterious effects on cardiac cells and tissues, two particularly undesirable sphingolipids are SPH and S-1-P. Enzymes that are inhibited for the purpose of lowering levels of SPH, S-1-P and/or other undesirable sphingolipids are assigned to different classes based on the product(s) of the reaction that they catalyze.

Similarly, there are several enzymes involved in sphingolipid metabolism that can be stimulated in order to reduce the amount of undesirable sphingolipids including but not limited to SPH and S-1-P. Stimulation of these enzymes leads to a more rapid degradation of undesirable sphingolipids. Enzymes that are stimulated for the purpose of lowering levels of SPH, S-1-P and other undesirable sphingolipids are assigned to different classes based on whether they promote the production or degradation of a selected undesirable, toxic and/or cardiotoxic sphingolipid or a precursor thereof. In general, enzymes that catalyze the production of a undesirable, toxic and/or cardiotoxic sphingolipid or its precursor are inhibited, whereas enzymes that catalyze the degradation of the undesirable, toxic and/or cardiotoxic sphingolipid are stimulated.

Binding Sphingolipids, and Receptors thereof, for Therapeutic Benefit

One way to control the amount of undesirable sphingolipids in a patient is by providing a composition that binds one or more sphingolipids, or receptors thereof.

Antibodies and other compounds that bind to undesirable sphingolipids may be used as therapeutic "sponges" that reduce the level of free undesirable sphingolipids. When a compound is stated to be "free," the compound is not in any way restricted from reaching the site or sites where it exerts its undesirable effects. Typically, a free compound is present in the cardiovascular system, which either is or contains the site(s) of action of the free compound, or from which a compound can freely migrate to its site(s) of action. A free compound may also be available to be acted upon by any enzyme that converts the compound into an undesirable compound.

Antibodies and other compounds that bind to cellular receptors of undesirable sphingolipids may be used to compete with and/or prevent sphingolipids from binding to receptors and thereby causing or enhancing undesirable cellular or biochemical events. Such events include, but are not limited to, the entry of undesirable sphingolipids into cells, initiation of a signal cascade pathway that has an undesirable outcome, and a reaction, which may be catalyzed by an enzyme, that produces an undesirable product. Receptors of interest include but are not limited to Edg receptors, SCaMPER. and other receptors that bind sphingolipids, and receptors for cytokines, including but not limited to the TNFα receptor.

Antibodies

Several antibodies have recently been approved for therapeutic use in humans by the Federal Drug Administration (Kling, Mod. Drug Disc. 2:33-45, 1999). In one aspect of sphingolipid-based cardiovascular therapy, antibodies that bind sphingolipids can be delivered to a patient, e.g., incorporation into pharmaceutical compositions, medical devices, and the like, for use in sphingolipid-based cardiovascular therapy. Such methods may, by way of non-limiting example, (1) modulate the effective concentration of a undesirable, toxic and/or cardiotoxic sphingolipid or a metabolic precursor thereof; (2) sterically inhibit the binding of a sphingolipid to a cellular receptor therefor, or to lower the concentration of a sphingolipid that is available for binding to such a receptor; (3) sterically inhibit the enzymatic conversion of a metabolic precursor of a undesirable, toxic and/or cardiotoxic sphingolipid, or lower the concentration of such a precursor that is available for enzymatic conversion into a undesirable, toxic and/or cardiotoxic sphingolipid; and (4) remove undesirable, toxic and/or cardiotoxic sphingolipids and their metabolic precursors from blood in vivo or ex vivo.

The term "antibody" is meant to encompass an immunoglobulin molecule obtained by in vitro or in vivo generation of an immunogenic response, and includes polyclonal, monospecific and monoclonal antibodies, as well as T cell receptors, and fragments and derivatives thereof. An "immunogenic response" is one that results in the production of antibodies directed to one or more proteins after the appropriate cells have been contacted with such proteins, or polypeptide derivatives thereof, in a manner such that one or more portions of the protein function as epitopes. An epitope is a single antigenic determinant in a molecule. In proteins, particularly denatured proteins, an epitope is typically defined and represented by a contiguous amino acid sequence. However, in the case of nondenatured proteins, epitopes also include structures, such as active sites, that are formed by the three-dimensional folding of a protein in a manner such that amino acids from separate portions of the amino acid sequence of the protein are brought into close physical contact with each other.

Polyclonal antibodies are generated in a immunogenic response to a protein having many epitopes, and thus include a variety of different antibodies directed to different epitopes within the protein. Methods for producing polyclonal antibodies are known in the art (see, e.g., Cooper et al., Section III of Chapter 11 in: Short Protocols in Molecular Biology, 2nd Ed., Ausubel et al., eds., John Wiley and Sons, New York, 1992, pages 11-37 to 11-41).

Monospecific antibodies (a.k.a. antipeptide antibodies) are generated in a humoral response to a short (typically, 5 to 20 amino acids) immunogenic polypeptide that corresponds to a few (preferably one) isolated epitopes of the protein from which it is derived. A plurality of monospecific antibodies includes a variety of different antibodies directed to a specific portion of the protein, i.e., to an amino acid sequence that contains at least one, preferably only one, epitope. Methods for producing monospecific antibodies are known in the art (see, e.g., Id., pages 11-42 to 11-46).

A monoclonal antibody is a specific antibody that recognizes a single specific epitope of an immunogenic protein. In a plurality of a monoclonal antibody, each antibody molecule is identical to the others in the plurality. In order to isolate a monoclonal antibody, a clonal cell line that expresses, displays and/or secretes a particular monoclonal antibody is first identified; this clonal cell line can be used in one method of producing the antibodies of the invention. Methods for the preparation of clonal cell lines and of monoclonal antibodies expressed thereby are known in the art (see, for example, Fuller et al., Section II of Chapter 11 in: Short Protocols in Molecular Biology, 2nd Ed., Ausubel et al., eds., John Wiley and Sons, New York, 1992, pages 11-22 to 11-11-36).

T cell receptors (TCR) are a distinct class of proteins that are genetically and structurally related to antibodies. TCR proteins belong to the immunoglobulin superfamily of proteins and have molecular structures similar to those of antibodies and, like antibodies, specifically recognize (i.e., specifically and bind) specific ligands. Complexes of TCR are displayed on T cells and bind specific antigens for the purpose of triggering molecular events associated with T cell differentiation and activation. Like antibodies, TCR proteins recognize particular antigens. However, because of differences in the precise structures of the portions of TCR proteins that bind ligands and the amino acid sequences associated with those structures, as well as different mechanisms by which genes encoding a protein are diversified by rearrangement and mutation. Thus, the "molecular rules" for specific binding of TCR molecules to their ligands are different from those of antibodies, and the use of TCR proteins expands the population of potential sphingolipid-binding proteins.

Antibody fragments and derivatives are proteins that are derived from antibodies and T-cell receptors and which retain the ability to specifically recognize the ligand recognized by the "parent" antibody or TCR (see Gavilondo et al., BioTechniques 29:128-145, 2000, and Morrow, Amer. Lab. 32:15-19, 2000). Preferred fragments include Fab fragments (i.e., an antibody fragment that contains the antigen-binding domain and comprises a light chain and part of a heavy chain bridged by a disulfide bond); Fab' (an antibody fragment containing a single anti-binding domain comprising an Fab and an additional portion of the heavy chain through the hinge region); F(ab')2 (two Fab' molecules joined by interchain disulfide bonds in the hinge regions of the heavy chains; the Fab' molecules may be directed toward the same or different epitopes); a bispecific Fab (an Fab molecule having two antigen binding domains, each of which may be directed to a different epitope); and camelized VH domains (the variable, antigen-binding determinative region of a single heavy chain of an antibody in which some amino acids at the VH interface are those found in the heavy chain of naturally occurring camel antibodies).

Single chain antibodies (scFv) comprise a variable region, a.k.a., a scFv (the variable, antigen-binding determinative region of a single light and heavy chain of an antibody linked together by a chain of 10-25 amino acids). For reviews, see Raag et al., Single-chain Fvs. FASEB J. 9:73-80, 1995, and Hudson, Recombinant antibody fragments. Curr. Op. Biotechnol. 9, 395-402, 1999. See also Bird et al., Single-chain antigen-binding proteins. Science 242, 423-426, 1988, and U.S. Pat. Nos. 5,260,203; 5,869,620; 5,455,030; 5,518,889; 5,534,621; 4,946,778; 6,025,165; and 6,027,725.

The well-known technique of phage display is used to prepare scFv molecules. For reviews, see Winter et al., Making antibodies by phage display technology. Annu. Rev. Immunol. 12:433-455, 1994; Little et al., Surface display of antibodies. Biotechn. Adv. 12:539-555, 1994; and Burton et al., Human antibodies from combinatorial libraries. Adv. Immunol. 57:191-280, 1994. See also U.S. Pat. Nos. 5,821, 047; 5,702,892; 6,031,071; and 6,310,191.

Complexes of single chain antibodies are also within the scope of the invention and include, but are not limited to, a disulfide-linked Fv, or dsFv (the variable, antigen-binding determinative region of a single light and heavy chain of an antibody linked together by a disulfide bond; a bispecific sFv (a scFv or a dsFv molecule having two antigen-binding domains, each of which may be directed to a different epitope); a diabody (a dimerized scFv formed when the VH domain of a first scFv assembles with the VL domain of a second scFv and the VL domain of the first scFv assembles with the VH domain of the second scFv; the two antigen-binding regions of the diabody may be directed towards the same or different epitopes); and a triabody (a trimerized sFv, formed in a manner similar to a diabody, but in which three antigen-binding domains are created in a single complex; the three antigen binding domains may be directed towards the same or different epitopes).

The term "antibody" also includes genetically engineered antibodies and/or antibodies produced by recombinant DNA techniques and "humanized" antibodies. Humanized antibodies have been modified, by genetic manipulation and/or in vitro treatment to be more human, in terms of amino acid sequence, glycosylation pattern, etc., in order to reduce the antigenicity of the antibody or antibody fragment in an animal to which the antibody is intended to be administered (Gussow et al., Methods Enz. 203:99-121, 1991).

Methods of Preparing Antibodies and Antibody Variants

The antibodies and antibody fragments of the invention may be produced by any suitable method, for example, in vivo (in the case of polyclonal and monospecific antibodies), in cell culture (as is typically the case for monoclonal antibodies, wherein hybridoma cells expressing the desired antibody are cultured under appropriate conditions), in in vitro translation reactions, and in recombinant DNA expression systems (Johnson et al., Methods Enz. 203:88-98, 1991). Antibodies and antibody variants can be produced from a variety of animal cells, preferably from mammalian cells, with murine and human cells being particularly preferred. Antibodies that include non-naturally occurring antibody and T-cell receptor variants that retain only the desired antigen targeting capability conferred by an antigen binding site(s) of an antibody can be produced by known cell culture techniques and recombinant DNA expression systems (see, e.g., Johnson et al., Methods in Enzymol. 203:88-98, 1991; Molloy et al., Mol. Immunol. 32:73-81, 1998; Schodin et al., J. Immunol. Methods 200:69-77, 1997). Recombinant DNA expression systems are typically used in the production of antibody variants such as, e.g., bispecific antibodies and sFv molecules. Preferred recombinant DNA expression systems include those that utilize host cells and expression constructs that have been engineered to produce high levels of a particular protein. Preferred host cells and expression constructs include *Escherichia coli*; harboring expression constructs derived from plasmids or viruses (bacteriophage); yeast such as *Sacharomyces cerevisieae* or *Fichia pastoras* harboring episomal or chromosomally integrated expression constructs; insect cells and viruses such as Sf9 cells and baculovirus; and mammalian cells harboring episomal or chromosomally integrated (e.g., retroviral) expression constructs (for a review, see Verma et al., J. Immunol. Methods 216:165-181, 1998). Antibodies can also be produced in plants (U.S. Pat. No. 6,046,037; Ma et al., Science 268:716-719, 1995) or by phage display technology (Winter et al., Annu. Rev. Immunol. 12:433-455, 1994).

XenoMouse strains are genetically engineered mice in which the murine IgH and Igk loci have been functionally replaced by their Ig counterparts on yeast artificial YAC transgenes. These human Ig transgenes can carry the majority of the human variable repertoire and can undergo class switching from IgM to IgG isotypes. The immune system of the xenomouse recognizes administered human antigens as foreign and produces a strong humoral response. The use of XenoMouse in conjunction with well-established hybridomas techniques, results in fully human IgG mAbs with subnanomolar affinities for human antigens (see U.S. Pat. Nos. 5,770,429, entitled "Transgenic non-human animals capable of producing heterologous antibodies"; 6,162,963, entitled "Generation of Xenogenetic antibodies"; 6,150,584, entitled "Human antibodies derived from immunized xenomice"; 6,114,598, entitled Generation of xenogeneic antibodies; and 6,075,181, entitled "Human antibodies derived from immunized xenomice"; for reviews, see Green, Antibody engineering via genetic engineering of the mouse: XenoMouse strains are a vehicle for the facile generation of therapeutic human monoclonal antibodies, J. Immunol. Methods 231:11-23, 1999; Wells, Eek, a XenoMouse: Abgenix, Inc., Chem Biol 2000 August; 7(8):R185-6; and Davis et al., Transgenic mice as a source of fully human antibodies for the treatment of cancer Cancer Metastasis Rev 1999;18(4):421-5).

Soluble Receptor Fragments

Soluble polypeptides derived from membrane bound, typically hydrophobic, sphingolipid receptors that retain the receptor's ability to bind sphingolipids may also be used to bind sphingolipids and sphingolipid metabolites. In the case of Edg receptors, in some instances, particular amino acid residues may be involved in the specificity of sphingolipid binding, i.e., the amino acids that determine which sphingolipid is bound by a specific receptor (Parrill et al., "Identification of Edg1 Receptor Residues That Recognize Sphingosine 1-Phosphate", J. Biol. Chem. 275:39379-39384, 2000; and Wang et al., "A Single Amino Acid Determines Lysophospholipid Specificity of the S1P1 (EDG1) and LPA1 (EDG2) Phospholipid Growth Factor Receptors", JBC Papers in Press Published Oct. 16, 2001 as Manuscript M107301200). Such information may be used to provide soluble receptor fragments comprising receptor residues of interest, i.e., the stretches of amino acids that bind the sphingolipid. Soluble receptor fragments derived from the naturally soluble TNFα receptor have been prepared and at least one of these, ENBREL® (Etanercept) is in development as a therapeutic agent for arthritis. In addition, modification of such residues may permit the skilled artisan to tailor the binding specificities and/or affinity of soluble receptor fragments.

Soluble receptor fragments of particular interest include Edg-1, Edg-3, Edg-5, Edg-6 and Edg-8, all of which bind the undesirable sphingolipid sphingosine-1-phosphate (S-1-P). The Edg-1, Edg-3, Edg-5 receptors are of particular interest because binding of S-1-P thereto seems to stimulate the production of intracellular S-1-P (Heringdorf et al., Stimulation of intracellular sphingosine-1-phosphate production by G-protein-coupled sphingosine-1-phosphate receptors, Eur J Pharmacol. 414:145-54, 2001). The P2Y(2) receptor is of interest as it also increases intracellular production of S-1-P (Alemany et al., Stimulation of sphingosine-1-phosphate formation by the P2Y(2) receptor in HL-60 cells: Ca(2+) requirement and implication in receptor-mediated Ca(2+) mobilization, but not MAP kinase activation, Mol Pharmacol. 58:491-7, 2000).

Soluble receptor fragments may be prepared in various ways including but not limited to proteolytic digestion of cells or cellular membrane preparations comprising the receptor (Bartfeld et al., Active acetylcholine receptor fragment obtained by tryptic digestion of acetylcholine receptor from Torpedo californica, Biochem Biophys Res Commun. 89:512-9, 1979; Borhani et al., Crystallization and X-ray diffraction studies of a soluble form of the human transferrin receptor, J Mol Biol. 218:685-9, 1991), recombinant DNA technologies (Marlovits et al., Recombinant soluble low-density lipoprotein receptor fragment inhibits common cold infection, J Mol Recognit. 11:49-51, 1998; Huang et al., Expression of a human thyrotrophin receptor fragment in *Escherichia coli* and its interaction with the hormone and autoantibodies from patients with Graves' disease, J Mol Endocrinol. 8:137-44, 1992), or by in vitro synthesis of oligopeptides.

Nucleic Acids

Traditionally, techniques for detecting and purifying target molecules have used polypeptides, such as antibodies, that specifically bind such targets. While nucleic acids have long been known to specifically bind other nucleic acids (e.g., ones having complementary sequences), aptamers (i.e., nucleic acids that bind non-nucleic target molecules) have been disclosed. See, e.g., Blackwell et al., Science (1990) 250:1104-1110; Blackwell et al., Science (1990) 250:1149-1152; Tuerk et al., Science (1990) 249:505-510; Joyce, Gene (1989) 82:83-87; and U.S. Pat. No. 5,840,867 entitled "Aptamer analogs specific for biomolecules".

As applied to aptamers, the term "binding" specifically excludes the "Watson-Crick"-type binding interactions (i.e., A:T and G:C base-pairing) traditionally associated with the DNA double helix. The term "aptamer" thus refers to a nucleic acid or a nucleic acid derivative that specifically binds to a target molecule, wherein the target molecule is either (i) not a nucleic acid, or (ii) a nucleic acid or structural element thereof that is bound through mechanisms other than duplex- or triplex-type base pairing. Such a molecule is called a "non-nucleic molecule" herein.

Structures of Nucleic Acids

"Nucleic acids," as used herein, refers to nucleic acids that are isolated a natural source; prepared in vitro, using techniques such as PCR amplification or chemical synthesis; prepared in vivo, e.g., via recombinant DNA technology; or by any appropriate method. Nucleic acids may be of any shape (linear, circular, etc.) or topology (single-stranded, double-stranded, supercoiled, etc.). The term "nucleic acids" also includes without limitation nucleic acid derivatives such as peptide nucleic acids (PNA's) and polypeptide-nucleic acid conjugates; nucleic acids having at least one chemically modified sugar residue, backbone, internucleotide linkage, base, nucleoside, or nucleotide analog; as well as nucleic acids having chemically modified 5' or 3' ends; and nucleic acids having two or more of such modifications. Not all linkages in a nucleic acid need to be identical.

Nucleic acids that are aptamers are often, but need not be, prepared as oligonucleotides. Oligonucleotides include without limitation RNA, DNA and mixed RNA-DNA molecules having sequences of lengths that have minimum lengths of 2, 4, 6, 8, 10, 11, 12, 13, 14, 15, 17, 18, 19, 20, 21, 22, 23, 24 or 25 nucleotides, and maximum lengths of about 100, 75, 50, 40, 25, 20 or 15 or more nucleotides, irrespectively. In general, a minimum of 6 nucleotides, preferably 10 nucleotides, more preferably 14 to 20 nucleotides, is necessary to effect specific binding.

In general, the oligonucleotides may be single-stranded (ss) or double-stranded (ds) DNA or RNA, or conjugates (e.g., RNA molecules having 5' and 3' DNA "clamps") or hybrids (e.g., RNA:DNA paired molecules), or derivatives (chemically modified forms thereof). However, single-stranded DNA is preferred, as DNA is often less labile than RNA. Similarly, chemical modifications that enhance an aptamer's specificity or stability are preferred.

Chemical Modifications of Nucleic Acids

Chemical modifications that may be incorporated into aptamers and other nucleic acids include, with neither limitation nor exclusivity, base modifications, sugar modifications, and backbone modifications.

Base modifications: The base residues in aptamers may be other than naturally occurring bases (e.g., A, G, C, T, U, 5MC, and the like). Derivatives of purines and pyrimidines are known in the art; an exemplary but not exhaustive list includes aziridinylcytosine, 4-acetylcytosine, 5-fluorouracil, 5-bromouracil, 5-carboxymethylaminomethyl-2-thiouracil, 5-carboxymethylaminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine (5MC), N6-methyladenine, 7-methylguanine, 5-methylaminomethyluracil, 5-methoxyaminomethyl-2-thiouracil, beta-D-mannosylqueosine, 5-methoxyuracil, 2-methylthio-N-6-isopentenyladenine, uracil-5-oxyacetic acid methylester, pseudouracil, queosine, 2-thiocytosine, 5-methyl-2-thiouracil, 2-thiouracil, 4-thiouracil, 5-methyluracil, uracil-5-oxyacetic acid, and 2,6-diaminopurine. In addition to nucleic acids that incorporate one or more of such base derivatives, nucleic acids having nucleotide residues that are devoid of a purine or a pyrimidine base may also be included in aptamers.

Sugar modifications: The sugar residues in aptamers may be other than conventional ribose and deoxyribose residues. By way of non-limiting example, substitution at the 2'-position of the furanose residue enhances nuclease stability. An exemplary, but not exhaustive list, of modified sugar residues includes 2' substituted sugars such as 2'-O-methyl-, 2'-O-alkyl, 2'-O-allyl, 2'-S-alkyl, 2'-S-allyl, 2'-fluoro-, 2'-halo, or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and abasic nucleoside analogs such as methyl riboside, ethyl riboside or propylriboside.

Backbone modifications: Chemically modified backbones include, by way of non-limiting example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Chemically modified backbones that do not contain a phosphorus atom have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages, including without limitation morpholino linkages; siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; and amide backbones.

Preparation and Identification of Aptamers

In general, techniques for identifying aptamers involve incubating a preselected non-nucleic target molecule with mixtures (2 to 50 members), pools (50 to 5,000 members) or libraries (50 or more members) of different nucleic acids that are potential aptamers under conditions that allow complexes of target molecules and aptamers to form. By "different nucleic acids" it is meant that the nucleotide sequence of each potential aptamer may be different from that of any other member, that is, the sequences of the potential aptamers are random with respect to each other. Randomness can be introduced in a variety of manners such as, e.g., mutagenesis, which can be carried out in vivo by exposing cells harboring a nucleic acid with mutagenic agents, in vitro by chemical treatment of a nucleic acid, or in vitro by biochemical replication (e.g., PCR) that is deliberately allowed to proceed under conditions that reduce fidelity of replication process; randomized chemical synthesis, i.e., by synthesizing a plurality of nucleic acids having a preselected sequence that, with regards to at least one position in the sequence, is random. By "random at a position in a preselected sequence" it is meant that a position in a sequence that is normally synthesized as, e.g., as close to 100% A as possible (e.g., 5'-C-T-T-A-G-T-3') is allowed to be randomly synthesized at that position (C-T-T-N-G-T, wherein N indicates a randomized position where, for example, the synthesizing reaction contains 25% each of A,T,C and G; or x % A, w % T, y % C and z % G, wherein x+w+y+z=100. In later stages of the process, the sequences are increasingly less randomized and consensus sequences may appear; in any event, it is preferred to ultimately obtain an aptamer having a unique nucleotide sequence.

Aptamers and pools of aptamers are prepared, identified, characterized and/or purified by any appropriate technique, including those utilizing in vitro synthesis, recombinant DNA techniques, PCR amplification, and the like. After their formation, target:aptamer complexes are then separated from the uncomplexed members of the nucleic acid mixture, and the nucleic acids that can be prepared from the complexes are candidate aptamers (at early stages of the technique, the aptamers generally being a population of a multiplicity of nucleotide sequences having varying degrees of specificity for the target). The resulting aptamer (mixture or pool) is then substituted for the starting apatamer (library or pool) in repeated iterations of this series of steps. When a limited number (e.g., a pool or mixture, preferably a mixture with less than 10 members, most preferably 1) of nucleic acids having satisfactory specificity is obtained, the aptamer is sequenced and characterized. Pure preparations of a given aptamer are generated by any appropriate technique (e.g., PCR amplification, in vitro chemical synthesis, and the like).

For example, Tuerk and Gold (Science (1990) 249:505-510) disclose the use of a procedure termed "systematic evolution of ligands by exponential enrichment" (SELEX). In this method, pools of nucleic acid molecules that are randomized at specific positions are subjected to selection for binding to a nucleic acid-binding protein (see, e.g., PCT International Publication No. WO 91/19813 and U.S. Pat. No. 5,270,163). The oligonucleotides so obtained are sequenced and otherwise characterization. Kinzler, K. W., et al. (Nucleic Acids Res. (1989) 17:3645-3653) used a similar technique to identify synthetic double-stranded DNA molecules that are specifically bound by DNA-binding polypeptides. Ellington, A. D., et al. (Nature (1990) 346: 818-822) disclose the production of a large number of random sequence. RNA molecules and the selection and identification of those that bind specifically to specific dyes such as Cibacron blue.

Another technique for identifying nucleic acids that bind non-nucleic target molecules is the oligonucleotide combinatorial technique disclosed by Ecker, D. J. et al. (Nuc. Acids Res. 21, 1853 (1993)) known as "synthetic unrandomization of randomized fragments" (SURF), which is based on repetitive synthesis and screening of increasingly simplified sets of oligonucleotide analogue libraries, pools and mixtures (Tuerk, C. and Gold, L. (Science 249, 505 (1990)). The starting library consists of oligonucleotide analogues of defined length with one position in each pool containing a known analogue and the remaining positions containing equimolar mixtures of all other analogues. With each round of synthesis and selection, the identity of at least one position of the oligomer is determined until the sequences of optimized nucleic acid ligand aptamers are discovered.

Once a particular candidate aptamer has been identified through a SURF, SELEX or any other technique, its nucleotide sequence can be determined (as is known in the art), and its three-dimensional molecular structure can be examined by nuclear magnetic resonance (NMR). These techniques are explained in relation to the determination of the three-dimensional structure of a nucleic acid ligand that binds thrombin in Padmanabhan, K. et al., J. Biol. Chem. 24, 17651 (1993); Wang, K. Y. et al., Biochemistry 32, 1899 (1993); and Macaya, R. F. et al., Proc. Nat'l. Acad. Sci. USA 90, 3745 (1993). Selected aptamers may be resynthesized using one or more modified bases, sugars or backbone linkages. Aptamers consist essentially of the minimum sequence of nucleic acid needed to confer binding specificity, but may be extended on the 5' end, the 3' end, or both, or may be otherwise derivatized or conjugated.

Small Molecules

The term "small molecule" includes any chemical or other moiety, other than polypeptides and nucleic acids, that can act to affect biological processes. Small molecules can include any number of therapeutic agents presently known and used, or can be small molecules synthesized in a library of such molecules for the purpose of screening for biological function(s). Small molecules are distinguished from macromolecules by size. The small molecules of this invention usually have molecular weight less than about 5,000 daltons (Da), preferably less than about 2,500 Da, more preferably less than 1,000 Da, most preferably less than about 500 Da.

Small molecules include without limitation organic compounds, peptidomimetics and conjugates thereof. As used herein, the term "organic compound" refers to any carbon-based compound other than macromolecules such nucleic acids and polypeptides. In addition to carbon, organic compounds may contain calcium, chlorine, fluorine, copper, hydrogen, iron, potassium, nitrogen, oxygen, sulfur and other elements. An organic compound may be in an aromatic or aliphatic form. Non-limiting examples of organic compounds include acetones, alcohols, anilines, carbohydrates, monosaccharides, oligosaccharides, polysaccharides, amino acids, nucleosides, nucleotides, lipids, retinoids, steroids, proteoglycans, ketones, aldehydes, saturated, unsaturated and polyunsaturated fats, oils and waxes, alkenes, esters, ethers, thiols, sulfides, cyclic compounds, heterocyclic compounds, imidizoles and phenols. An organic compound as used herein also includes nitrated organic compounds and halogenated (e.g., chlorinated) organic compounds. Methods for preparing peptidomimetics are described below. Collections of small molecules, and small molecules identified according to the invention are characterized by techniques such as accelerator mass spectrometry (AMS; see Turteltaub et al., Curr Pharm Des 2000 6:991-1007, Bioanalytical applications of accelerator mass spectrometry for pharmaceutical research; and Enjalbal et al., Mass Spectrom Rev 2000 19:139-61, Mass spectrometry in combinatorial chemistry.)

Preferred small molecules are relatively easier and less expensively manufactured, formulated or otherwise prepared. Preferred small molecules are stable under a variety of storage conditions. Preferred small molecules may be placed in tight association with macromolecules to form molecules that are biologically active and that have improved pharmaceutical properties. Improved pharmaceutical properties include changes in circulation time, distribution, metabolism, modification, excretion, secretion, elimination, and stability that are favorable to the desired biological activity. Improved pharmaceutical properties include changes in the toxicological and efficacy characteristics of the chemical entity.

Peptidomimetics

In general, a polypeptide mimetic ("peptidomimetic") is a molecule that mimics the biological activity of a polypeptide, but that is not peptidic in chemical nature. While, in certain embodiments, a peptidomimetic is a molecule that contains no peptide bonds (that is, amide bonds between amino acids), the term peptidomimetic may include molecules that are not completely peptidic in character, such as pseudo-peptides, semi-peptides and peptoids. Examples of some peptidomimetics by the broader definition (e.g., where part of a polypeptide is replaced by a structure lacking peptide bonds) are described below. Whether completely or partially non-peptide in character, peptidomimetics according to this invention may provide a spatial arrangement of reactive chemical moieties that closely resembles the three-dimensional arrangement of active groups in a polypeptide. As a result of this similar active-site geometry, the peptidomimetic may exhibit biological effects that are similar to the biological activity of a polypeptide.

There are several potential advantages for using a mimetic of a given polypeptide rather than the polypeptide itself. For example, polypeptides may exhibit two undesirable attributes, i.e., poor bioavailability and short duration of action. Peptidomimetics are often small enough to be both orally active and to have a long duration of action. There are also problems associated with stability, storage and immunoreactivity for polypeptides that may be obviated with peptidomimetics.

Candidate, lead and other polypeptides having a desired biological activity can be used in the development of peptidomimetics with similar biological activities. Techniques of developing peptidomimetics from polypeptides are known. Peptide bonds can be replaced by non-peptide bonds that allow the peptidomimetic to adopt a similar structure, and therefore biological activity, to the original polypeptide. Further modifications can also be made by replacing chemical groups of the amino acids with other chemical groups of similar structure, shape or reactivity. The development of peptidomimetics can be aided by determining the tertiary structure of the original polypeptide, either free or bound to a ligand, by NMR spectroscopy, crystallography and/or computer-aided molecular modeling. These techniques aid in the development of novel compositions of higher potency and/or greater bioavailability and/or greater stability than the original polypeptide (Dean (1994), BioEssays, 16: 683-687; Cohen and Shatzmiller (1993), J. Mol. Graph., 11: 166-173; Wiley and Rich (1993), Med. Res. Rev., 13: 327-384; Moore (1994), Trends Pharmacol. Sci., 15: 124-129; Hruby (1993), Biopolymers, 33: 1073-1082; Bugg et al. (1993), Sci. Am., 269: 92-98, all incorporated herein by reference].

Specific examples of peptidomimetics are set forth below. These examples are illustrative and not limiting in terms of the other or additional modifications.

Peptides with a Reduced Isostere Pseudopeptide Bond

Proteases act on peptide bonds. Substitution of peptide bonds by pseudopeptide bonds may confer resistance to proteolysis or otherwise make a compound less labile. A number of pseudopeptide bonds have been described that in general do not affect polypeptide structure and biological activity. The reduced isostere pseudopeptide bond is a suitable pseudopeptide bond that is known to enhance stability to enzymatic cleavage with no or little loss of biological activity (Couder, et al. (1993), Int. J. Polypeptide Protein Res. 41:181-184, incorporated herein by reference). Thus, the amino acid sequences of these compounds may be identical to the sequences of their parent L-amino acid polypeptides, except that one or more of the peptide bonds are replaced by an isostere pseudopeptide bond. Preferably the most N-terminal peptide bond is substituted, since such a substitution would confer resistance to proteolysis by exopeptidases acting on the N-terminus.

Peptides with a Retro-Inverso Pseudopeptide Bond

To confer resistance to proteolysis, peptide bonds may also be substituted by retro-inverso pseudopeptide bonds (Dalpozzo, et al. (1993), Int. J. Polypeptide Protein Res. 41:561-566, incorporated herein by reference). According to this modification, the amino acid sequences of the compounds may be identical to the sequences of their L-amino acid parent polypeptides, except that one or more of the peptide bonds are replaced by a retro-inverso pseudopeptide bond. Preferably the most N-terminal peptide bond is substituted, since such a substitution will confer resistance to proteolysis by exopeptidases acting on the N-terminus.

Peptoid Derivatives

Peptoid derivatives of polypeptides represent another form of modified polypeptides that retain the important structural determinants for biological activity, yet eliminate the peptide bonds, thereby conferring resistance to proteolysis (Simon, et al., 1992, Proc. Natl. Acad. Sci. USA, 89:9367-9371 and incorporated herein by reference). Peptoids are oligomers of N-substituted glycines. A number of N-alkyl groups have been described, each corresponding to the side chain of a natural amino acid.

Polypeptides

The polypeptides of this invention, including the analogs and other modified variants, may generally be prepared following known techniques. Preferably, synthetic production of the polypeptide of the invention may be according to the solid phase synthetic method. For example, the solid phase synthesis is well understood and is a common method for preparation of polypeptides, as are a variety of modifications of that technique [Merrifield (1964), J. Am. Chem. Soc., 85: 2149; Stewart and Young (1984), Solid Phase polypeptide Synthesis, Pierce Chemical Company, Rockford, Ill.; Bodansky and Bodanszky (1984), The Practice of polypeptide Synthesis, Springer-Verlag, New York; Atherton and Sheppard (1989), Solid Phase polypeptide Synthesis: A Practical Approach, IRL Press, New York].

Alternatively, polypeptides of this invention may be prepared in recombinant systems using polynucleotide sequences encoding the polypeptides. For example, fusion proteins are typically prepared using recombinant DNA technology.

Polypeptide Derivatives

A "derivative" of a polypeptide is a compound that is not, by definition, a polypeptide, i.e., it contains at least one chemical linkage that is not a peptide bond. Thus, polypeptide derivatives include without limitation proteins that naturally undergo post-translational modifications such as, e.g., glycosylation. It is understood that a polypeptide of the invention may contain more than one of the following modifications within the same polypeptide. Preferred polypeptide derivatives retain a desirable attribute, which may be biological activity; more preferably, a polypeptide derivative is enhanced with regard to one or more desirable attributes, or has one or more desirable attributes not found in the parent polypeptide.

Mutant Polypeptides: A polypeptide having an amino acid sequence identical to that found in a protein prepared from a natural source is a "wildtype" polypeptide. Mutant oligopeptides can be prepared by chemical synthesis, including without limitation combinatorial synthesis.

Mutant polypeptides larger than oligopeptides can be prepared using recombinant DNA technology by altering the nucleotide sequence of a nucleic acid encoding a polypeptide. Although some alterations in the nucleotide sequence will not alter the amino acid sequence of the polypeptide encoded thereby ("silent" mutations), many will result in a polypeptide having an altered amino acid sequence that is altered relative to the parent sequence. Such altered amino acid sequences may comprise substitutions, deletions and additions of amino acids, with the proviso that such amino acids are naturally occurring amino acids.

Thus, subjecting a nucleic acid that encodes a polypeptide to mutagenesis is one technique that can be used to prepare mutant polypeptides, particularly ones having substitutions of amino acids but no deletions or insertions thereof. A variety of mutagenic techniques are known that can be used in vitro or in vivo including without limitation chemical mutagenesis and PCR-mediated mutagenesis. Such mutagenesis may be randomly targeted (i.e., mutations may occur anywhere within the nucleic acid) or directed to a section of the nucleic acid that encodes a stretch of amino acids of particular interest. Using such techniques, it is possible to prepare randomized, combinatorial or focused compound libraries, pools and mixtures.

Polypeptides having deletions or insertions of naturally occurring amino acids may be synthetic oligopeptides that result from the chemical synthesis of amino acid sequences that are based on the amino acid sequence of a parent polypeptide but which have one or more amino acids inserted or deleted relative to the sequence of the parent polypeptide. Insertions and. deletions of amino acid residues in polypeptides having longer amino acid sequences may be prepared by directed mutagenesis.

Chemically Modified Polypeptides: As contemplated by this invention, the term "polypeptide" includes those having one or more chemical modification relative to another polypeptide, i.e., chemically modified polypeptides. The polypeptide from which a chemically modified polypeptide is derived may be a wildtype protein, a mutant protein or a mutant polypeptide, or polypeptide fragments thereof; an antibody or other polypeptide ligand according to the invention including without limitation single-chain antibodies, bacterial proteins and polypeptide derivatives thereof; or polypeptide ligands prepared according to the disclosure. Preferably, the chemical modification(s) confer(s) or improve(s) desirable attributes of the polypeptide but does not substantially alter or compromise the biological activity thereof. Desirable attributes include but are limited to increased shelf-life; enhanced serum or other in vivo stability; resistance to proteases; and the like. Such modifications include by way of non-limiting example N-terminal acetylation, glycosylation, and biotinylation.

Polypeptides with N-Terminal or C-Terminal Chemical Groups: An effective approach to confer resistance to peptidases acting on the N-terminal or C-terminal residues of a polypeptide is to add chemical groups at the polypeptide termini, such that the modified polypeptide is no longer a substrate for the peptidase. One such chemical modification is glycosylation of the polypeptides at either or both termini. Certain chemical modifications, in particular N-terminal glycosylation, have been shown to increase the stability of polypeptides in human serum (Powell et al. (1993), Pharma. Res. 10: 1268-1273). Other chemical modifications which enhance serum stability include, but are not limited to, the addition of an N-terminal alkyl group, consisting of a lower alkyl of from 1 to 20 carbons, such as an acetyl group, and/or the addition of a C-terminal amide or substituted amide group.

Polypeptides with a Terminal D-Amino Acid: The presence of an N-terminal D-amino acid increases the serum stability of a polypeptide that otherwise contains L-amino acids, because exopeptidases acting on the N-terminal residue cannot utilize a D-amino acid as a substrate. Similarly, the presence of a C-terminal D-amino acid also stabilizes a polypeptide, because serum exopeptidases acting on the C-terminal residue cannot utilize a D-amino acid as a substrate. With the exception of these terminal modifications, the amino acid sequences of polypeptides with N-terminal and/or C-terminal D-amino acids are usually identical to the sequences of the parent L-amino acid polypeptide.

Polypeptides With Substitution of Natural Amino Acids By Unnatural Amino Acids: Substitution of unnatural amino acids for natural amino acids in a subsequence of a polypeptide can confer or enhance desirable attributes including biological activity. Such a substitution can, for example, confer resistance to proteolysis by exopeptidases acting on the N-terminus. The synthesis of polypeptides with unnatural amino acids is routine and known in the art (see, for example, Coller, et al. (1993), cited above).

Post-Translational Chemical Modifications: Different host cells will contain different post-translational modification mechanisms that may provide particular types of post-translational modification of a fusion protein if the amino acid sequences required for such modifications is present in the fusion protein. A large number (~100) of post-translational modifications have been described, a few of which are discussed herein. One skilled in the art will be able to choose appropriate host cells, and design chimeric genes that encode protein members comprising the amino acid sequence needed for a particular type of modification.

Glycosylation is one type of post-translational chemical modification that occurs in many eukaryotic systems, and may influence the activity, stability, pharmacogenetics, immunogenicity and/or antigenicity of proteins. However, specific amino acids must be present at such sites to recruit the appropriate glycosylation machinery, and not all host cells have the appropriate molecular machinery. *Saccharomyces cerevisieae* and *Pichia pastoris* provide for the production of glycosylated proteins, as do expression systems that utilize insect cells, although the pattern of glycosylation may vary depending on which host cells are used to produce the fusion protein.

Another type of post-translation modification is the phosphorylation of a free hydroxyl group of the side chain of one or more Ser, Thr or Tyr residues. Protein kinases catalyze such reactions. Phosphorylation is often reversible due to the action of a protein phosphatase, an enzyme that catalyzes the dephosphorylation of amino acid residues.

Differences in the chemical structure of amino terminal residues result from different host cells, each of which may have a different chemical version of the methionine residue encoded by a start codon, and these will result in amino termini with different chemical modifications.

For example, many or most bacterial proteins are synthesized with an amino terminal amino acid that is a modified form of methionine, i.e, N-formyl-methionine (fMet). Although the statement is often made that all bacterial proteins are synthesized with an fMet initiator amino acid; although this may be true for *E. coli*, recent studies have shown that it is not true in the case of other bacteria such as *Pseudomonas aeruginosa* (Newton et al., J. Biol. Chem. 274: 22143-22146, 1999). In any event, in *E. coli*, the formyl group of fMet is usually enzymatically removed after translation to yield an amino terminal methionine residue, although the entire fMet residue is sometimes removed (see Hershey, Chapter 40, "Protein Synthesis" in: *Escherichia Coli* and *Salmonella Typhimurium*: Cellular and Molecular Biology, Neidhardt, Frederick C., Editor in Chief, American Society for Microbiology, Washington, D.C., 1987, Volume 1, pages 613-647, and references cited therein.) *E. coli* mutants that lack the enzymes (such as, e.g., formylase) that catalyze such post-translational modifications will produce proteins having an amino terminal fMet residue (Guillon et al., J. Bacteriol. 174:4294-4301, 1992).

In eukaryotes, acetylation of the initiator methionine residue, or the penultimate residue if the initiator methionine has been removed, typically occurs co- or post-translationally. The acetylation reactions are catalyzed by N-terminal acetyltransferases (NATs, a.k.a. N-alpha-acetyltransferases), whereas removal of the initiator methionine residue is catalyzed by methionine aminopeptidases (for reviews, see Bradshaw et al., Trends Biochem. Sci. 23:263-267, 1998; and Driessen et al., CRC Crit. Rev. Biochem. 18:281-325, 1985). Amino terminally acetylated proteins are said to be "N-acetylated," "N alpha acetylated" or simply "acetylated."

Another post-translational process that occurs in eukaryotes is the alpha-amidation of the carboxy terminus. For reviews, see Eipper et al. Annu. Rev. Physiol. 50:333-344, 1988, and Bradbury et al. Lung Cancer 14:239-251, 1996. About 50% of known endocrine and neuroendocrine peptide hormones are alpha-amidated (Treston et al., Cell Growth Differ. 4:91 1-920, 1993). In most cases, carboxy alpha-amidation is required to activate these peptide hormones.

Aminoglycosides

A class of small molecules of particular interest are known as aminoglycosides, particularly those that inhibit a sphingomyelinase (SMase), particularly a neutral SMase. Example 13 describes the use of the screening methods of the invention to prepare novel therapeutic agents using chemical libraries based on the aminoglycoside structure.

Aminoglycosides were first identified as antibiotics produced by microorganisms of the genus *Micromonospora*. The antibiotics, recovered from the *Micromonospora* culture media, included Gentamicin (Weinstein et al., Antimicrobial Agents and Chemotherapy, 1963, page 1; Cooper et al., J. Infect. Dis. 119:342, 1969; Waitz: Antimicrobial Agents and Chemotherapy 2:464, 1972), Antibiotic No. 460 (Japanese Pat. No. 16153/71), Sisomicin (Weinstein et al., J. Antibiotics 23:551, 555, 559, 1970), Kanamycin, Neomycin, and many others as described below. For a review, see Edson et al., The Aminoglycosides, Mayo Clin Proc 74:519-528, 1999.

Aminoglycosides are a group of antibiotics that exert their bactericidal activity primarily by inhibition of protein synthesis. Aminoglycoside molecules bind to the bacterial 30S ribosomal subunit rendering the ribosomes unavailable for translation, which results in cell death.

The first aminoglycoside, streptomycin, was isolated from *Streptomyces griseus* in 1943. Neomycin, isolated from *Streptomyces fradiae*, had better activity than streptomycin against aerobic gram-negative bacilli but, because of its formidable toxicity, could not safely be used systemically. Gentamicin, isolated from *Micromonospora* in 1963, was a breakthrough in the treatment of gram-negative bacillary infections, including those caused by *Pseudomonas aeruginosa*. Other aminoglycosides were subsequently developed, including amikacin (Amikin), netilmicin (Netromycin) and tobramycin (Nebcin), which are all currently available for systemic use in the United States.

Within the aminoglycoside family, the suffix "-mycin" is used in the name when the antibiotic is produced by *Streptomyces* species and "micin," when produced by *Micromonospora* species.

Structure of Aminoglycosides

Aminoglycosides are water soluble weak bases that are polycations at body pH. They are chemically similar in that they have one of two bases to which is attached two or three aminosugars. The aminosugars are linked to the by glycosidic bonds, hence the group name. The base in streptomycin is streptidine, but all of the others have 2-deoxystreptamine so that most of the members differ in the number and nature of the aminosugars attached to the 2-deoxystreptamine.

The terms "aminoglycoside" is used herein according to its conventional chemical meanings, as described in various standard texts on organic chemistry. The following is a condensed summary of these terms.

As implied by the term, an aminosaccharide is a saccharide molecule (the term saccharide is used interchangeably with sugar) having at least one amine group coupled to it, either directly or indirectly. Saccharide molecules (i.e., polyhydroxylated aldehydes or ketones) exist as both straight chains and ring structures, which spontaneously convert back and forth between straight and ring forms in an equilibrium-type "tautomeric" mode. Since the equilibria between straight and ring structures tends to generate more ring structures than straight chains at any given moment when dissolved in an aqueous solvent, most saccharides are usually drawn and discussed as ring structures.

Saccharide rings are called furanose rings if the ring structure itself (excluding any pendant groups) contains five atoms, and pyranose rings if the ring contains six atoms. Most furanose molecules are derived from pentose sugars (i.e., sugars which contain five carbon atoms, such as ribose, arabinose, or xylose). In a pentose molecule, one of the atoms in the ring form of the molecule is an oxygen atom; the fifth carbon atom is attached to the ring in a pendant structure, usually as a hydroxylated methyl group. In the same manner, most pyranose molecules (with six-membered rings) are hexose sugars such as glucose, galactose, and mannose, or derivatives thereof. Hexose sugars contain six carbon atoms; in the most common pyranose ring, five carbons are in the ring along with an oxygen atom; the sixth carbon atom is attached to the ring in a pendant group.

A glycoside molecule contains at least one saccharide component (usually drawn as a ring) attached through an oxygen atom (which can be regarded as an ether linkage) to a second molecular group having at least one carbon atom. If a glycoside molecule is chemically hydrolyzed to break the ether linkage(s), it will release at least one saccharide molecule. Usually, the glycoside linkage is between adjacent saccharide rings, to form disaccharides, trisaccharides, polysaccharides, etc.

As implied by the name, an aminoglycoside is a glycoside with one or more amino groups. Because of their biological properties, aminoglycosides are an important class of aminosaccharides. Neomycin A (neamine), Neomycin B and C, Gentamicin, sisomycin, streptomycin, and tobramycin are all aminoglycosides, since they have the requisite amine groups, saccharide rings, and oxygen linkages. Most aminoglycosides were initially identified due to the anti-bacterial activities of various microbes that synthesize such compounds in nature. Many of these aminoglycoside antibiotics can be altered or derivatized in various ways that do not destroy their antibiotic activity; for example, if Neomycin B or Neomycin C is cleaved between the disaccharide structure and the pentose ring, the two cleavage products are Neomycin A (a disaccharide, also known as neamine) and either Neobiosanine B or Neobiosamine C.

The aminoglycosides and derivatives thereof that are of particular interest to the present invention have the structure:

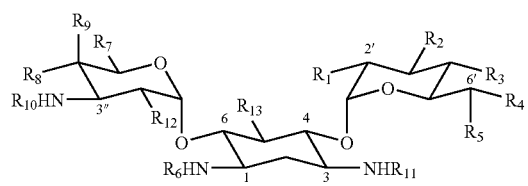

Wherein each of R1-R13 is independently hydrogen, alkyl, optionally substituted alkyl, alkenyl, optionally substituted alkenyl, alkynyl, optionally substituted alkynyl, aryl, optionally substituted aryl, cycloalkyl, optionally substituted cycloalkyl, alkoxy, optionally substituted alkoxy, heterocyclic, optionally substituted heterocyclic, heteroaryl, optionally substituted heteroaryl, hydroxyl, halogen, nitro, carboxyl, thioalkyl, amino, alkylamino, arylamino, amido, ammonium, alkylammonium, sulfonyl, aminosulfonyl, alkylsulfonyl, alkoxycarbonyl, acetyl, or acyl.

In one embodiment, each of R1-R13 is independently hydrogen, alkyl, optionally substituted alkyl, alkoxy, optionally substituted alkoxy, cycloalkyl, optionally substituted cycloalkyl, cyclooxyalkyl, optionally substituted cyclooxyalkyl, hydroxyl, halogen, amino, alkylamino, amido, ammonium, alkoxycarbonyl, acetyl, or acyl.

In another embodiment, each of R1-R13 is independently hydrogen, alkyl, optionally substituted alkyl, hydroxyl, alkoxy, optionally substituted alkoxy, halogen, amino, acetyl, or acyl. In a related embodiment, at least one of R1-R13 is independently acetyl.

In another embodiment, at least one of R2, R3, R6, R12, or R13 is halogen. In a related embodiment, the halogen is fluorine.

In another embodiment, at least one of R4, R5, or R6 is acyl.

In another embodiment, R7 is alkyl or optionally substituted alkyl. In a related embodiment, the optionally substituted alkyl is a $C_6$ to $C_{12}$ alkyl.

In another embodiment, each of R1-R13 is independently hydrogen, alkyl, optionally substituted alkyl, alkenyl, optionally substituted alkenyl, alkynyl, optionally substituted alkynyl, alkoxy, optionally substituted alkoxy, aryl, optionally substituted aryl, cycloalkyl, optionally substituted cycloalkyl, heterocyclic, optionally substituted heterocyclic, heteroaryl, optionally substituted heteroaryl, hydroxyl, halogen, nitro, carboxyl, thioalkyl, amino, alkylamino, arylamino, amido, ammonium, alkylammonium, sulfonyl, aminosulfonyl, alkylsulfonyl, alkoxycarbonyl, acetyl, or acyl, with the proviso that when R6=H, R7=H, R8=CH3, R9 OH, R10=CH3, R11=H, R12=OH, and R13=OH; if R1=NH2, R2=H, R3=H, and R4=CH3, then R5 is not NH2 or NHCH3; and if R1=OH, R2=OH, R3=OH, and R4 is H, then R5 is not NH2.

In another embodiment, R1=NH2, R2=H, R3=H, R4=CH3, R5=NH2 or NHCH3, R6=H, R7=H, R8=CH3, R9=OH, R10=CH3, R1=H, R12=OH, and R13=OH.

In another embodiment, R1=OH, R2=OH, R3=OH, R4=H, R5=NH2, R6=H, R7=H, R8=CH3, R9=OH, R10=CH3, R11=H, R12=OH, and R13=OH.

In addition to the above, some compounds are also called aminoglycosides even though they do not have a glycosidic oxygen linkage, since they are components of larger molecules which are true aminoglycosides, and they are commonly synthesized using bacterial aminoglycosides as starting reagents. Examples include 2,6-diamino-2,6-dideoxy-D-glucose (which can be obtained by hydrolyzing Neomycin) and streptidine (which can be obtained by hydrolyzing streptomycin). As used herein, the term "aminoglycoside" encompasses these compounds as well.

Gentamicin and derivatives thereof are one type of aminoglycoside of interest, as gentamicin is known to inhibit SMase (Ghosh et al., J. Biol. Chem. 262:12550-12556, 1987). Several isoforms of gentamicin are known, including Gentamicin C, Gentamicin C1a, Gentamicin C2, Gentamicin C26 and Gentamicin B (see Example 13 for the structures of these isoforms). Methods of preparing gentamicin isoforms and derivatives are disclosed in U.S. Pat. Nos. 3,984,395 (Method of isolating gentamicin C2a); 4,288,547 (Fermentative process for preparing antibiotics of the gentamicin class); and 5,814,488 (Semisynthetic 1-N-ethylgentamicin C1a and method for its preparation). Gentamicin derivatives are disclosed in U.S. Pat. Nos. 4,387,219 (2-Hydroxy gentamicin compounds); 4,283,528 (1-N-aminohydroxyacyl derivatives of gentamicin B); and 4,223,024 (4"-O-Alkylgentamicins and sagamicins). U.S. Pat. No. 4,150,949, (Immunoassay for gentamicin), discloses fluorescein-labelled gentamicins, including fluoresceinthiocarbanyl gentamicin.

Kanamycin and derivatives thereof are of interest. Many chemically modified derivatives of kanamycin are known; for a review, see Mingeot-Leclercq et al., Antimicrobial Agents and Chemoctherapy 43:727-737, 1999. Kanamycin derivatives are described in U.S. Pat. No. 4,873,225 (1-n-(4-amino-3-fluoro-2-hydroxybutyryl)-kanamycins); U.S Pat. No. 4,455,419 (2'-Modified kanamycins and production thereof); U.S Pat. No. 4,424,343 (Preparation of 1-N->.omega.-amino-. alpha.-hydroxyalkanoyllkanamycin polysilylates and products); U.S Pat. No. 4,337,336 (Derivative of kanamycin A and a process for the preparation thereof); U.S Pat. No. 4,195,170 (3',4'-Episulfido kanamycin B compounds); U.S. Pat. No. 4,178,437 (1-N-Kanamycin derivatives); U.S Pat. No. 4,170,642 (Derivatives of kanamycin A); U.S Pat. No. 4,140,849 (Kanamycin C derivatives); U.S Pat. No. 4,120,955 (Method for production of kanamycin C and its derivatives); U.S Pat. No. 3,974,137 (Process for the preparation of 1-[L-(−)-.gamma.-amino-.alpha.-hydroxybutyryl]-kanamycin A (RD-1341A)); U.S Pat. No. 3,940,382 (1,2'-Di-N-substituted kanamycin B compounds); U.S. Pat. No. 4,178,437 (1-N-Kanamycin derivatives); U.S. Pat. No. 4,140,849 (Kanamycin C derivatives); U.S. Pat. No. 4,181,797 (1-N-(.omega.-amino-.alpha.-hydroxyalkanoyl) derivatives of 4'-deoxy-6'-N-methylkanamycin A); and U.S Pat. No. 4,051,315 (6"-Deoxykanamycin B and 6"-deoxytobramycin).

Fortimicin and derivatives thereof are of interest. Fortimicin is a naturally occurring aminoglycoside antibiotic, first produced by fermentation of a microorganism belonging to the genus *Micromonospora*. Studies of fortimicin showed that blocking the 2-hydroxy group by inactivates the antibiotic. As a result, much attention was focused on developing chemical modifications to the aminoglycoside that position in order to develop more stable fortimicin derivatives. Fortimicin and chemical derivatives of Fortimicin are described in U.S. Pat. No. 4,214,079 (4-N, 2'-N and 4,2'-Di-N-fortimicin AL derivatives); U.S Pat. No. 4,214,078 (Fortimicin AL); U.S Pat. No. 4,214,076 (2'-N-Substituted fortimicin B and derivatives); 4,220,756 (Method of producing 3-O-demethylfortimicin B,4-N-alkylfortimicin B derivatives and related aminoglycoside antibiotics); U.S Pat. No. 4,219,644 (Fortimicins AH and AI); U.S Pat. No. 4,219,643 (Fortimicin AN); U.S Pat. No. 4,219,642 (Fortimicin AO); U.S. Pat. No. 4,214,080 (Fortimicins AM and AP); U.S. Pat. No. 4,214,075 (6'-Epi-fortimicin A and B derivatives); U.S. Pat. No. 4,213,974 (4-N,2'-N and 4,2'-Di-N-fortimicin AO derivatives); U.S Pat. No. 4,213,972 (4-N, 2'-N and 4,2'Di-N-fortimicins AH and AI); U.S. Pat. No. 4,213,971 (4-N, 2'-N and 4,2'-Di-N-fortimicin AD derivatives); U.S Pat. No. 4,207,415 (Method of producing 2-deoxyfortimicin A); U.S. Pat. No. 4,205,070 (6'N-Alkyl- and 6',6'-di-N-alkyl derivatives of fortimicins A and B); U.S Pat. No. 4,176,178 (2-Deoxy-2'-N-acyl and alkyl fortimicins A and B); U.S. Pat. No. 4,169,198 (2-Deoxyfortimicin B); U.S. Pat. No. 4,183,920 (4-N-Acyl, 2'-N-acyl and 4,2'-N,N'-diacylfortimicin E derivatives); U.S. Pat. No. 4,192,867 (2-Deoxyfortimicin A, 4-N-alkyl and 4-N-acyl-2-deoxyfortimicin B derivatives); U.S. Pat. No. 4,220,756 (Method of producing 3-O-demethylfortimicin B,4-N-alkyl-fortimicin B derivatives and related aminoglycoside antibiotics); U.S. Pat. No. 4,196,197 (2'N-Acyl and alkyl-6'-N-alkyl- and 6',6'-di-N-alkyl derivatives of fortimicins A and B); U.S Pat. No. 4,187,299 (Fortimicin E); U.S. Pat. No. 4,187,298 (2'N-acyl and alkyl fortimicin B and derivatives, 4,2'-N, N'diacyl and dialkyl fortimicin B derivatives 4-N-acyl-2'-N-alkyl and 4-N-alkyl-2'-N-acyl fortimicin B derivatives); U.S Pat. No. 4,187,297 (3-De-O-methyl-2-N-acyl and alkyl fortimicins A and B); U.S Pat. No. 4,187,296 (2-N-acyl and alkyl 6-epi-fortimicin B and derivatives); U.S Pat. No. 4,208,407 (5-Deoxyfortimicin A, 2,5-dideoxyfortimicin A and the corresponding 4-N-acyl and alkyl fortimicin B derivatives thereof and intermediates therefor); U.S Pat. No. 4,216,210 (Fortimicins AM and AP derivatives); U.S Pat. No. 4,319,022 (2-O-Substituted sulfonyl derivatives of fortimicin B); U.S Pat. No. 4,251,516 (2-Deoxy-3-O-Demethylfortimicins); U.S Pat. No. 4,251,511 (Antibiotic and fermentation process of preparing); U.S Pat. No. 4,250,304 (2-Deoxy-2-substituted fortimicin A and B and derivatives); U.S Pat. No. 4,317,904 (1,2-Epiminofortimicin B); U.S Pat. No. 4,255,421 (Fortimicin aminoglycosides, process for production thereof, and use thereof); U.S Pat. No. 4,252,972 (Fortimicin B-1, 2:4,5-bis-carbamates); U.S. Pat. No. 4,418,193 (Method of producing 2-epi-fortimicin A); and U.S Pat. No. 4,207,415 (Method of producing 2-deoxyfortimicin A).

Sisomicin and derivatives thereof are disclosed in U.S. Pat. No. 4,438,260 (Sisomicin compounds); U.S Pat. No. 4,369,251 (Method for the production of sisomicin); U.S Pat. No. 4,365,020 (Method for the preparation of antibiotic sisomicin); U.S Pat. No. 4,336,369 (Selectively protected 1-N-(.omega.-aminoalkoxycarbonyl)-sisomicin derivatives); U.S Pat. No. 4,312,859 (Sisomicin derivatives, processes for their production and their medicinal use); U.S Pat. No. 3,997,524 (Process for the manufacture of 6'-N-alkyl derivatives of sisomicin and verdamicin; novel intermediates useful therein, and novel 6'-N-alkylverdamicins prepared thereby); and U.S Pat. No. 3,988,316 (Antibiotics sisomicin and verdamicin I and complex containing same).

Amikacin and derivatives thereof are disclosed in U.S. Pat. No. 5,763,587 (Process for the synthesis of amikacin); U.S Pat. No. 5,656,735 (Process for the preparation of amikacin precursors); U.S Pat. No. 5,621,085 (Process for the preparation of amikacin precursors); U.S Pat. No. 4,985,549 (Process for preparing amikacin); and U.S Pat. No. 4,902,790 (Novel process for the synthesis of amikacin).

Dibekacin and derivatives thereof are disclosed in U.S. Pat. No. 5,618,795 (Dibekacin derivatives and arbekacin derivatives active against resistant bacteria, and the production thereof); and U.S Pat. No. 5,488,038 (Dibekacin derivatives and arbekacin derivatives active against resistant bacteria).

Other aminoglycosides are disclosed in U.S. Pat. No. 4,855,287 (Aminoglycoside compounds, processes for production thereof, and pharmaceutical composition containing the same); U.S. Pat. No. 5,442,047 (Process for preparing isepamicin); U.S Pat. No. 4,208,531 (Synthetic aminoglycosides); U.S Pat. No. 4,656,160 (Aminoglycoside derivatives); U.S Pat. No. 4,647,656 (Aminoglycoside compounds); U.S Pat. No. 4,645,760 (Activated aminoglycosides and aminoglycoside-aminocyclitols pharmaceutical compositions and method of use); U.S Pat. No. 4,617,293 (Flavonoid phosphate salts of aminoglycoside antibiotics); U.S Pat. No. 4,554,269 (Kasugamycin derivatives, pharmaceutical compositions and method of use); U.S Pat. No. 4,503,046 (1-Nitro-aminoglycoside derivatives, pharmaceutical compositions containing them and such derivatives for use as pharmaceuticals); U.S Pat. No. 4,493,831 (Aminoglycoside derivatives); U.S Pat. No. 4,486,418 (2'-Deamino aminoglycosides and composition thereof); U.S Pat. No. 4,468,513 (2'-N-Acylated and 2'-N-alkylated derivatives of 4-O-substituted-2-deoxystreptamine aminoglycosides); U.S Pat. No. 4,468,512 (1-N-Acylated and 1-N-alkylated derivatives of 4-O-substituted-2-deoxystreptamine aminoglycosides); U.S Pat. No. 4,438,107 (Aminoglycosides and use thereof); U.S Pat. No. 4,424,345 (1-N-Acylated and 1-N-alkylated derivatives of 4-O-substituted-2-deoxystreptamine aminoglycosides and process); U.S Pat. No. 4,424,344 (2-N-Acylated and 2-N-alkylated derivatives of 4-O-substituted-2-deoxystreptamine aminoglycosides and process); U.S Pat. No. 4,380,625 (Process for the preparation of purified aminoglycoside antibiotics); U.S Pat. No. 4,349,667.(Aminoglycoside antibiotic G-367-2); U.S Pat. No. 4,347,354 (Preparation of 1-N-[.omega.-amino-.alpha.-hydroxyalkanoyl]aminoglycoside polysilylated antibiotics and products obtained therefrom); U.S Pat. No. 4,330,673 (Process for producing 3-O-demethylaminoglycoside and novel 3-O-demethylfortimicin derivatives); U.S Pat. No. 4,297,486 (Aminoglycoside antibiotic G-367-1 and method for the production thereof); U.S Pat. No. 4,297,485 (Production of a selectively protected N-acylated derivative of an aminoglycosidic antibiotic); U.S Pat. No. 4,279,997 (Process for production of aminoglycoside antibiotics); U.S Pat. No. 4,273,923 (Process for preparing aminoglycoside derivatives); U.S Pat. No. 4,255,421 (Fortimicin aminoglycosides, process for production thereof, and use thereof); U.S Pat. No. 4,252,972 (Fortimicin B-1, 2:4,5-bis-carbamates); U.S Pat. No. 4,250,170 (Antibacterial agents Bu-2349A and B and method of using same); U.S Pat. No. 4,248,865 (Novel aminoglycoside derivatives); U.S Pat. No. 4,242,331 (Aminoglycosides and method of use); U.S Pat. No. 4,230,847 (Aminoglycoside antibiotic compounds); U.S Pat. No. 4,226,978 (beta.-Galactosyl-umbelliferone-labeled aminoglycoside antibiotics and intermediates in their preparation); U.S Pat. No. 4,223,022 Stabilized aminoglycoside antibiotic formulations); U.S Pat. No. 4,217,446 (.omega.Amino-2-hydroxyalkyl derivatives of aminoglycoside antibiotics); 4,214,074 Hydroxyalkyl derivatives of aminoglycoside antibiotics); U.S Pat. No. 4,212,859 (2'-Hydroxy-2'-desamino-4,6-di-O-(aminoglycosyl)-1,3-diaminocyclitols, methods for their manufacture, method for their use as antibacterial agents, and compositions useful therefor: U.S Pat. No. 4,209,511 (Aminoglycoside antibiotics and process for production thereof); U.S Pat. No. 4,207,314 (Isofortimicin); U.S Pat. No. 4,201,774 (Novel aminoglycoside derivatives); U.S Pat. No. 4,200,628 (Novel aminoglycoside derivatives); U.S Pat. No. 4,199,570 1-N-Hetero containing aminoglycoside derivatives); U.S Pat. No. 4,189,569 (Seldomycin factor 5 derivatives); U.S Pat. No. 4,187,372 (Seldomycin factor 5 derivative); U.S Pat. No. 4,187,299 (Fortimicin E); U.S Pat. No. 4,170,643 (Aminoglycoside-aminocyclitol derivatives and method of use); U.S Pat. No. 4,166,114 (Aminoglycoside antibiotic derivatives and method of use); U.S Pat. No. 4,146,617 (Desoxystreptamine derivatives, salts, pharmaceutical compositions and method of use); U.S Pat. No. 4,136,254 (Process of selectively blocking amino functions in aminoglycosides using transition metal salts and intermediates used thereby); U.S Pat. No. 4,125,707 (Protected pseudotrisaccharide intermediate for paromomycin and neomycin derivatives); U.S Pat. No. 4,117,221 (Aminoacyl derivatives of aminoglycoside antibiotics); U.S Pat. No. 4,107,435 (Process for .omega.-amino-2-hydroxyalkyl derivatives of aminoglycoside antibiotics); U.S Pat. No. 4,101,556 (Total synthesis of 2,5-dideoxystreptamines); U.S Pat. No. 4,085,208 (Process for preparing 4,6-di-O-(aminoglycosyl)-1,3-diaminocyclitols and novel 1-epimers and 1-N-alkyl derivatives produced thereby; methods for the use of the 1-epimer derivatives as antibacterial agents and compositions useful therefor); U.S Pat. No. 4,066,752 1-Desamino-1-hydroxy and 1-desamino-1-epi-hydroxy-4, 6-di-o-(aminoglycosyl)-1,3-diaminocyclitols; 1-desamino-1-oxo-4,6-di-o-(aminoglycosyl)-1, 3-diaminocyclitols, intermediates and use as antibacterial agents); U.S Pat. No. 4,065,615 (Deoxyaminoglycoside antibiotic derivatives); U.S Pat. No. 4,064,339 (Antibiotic aminoglycosides, processes of preparation and pharmaceutical compositions); U.S Pat. No. 4,049,498 (Methods for the preparation of semisynthetic aminocyclitol aminoglycoside antibiotics); U.S Pat. No. 4,044,123 (6'-N-alkyl-4,6-di-O-(aminoglycosyl)-1,3-diaminocyclitols, methods for their use as antibacterial agents and compositions useful therefor); U.S Pat. No. 4,038,478 (O-Glycoside ortho esters of neamine containing compounds); U.S Pat. No. 4,032,404 (Fermentation process for producing apramycin and nebramycin factor V'); U.S Pat. No. 4,031,210 (Antibiotic aminoglycosides, processes of preparation and pharmaceutical compositions); U.S Pat. No. 4,024,332 (Aminoglycoside antibiotics and intermediates therefor); U.S Pat. No. 4,020,269 (Epiminodeaminodeoxyaminoglycoside antibiotics and intermediates); U.S Pat. No. 4,012,576 (Antibiotic complex Bu 2183); U.S Pat. No. 4,011,390

(Semi-synthetic aminocyclitol aminoglycoside antibiotics and methods for the preparation thereof); U.S Pat. No. 4,009,328 (Aminoglycoside 66-40C, method for its manufacture, method for its use as an intermediate in the preparation of known antibiotics and novel antibacterials); U.S Pat. No. 4,003,922 (Synthesis of cis-1,4-cyclohexadiene dioxide); U.S Pat. No. 4,002,608 (1-N-alkyl-aminoglycoside-XK-88 derivatives and methods for their manufacture); U.S Pat. No. 3,996,205 (Aminoglycoside antibiotics and intermediates); U.S Pat. No. 3,984,393 (Aminoglycoside antibiotics); U.S Pat. No. 3,981,861 (Antibiotic aminoglycosides, processes of preparation and pharmaceutical compositions); U.S Pat. No. 3,978,214 (Novel 4,6-di-O-(aminoglycosyl)-2-deoxystreptamine, method for its manufacture, method for its use as an antiprotozoal agent and compositions useful thereof); 3,962,429 (Method for reducing side effects of aminoglycoside antibiotics and composition therefor); U.S Pat. No. 3,959,255 (Antibiotic aminoglycosides, and process of preparation); U.S Pat. No. 3,953,422 (Deoxyglucose derivatives); and U.S Pat. No. 3,953,293 (Process for the preparation of xylostasin).

Additional aminoglycosides are disclosed by Matsumoto et al., "Synthesis of novel 13-methyl-13-dihydroanthracyclines", Chem Pharm Bull (Tokyo), 34:4613-9, 1986; Israel et al., "Adriamycin analogues. Preparation and biological evaluation of some N-(trifluoroacetyl)-14-O-[(N-acetylamino)acyl]adriamycin derivatives", J Med Chem., 2:1273-6, 1986; Takahashi et al., "Production of novel antibiotic, dopsisamine, by a new subspecies of *Nocardiopsis mutabilis* with multiple antibiotic resistance", J Antibiot (Tokyo), 39:175-83, 1986; Yasuda et al., "Total synthesis of 3-O-demethylsporaricin A", J Antibiot (Tokyo), 38:1512-25, 1985; Tsunakawa et al., "Inosamycin, a complex of new aminoglycoside antibiotics. 1. Production, isolation and properties", J Antibiot (Tokyo), 38:1302-12, 1985; Matsuhashi et al., "In vitro and in vivo antibacterial activities of dactimicin, a novel pseudodisaccharide aminoglycoside, compared with those of other aminoglycoside antibiotics", Antimicrob Agents Chemother, 27:589-94, 1985; Matsunaga et al., "Bacterial uptake of habekacin, a novel aminoglycoside antibiotic", J Antibiot (Tokyo), 37:596-601, 1984; Tanaka et al., "Mechanism of action of habekacin, a novel amino acid-containing aminoglycoside antibiotic", Antimicrob Agents Chemother, 24:797-802, 1983; Dawson, "Activity of SC33428, a novel bishydrazone-bridged derivative of 4-demethoxydaunorubicin, against experimental tumors in mice", Cancer Res., 43:2880-3, 1983; Digranes et al., "N-formimidoyl thienamycin: in vitro comparison with cefoxitin and tobramycin against clinical, bacterial isolates", Acta Pathol Microbiol Immunol Scand [B], 91:141-4, 1983; FitzGerald et al., "3,4-Dihydroxybenzylamine: an improved dopamine analog cytotoxic for melanoma cells in part through oxidation products inhibitory to dna polymerase", J Invest Dermatol., 80:119-23, 1983; Israel et al., "Adriamycin analogues. Novel anomeric ribofuranoside analogues of daunorubicin", J Med Chem., 25:28-31, 1982; Tanaka, "Effects of habekacin, a novel aminoglycoside antibiotic, on experimental corneal ulceration due to *Pseudomonas aeruginosa*", J Antibiot (Tokyo), 34:892-7, 19881; Fujiwara et al., "Production of a new aminoglycoside antibiotic by a mutant of *Bacillus circulans*", J Antibiot (Tokyo), 33:836-41, 1980; Ohashi et al., "In vitro and in vivo antibacterial activity of KW1070, a new aminoglycoside antibiotic", Antimicrob Agents Chemother., 17:138-43, 1980; Inouye et al., "A novel aminoglycoside antibiotic, substance SF-2052", J Antibiot (Tokyo), 32:1355-6, 1979; Perzynski et al., "Effects of apramycin, a novel aminoglycoside antibiotic on bacterial protein synthesis", Eur J. Biochem., 99:623-8, 1979; Suzuki et al., "Preparation and some microbiological properties of novel kanamycin-glucoside derivatives", J Antibiot (Tokyo), 32:753-5, 1979; Smith et al., "Synthesis of daunorubicin analogues with novel 9-acyl substituents", J Med Chem., 22:40-4, 1979; Davies et al., "Semisynthetic aminoglycoside antibacterials. 6. Synthesis of sisomicin, Antibiotic G-52, and novel 6'-substituted analogues of sisomicin from aminoglycoside 6640C", J Med Chem., 21:189-93, 1978; Egan et al., "Fortimicins A and B, new aminoglycoside antibiotics. III. Structural identification",J Antibiot (Tokyo), 30:552-63, 1977; Okachi et al., "Fortimicins A and B, new aminoglycoside antibiotics. II. Isolation, physico-chemical and chromatographic properties", J Antibiot (Tokyo), 30:541-51, 1977; Kinumaki et al., "Macrolide antibiotics M-4365 produced by *Micromonospora*. II. Chemical structures", J Antibiot (Tokyo), 30:450-4, 1977; Okutani et al., "Conversion of aminoglycosidic antibiotics: Novel and efficient approaches to 3'-deoxyaminoglycosides via 3'-phosphoryl esters", J Am Chem. Soc., 99:1278-9, 1977; Hanessian et al., "Aminoglycoside antibiotics: oxidative degradations leading to novel biochemical probes and synthetic intermediates", J Antibiot (Tokyo), 28:835-7, 1975; Reimann et al., "The structure of sisomicin, a novel unsaturated aminocyclitol antibiotic from *Micromonospora inyoensis*", J Org. Chem., 39:1451-7, 1974; Kugelman et al., "Letter: The preparation of garamine, a novel pseudodisaccharide from sisomycin", J Antibiot (Tokyo), 26:394-5, 1973; Arcamone et al., "Adriamycin (14-hydroxydaunomycin), a novel antitumor antibiotic", Tetrahedron Lett., 13:1007-10, 1969; Matsumoto et al., "Synthesis of novel 13-methyl-13-dihydroanthracyclines", Chem Pharm Bull (Tokyo), 34:4613-9, 1986; Israel et al., "Adriamycin analogues. Preparation and biological evaluation of some N-(trifluoroacetyl)-14-O—[(N-acetylamino)acyl]adriamycin derivatives", J Med Chem., 29:1273-6, 1986; Takahashi et al., "Production of novel antibiotic, dopsisamine, by a new subspecies *of* Nocardiopsis mutabilis with multiple antibiotic resistance", J Antibiot (Tokyo), 39:175-83, 1986; Yasuda et al., "Total synthesis of 3-O-demethylsporaricin A", J Antibiot (Tokyo), 38:1512-25, 1985; Tsunakawa et al., "Inosamycin, a complex of new aminoglycoside antibiotics. 1. Production, isolation and properties", J Antibiot (Tokyo), 38:1302-12, 1985; Matsuhashi et al., "In vitro and in vivo antibacterial activities of dactimicin, a novel pseudodisaccharide aminoglycoside, compared with those of other aminoglycoside antibiotics", Antimicrob Agents Chemother., 27:589-94, 1985; Matsunaga et al., "Bacterial uptake of habekacin, a novel aminoglycoside antibiotic", J Antibiot (Tokyo), 37:596-601, 1984; Tanaka et al., "Mechanism of action of habekacin, a novel amino acid-containing aminoglycoside antibiotic", Antimicrob Agents Chemother., 24:797-802, 1983; Dawson, "Activity of SC33428, a novel bishydrazone-bridged derivative of 4-demethoxydaunorubicin, against experimental tumors in mice", Cancer Res., 43:2880-3, 1983; Digranes et al., "N-formimidoyl thienamycin: in vitro comparison with cefoxitin and tobramycin against clinical, bacterial isolates", Acta Pathol Microbiol Immunol Scand [B]., 91:141-4, 1983; FitzGerald et al., "3,4-Dihydroxybenzylamine: an improved dopamine analog cytotoxic for melanoma cells in part through oxidation products inhibitory to dna polymerase", J Invest Dermatol., 80:119-23, 1983; Israel et al., "Adriamycin analogues. Novel anomeric ribofuranoside analogues of daunorubicin", J Med Chem., 25:28-31, 1982; Tanaka, "Effects of habekacin, a novel aminoglycoside antibiotic, on experimental corneal ulceration due to *Pseudomonas aeruginosa*", J Antibiot (Tokyo), 34:892-7, 1981; Fujiwara et al., "Production of a new aminoglycoside antibiotic by a mutant of *Bacillus circulans*", J Antibiot (Tokyo), 33:83641, 1980; Ohashi et al., "In vitro and in vivo antibacterial activity of KW1070, a new aminoglycoside antibiotic", Antimicrob Agents Chemother., 17:138-43, 1980; Inouye et al., "A novel aminoglycoside antibiotic, substance SF-2052", J Antibiot (Tokyo), 32:1355-6, 1979; Perzynski et al., "Effects of apramycin, a novel aminoglycoside antibiotic on bacterial protein synthesis", Eur J. Biochem., 99:623-8, 1979; Suzuki et al., "Preparation and some microbiological properties of novel kanamycin-glucoside derivatives", J Antibiot (Tokyo), 32:753-5, 1979; Smith et al., "Synthesis of daunorubicin analogues with novel 9-acyl substituents", J Med Chem., 22:40-4, 1979; Davies et al., "Semisynthetic aminoglycoside antibacterials. 6. Synthesis of sisomicin, Antibiotic G-52, and novel 6'-substituted analogues of sisomicin from aminoglycoside 66-40C", J Med Chem., 21:189-93, 1978; Egan et al., "Fortimicins A and B, new aminoglycoside antibiotics. III. Structural identification", J Antibiot (Tokyo), 30:552-63, 1977; Okachi et al., "Fortimicins A and B, new aminoglycoside antibiotics. II. Isolation, physico-chemical and chromatographic properties", J Antibiot (Tokyo), 30:541-51, 1977; Kinumaki et al., "Macrolide antibiotics M-4365 produced by *Micromonospora*. II. Chemical structures", J Antibiot (Tokyo), 30:450-4, 1977; Okutani et al., "Conversion of aminoglycosidic antibiotics: Novel and efficient approaches to 3'-deoxyaminoglycosides via 3'-phosphoryl esters", J Am Chem. Soc., 99:1278-9, 1977; Hanessian et al., "Aminoglycoside antibiotics: oxidative degradations leading to novel biochemical probes and synthetic intermediates", J Antibiot (Tokyo), 28:835-7, 1975; Reimann et al., "The structure of sisomicin, a novel unsaturated aminocyclitol antibiotic from *Micromonospora inyoensis*", J Org. Chem., 39:1451-7, 1974; Kugelman et al., "Letter: The preparation of garamine, a novel pseudodisaccharide from sisomycin", J Antibiot (Tokyo), 26:394-5, 1973; Arcamone et al., "Adriamycin (14-hydroxydaunomycin), a novel antitumor antibiotic", Tetrahedron Lett., 13:1007-10, 1969; Yew et al., "New antimycobacterial agents", Monaldi Arch Chest Dis., 51:394-404, 1996; Urban et al., "Comparative in-vitro activity of SCH 27899, a novel everninomicin, and vancomycin", J Antimicrob Chemother, 37:361-4, 1996; Lam et al., "Production and isolation of two novel esperamicins in a chemically defined medium", J Antibiot (Tokyo), 48:1497-501, 1995; Pelyvas et al., "Novel aminocyclitol antibiotics derived from natural carbohydrates", Carbohydr Res., 272:C5-9, 1995; Pelyvas et al., "Synthesis of new pseudodisaccharide aminoglycoside antibiotics from carbohydrates", J Antibiot (Tokyo), 48:683-95, 1995; Jones, "Isepamicin (SCH 21420, 1-N-HAPA gentamicin B): microbiological characteristics including antimicrobial potency of spectrum of activity", J. Chemother., 2:7-16, 1995 Suppl; Abe et al., "Novel antitumor antibiotics, saptomycins. II. Isolation, physico-chemical properties and structure elucidation", J Antibiot (Tokyo), 46:1536-49, 1993; Abe et al., "Novel antitumor antibiotics, saptomycins. 1. Taxonomy of the producing organism, fermentation, HPLC analysis and biological activities", J Antibiot (Tokyo), 46:1530-5, 1993; Phillipson et al., "Lanomycin and glucolanomycin, antifungal agents produced by *Pycnidiophora dispersa*. 11. Structure elucidation", J Antibiot (Tokyo), 45:313-9, 1992; Mariani et al., "In vitro activity of novel sulphonic derivatives of distamycin A", EXS., 61:455-8, 1992; Abe et al., "Novel antitumor antibiotics, saptomycins D and E", J Antibiot (Tokyo), 44:908-11, 1991; Priebe et al., "3'-Hydroxyesorubicin. Synthesis and antitumor activity", J Antibiot (Tokyo), 43:838-46, 1990; Brill et al., "Altromycins, novel pluramycin-like antibiotics. II. Isolation and elucidation of structure", J Antibiot (Tokyo), 43:229-37, 1990; Jackson et al., "Altromycins, novel pluramycin-like antibiotics. I. Taxonomy of the producing organism, fermentation and antibacterial activity", J Antibiot (Tokyo), 43(3):223-8, 1990; Flynn et al., "The chiral synthesis and biochemical properties of electron rich phenolic sulfoxide analogs of sparsomycin", Biochem Biophys Res Commun., 166:673-80, 1990; Kitamura et al., "Pirarubicin, a novel derivative of doxorubicin. THP-COP therapy for non-Hodgkin's lymphoma in the elderly", Am J Clin Oncol., 13 Suppl 1:S15-9, 1990; Gu et al., "In vitro activity of dactimicin, a novel pseudodisaccharide aminoglycoside, compared with activities of other aminoglycosides", Antimicrob Agents Chemother, 33:1998-2003, 1989; Lam, "Biosynthesis of elsamicin A, a novel antitumor antibiotic", J Nat Prod., 52:1015-21, 1989; Rolston et al., "In vitro activity of trospectomycin (U-63366F), a novel spectinomycin analog, against gram-positive isolates from cancer patients", Eur J Clin Microbiol Infect Dis., 8:254-60, 1989; Gupta et al., "Synthesis, cytotoxicity, and antiviral activity of some acyclic analogues of the pyrrolo[2,3-d]pyrimidine nucleoside antibiotics tubercidin, toyocamycin, and sangivamycin", J Med Chem., 32:402-8, 1989; Hochlowski et al., "Phenelfamycins, a novel complex of elfamycin-type antibiotics. II. Isolation and structure determination" J Antibiot (Tokyo), 41:1300-15, 1988; Jackson et al., "Phenelfamycins, a novel complex of elfamycin-type antibiotics. I. Discovery, taxonomy and fermentation", J Antibiot (Tokyo), 41:1293-9, 1988; Saitoh et al., "Boholmycin, a new aminoglycoside antibiotic. 1. Production, isolation and properties", J Antibiot (Tokyo), 41:855-61, 1988; Matsumoto et al., "Synthesis of novel 13-methyl-13-dihydroanthracyclines", Chem Pharm Bull (Tokyo), 34:4613-9, 1986; Israel et al., "Adriamycin analogues. Preparation and biological evaluation of some N-(trifluoroacetyl)-14-.O—[(N-acetylamino)acyl]adriamycin derivatives", J Med Chem., 29:1273-6, 1986; Takahashi et al., "Production of novel antibiotic, dopsisamine, by a new subspecies of Nocardiopsis mutabilis with multiple antibiotic resistance", Antibiot (Tokyo), 39:175-83, 1986; Yasuda et al., "Total synthesis of 3-O-demethylsporaricin A", J Antibiot (Tokyo), 38:1512-25, 1985; Tsunakawa et al., "Inosamycin, a complex of new aminoglycoside antibiotics. I. Production, isolation and properties", J Antibiot (Tokyo), 38:1302-12, 1985; Matsuhashi et al., "In vitro and in vivo antibacterial activities of dactimicin, a novel pseudodisaccharide aminoglycoside, compared with those of other aminoglycoside antibiotics", Antimicrob Agents Chemother., 27:589-94, 1985; Matsunaga et al., "Bacterial uptake of habekacin, a novel aminoglycoside antibiotic", J Antibiot (Tokyo), 37:596-601, 1984; Tanaka et al., "Mechanism of action of habekacin, a novel amino acid-containing aminoglycoside antibiotic", Antimicrob Agents Chemother., 24:797-802, 1983; Dawson, "Activity of SC33428, a novel bishydrazone-bridged derivative of 4-demethoxydaunorubicin, against experimental tumors in mice", Cancer Res., 43:2880-3, 1983; Digranes et al., "N-formimidoyl thienamycin: in vitro comparison with cefoxitin and tobramycin against clinical, bacterial isolates", Acta Pathol Microbiol Immunol Scand [B], 91:141-4, 1983; FitzGerald et al., "3,4-Dihydroxybenzylamine: an improved dopamine analog cytotoxic for melanoma cells in part through oxidation products inhibitory to dna polymerase", J Invest Dermatol., 80:119-23, 1983; Israel et al., "Adriamycin analogues. Novel anomeric ribofuranoside analogues of daunorubicin", J Med Chem., 25:28-31, 1982; Tanaka, "Effects of habekacin, a novel aminoglycoside antibiotic, on experimental corneal ulceration due to *Pseudomonas aeruginosa*", J Antibiot (Tokyo), 34:892-7, 1981; Fujiwara et al., "Production of a new aminoglycoside antibiotic by a mutant of *Bacillus circulans*", J Antibiot (Tokyo), 33:836-41, 1980; Ohashi et al., "In vitro and in vivo antibacterial activity of KW1070, a new aminoglycoside antibiotic", Antimicrob Agents Chemother., 17:138-43, 1980; Inouye et al., "A novel aminoglycoside antibiotic, substance SF-2052", J Antibiot (Tokyo), 32:1355-6, 1979; Perzynski et al., "Effects of apramycin, a novel aminoglycoside antibiotic on bacterial protein synthesis", Eur J Biochem., 99:623-8, 1979; Suzuki et al., "Preparation and some microbiological properties of novel kanamycin-glucoside derivatives", J. Antibiot (Tokyo), 32:753-5, 1979; Smith et al., "Synthesis of daunorubicin analogues with novel 9-acyl substituents", J Med Chem., 22:40-4, 1979; Davies et al., "Semisynthetic aminoglycoside antibacterials. 6. Synthesis of sisomicin, Antibiotic G-52, and novel 6'-substituted analogues of sisomicin from aminoglycoside 66-40C", J Med Chem., 21:189-93, 1978; Egan et al., "Fortimicins A and B, new aminoglycoside antibiotics. III. Structural identification", J Antibiot (Tokyo), 30:552-63, 1977; Okachi et al., "Fortimicins A and B, new aminoglycoside antibiotics. II. Isolation, physicochemical and chromatographic properties", J Antibiot (Tokyo), 30:541-51, 1977; Kinumaki et al., "Macrolide antibiotics M-4365 produced by *Micromonospora*. II. Chemical structures", J Antibiot (Tokyo), 30:4504, 1977; Okutani et al., "Conversion of aminoglycosidic antibiotics: Novel and efficient approaches to 3'-deoxyaminoglycosides via 3'-phosphoryl esters", J Am Chem Soc., 99:1278-9, 1977; Hanessian et al., "Aminoglycoside antibiotics: oxidative degradations leading to novel biochemical probes and synthetic intermediates", J Antibiot (Tokyo), 28:835-7, 1975; Reimann et al., "The structure of sisomicin, a novel unsaturated aminocyclitol antibiotic from *Micromonospora inyoensis*", J Org Chem., 39:1451-7, 1974; Kugelman et al., "Letter: The preparation of garamine, a novel pseudodisaccharide from sisomycin", J Antibiot (Tokyo), 26:394-5, 1973; Arcamone et al., "Adriamycin (14-hydroxydaunomycin), a novel antitumor antibiotic", Tetrahedron Lett., 13:1007-10, 1969; Yew et al., "New antimycobacterial agents", Monaldi Arch Chest Dis., 51:394-404, 1996; Urban et al., "Comparative in-vitro activity of SCH 27899, a novel everninomicin, and vancomycin", J Antimicrob Chemother., 37:3614, 1996; Lam et al., "Production and isolation of two novel esperamicins in a chemically defined medium", J Antibiot (Tokyo), 48:1497-501, 1995; Pelyvas et al., "Novel aminocyclitol antibiotics derived from natural carbohydrates", Carbohydr Res., 272:C5-9, 1995; Pelyvas et al., "Synthesis of new pseudodisaccharide aminoglycoside antibiotics from carbohydrates", J Antibiot (Tokyo), 48:683-95, 1995; Jones, "Isepamicin (SCH 21420, 1-N-HAPA gentamicin B): microbiological characteristics including antimicrobial potency of spectrum of activity", J Chemother., 7 Suppl 2:7-16, 1995; Abe et al., "Novel antitumor antibiotics, saptomycins. II. Isolation, physico-chemical properties and structure elucidation", J Antibiot (Tokyo), 46:1536-49, 1993; Abe et al., "Novel antitumor antibiotics, saptomycins. 1. Taxonomy of the producing organism, fermentation, HPLC analysis and biological activities", J Antibiot (Tokyo), 46:1530-5, 1993; Phillipson et al., "Lanomycin and glucolanomycin, antifungal agents produced by *Pycnidiophora dispersa*. II. Structure elucidation", J Antibiot (Tokyo), 45:313-9, 1992; Mariani et al., "In vitro activity of novel sulphonic derivatives of distamycin A", EXS., 61:455-8, 1992; Abe et al., "Novel antitumor antibiotics, saptomycins D and E", J Antibiot (Tokyo), 44:908-11, 1989; Priebe et al., "3'-Hydroxyesorubicin. Synthesis and antitumor activity", J Antibiot (Tokyo), 43:838-46, 1990; Brill et al., "Altromycins, novel pluramycin-like antibiotics. II. Isolation and elucidation of structure", J Antibiot (Tokyo), 43:229-37, 1990; Jackson et al., "Altromycins, novel pluramycin-like antibiotics. I. Taxonomy of the producing organism, fermentation and antibacterial activity", J Antibiot (Tokyo), 43:223-8, 1990; Flynn et al., "The chiral synthesis and biochemical properties of electron rich phenolic sulfoxide analogs of sparsomycin", Biochem Biophys Res Commun., 166:673-80, 1990; Kitamura et al., "Pirarubicin, a novel derivative of doxorubicin. THP-COP therapy for non-Hodgkin's lymphoma in the elderly", Am J Clin Oncol., 13 Suppl 1:S15-9, 1990; Gu et al., "In vitro activity of dactimicin, a novel pseudodisaccharide aminoglycoside, compared with activities of other aminoglycosides", Antimicrob Agents Chemother., 33:1998-2003, 1989; Lam et al., "Biosynthesis of elsamicin A, a novel antitumor antibiotic", J Nat Prod. 52:1015-21, 1989; Rolston et al., "In vitro activity of trospectomycin (1'-63366F), a novel spectinomycin analog, against gram-positive isolates from cancer patients", Eur Clin Microbiol Infect Dis., 8:254-60, 1989; Gupta et al., "Synthesis, cytotoxicity, and antiviral activity of some acyclic analogues of the pyrrolo[2,3-d]pyrimidine nucleoside antibiotics tubercidin, toyocamycin, and sangivamycin", J Med Chem., 32:402-8, 1989; Hochlowski et al., "Phenelfamycins, a novel complex of elfamycin-type antibiotics. 11. Isolation and structure determination", J Antibiot (Tokyo), 41:1300-15, 1988; Jackson et al., "Phenelfamycins, a novel complex of elfamycin-type antibiotics. I. Discovery, taxonomy and fermentation", J Antibiot (Tokyo), 41(10):1293-9, 1988; Saitoh et al., "Boholmycin, a new aminoglycoside antibiotic. I. Production, isolation and properties", J Antibiot (Tokyo), 41:855-61, 1988; Yew et al., "New antimycobacterial agents", Monaldi Arch Chest Dis., 51(5): 394-404, 1996; Urban et al., "Comparative in-vitro activity of SCH 27899, a novel everninomicin, and vancomycin", J Antimicrob Chemother, 37:361-4, 1996; Lam et al., "Production and isolation of two novel esperamicins in a chemically defined medium", J Antibiot (Tokyo), 148:1497-501, 1995; Pelyvas et al., "Novel aminocyclitol antibiotics derived from natural carbohydrates", Carbohydr Res., 272:C5-9, 1995; Plyvas et al., "Synthesis of new pseudodisaccharide aminoglycoside antibiotics from carbohydrates", J Antibiot (Tokyo), 48:683-95, 1995; Jones, "Isepamicin (SCH 21420, 1-N-HAPA gentamicin B): microbiological characteristics including antimicrobial potency of spectrum of activity", J Chemother., 7 Suppl 2:7-16, 1995; Abe et al., "Novel antitumor antibiotics, saptomycins. II. Isolation, physico-chemical properties and structure elucidation", J Antibiot (Tokyo), 46:1536-49, 1993; Abe et al., "Novel antitumor antibiotics, saptomycins. I. Taxonomy of the producing organism, fermentation, HPLC analysis and biological activities", J Antibiot (Tokyo), 46:1530-5, 1993; Phillipson et al., "Lanomycin and glucolanomycin, antifungal agents produced by *Pycnidiophora dispersa*. II. Structure elucidation", J Antibiot (Tokyo), 45:313-9, 1992; Mariani et al., "In vitro activity of novel sulphonic derivatives of distamycin A", EXS., 61:455-8, 1992; Abe et al., "Novel antitumor antibiotics, saptomycins D and E", J Antibiot (Tokyo), 44:908-11, 1991; Priebe et al., "3'-Hydroxyesorubicin. Synthesis and antitumor activity", J Antibiot (Tokyo), 43:838-46, 1990; Brill et al., "Altromycins, novel pluramycin-like antibiotics. II. Isolation and elucidation of structure", J Antibiot (Tokyo), 43:229-37, 1990; Jackson et al., "Altromycins, novel pluramycin-like antibiotics. I. Taxonomy of the producing organism, fermentation and antibacterial activity", J Antibiot (Tokyo), 43:223-8, 1990; Flynn et al., "The chiral synthesis and biochemical properties of electron rich phenolic sulfoxide analogs of sparsomycin", Biochem Biophys Res Commun., 166:673-80, 1990; Kitamura et al., "Pirarubicin, a novel derivative of doxorubicin. THP-COP therapy for non-Hodgkin's lymphoma in the elderly", Am J Clin Oncol., 13 Suppl 1:S15-9, 1990; Gu et al., "In vitro activity of dactimicin, a novel pseudodisaccharide aminoglycoside, compared with activities of other aminoglycosides",.Antimicrob Agents Chemother., 33:1998-2003, 1989; Lam et al., "Biosynthesis of elsamicin A, a novel antitumor antibiotic", J Nat Prod., 52:1015-21, 1989; Rolston et al., "In vitro activity of trospectomycin (U-63366F), a novel spectinomycin analog, against gram-positive isolates from cancer patients", Eur Clin Microbiol Infect Dis., 8:254-60, 1989; Gupta et al., "Synthesis, cytotoxicity, and antiviral activity of some acyclic analogues of the pyrrolo[2,3-d]pyrimidine nucleoside antibiotics tubercidin, toyocamycin, and sangivamycin", J Med Chem., 32:402-8, 1989; Hochlowski et al., "Phenelfamycins, a novel complex of elfamycin-type antibiotics. II. Isolation and structure determination", J Antibiot (Tokyo), 41:1300-15, 1988; Jackson et al., "Phenelfamycins, a novel complex of elfamycin-type antibiotics. I. Discovery, taxonomy and fermentation", J Antibiot (Tokyo), 41:1293-9, 1988; Saitoh et al., "Boholmycin, a new aminoglycoside antibiotic. I. Production, isolation and properties", J Antibiot (Tokyo), 41:855-61, 1988; Miller et al., "Clinical pharmacology and toxicity of 4'-O-tetrahydropyranyladriamycin", Cancer Res., 47:1461-5, 1987; Stefani et al., "First microbiological approach to dactimicin, a novel aminoglycoside antibiotic", Drugs Exp Clin Res., 13:727-9, 1987; Matsumoto et al., "Synthesis of novel 13-methyl-13-dihydroanthracyclines", Chem Pharm Bull (Tokyo), 34:4613-9, 1986; Israel et al., "Adriamycin analogues. Preparation and biological evaluation of some N-(trifluoroacetyl)-14-O—[(N-acetylamino)acyl]adriamycin derivatives", J Med Chem., 29:1273-6, 1986; Takahashi et al., "Production of novel antibiotic, dopsisamine, by a new subspecies of *Nocardiopsis mutabilis* with multiple antibiotic resistance", J Antibiot (Tokyo), 39:175-83, 1986; Yasuda et al., "Total synthesis of 3-O-demethylsporaricin A", J Antibiot (Tokyo), 38:1512-25, 1985; Tsunakawa et al., "Inosamycin, a complex of new aminoglycoside antibiotics. I. Production, isolation and properties", J Antibiot (Tokyo), 38:1302-12, 1985; Matsuhashi et al., "In vitro and in vivo antibacterial activities of dactimicin, a novel pseudodisaccharide aminoglycoside, compared with those of other aminoglycoside antibiotics", Antimicrob Agents Chemother., 27:589-94, 1985; Matsunaga et al., "Bacterial uptake of habekacin, a novel aminoglycoside antibiotic", J Antibiot (Tokyo), 37:596-601, 1984; Tanaka et al., "Mechanism of action of habekacin, a novel amino acid-containing aminoglycoside antibiotic", Antimicrob Agents Chemother., 24:797-802, 1983; Dawson, "Activity of SC33428, a novel bishydrazone-bridged derivative of 4-demethoxydaunorubicin, against experimental tumors in mice", Cancer Res., 43:2880-3, 1983; Digranes et al., "N-formimidoyl thienamycin: in vitro comparison with cefoxitin and tobramycin against clinical, bacterial isolates", Acta Pathol Microbiol Immunol Scand [B], 91:141-4, 1983; FitzGerald et al., "3,4-Dihydroxybenzylamine: an improved dopamine analog cytotoxic for melanoma cells in part through oxidation products inhibitory to dna polymerase", J Invest Dermatol., 80:119-23, 1983; Israel et al., "Adriamycin analogues. Novel anomeric ribofuranoside analogues of daunorubicin", J Med Chem.e 25:28-31, 1982; Tanaka. "Effects of habekacin, a novel aminoglycoside antibiotic, on experimental corneal ulceration due to *Pseudomonas aeruginosa*", J Antibiot (Tokyo), 34:892-7, 1981; Fujiwara et al., "Production of a new aminoglycoside antibiotic by a mutant of *Bacillus circulans*", J Antibiot (Tokyo), 33:836-41, 1980; Ohashi et al., "In vitro and in vivo antibacterial activity of KW1070, a new aminoglycoside antibiotic", Antimicrob Agents Chemother, 17:138-43, 1980; Inouye et al., "A novel aminoglycoside antibiotic, substance SF-2052", J Antibiot (Tokyo), 32:1355-6, 1979; Perzynski et al., "Effects of apramycin, a novel aminoglycoside antibiotic on bacterial protein synthesis", Eur J Biochem, 99:623-8, 1979; Suzuki et al., "Preparation and some microbiological properties of novel kanamycin-glucoside derivatives", J Antibiot (Tokyo), 32:753-5, 1979; Smith et al., "Synthesis of daunorubicin analogues with novel 9-acyl substituents", J Med Chem., 22:40-4, 1979; Davies et al., "Semisynthetic aminoglycoside antibacterials. 6. Synthesis of sisomicin, Antibiotic G-52, and novel 6'-substituted analogues of sisomicin from aminoglycoside 66-40C", J Med Chem., 21:189-93, 1978; Egan et al., "Fortimicins A and B, new aminoglycoside antibiotics. III. Structural identification", J Antibiot (Tokyo), 30:552-63, 1977; Okachi et al., "Fortimicins A and B, new aminoglycoside antibiotics. II. Isolation, physico-chemical and chromatographic properties", J Antibiot (Tokyo), 30:541-51, 1977; Kinumaki et al., "Macrolide antibiotics M-4365 produced by *Micromonospora*. II. Chemical structures", J Antibiot (Tokyo), 30:450-4. 1977; Okutani et al., "Conversion of aminoglycosidic antibiotics: Novel and efficient approaches to 3'-deoxyaminoglycosides via 3'-phosphoryl esters", J Am Chem Soc., 99(4):1278-9, 1977; Hanessian et al., "Aminoglycoside antibiotics: oxidative degradations leading to novel biochemical probes and synthetic intermediates", J Antibiot (Tokyo), 28:835-7, 1975; Reimann et al., "The structure of sisomicin, a novel unsaturated aminocyclitol antibiotic from *Micromonospora inyoensis*", J Org Chem., 39:1451-7, 1974; Kugelman et al., "Letter: The preparation of garamine, a novel pseudodisaccharide from sisomycin", J Antibiot (Tokyo), 26:394-5, 1973; Arcamone et al., "Adriamycin (14-hydroxydaunomycin), a novel antitumor antibiotic", Tetrahedron Lett., 13:1007-10, 1969; Marchini et al., "4-Demethoxy-3'-deamino-3'-aziridinyl-4'-methylsulphonyl-daunorubicin (PNU-159548), a novel anticancer agent active against tumor cell lines with different resistance mechanisms", Cancer Res., 61:1991-5, 2001; Sunada et al., "Acetylation of aminoglycoside antibiotics with 6'-methylamino group, istamycin B and micronomicin, by a novel aminoglycoside 6'-acetyltransferase of actinomycete origin", J Antibiot (Tokyo), 53:1416-9, 2000; Ganguly, "Ziracin, a novel oligosaccharide antibiotic", J Antibiot (Tokyo), 53:1038-44, 2000; Nicolaou et al., "Total synthesis of everninomicin 13, 384-1—Part 2: synthesis of the FGHA2 fragment", Chemistry, 6:3116-48, 2000; Nicolaou et al., "Total synthesis of everninomicin 13, 384-1—Part 1: retrosynthetic analysis and synthesis of the A1B(A)C fragment", Chemistry, 6:3095-115, 2000; Wang et al., "In vivo activity and pharmacokinetics of ziracin (SCH27899), a new long-acting everninomicin antibiotic, in a murine model of penicillin-susceptible or penicillin-resistant pneumococcal pneumonia", Antimicrob Agents Chemother., 44:1010-8, 2000; Ganguly et al., "Chemical modifications and structure activity studies of ziracin and related everninomicin antibiotics", Bioorg Med Chem Lett., 9:1209-14, 1999; and Hotta et al., "The novel enzymatic 3"-N-acetylation of arbekacin by an aminoglycoside 3-N-acetyltransferase of *Streptomyces* origin and the resulting activity", J Antibiot (Tokyo), 51 :735-42, 1998.

Aminoglycosides Pharmacology

After injection, aminoglycosides are distributed mainly in the ECF. Protein binding is low. Even with inflammation, concentrations in tissues and secretions are much less than those in plasma levels.

Aminoglycosides are excreted unchanged into the urine by glomerular filtration. They generally have the same half-life in plasma of 2 to 3 h; with renal insufficiency and in the elderly, the half-life rises markedly. To avoid toxicity, the maintenance dosages of aminoglycosides in patients with renal insufficiency must be modified by either decreasing the dose or increasing the interval between doses or both.

Because of the distribution properties of aminoglycosides, dosing in obese patients should be based on a weight equal to lean body weight plus 50% of the adipose mass. In patients with excessive ECF, as in edema, the dose should be calculated based on total body weight. Patients with burns and cystic fibrosis have decreased plasma levels and may require higher doses. Anemia tends to increase plasma levels.

One large aminoglycoside dose given once daily rather than several divided doses given on multiple occasions throughout the day is believed to result in less net transfer of aminoglycoside from the blood into the tissue. This is believed to be accomplished by saturating the rate by which aminoglycoside is moved into the tissue.

Treatment of patients with certain aminoglycosides results in the undesirable side effects of nephrotoxicity and ototoxicity. (For a review, see Mingeot-Leclerq et al., Antimicrobial Agents and Chemotherapy 43:1003-1012, 1999). The compounds used in the methods of the invention are preferably not toxic, in particular because they would not typically be given for prolonged periods of time. Compounds identified by the screening assays of the invention are tested for their toxicity in animal models in order to identify nontoxic compounds. Aminoglycosides having undesirable side-effects can be administered to a patient with one or. more agents that ameriolate or prevent the undesirable side effects. Additionally or alternatively, in the methods of the invention, the compounds are administered using a dosage regimen that is designed to minimize or avoid toxicity or any other undesirable side effects.

Modulation of the Sphingomyelin Signaling Pathway for Therapeutic Benefit

The sphingomyelin signaling pathway (a.k.a. the SM pathway or the ceramide signaling pathway) is a "cascade" of biochemical events in which proteins in the pathway are activated (by enzymatic chemical modification or otherwise) with the end result that sphingosine metabolism is affected. In most instances, activation of the SM pathway leads to increased production of ceramide. For reviews of the molecular biology of the sphingomyelin signaling pathway, see Hannun et al., Adv. Lipid Res. 25:27-41, 1993; Liu et al., Crit. Rev. Clin. Lab. Sci. 36:511-573, 1999; Igarashi, J. Biochem. 122:1080-1087, 1997; and Oral et al., J. Biol. Chem. 272: 4836-4842, 1997.

It has been suggested that the sphingomyelin signal transduction pathway is activated during cardiac ischemia/hypoxia (Bielawska et al., Am. J. Pathol. 151:1257-1263, 1997; Meldrum, Am. J. Physiol. 274:R577-R595, 1998; and Cain et al., J. Mol. Cell. Cardiol. 31:931-947, 1999). If so, one or more factors or processes may mediate the ischemia-induced SPH production. One likely candidate for such a mediator is the pro-inflammatory cytokine, tumor necrosis factor alpha (TNFα). In various animal models of ischemia, the myocardium produces TNFα (Squadrito et al., Eur. J. Pharmacol. 237:223-230, 1993; Herrmann et al., European Journal of Clinical Investigation 28:59-66, 1998; Meldrum et al., Ann. Thorac. Surg. 65:439-443, 1998). Recent evidence demonstrates that the cardiomyocytes themselves produce TNFα and secrete the cytokine into the extracellular fluid (Comstock et al., J. Mol. Cell Cardiol. 30:2761-2775, 1998). Since TNFα receptors are expressed by cardiomyocytes (Krown et al., FEBS Letters 376:24-30, 1995; Torre-Amione et al., Circulation 92:1487-1493, 1995), an autocrine/paracrine role for TNFα has been suggested (Meldrum et al., Ann. Thorac. Surg. 65:439-443, 1998). Significantly, TNFα induces SPH production and apoptosis in cardiac myocytes (Krown et al., J. Clin. Invest. 98:2854-2865, 1996), presumably by acting by binding to the cardiomyocyte complement of TNFα receptors Activation of the sphingomyelin signal transduction cascade may be a key early event in the cytotoxic (apoptotic) effects of the cytokine TNFα (Zhang et al., Endo. 136:4157-4160, 1995). TNFα can cause significant apoptosis in cultured rat cardiomyocytes and it has been suggested that TNFα-induced SPH production is responsible for the cell death triggered by TNFα (Krown et al., J. Clin. Invest. 98:2854-2865, 1996).

The SM pathway, many steps of which occur intracellularly, is induced by a variety of extracellular stimuli. In sphingolipid-based cardiovascular therapy, such stimuli may be inhibited or completely blocked. SM pathway-inducing agents, the function of which may be modulated, include but are not limited to cytokines. Cytokines of particular interest include but are not limited to pro-inflammatory cytokines, interferons and chemokines.

Methods of Screening for Novel Sphingolipid-Based Therapeutic Agents

The sphingolipid targets of the invention are readily adaptable for use in high-throughput screening assays for screening candidate compounds to identify those which have a desired activity, e.g., inhibiting an enzyme that catalyzes a reaction that produces an undesirable sphingolipid, or blocking the binding of a sphingolipid to a receptor therefor. The compounds thus identified can serve as conventional "lead compounds" or can themselves be used as therapeutic agents.

The methods of screening of the invention comprise using screening assays to identify, from a library of diverse molecules, one or more compounds having a desired activity. A "screening assay" is a selective assay designed to identify, isolate, and/or determine the structure of, compounds within a collection that have a preselected activity. By "identifying" it is meant that a compound having a desirable activity is isolated, its chemical structure is determined (including without limitation determining the nucleotide and amino acid sequences of nucleic acids and polypeptides, respectively) the structure of and, additionally or alternatively, purifying compounds having the screened activity). Biochemical and biological assays are designed to test for activity in a broad range of systems ranging from protein-protein interactions, enzyme catalysis, small molecule-protein binding, to cellular functions. Such assays include automated, semi-automated assays and HTS (high throughput screening) assays.

In HTS methods, many discrete compounds are preferably tested in parallel by robotic, automatic or semi-automatic methods so that large numbers of test compounds are screened for a desired activity simultaneously or nearly simultaneously. It is possible to assay and screen up to about 6,000 to 20,000, and even up to about 100,000 to 1,000,000 different compounds a day using the integrated systems of the invention.

Typically in HTS, target molecules are contained in each well of a multi-well microplate; in the case of enzymes, reactants are also present in the wells. Currently, the most widely established techniques utilize 96-well microtiter plates. In this format, 96 independent tests are performed simultaneously on a single 8 cm×12 cm plastic plate that contains 96 reaction wells. One or more blank wells contains all of the reactants except the candidate compound. Each of the non-standard wells contain at least one candidate compound.

These wells typically require assay volumes that range from 50 to 500 ul. In addition to the plates, many instruments, materials, pipettors, robotics, plate washers and plate readers are commercially available to fit the 96-well format to a wide range of homogeneous and heterogeneous assays. Microtiter plates with more wells, such as 384-well microtiter plates, are also used, as are emerging methods such as the nanowell method described by Schullek et al. (Anal Biochem., 30 246, 20-29, 1997).

In one modality, screening comprises contacting a sphingolipid target with a diverse library of member compounds, some of which are ligands of the target, under conditions where complexes between the target and ligands can form, and identifying which members of the libraries are present in such complexes. In another non limiting modality, screening comprises contacting a target enzyme with a diverse library of member compounds, some of which are inhibitors (or activators) of the target, under conditions where a product or a reactant of the reaction catalyzed by the enzyme produce a detectable signal. In the latter modality, inhibitors of target enzyme decrease the signal from a detectable product or increase a signal from a detectable reactant (or vice-versa for activators).

Chemical Libraries

Developments in combinatorial chemistry allow the rapid and economical synthesis of hundreds to thousands of discrete compounds. These compounds are typically arrayed in moderate-sized libraries of small organic molecules designed for efficient screening. Combinatorial methods, can be used to generate unbiased libraries suitable for the identification of novel inhibitors. In addition, smaller, less diverse libraries can be generated that are descended from a single parent compound with a previously determined biological activity. In either case, the lack of efficient screening systems to specifically target therapeutically relevant biological molecules produced by combinational chemistry such as inhibitors of important enzymes hampers the optimal use of these resources.

A combinatorial chemical library is a collection of diverse chemical compounds generated by either chemical synthesis or biological synthesis, by combining a number of chemical "building blocks," such as reagents. For example, a linear combinatorial chemical library, such as a polypeptide library, is formed by combining a set of chemical building blocks (amino acids) in a large number of combinations, and potentially in every possible way, for a given compound length (i.e., the number of amino acids in a polypeptide compound). Millions of chemical compounds can be synthesized through such combinatorial mixing of chemical building blocks.

A "library" may comprise from 2 to 50,000,000 diverse member compounds. Preferably, a library comprises at least 48 diverse compounds, preferably 96 or more diverse compounds, more preferably 384 or more diverse compounds, more preferably, 10,000 or more diverse compounds, preferably more than 100,000 diverse members and most preferably more than 1,000,000 diverse member compounds. By "diverse" it is meant that greater than 50% of the compounds in a library have chemical structures that are not identical to any other member of the library. Preferably, greater than 75% of the compounds in a library have chemical structures that are not identical to any other member of the collection, more preferably greater than 90% and most preferably greater than about 99%.

The preparation of combinatorial chemical libraries is well known to those of skill in the art. For reviews, see Thompson et al., Synthesis and application of small molecule libraries, Chem Rev 96:555-600, 1996; Kenan et al., Exploring molecular diversity with combinatorial shape libraries, Trends Biochem Sci 19:57-64, 1994; Janda, Tagged versus untagged libraries: methods for the generation and screening of combinatorial chemical libraries, Proc Natl Acad Sci USA. 91:10779-85, 1994; Lebl et al., One-bead-one-structure combinatorial libraries, Biopolymers 37:177-98, 1995; Eichler et al., Peptide, peptidomimetic, and organic synthetic combinatorial libraries, Med Res Rev. 15:481-96, 1995; Chabala, Solid-phase combinatorial chemistry and novel tagging methods for identifying leads, Curr Opin Biotechnol. 6:632-9, 1995; Dolle, Discovery of enzyme inhibitors through combinatorial chemistry, Mol Divers. 2:223-36, 1997; Fauchere et al., Peptide and nonpeptide lead discovery using robotically synthesized soluble libraries, Can J Physiol Pharmacol. 75:683-9, 1997; Eichler et al., Generation and utilization of synthetic combinatorial libraries, Mol Med Today 1:174-80, 1995; and Kay et al., Identification of enzyme inhibitors from phage-displayed combinatorial peptide libraries, Comb Chem High Throughput Screen 4:535-43, 2001.

Such combinatorial chemical libraries include, but are not limited to, peptide libraries (see, e.g., U.S. Pat. No. 5,010,175, Furka, Int. J. Pept. Prot. Res., 37:487-493 (1991) and Houghton, et. al., Nature, 354:84-88 (1991)). Other chemistries for generating chemical diversity libraries can also be used. Such chemistries include, but are not limited to, peptoids (PCT Publication No. WO 91119735); encoded peptides (PCT Publication WO 93/20242); random bio-oligomers (PCT Publication No. WO 92/00091); benzodiazepines (U.S. Pat. No. 5,288,514); diversomers, such as hydantoins, benzodiazepines and dipeptides (Hobbs, et al., Proc. Nat. Acad. Sci. USA, 90:6909-6913 (1993)); vinylogous polypeptides (Hagihara, et al., J. Amer. Chem. Soc. 114:6568 (1992)); nonpeptidal peptidomimetics with .beta.-D-glucose scaffolding (Hirschmann, et al., J. Amer. Chem. Soc., 114:9217-9218 (1992)); analogous organic syntheses of small compound libraries (Chen, et al., J. Amer. Chem. Soc., 116:2661 (1994)); oligocarbamates (Cho, et al., Science, 261:1303 (1993)); and/or peptidyl phosphonates (Campbell, et al., J. Org. Chem. 59:658 (1994)); nucleic acid libraries (see, Ausubel, Berger and Sambrook, all supra); peptide nucleic acid libraries (see, e.g., U.S. Pat. No. 5,539,083); antibody libraries (see, e.g., Vaughn, et al., Nature Biotechnology, 14(3):309-314 (1996) and PCT/US96/10287); carbohydrate libraries (see, e.g., Liang, et al., Science, 274:1520-1522 (1996) and U.S. Pat. No. 5,593,853); small organic molecule libraries (see, e.g., benzodiazepines, Baum C&E News, January 18, page 33 (1993); isoprenoids (U.S. Pat. No. 5,569, 588); thiazolidinones and metathiazanones (U.S. Pat. No. 5,549,974); pyrrolidines (U.S. Pat. Nos. 5,525,735 and 5,519, 134); morpholino compounds (U.S. Pat. No. 5,506,337); benzodiazepines (U.S. Pat. No. 5,288,514); and the like.

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Bio sciences, Columbia, Md., etc.).

Bioactive Lipid Libraries

Naturally occurring or synthetic lipids, particularly sphingolipids, are known that modulate processes in sphingolipid biosynthesis and intracellular signaling by ceramide, S-1-P and other sphingolipids (for reviews of sphingolipid-mediated cell signaling processes and consequences arising therefrom, see Linn et al., "Regulation of de novo sphingolipid biosynthesis and the toxic consequences of its disruption", Biochemical Society, 831-835, 2001; Luberto et al., "Sphingolipid Metabolism in the Regulation of Bioactive Molecules", Lipids, 34:S5-S11, 1999; Kester, "Sphingolipid Metabolites and the Cellular Phenotype", Trends in Glycoscience and Glycotechnology, 9:447-460, 1997; Ariga et al., "Role of Sphingolipid-mediated cell death in neurodegenerative diseases", Journal of Lipid Research, 39:1-16, 1998; Chan et al., "Ceramid Path in Human Lung Cell Death", Am. J. Respir. Cell Mol. Biol., 22:460-468, 2000; and Hannun et al., "Ceramide in the eukaryotic stress response", Cell Biology, 10:73-80, 2000; see also Brownlee, Current Biology 11:R535-R538, 2001).

See, for example, Usta et al., "Structural Requirements of Cermaide and Sphingosine Based Inhibitors of Mitochondrial Ceramidase", Biochemistry, 40:9657-9668, 2000; Hannun et al., "Method of Inducing Cellular Differentiations and Altering Cell Phenotype Using Ceramide Analogs", U.S. Pat. No. 5,369,030, issued Nov. 29, 1994; Wei et al., "Pharmaceutically Active Ceramide-Related Compounds", U.S. Pat. No. 5,631,394, issued May 20, 1997; Wei et al., "Methods of Treatment Using Pharmaceutically Active Ceramide-Related Compositions", U.S. Pat. No. 5,677,337, issued Oct. 14, 1997; Carson et al., "Compounds for Inhibition of Ceramide-Mediated Signal Transduction", U.S. Pat. No. 6,323,201 B1, issued Nov. 27, 2001; Bell et al., "Inhibition of Protein Kinase C By Long-Chain Bases", U.S. Pat. No. 4,937,232, issued Jun. 26, 1990; Bell et al., "Inhibition of Protein Kinase C By Long-Chain Bases", U.S. Pat. No. 4,816,450, issued Mar. 28, 1989; Hannun et al., "Ceramidase Compositions and Methods Based Thereon", PCT/US01/02866 published as WO01/55410 on Aug. 2, 2001; Kimura et al., "Effect of N,N,N,-trimethylsphingosine on Protein Kinase-C Activity; Melanoma Cell Growth In Vitro; Metastatic Potential In Vivo and Human Platelet Aggregation", U.S. Pat. No. 5,331,014, dated Jul. 19, 1994; Igarashi et al., "Effect of N,N,N,-trimethylsphingosine on Protein Kinase C Activity Melanoma Cell Growth In Vitro; Metastatic Potential In Vivo and Human Platelet Aggregation", Patent No. 5,137,919 dated Aug. 11, 1992; Handa et al., "Effect of N,N,N,-trimethylsphingosine on Protein Kinase-C Activity, Melanoma Cell Growth In Vitro, Metastatic Potential In Vivo and Human Platelet Aggregation", U.S. Pat. No. 5,151,360 dated Sep. 29, 1992; Takesako et al., "Sphingosine Analogues", PCT/JP98/01038, published as WO98/40349 on Sep. 16, 1998; Kobori et al., "Sphingosine Derivatives", PCT/JP00/08229, published as WO01/38295 on May 31, 2001; Takesako et al., "Sphingosine Derivatives and Medicinal Composition", PCT/JP98/04093, published as WO99/12890 on Mar. 18, 1999; Liotta et al., "Sphingolipid Derivatives and Their Methods of Use", PCT/US99/03093, published as WO99/41266 on Aug. 19, 1999; Macchia et al., "Ceramide Analogs, Process for their Preparation and their Use as Antitumor Agents", PCT/EP00/07023, published as WO01/07418 on Feb. 1, 2001; Shayman et al., "Amino Ceramide-Like Compounds and Therapeutic Methods of Use", PCT/US00/18935, published as WO01/04108 on Jan. 18, 2001; Bielawska et al., "(1S,2R)-D-erythro-2-(N-Myristoylamino)-1-phenyl-1-propanol as an Inhibitor of Ceramidase", The Journal of Biological Chemistry, Vol. 271, May 24, 1996, pp. 12646-12654; Wanebo et al., "Ceramide and Chemotherapeutic Agents for Inducing Cell Death", PCT/US00/09440, published as WO00/59517 on Oct. 12, 2000; Ali et al., "Ceramide Derivatives and Method of Use", PCT/US01/09894, published as WO01/72701 on Oct. 4, 2001; Eibl et al., "Pseudoceramides", PCT/EP99/07698, published as WO00/21919 on Apr. 20, 2000; Jonghe et al., "Structure-Activity Relationship of Short-Chain Sphingoid Bases As Inhibitors of Sphingosine Kinase", Bioorganic & Medicinal Chemistry Letters 9:3175-3180, 1999; Arenz et al., "Synthese des ersten selektiven irreverilben Inhibitors der neutralen Sphingomyelinase", Angew Chem., 112:1498-1500, 2000; and Abe et al., "Use of Sulfobutyl Ether □-Cyclodextrin as a Vehicle for D-threo-1-Phenyl-2-decanoylamino-3-morpholinopropanol-Related Glucosylceramide Synthase Inhibitors", Analytical Biochemistry, 287:344-347, 2000.

One aspect of the invention involves identifying sphingolipids that are useful in sphingolipid-based therapy. This can done by testing commercially available or otherwise obtainable sphingolipids in assays that measure the activity of enzymes involved in sphingolipid metabolism and/or intracellular signalling.

Commercially available sphingolipids (Avanti Polar Lipids, Inc., Alabaster, AL) include without limitation synthetic D-erythro (C-18) derivatives of sphingosine, e.g., D-erythro Sphingosine (synthetic), Sphingosine-1-Phosphate, D-erythro Ceramide-1-Phosphate, N,N-Dimethylsphingosine, N,N,N-Trimethylsphingosine, Sphingosylphosphorylcholine, Sphingomyelin, and Ceramides; D-erythro (C-18) derivatives of sphinganine (dihydrosphingosine), e.g., Sphinganine-1-Phosphate, D-erythro Sphinganine, N-Acyl-Sphinganine C2, N-Acyl-Sphinganine C8, N-acyl-Sphinganine C16, N-Acyl-Sphinganine C18, N-Acyl-Sphinganine C24, and N-Acyl-Sphinganine C24:1; glycosylated (C18) sphingosine and phospholipid derivatives, e.g., glycosylated sphingosine, ceramide and phosphatidylethanolamine, beta D-glucosyl-sphingosine, and beta D-galactosyl-sphingosine; D-erythro (C17) derivatives, e.g., D-erythro Sphingosine and D-erythro Sphingosine-1-phosphate; D-erythro (C20) derivatives, such as D-erythro sphingosine; and L-threo (C18) derivatives such as L-threo Sphingosine and L-threo Dihydrosphingosine (Safingol). Phytosphingosine derivatives from yeast. e.g., Phytosphingosine, D-ribo-Phytosphingosine-1-Phosphate, N-Acyl Phytosphingosine C2, N-Acyl Phytosphingosine C8 and N-Acyl Phytosphingosine C18 may also be used.

A variety of methods for synthesizing sphingolipids and sphingolipid-related molecules are known. In addition to the above-cited references, see Szulc et al., "A facile regioselective synthesis of sphingosine 1-phosphate and ceramide 1-phosphate, Tetrahedron Letter 41:7821-7824, 2000; Igarashi et al., "Sphingosine-1-Phosphate Essentially Free of L-Threo Isomer, U.S. Pat. No. 5,663,404, issued Sep. 2, 1997; Boumendjel et al., "Method For Preparation of Sphingoid Bases", U.S. Pat. No. 5,430,160, issued Jul. 4, 1995; Ito et al., "Process for the Preparation of Sphingolipids and Sphingolipid Derivatives", PCT/JP97/02483, published as WO98/03529 on Jan. 29, 1998; and Igarashi et al., "Method of Preparing N,N,N,-trimethylsphingosine", U.S. Pat. No. 5,248,824 dated Sep. 28, 1993.

In a preferred embodiment, sphingolipids having a desired activity are identified by high throughput screening (HTS) of combinatorial libraries of sphingolipid-related compounds. Combinatorial sphingolipid libraries are prepared according to methods known in the art, or may be purchased commercially. One type of combinatorial sphingolipid library that may be used is the BIOMOL Bioactive Lipid Library (Affiniti Research Products Ltd., Mamhead, U.K.).

High Throughput Screening (HTS) Assays

HTS typically uses automated assays to search through large numbers of compounds for a desired activity. Typically HTS assays are used to find new drugs by screening for chemicals that act on a particular enzyme or molecule. For example, if a chemical inactivates an enzyme it might prove to be effective in preventing a process in a cell which causes a disease. High throughput methods enable researchers to try out thousands of different chemicals against each target very quickly using robotic handling systems and automated analysis of results.

As used herein, "high throughput screening" or "HTS" refers to the rapid in vitro screening of large numbers of compounds (libraries); generally tens to hundreds of thousands of compounds, using robotic screening assays. Ultra high-throughput Screening (uHTS) generally refers to the high-throughput screening accelerated to greater than 100,000 tests per day.

To achieve high-throughput screening, it is best to house samples on a multicontainer carrier or platform. A multicontainer carrier facilitates measuring reactions of a plurality of candidate compounds simultaneously. Multi-well microplates may be used as the carrier. Such multi-well microplates, and methods for their use in numerous assays, are both known in the art and commercially available.

Screening assays may include controls for purposes of calibration and confirmation of proper manipulation of the components of the assay. Blank wells that contain all of the reactants but no member of the chemical library are usually included. As another example, a known inhibitor (or activator) of an enzyme for which modulators are sought, can be incubated with one sample of the assay, and the resulting decrease (or increase) in the enzyme activity determined according to the methods herein. It will be appreciated that modulators can also be combined with the enzyme activators or inhibitors to find modulators which inhibit the enzyme activation or repression that is otherwise caused by the presence of the known the enzyme modulator. Similarly, when ligands to a sphingolipid target are sought, known ligands of the target can be present in control/calibration assay wells.

Measuring Enzymatic and Binding Reactions During Screening Assays

Techniques for measuring the progression of enzymatic and binding reactions in multicontainer carriers are known in the art and include, but are not limited to, the following.

Spectrophotometric and spectrofluorometric assays are well known in the art. Examples of such assays include the use of calorimetric assays for the detection of peroxides, as disclosed in Example 1(b) and Gordon, A. J. and Ford, R. A., The Chemist's Companion: A Handbook Of Practical Data, Techniques, And References, John Wiley and Sons, N.Y., 1972, Page 437.

Fluorescence spectrometry may be used to monitor the generation of reaction products. Fluorescence methodology is generally more sensitive than the absorption methodology. The use of fluorescent probes is well known to those skilled in the art. For reviews, see Bashford et al., Spectrophotometry and Spectrofluorometry: A Practical Approach, pp. 91-114, IRL Press Ltd. (1987); and Bell, Spectroscopy In Biochemistry, Vol. 1, pp. 155-194, CRC Press (1981).

In spectrofluorometric methods, enzymes are exposed to substrates that change their intrinsic fluorescence when processed by the target enzyme. Typically, the substrate is non-fluorescent and converted to a fluorophore through one or more reactions. As a non-limiting example, SMase activity can be detected using the Amplex® Red reagent (Molecular Probes, Eugene, Oreg.). In order to measure sphingomyelinase activity using Amplex Red, the following reactions occur. First, SMase hydrolyzes sphingomyelin to yield ceramide and phosphorylcholine. Second, alkaline phosphatase hydrolyzes phosphorylcholine to yield choline. Third, choline is oxidized by choline oxidase to betaine. Finally, $H_2O_2$, in the presence of horseradish peroxidase, reacts with Amplex Red to produce the fluorescent product, Resorufin, and the signal therefrom is detected using spectrofluorometry.

Fluorescence polarization (FP) is based on a decrease in the speed of molecular rotation of a fluorophore that occurs upon binding to a larger molecule, such as a receptor protein, allowing for polarized fluorescent emission by the bound ligand. FP is empirically determined by measuring the vertical and horizontal components of fluorophore emission following excitation with plane polarized light. Polarized emission is increased when the molecular rotation of a fluorophore is reduced. A fluorophore produces a larger polarized signal when it is bound to a larger molecule (i.e. a receptor), slowing molecular rotation of the fluorophore. The magnitude of the polarized signal relates quantitatively to the extent of fluorescent ligand binding. Accordingly, polarization of the "bound" signal depends on maintenance of high affinity binding.

FP is a homogeneous technology and reactions are very rapid, taking seconds to minutes to reach equilibrium. The reagents are stable, and large batches may be prepared, resulting in high reproducibility. Because of these properties, FP has proven to be highly automatable, often performed with a single incubation with a single, premixed, tracer-receptor reagent. For a review, see Owicki et al., Application of Fluorescence Polarization Assays in High-Throughput Screening, Genetic Engineering News, 17:27, 1997.

FP is particularly desirable since its readout is independent of the emission intensity (Checovich, W. J., et al., Nature 375:254-256, 1995; Dandliker, W. B., et al., Methods in Enzymology 74:3-28, 1981) and is thus insensitive to the presence of colored compounds that quench fluorescence emission. FP and FRET (see below) are well-suited for identifying compounds that block interactions between sphingolipid receptors and their ligands. See, for example, Parker et al., Development of high throughput screening assays using fluorescence polarization: nuclear receptor-ligand-binding and kinase/phosphatase assays, J Biomol Screen 5:77-88, 2000.

Fluorophores derived from sphingolipids that may be used in FP assays are commercially available. For example, Molecular Probes (Eugene, Oreg.) currently sells sphingomyelin and one ceramide fluorophores. These are, respectively, N-(4,4-difluoro-5,7-dimethyl-4-bora-3a,4a-diaza-s-indacene-3-pentanoyl)sphingosyl phosphocholine (BODIPY® FL C5-sphingomyelin); N-(4,4-difluoro-5,7-dimethyl-4-bora-3a,4a-diaza-s-indacene-3-dodecanoyl)sphingosyl phosphocholine (BODIPY® FL C12-sphingomyelin); and N-(4,4-difluoro-5,7-dimethyl-4-bora-3a,4a-diaza-s-indacene-3-pentanoyl)sphingosine (BODIPY® FL C5-ceramide). U.S. Pat. No. 4,150,949, (Immunoassay for gentamicin), discloses fluorescein-labelled gentamicins, including fluoresceinthiocarbanyl gentamicin. Additional fluorophores may be prepared using methods well known to the skilled artisan.

Exemplary normal-and-polarized fluorescence readers include the POLARION fluorescence polarization system (Tecan AG, Hombrechtikon, Switzerland). General multiwell plate readers for other assays are available, such as the VERSAMAX reader and the SPECTRAMAX multiwell plate spectrophotometer (both from Molecular Devices).

Fluorescence resonance energy transfer (FRET) is another useful assay for detecting interaction and has been described previously. See, e.g., Heim et al., Curr. Biol. 6:178-182, 1996; Mitra et al., Gene 173:13-17 1996; and Selvin et al., Meth. Enzymol. 246:300-345, 1995. FRET detects the transfer of energy between two fluorescent substances in close proximity, having known excitation and emission wavelengths. As an example, a protein can be expressed as a fusion protein with green fluorescent protein (GFP). When two fluorescent proteins are in proximity, such as when a protein specifically interacts with a target molecule, the resonance energy can be transferred from one excited molecule to the other. As a result, the emission spectrum of the sample shifts, which can be measured by a fluorometer, such as a fMAX multiwell fluorometer (Molecular Devices, Sunnyvale Calif.).

Scintillation proximity assay (SPA) is a particularly useful assay for detecting an interaction with the target molecule. SPA is widely used in the pharmaceutical industry and has been described (Hanselman et al., J. Lipid Res. 38:2365-2373 (1997); Kahl et al., Anal. Biochem. 243:282-283 (1996); Undenfriend et al., Anal. Biochem. 161:494-500 (1987)). See also U.S. Pat. Nos. 4,626,513 and 4,568,649, and European Patent No. 0,154,734. One commercially available system uses FLASHPLATE scintillant-coated plates (NEN Life Science Products, Boston, Mass.).

The target molecule can be bound to the scintillator plates by a variety of well known means. Scintillant plates are available that are derivatized to bind to fusion proteins such as GST, His6 or Flag fusion proteins. Where the target molecule is a protein complex or a multimer, one protein or subunit can be attached to the plate first, then the other components of the complex added later under binding conditions, resulting in a bound complex.

In a typical SPA assay, the gene products in the expression pool will have been radiolabeled and added to the wells, and allowed to interact with the solid phase, which is the immobilized target molecule and scintillant coating in the wells. The assay can be measured immediately or allowed to reach equilibrium. Either way, when a radiolabel becomes sufficiently close to the scintillant coating, it produces a signal detectable by a device such as a TOPCOUNT NXT microplate scintillation counter (Packard BioScience Co., Meriden Conn.). If a radiolabeled expression product binds to the target molecule, the radiolabel remains in proximity to the scintillant long enough to produce a detectable signal.

In contrast, the labeled proteins that do not bind to the target molecule, or bind only briefly, will not remain near the scintillant long enough to produce a signal above background. Any time spent near the scintillant caused by random Brownian motion will also not result in a significant amount of signal. Likewise, residual unincorporated radiolabel used during the expression step may be present, but will not generate significant signal because it will be in solution rather than interacting with the target molecule. These non-binding interactions will therefore cause a certain level of background signal that can be mathematically removed. If too many signals are obtained, salt or other modifiers can be added directly to the assay plates until the desired specificity is obtained (Nichols et al., Anal. Biochem. 257:112-119, 1998).

Assays for Enzymes Involved in Sphingolipid Metabolism

SMase: A variety of methods are available to measure SMase activity. It is possible to assay the SMase activity in vivo through labeling the cells with a radioactive substrate for SMase and then determining the level of radiolabel in the enzymatic products. Liu, B., and Y. A. Hannun. "Sphingomyelinase Assay Using Radiolabeled Substrate." Sphingolipid Metabolism and Cell Signaling, Pt a., 164-67. Methods in Enzymology, vol. 311, 2000. HTS assays of SMase activity are described by Lin et al., "Sphingomyelinase Assay Using Radiolabeled Substrate", p. 164, Liu et al., Barbone et al., "Robotic Assay of Sphingomyelinase for High-Throughput Screening", p. 168, and Hessler et al., "A High Throughput Sphingomyelinase Assay", p. 176 In: Sphingolipid Metabolism and Cell Signaling, Hannun, Yusaf A. (editor); Merrill, Alfred H. (editor), Academic Press (1999). The activity of SMase can be also determined in vitro either using radiolabelled SM, or a chromogenic analog of SM or colored and fluorescent derivatives of natural SM. Torley et al., (A turbidometric assay for phospholipase C and sphingomyelinase, Anal Biochem 222:461-464, 1994) describe a turbidometric assay for SMase suitable for high-volume screening using unmodified substrates.

SPH Kinase: Assays for SPH kinase are described by Olivera et al., "Assaying Sphingosine Kinase Activity", Methods in Enzymology, 311:215-223, 1999; and Caligan et al., "A High-Performance Liquid Chromatographic Method to Measure Sphingosine 1-Phosphate and Related Compounds from Sphingosine Kinase Assays and Other Biological Samples", Analytical Biochemistry, 281:36-44, 2000.

CER Kinase: Assays for CER kinase are disclosed by Bajjalieh et al., "Ceramide Kinase", Methods in Enzymology, 311:207-215, 1999.

Ceramidase: Assays for Ceramidase are disclosed by Zhang et al., "Human Acid Ceramidase Gene Novel Mutations in Farber Disease", Molecular Genetics and Metabolism, 70:301-309, 2000.

CER Synthase: Assays for CER synthase are disclosed by Bose et al., "Measurement of Ceramide Synthase Activity", Methods in Enzymology, 322:378-382, 2000.

Glucosylceramide Synthase: Assays for glucosylceramide synthase are disclosed by Shayman et al., "Glucosylceramide Synthase: Assay and Properties", Methods in Enzymology, 311:42-49, 1999.

Assays for Sphingolipids

S-1-P assays are disclosed by Ruwisch et al., "An improved high-performance liquid chromatographic method for the determination of sphingosine-1-phosphate in complex biological materials", Naunyn-Schmiedeberg's Arch Pharmacol, 363:358-363, 2001; Edsall et al., "Enzymatic Measurement of Sphingosine 1-Phosphate", Analytical Biochemistry, 272:80-86, 1999; and Edsall et al., "Enzymatic Method for Measurement of Sphingosine 1-Phosphate", Methods in Enzymology, 312:9-16, 2000.

SPH assays are disclosed by Chmura et al. (Down-Regulation of Ceramide Production Abrogates Ionizing Radiation-Induced Cytochrome c Release and Apoptosis, Molecular Pharmacology, 57:792-796, 2001); U.S. Pat. No. 5,677,189, and Shephard et al. (Liquid chromatographic determination of the sphinganine/sphingosine ratio in serum, Journal of Chromatography B, 710:291-222, 1998).

Pharmaceutical Compositions

Another aspect of the invention is drawn to compositions, including but not limited to pharmaceutical and/or biological compositions. According to the invention, a "composition" refers to a mixture comprising at least one carrier, preferably a physiologically acceptable carrier, and one or more therapeutic agents according to the invention. The term "carrier" defines a chemical compound that does not inhibit or prevent the incorporation of therapeutic agents into cells or tissues. A carrier typically is an inert substance that allows an active ingredient to be formulated or compounded into a suitable dosage form (e.g., a pill, a capsule, a gel, a film, a tablet, a microparticle (e.g., a microsphere), a solution etc.). A "physiologically acceptable carrier" is a carrier suitable for use under physiological conditions that does not abrogate (reduce, inhibit, or prevent) the biological activity and properties of the compound. For example, dimethyl sulfoxide (DMSO) is a carrier as it facilitates the uptake of many organic compounds into the cells or tissues of an organism. Preferably, the carrier is a physiologically acceptable carrier, preferably a pharmaceutically or veterinarily acceptable carrier, in which the therapeutic agent is disposed. A "pharmaceutical composition" refers to a composition wherein the carrier is a pharmaceutically acceptable carrier, while a "veterinary composition" is one wherein the carrier is a veterinarily acceptable carrier. The term "pharmaceutically acceptable carrier" or "veterinarily acceptable carrier" includes any medium or material that is not biologically or otherwise undesirable, i.e., the carrier may be administered to an organism along with a therapeutic agent, composition or compound without causing any undesirable biological effects or interacting in a deleterious manner with the complex or any of its components or the organism. Examples of pharmaceutically acceptable reagents are provided in The United States Pharmacopeia, The National Formulary, United States Pharmacopeial Convention, Inc., Rockville, Md. 1990, hereby incorporated by reference herein into the present application. The terms "therapeutically effective amount" or "pharmaceutically effective amount" mean an amount sufficient to induce or effectuate a measurable response in the target cell, tissue, or organism. What constitutes a therapeutically effective amount will depend on a variety of factors which the knowledgeable practitioner will take into account in arriving at the desired dosage regimen.

The compositions of the invention can further comprise other chemical components, such as diluents and excipients. A "diluent" is a chemical compound diluted in a solvent, preferably an aqueous solvent, that facilitates dissolution of the therapeutic agent in the solvent, and it may also serve to stabilize the biologically active form of the therapeutic agent or one or more of its components. Salts dissolved in buffered solutions are utilized as diluents in the art. For example, preferred diluents are buffered solutions containing one or more different salts. A preferred buffered solution is phosphate buffered saline (particularly in conjunction with compositions intended for pharmaceutical administration), as it mimics the salt conditions of human blood. Since buffer salts can control the pH of a solution at low concentrations, a buffered diluent rarely modifies the biological activity of a therapeutic agent.

An "excipient" is any more or less inert substance that can be added to a composition in order to confer a suitable property, for example, a suitable consistency or to form a drug. Suitable excipients and carriers include, in particular, fillers such as sugars, including lactose, sucrose, mannitol, or sorbitol cellulose preparations such as, for example, maize starch, wheat starch, rice starch, agar, pectin, xanthan gum, guar gum, locust bean gum, hyaluronic acid, casein potato starch, gelatin, gum tragacanth, methyl cellulose, hydroxypropylmethyl-cellulose, polyacrylate, sodium carboxymethylcellulose, and/or polyvinylpyrrolidone (PVP). If desired, disintegrating agents can also be included, such as cross-linked polyvinyl pyrrolidone, agar, or alginic acid or a salt thereof such as sodium alginate. Other suitable excipients and carriers include hydrogels, gellable hydrocolloids, and chitosan. Chitosan microspheres and microcapsules can be used as carriers. See WO 98/52547 (which describes microsphere formulations for targeting compounds to the stomach, the formulations comprising an inner core (optionally including a gelled hydrocolloid) containing one or more active ingredients, a membrane comprised of a water insoluble polymer (e.g., ethylcellulose) to control the release rate of the active ingredient(s), and an outer layer comprised of a bioadhesive cationic polymer, for example, a cationic polysaccharide, a cationic protein, and/or a synthetic cationic polymer; U.S. Pat. No. 4,895,724. Typically, chitosan is cross-linked using a suitable agent, for example, glutaraldehyde, glyoxal, epichlorohydrin, and succinaldehyde. Compositions employing chitosan as a carrier can be formulated into a variety of dosage forms, including pills, tablets, microparticles, and microspheres, including those providing for controlled release of the active ingredient(s). Other suitable bioadhesive cationic polymers include acidic gelatin, polygalactosamine, polyamino acids such as polylysine, polyhistidine, polyomithine, polyquaternary compounds, prolamine, polyimine, diethylaminoethyldextran (DEAE), DEAE-imine, DEAE-methacrylate, DEAE-acrylamide, DEAE-dextran, DEAE-cellulose, poly-p-aminostyrene, polyoxethane, copolymethacrylates, polyamidoamines, cationic starches, polyvinylpyridine, and polythiodiethylaminomethylethylene.

The compositions of the invention can be formulated in any suitable manner. Therapeutic agents may be uniformly (homogeneously) or non-uniformly (heterogeneously) dispersed in the carrier. Suitable formulations include dry and liquid formulations. Dry formulations include freeze dried and lyophilized powders, which are particularly well suited for aerosol delivery to the sinuses or lung, or for long term storage followed by reconstitution in a suitable diluent prior to administration. Other preferred dry formulations include those wherein a composition according to the invention is compressed into tablet or pill form suitable for oral administration or compounded into a sustained release formulation. When the composition is intended for oral administration but the therapeutic agent is to be delivered to epithelium in the intestines, it is preferred that the formulation be encapsulated with an enteric coating to protect the formulation and prevent premature release of the therapeutic agents included therein. As those in the art will appreciate, the compositions of the invention can be placed into any suitable dosage form. Pills and tablets represent some of such dosage forms. The compositions can also be encapsulated into any suitable capsule or other coating material, for example, by compression, dipping, pan coating, spray drying, etc. Suitable capsules include those made from gelatin and starch. In turn, such capsules can be coated with one or more additional materials, for example, and enteric coating, if desired. Liquid formulations include aqueous formulations, gels, and emulsions.

In one embodiment, the pharmaceutical composition is formulated for rapid cardiac delivery. One type of pharmaceutical composition that is formulated for rapid cardiac delivery is an injectable pharmaceutical composition. Liquid pharmaceutical compositions which are sterile solutions or suspensions can be utilized by for example, intramuscular, intrathecal, epidural, intraperitoneal or subcutaneous injection. Sterile solutions can also be administered intravenously. The active ingredient may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

Some preferred embodiments concern compositions that comprise a bioadhesive, preferably a mucoadhesive, coating. A "bioadhesive coating" is a coating that allows a substance (e.g., a composition or therapeutic agent according to the invention) to adhere to a biological surface or substance better than occurs absent the coating. A "mucoadhesive coating" is a preferred bioadhesive coating that allows a substance, for example, a composition according to the invention, to adhere better to mucosa occurs absent the coating. For example, micronized particles (e.g., particles having a mean diameter of about 0.01, 0.1, 0.2, 0.3, 0.4, 0.5, 1, 5, 10, 25, 50, or 100 um) can be coated with a mucoadhesive. In instances wherein the therapeutic agent is a soluble molecule, including but not limited to soluble receptor fragments, antibodies and antibody derivatives or other soluble polypeptides, preferred diameters include but are not limited to about 0.1, 0.3, 0.5, 0.6, 0.7, 0.8, 0.9, and 1.0 um. In instances where the therapeutic agent is a soluble molecule, including but nor limited to soluble receptor fragments and derivatives, antibodies and antibody derivatives and other soluble polypeptides, preferred diameters are about 0.1, 0.3, 0.5, 0.6, 0.7, 0.8, 0.9 and 1.0 um. The coated particles can then be assembled into a dosage form suitable for delivery to an organism. Preferably, and depending upon the location where the cell surface transport moiety to be targeted is expressed, the dosage form is then coated with another coating to protect the formulation until it reaches the desired location, where the mucoadhesive enables the formulation to be retained while the therapeutic agents interact with the target cell surface transport moiety.

Those skilled in the art will appreciate that when the compositions of the present invention are administered as agents to achieve a particular desired biological result, which may include a therapeutic or protective effect(s) (including vaccination), it may be necessary to combine the therapeutic agents of the invention with a suitable pharmaceutical carrier. The choice of pharmaceutical carrier and the preparation of the therapeutic agent as a therapeutic or protective agent will depend on the intended use and mode of administration. Suitable formulations and methods of administration of therapeutic agents include those for oral, pulmonary, nasal, buccal, occular, dermal, rectal, or vaginal delivery.

Depending on the mode of delivery employed, the context-dependent functional entity can be delivered in a variety of pharmaceutically acceptable forms. For example, the context-dependent functional entity can be delivered in the form of a solid, solution, emulsion, dispersion, micelle, liposome, and the like, incorporated into a pill, capsule, tablet, suppository, aerosol, droplet, or spray. Pills, tablets, suppositories, aerosols, powders, droplets, and sprays may have complex, multilayer structures and have a large range of sizes. Aerosols, powders, droplets, and sprays may range from small (1 micron) to large (200 micron) in size.

Pharmaceutical compositions of the present invention can be used in the form of a solid, a solution, an emulsion, a dispersion, a micelle, a liposome, and the like, wherein the resulting composition contains one or more of the compounds of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Examples of a stabilizing dry agent includes triulose, preferably at concentrations of 0.1% or greater (See, e.g., U.S. Pat. No. 5,314,695).

Pharmaceutical compositions that preferentially target cardiac tissues are generally preferred. As a non-limiting example, U.S. Pat. No. 5,876,747 to Stracher et al. claims liposomes that preferentially travel to cardiac and skeletal muscle.

Medical Devices and Kits

Medical devices that incorporate the therapeutic agents of the invention may be prepared and used. Such devices and kits may be designed for use by trained medical personnel in, e.g., hospitals, ambulances, and the like. Additionally or alternatively, such devices and kits may be designed to be used by untrained individuals, including a patient in need of treatment, in situations where trained medical personnel are not available. Non-limiting examples of such devices and kits are disclosed in U.S. Pat. No. 4,658,830 to Sarnoff. Such devices and kits may further include other (supplementary) devices and formulations useful for treating cardiac disorders. A non-limiting example of one such supplementary device is a portable defibrillator and similar devices, such as is disclosed in U.S. Pat. No. RE 30,750 to Diack et al. A non-limiting example of a supplementary formulation is one that includes compounds useful for treating conditions associated with cardiac disorders, such as those that are disclosed in U.S. Pat. No. 6,130,235 to Mavunkel et al.

Medical devices that incorporate sphingolipid-binding ligands, such as antibodies, according to the invention include those that are commonly referred to as "dialysis machines" (see, e.g., U.S. Pat. No. 6,080,321). In this type of sphingolipid-based cardiac medical device, sphingolipid ligands are immobilized onto a surface in the device. A patient's blood is pumped into the device in such a way as to bring blood into contact with the sphingolipid ligands. Undesirable, toxic and/or cardiotoxic sphingolipids and/or their metabolic precursors in the blood bind to the immobilized sphingolipid ligands, thus removing undesirable, toxic and/or cardiotoxic sphingolipids and/or their less toxic metabolic precursors from the blood. The blood, which is returned to the patient after passing through the device, leaves the device while the targeted sphingolipid remains bound to, and thus retained by, the immobilized sphingolipid ligands. The patient's blood re-enters the patient's body relatively or completely depleted of the targeted sphingolipid. The passage of a patient's blood through the device is repeated as many times as is needed in order to achieve the desired effect of lowering the concentration of undesirable, toxic and/or cardiotoxic sphingolipids and their metabolic precursors.

An in-dwelling catheter would be inserted to the area at risk in the heart. The catheter would have a smaller inner catheter which would subsequently inserted. The smaller catheter would be coated with an antibody or other sphingolipid binding ligands which would act as a sink to remove the sphingolipids in the focused area. This leads to a localized depletion or complete removal of undesirable sphingolipids.

The invention provides for diagnostic and therapeutic kits related to sphingolipid-based therapy. In one embodiment, the invention relates to kits for determining the diagnosis or prognosis of a patient. These kits preferably comprise devices and reagents for measuring one or more marker levels in a test sample from a patient, and instructions for performing the assay. Optionally, the kits may contain one or more means for converting marker level(s) to a prognosis. Such kits preferably contain sufficient reagents to perform one or more such determinations.

More specifically, a diagnostic kit of the invention comprises any of the following reagents and/or components in any combination.

1. A detectable or detectably labeled first reagent that binds a sphingolipid or sphingolipid metabolite of interest. The sphingolipid-binding reagent can, but need not, be an antibody or an antibody derivative comprising a detectable moiety. The sphingolipid-binding reagent is stored in an openable container in the kit, or is bound to a surface of a substrate such that it is accessible to other reagents. Examples of the latter include test strips.

2. If the first reagent in neither detectable nor detectably labeled, the kit may comprise a detectable or detectably labeled second reagent that binds to the first reagent (e.g., a secondary antibody) or which produces a detectable signal when in close proximity to the first reagent (e.g., as results from fluorescent resonance energy transfer FRET). In either case, the signal produced from the second reagent correlates with the amount of sphingolipid in the sample.

3. One or more positive control reagents. Typically, these reagents comprise a compound that is known to produce a signal in the assay. In one embodiment, the positive control reagents are standards, i.e., comprise a known amount of a detectable or detectably labeled compound, the signal from which may be compared to the signal from a test sample. In addition to serving as positive control reagents, they may be used to develop calibration curves that relate the amount of signal to the known concentration of a detectable or detectably labeled compound. The signal from a test sample is compared to the calibration curve in order to determine what concentration of the detectable or detectably labeled compound corresponds to the signal from the test sample. In this embodiment, the kit provides quantitative measurements of the amount of a sphingolipid in a test sample.

4. One or more negative control reagents. Typically, these control reagents may comprise buffer or another solution that does not contain any of the detectable or detectably labeled first or second reagents and should thus not produce any detectable signal. Any signal that is detected reflects the background level of "noise" in the assay. Another type of negative control reagent contains most of the components necessary for the signal of the assay to be produced, but lacks at least one such component and therefor should not produce a signal. Yet another type of negative control reagent contains all of the components necessary for the signal of the assay to be produced, but also contains an inhibitor of the process that produced the signal.

5. One or more auxiliary reagents for use in the diagnostic assays of the kit, e.g., buffers, alcohols, acid solutions, etc. These reagents are generally available in medical facilities and thus are optional components of the kit. However, these reagents preferably are included in the kit to ensure that reagents of sufficient purity and sterility are used, since the resulting protein conjugates are to be administered to mammals, including humans, for medical purposes, and to provide kits that can be used in situations where medical facilities are not readily available, e.g., when hiking in places located far from medical facilities, or in situations where the presence of these auxiliary reagents allows for the immediate treatment of a patient outside of a medical facility as opposed to treatment that arrives at some later time:

6. Instructions to a person using a kit for its use. The instructions can be present on one or more of the kit components, the kit packaging and/or a kit package insert.

A therapeutic kit of the invention comprises any of the following reagents and/or components in any combination.

1. One or more therapeutic agents.

2. If the therapeutic agent(s) are not formulated for delivery via the alimentary canal, which includes but is not limited to sublingual delivery, a device capable of delivering the therapeutic agent through some other routes. One type of device for parenteral delivery is a syringe that is used to inject the therapeutic agent into the body of an animal in need of the therapeutic agent. Inhalation devices may also be used, including a device for delivering gentamicin to a patient via inhalation.

3. Separate containers, each of which comprises one or more reagents of the kit. In a preferred embodiment, the containers are vials contain sterile, lyophilized formulations of a therapeutic composition that are suitable for reconstitution.

4. Instructions to a person using a kit for its use. The instructions can be present on one or more of the kit components, the kit packaging and/or a kit package insert.

For a better understanding of the present invention, reference is made to the accompanying drawings and detailed description and its scope will be pointed out in the appended claims. All references cited herein are hereby incorporated by reference.

EXAMPLES

The following examples are non-limiting and are merely representative of various aspects and features of the present invention.

Example 1

Sphingosine Production in Rabbits Increases in Cardiac Ischemia

Tissue levels of sphingosine (SPH) in adult rabbit hearts under various conditions were determined as follows. Rabbits were subjected to retrograde coronary perfusion with hypoxic (low oxygen) conditions (i.e., 95% $CO_2$; 5% $O_2$) or normal Kreb's buffers (equilibrated with 95% $O_2$; 5% $CO_2$). The rabbits were sacrificed, and hearts were removed and quickly homogenized. Sphingolipids were extracted from homogenates using protocols essentially as described by Sabbadini et al., Biochem. Biophys. Res. Comm. 193:752-758, 1993. HPLC analysis of the extracted lipids revealed significant increases in tissue SPH levels for hearts perfused with $CO_2$ when compared to hearts exposed to control conditions (20-fold, $p<0.001$). These increases occurred after only 5 minutes of hypoxia.

Example 2

Sphingosine Production in Humans

Serum levels of SPH levels in human patients experiencing cardiac ischemia were examined as follows. Serum samples were taken from patients presenting themselves to the emergency department of the Naval Medical Center of San Diego using strict human subjects protocols. Sphingolipids in the blood samples were extracted and analyzed as described above. Patients with confirmed myocardial ischemia had significantly higher SPH levels than any of the control groups.

Serum SPH levels in six "well-conditioned athletes" were combined as one control group. These subjects were Navy special forces (Navy Seals) and Olympic athletes from the Olympic Training Center who were exercised to exhaustion on treadmills at 49° C. In the case of the Olympic athletes, individuals at rest were also evaluated. The well-conditioned athletic control group had serum SPH levels of 4.18±1.8 μmol/mL, ranging from the lower limit of detection (5 μmol/mL) to 16.4 μmol/mL.

An age-matched (47-79 yrs) control group consisted of fifteen subjects enrolled in the San Diego State University (SDSU) Adult Fitness Program who tested negative for exercise stress (treadmill) and no symptoms of acute coronary syndrome (e.g., chest pain). The age-matched control group had a mean serum level of SPH of 99.3±32.4 pmol/mL, ranging from the lower limit of detection to 369 pmol/mL.

A group of ischemic patients (n=19) were individuals who had myocardial ischemia, tested positive for exercise stress for exercise treadmill testing and/or were referred to the catherization lab for percutaneous coronary revascularization (angioplasty). The ischemic patients had a mean serum SPH level of 697±80.7 pmol/mL.

The ischemic patient subgroup with angina symptoms who underwent angioplasty had average pre-procedure serum SPH levels of 885±123 pmol/mL (ranging from 447 to 1122 pmol/mL). The patient serum SPH levels were significantly ($p<0.001$) higher than the SPH levels of the age-matched control group. When the control group of ischemic patients was examined, an average serum SPH level of 697±80.7 pmol/mL was obtained. This value is ~7-fold higher than the age-matched control group ($p<0.001$) and ~160-fold higher than well-conditioned athletes.

Example 3

Hypoxic Effects on the Sphingomyelin Signal Transduction Cascade

TNFα, acting via TNFα receptors, has been shown to utilize the sphingomyelin signal transduction cascade in cardiomyocytes (Oral et al., J. Biol. Chem. 272:4836-4842, 1997; Krown et al., J. Clin. Invest. 98:2854-2865, 1996). The following experiments were carried out in order to determine if this signaling system could also be activated by hypoxia, and if sphingolipids were produced before cell death as is the case for TNFα, as described in the Detailed Description of the Invention.

Adult rat cardiomyocytes were subjected to hypoxic conditions as described above and assayed for their ability to produce sphingolipid bases involved in the sphingomyelin signal transduction cascade.

Cardiomyocytes were cultured on plastic dishes that were placed in a humidified modular incubator chamber (ICN Biomedicals, Aurora, Ohio) pressurized to 0.04-0.05 psi by the particular gas mixture used in the treatment. Warm (37° C.) Tyrode's solution containing 0.2 mM BSA, ampicillin (50 mg/mL), kanamycin (100 mg/mL) and fungizone (20 μg/mL) was gassed in a 50 mL sterile conical for 15 minutes with 95% N2/5% CO2 prior to adding the solution to the cultured cells. The $pO_2$ was monitored by a Micro $pO_2$ System oxygen electrode (Lasar Research Labs, Los Angeles, Calif.) and found to be 4.0 PPM for the duration of the hypoxia condition. The chamber was maintained at 37° C. for the designated times. Control (normoxia) cells were treated the same except for the use of 95% $O_2$/5% $CO_2$ and incubated in a standard incubator. The $pO_2$ of the normoxia treatment was 7.3 PPM. The pH of control and experimental cell cultures was monitored with a micro pH electrode (Beetrode pH Electrodes, Sarasota, Fla.) and remained constant at pH=7.26+/−0.02 for normoxic cells and 7.15+/−0.03 for hypoxic cells throughout the experiment. Because the cells were incubated in Tyrode's lacking glucose, these experiments represent a model of hypoxia with metabolic inhibition. In selected experiments with neonatal rat cardiomyocytes, a third treatment following hypoxia was employed to simulate reperfusion. This treatment consisted of 5 hours of reoxygenation with 95% $O_2$/5% $CO_2$ in the incubation chamber. At the end of each incubation period, the cell-conditioned media was aspirated and saved for analysis. In selected experiments, the cells were scraped in the presence of 800 μl 1-butanol for the determination of both cellular and extracellular (cell-conditioned media) content of sphingolipids.

For the extraction of sphingolipids, 100-300 μl samples of tissue, serum or cell extracts were deproteinized by adding warmed butanol (70° C., 800 μl), vortexing and incubating at 70° C. while rocking. The mixture was then placed in a sonicating water bath for 10 minutes. Denatured protein and aqueous phase were separated from the butanol layer by centrifugation at 15,300×g. The upper butanol layer was transferred into a new extraction tube and saponified by the addition 0.5 M KOH (200 μl). After vortexing, samples were incubated at 70° C. while rocking for 1 hour with intermittent vortexing and sonicating. Nanopure water (400 μl) was added to each sample and returned to the incubator for 10 minutes. After sonicating for 1 minute, the layers were separated by centrifuging at 15,300×g for 3 minutes. The butanol layers was transferred to a new tube and dried down using a Savant (Holbrook, N.Y.) SpeedVac Plus. Dried samples were completely resuspended in methanol (375 μl) and agitated in a bath sonicator for 2 minutes. The extracts were then derivatized with O-phthalaldehyde (OPA) (Molecular Probes, Eugene, Oreg.). In brief, 50 mg of OPA were dissolved in ethanol (1.0 mL). Into 0.5 M boric acid (24.75 mL), 0.25 mL of the OPA in ethanol was added and mixed. Finally, 2-mercaptoethanol (13 μl) was added and mixed to make up the OPA derivatization solution. To each sample 10 mM disodium EDTA (50 μl) was added followed by 0.5 M boric acid (50 μl) and OPA solution (25 μl). Samples were incubated at room temperature protected from light for 20 minutes.

The HPLC analysis was performed using a Beckman (Fullerton, Calif.) System Gold 118 Solvent Module and 507e Autosampler. A Jasco (Easton, Md.) FP-920 Intelligent Fluorescence Detector was used with an excitation wavelength of 330 nm and emission wavelength of 455 nm. The derivatized samples (50 μl injection) were separated on a Beckman (Fullerton, Calif.) Ultrasphere ODS 4.6 mm×25 cm column with a 1.5 cm Perkin Elmer (Norwalk, Conn.) NewGuard RP-18 guard column. The solvent system was methanol, glacial acetic acid, 1 M tetrabutlyammonium dihydrogen phosphate, Nanopure water (82.9:1.5:0.9:14.7, v/v) run at 1.5 mL/minute. Chromatograms were analyzed using the Beckman System Gold Nouveau software. Results are shown in Table 1.

The only sphingolipid base that accumulated in cardiomyocytes in response to hypoxia was sphingosine (SPH). Levels of S-1-P and SPC were not increased by hypoxia. Cumulative data from several experiments demonstrated that hypoxia produces a 6.4-fold increase in SPH production. The increase in total cell SPH is not reflected in an increased intracellular content. Instead, the majority of the SPH produced in response to hypoxia is released from the cells into the cell-conditioned media. These data demonstrate a 18-fold increase in the extracellular SPH content of hypoxic cardiomyocytes.

The short time (5 hrs) of hypoxia employed did not result in appreciable necrotic or apoptotic cell death but was associated with significant TNFα release. Pretreatment with the TNFRII:Fc receptor fragment (Mohler et al., J. Immunol. 151:1548-1561, 1993), resulted in the significant ($p<0.001$) reduction (~3-fold) of the SPH release. TNFα receptor fragment pretreatment did not mitigate SPH-triggered apoptosis (SPH only, no TNF), indicating that SPH production is a step in the signal cascade that is "downstream" from TNFα binding to its receptors.

Example 4

Blood Sph is Converted to S-1-P

Studies with human blood obtained from normal subjects suggest that blood platelets are capable of converting SPH to S-1-P because of their rich source of sphingosine kinase (Yatomi et al., J. Biochem. 121:969-973, 1997; Yatomi et al., J. Biol. Chem. 272:5291-5297, 1997; Yatomi et al., Blood 86:193-202, 1995). In such experiments, commercially supplied SPH was added to blood serum which, in the absence of cellular components, was found to be unable to convert SPH to S-1-P. Without wishing to be bound by any particular theory, applicants believe that the ischemic heart is the major source of serum SPH and that cardiac-derived SPH could be converted to S-1-P by blood platelets (U.S. Pat. No. 6,210,976 B1, and published PCT patent application WO 98/57179).

Experiments were carried out to determine the fate of any SPH that might be released from cells or platelets into the extracellular compartment. Whole blood samples were incubated in vitro for up to 15 hours with 3H-SPH, followed by thin layer chromatography (TLC) to examine which, if any, of the known metabolic products of the sphingomyelin pathway were radiolabeled as a result of metabolism of radiolabeled SPH.

Figure 3:
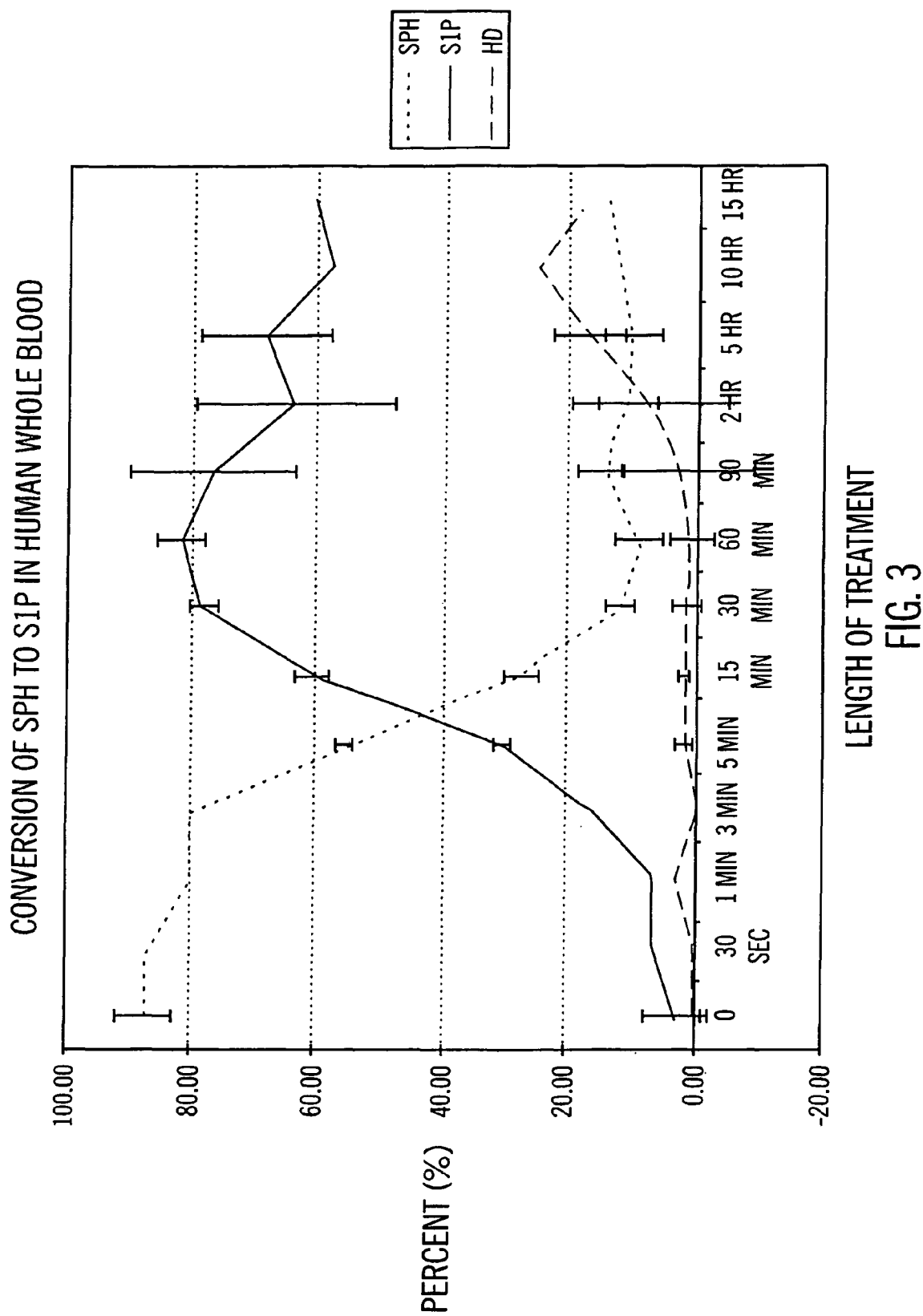
FIG. 3 shows the fate of 3H-labeled SPH in whole blood. After labeled sphingosine (SPH) is added to human whole blood, the concentration of SPH drops while the concentration of labeled sphingosine-1-phosphate (S1P) increases, suggesting that SPH is converted into S-1-P in blood; in contrast, little of the label is detected as labeled hexadecanal (HD). Symbols: solid line, S1P; line with long dashes, HD; line with short dashes, SPH.

The results (FIG. 3) indicate that, in whole blood, the radiolabeled SPH was not converted to ceramide or sphingomyelin, nor was it metabolized to dimethylsphingosine or dihydrosphingosine (see FIG. 2). The major metabolite of the pathway that was appreciably labeled was sphingosine-1-phosphate (S-1-P), presumably due to the action of the very active sphingosine kinase present in blood platelets (Yatomi et al., J. Biochem. 121:969-973, 1997; Yatomi et al., J. Biol. Chem. 272:5291-5297, 1997; Yatomi et al., Blood 86:193-202, 1995).

A substantial amount of the time-dependent conversion of 3H-SPH to 3H-S-1-P occurred within 20 minutes and represented a conversion of 86%.

TABLE 1

Sphingolipid Production in Cultured Cardiomyocytes During Normoxia, Hypoxia and Reoxygenation

| | Normoxia | Hypoxia 12 hours for neonates 7 hours for adults | Reoxygenation 5 hrs |
|---|---|---|---|
| Neonatal cardiomyocytes | | | |
| % Permeabilized cells | 1.7 + 1.3 | 3.15 + 1.3 | 7.45 + 2.5 |
| % Apoptotic cells | 1.17 + 0.37 | 4.58 + 0.74 | *23.5 + 2.7 |
| TNFα (pg/106 cells) | 561 + 13.4 | *979 + 26.7 | — |
| SPH (pmol/106 cells) | 5.8 + 0.43 | *77.6 + 6.24 | — |
| Adult cardiomyocytes | | | |
| % Permeabilized cells | 4.71 + 1.18 | 9.5 + 2.9 | — |
| % Apoptotic cells | 8.12 + 1.76 | *26.7 + 2.9 | — |
| TNFα (pg/106 cells) | 810 + 155 | *8660 + 3150 | — |
| SPH (pmol/106 cells) | 238 + 39 | *3860 + 547 | — |

*Significant at the p < 0.05 level or greater.

The data also demonstrate that S-1-P was very stable in whole blood for the 15-hour time course of the experiment. Only after several hours was it evident that a small but measurable amount of t-2-hexadecanal (a.k.a. palmitaldehyde) was produced as a consequence of the low level of S-1-P lyase present in platelets that can convert S-1-P to hexadecanal and ethanolamine phosphate (Yatomi et al., J. Biochem. 121:969-973, 1997; Yatomi et al., J. Biol. Chem. 272:5291-5297, 1997; Yatomi et al., Blood 86:193-202, 1995).

It is possible that blood platelets were the major reservoir of SPH-derived S-1-P (Yatomi et al., J. Biochem. 121:969-973, 1997). Another possible reservoir of S-1-P could be heart cells. Some studies have indicated that SPH is produced intracellularly by cultured cardiomyocytes, although these studies did not present evidence of S-1-P release/secretion (U.S. Pat. No. 6,210,976 B1 and Published PCT Application WO 98/57179).

Example 5

Blood S-1-P is Cardiotoxic AND Dependent on S-1-P Receptors

During ischemia-induced myocardial infarction, several important events occur as a consequence of the pathophysiology. In 74% of the cases of AMI, the sudden cardiac death is associated with significant thrombus (blood clot) in the coronary artery supplying blood to the infarcted region of the myocardium (Davies et al., N. Engl. J. Med. 310:1137-1140, 1984). "Infarcted" areas are those in which cells are dead or have sustained so much damage that they are fated to die. There is a profound negative inotropic effect (i.e., loss of contractility) on the myocardial cells induced by the ischemia itself. Intracellular calcium control is deregulated with diastolic (resting) calcium steadily rising in an uncontrolled fashion accompanied by a decrease in systolic (contractile) calcium leading to an eventual 'calcium overload'.

Without wishing to bound by any particular theory, applicants believe that these effects are a consequence of the initial SPH production by pre-AMI and post-AMI ischemic cardiac cells and the subsequent production of S-1-P by nearby platelets. It is also believed that S-1-P activates nearby platelets through calcium deregulation of the platelets and that platelet-derived S-1-P is released into the serum.

Exogenously applied S-1-P is capable of activating blood platelets (Yatomi et al., J. Biol. Chem. 272:5291-5297, 1997; Yatomi et al., Blood 86:193-202, 1995). It has been suggested that the increased serum S-1-P has two major actions, both of which are cardiotoxic. The first is to act on the platelets to promote the clotting response and further exacerbate the ischemia. Secondly, the platelet-derived S-1-P acts in a paracrine fashion on neighboring endothelial and myocardial cells to promote calcium deregulation and apoptosis. On the cardiomyocytes, the consequence is to promote calcium overload. The endothelial cell response is to promote vasoconstriction and further limit the blood supply through the coronary vasculature. It has demonstrated that S-1-P applied to cultured cardiomyocytes resulted in apoptosis and dramatic increases in diastolic calcium followed in minutes by decreases in systolic calcium and eventual calcium overload reminiscent of what happens to the ischemic myocardium. It has also demonstrated that both rat and human cardiac tissue express genes for the recently identified S-1-P receptors of the EDG (endothelial differentiation gene) family, and that these receptors mediate the calcium deregulation (Nakajima et al., Biophysical J. 78:319 A, 2000).

Extracellular S-1-P is the ligand for a novel class of G protein-coupled receptors (GPCRs). Such receptors were first described as an orphan GPCRs cloned from human umbilical vein endothelial cells (Hla et al., J. Biol. Chem. 265:9308-9313, 1990; Lynch et al., Trends Pharmacol. Sci. 20:473-475, 1999). Tissue expression of the EDG-1/3/5 genes in the murine system indicates that heart and lung have the highest overall expression of these three genes (Zhang et al., Gene 227:89-99, 1999). However, cardiac tissues are composed of diverse cell types, including endothelial cells, which have high levels of EDG-1 expression (Hla et al., J. Biol. Chem. 265:9308-9313, 1990). Although EDG-1/3/5 are expressed in C2C12 skeletal muscle myoblasts (Meacci et al., FEBS Letters 457:184-188, 1999), cardiomyocyte-specific expression of the EDG genes has not been elucidated. Recently a EDG-1 gene and its protein expression were determined in primary cultures of neonatal rat cardiomyocytes and in adult rat ventricular tissue (Nakajima et al., Biophysical J. 78:319 A, 2000). Cultured cardiomyocytes were used to evaluate the functional role of EDG receptors, including the ability of S-1-P to modulate intracellular calcium levels.

Importantly, the calcium deregulatory responses evoked by S-1-P in cultured cardiomyocytes are quite similar to the calcium deregulation seen in models of acute myocardial infarction (Lee et al., Circ. 78:1047-1059, 1988; Smith et al., Amer. Heart J. 103:716-723, 1982; Kihara et al., Circ. Res. 65:1029-1044, 1989). These characteristic responses include: increases in diastolic calcium (and calcium overload), decreases in systolic calcium (the negative inotropic state) and the production of abnormal oscillatory beating behavior (arrhythmias) and cessation of activity, all of which were seen in the cardiomyocytes when treated with S-1-P. Additionally, the average calcium level combining both diastolic and systolic responses is significantly increased by S-1-P treatment. Taken together, these data suggest that S-1-P, possibly acting via EDGRs, increases the influx of extracellular calcium which then causes the calcium overload.

It is well known that calcium deregulation is a prerequisite to apoptosis (Magnelli et al., Bioch. Biophys. Res. Comm. 204:84-90, 1994). Previously published data indicate that rat cardiomyocytes in culture undergo apoptotic cell death when exposed to sphingosine (Krown et al., J. Clin. Invest. 98:2854-2865, 1996). It is also suggested that the S-1-P present in putative high levels in cardiac circulation could act on cardiac cell S-1-P receptors to produce profound negative inotropic effects and cell death by apoptosis.

Thus, it is likely that the pre-AMI ischemic myocardium produces the initial instruments of its own destruction, namely, various cytokines and, importantly, SPH. The secreted SPH, acting indirectly through platelet-derived S-1-P, promotes the activation of S-1-P receptors on platelets, endothelial cells and cardiomyocytes. Blood clotting, vasoconstriction and myocardial calcium overload are the consequences with myocardial infarction as the ultimate result. As the growing ischemia and the area of infarction challenges more cardiac tissue, additional SPH is released and a positive feedback loop results until substantial cell death occurs.

Although not wishing to be bound to any particular theory, it is possible that during low levels of ischemia and cardiac stress (e.g., hypertension), the cardiac cells produce cytokines and sphingolipids as extracellular signaling molecules that serve to precondition the heart to these stresses. Protection can come from preconditioning the heart itself via protection against calcium overload, cell death and arrythmias or by producing a hypernatating myocardial state to lower energy demands during ischemia.

Example 6

Use of Antibodies in Sphingolipid-Based Therapy

This Example describes how sphingolipid-based cardiovascular therapy can be realized by the use of antibodies and derivatives thereof (single-chain Fv's, CDR's, etc.) that specifically bind certain molecules as therapeutic agents. Such antibodies are directed to, by way of non-limiting example, antibodies to sphingolipids and receptors thereof.

Antibodies to Sphingolipid Receptors

One type of therapeutic antibody specifically sphingolipid receptors that carry out the cellular internalization of undesirable sphingolipids. In some cases, the delivery into the cell of an undesirable sphingolipid results in a sequence of events having an undesirable effect. Antibodies to such receptors prevent the entry of the undesirable sphingolipid into cells, thus avoiding the undesirable consequences of such entry. For example, the undesirable, toxic and/or cardiotoxic sphingolipid S-1-P has many actions that are dependent upon binding to sphingolipid receptors, including without limitation Edg receptors (Example 15). Antibodies to receptors that block the binding of a undesirable, toxic and/or cardiotoxic sphingolipid are developed and tested for their ability to inhibit the binding of S-1-P to its receptors, as well as for their ability to block post-binding events that lead to cardiotoxic effects. Antibodies to Edg receptors are known, and are in some instances commercially available. For example, antibodies to Edg-1, -7 and -8 are available from Oncogene Research Products; antibodies to Edg-2 are available from Calbiochem; antibodies to Edg-4 are available from Antibody Solutions (Palo Alto, Calif.); and antibodies to Edg-5 are available from Exalpha Biologicals, Inc. (Boston, Mass.).

Antibodies to Sphingolipids

One type of therapeutic antibody specifically binds undesirable sphingolipids. Such antibodies bind sphingolipids in order to achieve beneficial effects such as, e.g., (1) lowering the effective concentration of available (i.e., unbound) undesirable, toxic and/or cardiotoxic sphingolipids (and/or the concentration of their metabolic precursors) that would otherwise be free to exert their harmful effects on cells (including, by way of non-limiting example, removing undesirable, toxic and/or cardiotoxic sphingolipids and their metabolic precursors from blood via ex vivo treatments); (2) to inhibit the binding of an undesirable, toxic and/or cardiotoxic sphingolipid to a cellular receptor therefor, and/or to lower the concentration of a sphingolipid that is available for binding to such a receptor; and/or (3) preventing the metabolic conversion of a first sphingolipid into a second and more undesirable, toxic and/or cardiotoxic sphingolipid, and/or to lower the concentration of such a precursor that is available for enzymatic conversion into a undesirable, toxic and/or cardiotoxic sphingolipid.

Examples of such therapeutic effects include but are not limited to the use of (i) anti-S-1-P antibodies to lower the concentration of available S-1-P, thereby blocking or at least limiting S-1-P's cardiotoxic and thrombogenic effects, and/ or (ii) anti-SPH antibodies to prevent the metabolic conversion of SPH to the more undesirable, toxic and/or cardiotoxic sphingolipid S-1-P.

To produce mAb to phospholipids, acid-treated *Salmonella minnesota* are administered directly into a mouse spleen using protocols essentially according to the methods of Umeda et al. that have been used to make mAbs to phosphatidylserine (J. Immunol. 143:2273-2279, 1989; see also Reza et al., FEBS Lett. 339:229-233, 1994).

For production of anti-SPH antibodies, the acid-treated *S. Minnesota* are coated with SPH and injected into the mouse spleen prior to cell fusion to produce a hybridoma that secretes anti-SPH mAb. Similar methods are used to produce anti-S-1-P mAb and anti-SPC mAb.

Additionally or alternatively, fatty acid free BSA-sphingolipid conjugates are used as the immunogen in order to present unique epitopes to the animal. Appropriate steps are taken to ensure that the mAbs produced in this fashion are directed to sphingolipids of choice and not to oxidized lipid or protein-lipid adducts (Horkko et al., J. Clin. Invest. 98:815-825, 1996; Palinski et al., J. Clin. Invest. 98:800-814, 1996).

Antibodies to S-1-P

In order to develop antibodies to S-1-P, guinea pigs were immunized IP once a week for 4 weeks with 1 mg of KLH-derivatized sphingolipid. The protocols that were used are essentially those of Horkko et al. (J. Clin. Invest. 98:815-825, 1996) and Palinski et al. (J. Clin. Invest. 98:800-814, 1996).

In brief, the animals were given weekly injections over a period of several weeks. In the first week, 150 ug of immunogen in Complete Freund's adjuvant was injected. During the second, third, fourth, fifth and sixth weeks, 100 ug of immunogen in Incomplete Freund's adjuvant was injected into the guinea pigs. Serum samples collected from the immunized guinea pigs were shown to contain antibodies to S-1-P by use of an ELISA assay. The ELISA was carried out essentially according to the procedures described by Horkko et al., (J. Clin. Invest. 98:815-825, 1996) and Palinski et al. (J. Clin. Invest. 98:800-814, 1996). The serum samples had a titer of 140,000 Relative Luminescent Units/100 ms.

Example 7

Modulation of Sphingosine-1-Phosphate (S-1-P) Metabolism

The concentration of the undesirable, toxic and/or cardiotoxic sphingolipid S-1-P is lowered (i) by stimulating reactions that utilize S-1-P as a reactant (i.e., reactions that degrade S-1-P, e.g., Rxns. #1 and #2 in FIG. 2) and, additionally or alternatively, (ii) by inhibiting chemical reactions that yield S-1-P as a product (i.e., reactions that produce S-1-P, e.g. Rxn. #3 in FIG. 2). Such stimulation and/or inhibition is achieved by, for example, (1) increasing the amount of, and/or enhancing the activity of, enzymes that catalyze the catabolism (degradation) of S-1-P and, additionally or alternatively, (2) reducing the amount of, and/or or inhibiting or completely blocking the activity of, enzymes that catalyze the anabolism (production) of S-1-P.

In instances where the goal is to increase the concentration enzymes that degrade S-1-P, pharmaceutical formulations of such enzymes are administered to a patient. S-1-P-degrading enzymes are purified from a variety of mammals and other animals, or produced in vitro from cells using recombinant DNA techniques.

Inhibition of Production of S-1-P

The inhibition of enzymes that catalyze reactions that yield S-1-P (i.e., reactions that have S-1-P as a product) is expected to result in the reduction or complete inhibition of the production of S-1-P. Such enzymes include but are not limited to the following:

Sphingosine Kinase (SPH kinase) catalyzes the conversion of SPH to S-1-P (Rxn. #3 in FIG. 2; see also FIG. 1). A genetic sequence encoding human SPH-kinase has been described (Melendez et al., Gene 251:19-26, 2000). Three human homologs of SPH kinase (SKA, SKB and SKC) have been described (published PCT patent application WO 00/52173). Murine SPH kinase has also been described (Kohama et al., J. Biol. Chem. 273:23722-23728, 1998; and published (PCT patent application WO 99/61581). Published PCT patent application WO 99/61581 to Spiegel is stated to describe nucleic acids encoding a sphingosine kinase. Published PCT patent application WO 00/52173 to Munroe et al. is stated to describe nucleic acids encoding homologues of sphingosine kinase. Other SPH Kinases are described by Pitson et al., "Human sphingosine kinase: purification, molecular cloning and characterization of the native and recombinant enzymes", Biochem J. 350:429-441, 2000; and published PCT application WO 00/70028 to Pitson et al.; and Liu et al., "Molecular Cloning and Functional Characterization of a Novel Mammalian Sphingosine Kinase Type 2 Isoform", The Journal of Biological Chemistry, 275:19513-19520, 2000; Vadas et al., "Sphingosine Kinase and Uses Thereof", PCT/AU01/00539, published as WO 01/85953 on Nov. 15, 2001; Rastelli, "Novel Sphingosine Kinases", PCT/US01/04789, published as WO 01/60990 on Aug. 23, 2001; Allen et al., "Human Sphingosine Kinase Gene", PCT/EP00/09498, published as WO 01/31029 on May 3, 2001.

Inhibitors of SPH kinase include but are not limited to N,N-dimethylsphingosine (DMS) (Edsall et al., Biochem. 37:12892-12898, 1998); D-threo-dihydrosphingosine (Olivera et al., Nature 365:557-560, 1993); and Sphingoid bases (Jonghe et al., "Structure-Activity Relationship of Short-Chain Sphingoid Bases As Inhibitors of Sphingosine Kinase", Bioorganic & Medicinal Chemistry Letters 9:3175-3180, 1999)

Assays of SPH kinase useful for evaluating these and other known or potential SPH kinase inhibitors include those disclosed by Olivera et al., "Assaying Sphingosine Kinase Activity", Methods in Enzymology, 311:215-223, 1999; Caligan et al., "A High-Performance Liquid Chromatographic Method to Measure Sphingosine 1-Phosphate and Related Compounds from Sphingosine Kinase Assays and Other Biological Samples", Analytical Biochemistry, 281:36-44, 2000.

Pharmaceutical compositions of these and other inhibitors of SPH kinase, especially those that are formulated for rapid cardiac delivery, are used for this form of sphingolipid-based cardiovascular therapy.

Inhibition of SPH kinase may lead to an accumulation of its substrate, SPH, which is also an undesirable sphingolipid, albeit generally less harmful than S-1-P. In order to avoid or mitigate this effect should it occur, additional agents are concurrently administered to (i) stimulate an enzyme that has SPH as a substrate, with the proviso that the enzyme should not be one that has S-1-P as a product (such as, e.g., ceramide synthase; see below); and, additionally or alternatively, (ii) inhibit an enzyme that has SPH as a product.

Stimulation of Destruction of S-1-P

The stimulation of enzymes that catalyze reactions that degrade S-1-P (i.e., reactions that have S-1-P as a reactant) is expected to result in the stimulation of degradation of S-1-P molecules. Such enzymes include but are not limited to the following:

S-1-P Lyase catalyzes the conversion of S-1-P to ethanolamine-P and (a.k.a. t-2-hexadecanal) palmitaldehyde (Veldhoven et al., Adv. Lipid Res. 26:67-97, 1993; Van Veldhoven, "Sphingosine-1-phosphate Lyase" Methods in Enzymology, 311:244-254, 1999; Rxn. #1 in FIG. 2). Yeast (Lanterman et al., Biochem. J. 332:525-531, 1998), murine (Zhou et al., Biochem. Biophys. Res. Comm. 242:502-507, 1998) and human (published PCT patent applications WO 99/38983 and WO 99/16888) S-1-P lyase genes have been described. Published PCT patent application WO 99/16888 to Saba et al. is stated to describe S-1-P lyase DNA and protein sequences. U.S. Pat. No. 6,187,562, Published PCT patent application WO 99/38983 to Duckworth et al. is stated to describe a S-1-P lyase. See also Van Veldhoven et al., "Human sphingosine-1-phosphate lyase: cDNA cloning, functional expression studies and mapping to chromosome 10q221", Biochimica et Biophysica Acta 1487:128-134, 20000); and Mandala et al., "Molecular cloning and characterization of a lipid phosphohydrolase that degrades sphingosine-1-phosphate and induces cell death", PNAS, 97:7859-7864, 2000.

Pharmaceutical compositions of agents that are stimulators of S-1-P lyase, especially those that are formulated for rapid cardiac delivery, are used for this form of sphingolipid-based cardiovascular therapy.

S-1-P Phosphatase (a.k.a. SPP phosphohydrolase) is a mammalian enzyme that catalyzes the conversion of S-1-P to sphingosine (Rxn. #2 in FIG. 2) (Mandala et al., Proc. Nat.

Acad. Sci. 95:150-155, 1998; Mandala et al., Proc. Nat. Acad. Sci. 97:7859-7864, 2000; Mandala, "Sphingosine-1-Phosphate Phosphatases", Prostaglandins & other Lipid Mediators, 64:143-156, 2001; Brindley et al., "Analysis of Ceramide 1-phosphate and Sphingosine-1-phosphate Phosphatase Activities", Methods in Enzymology, 311:233-244, 1999). Two S-1-P phosphatases, LBP1 and LBP2, have been isolated from yeast (Mandala et al., J. Biol. Chem. 272:32709-32714, 1997). Mandala et al., "Mammalian Sphingosine-1-Phosphate Phosphatase", PCT/UWO1/03879, published as WO01/57057 on Aug. 9, 2001.

Pharmaceutical compositions of agents that are stimulators of S-1-P phosphatase, especially those that are formulated for rapid cardiac delivery, are used for this form of sphingolipid-based cardiovascular therapy.

Example 8

Modulation of Sphingosine (SPH) Metabolism

The concentration of the undesirable, toxic and/or cardiotoxic sphingolipid SPH is lowered (i) by stimulating reactions that utilize SPH as a reactant (i.e., reactions that degrade SPH without producing S-1-P) and, additionally or alternatively, (ii) by inhibiting chemical reactions that yield SPH as a product (i.e., reactions that produce SPH, e.g., Rxn. #5 in FIG. 2). Such stimulation and/or inhibition is achieved by, for example, (1) increasing the amount of, and/or enhancing the activity of, enzymes that catalyze the catabolism (degradation) of SPH and, additionally or alternatively, (2) reducing the amount of, and/or or inhibiting or completely blocking the activity of, enzymes that catalyze the anabolism (production) of SPH. Because SPH is converted into S-1-P by enzymes such as SPH kinase (Rxn. #3 in FIG. 2), lowering the concentration of the undesirable, toxic and/or cardiotoxic sphingolipid SPH is not only therapeutic in its own right but, if done without converting SPH to S-1-P, has the additional therapeutic benefit of lowering the production of the more undesirable, toxic and/or cardiotoxic sphingolipid S-1-P.

In instances where the goal is to increase the concentration of enzymes that degrade SPH, pharmaceutical formulations of such enzymes are administered to a patient. SPH-degrading enzymes, such as SPH Kinase and ceramide synthase (Rxns. #3 and 4, respectively, in FIG. 2) are purified from a variety of mammals, including humans, and other animals; or are produced in vitro using, e.g., recombinant DNA techniques.

Inhibition of Production of SPH

The inhibition of enzymes that catalyze reactions that yield SPH (i.e., reactions that have SPH as a product) is expected to result in the reduction or complete inhibition of the production of SPH. Such enzymes include but are not limited to the following:

Ceramidase (CDase) catalyzes the conversion of ceramide to SPH (Rxn. #5 in FIG. 2; see also FIG. 1). For a review, see Nikolova-Karakashian et al., "Ceramidases", Methods in Enzymology, 311:194-201, 1999. At least two types of ceramidases are known in the art, ceramidase I and ceramidase II, which differ in terms of pH optima (Sugita et al., Biochim. Biophys. Acta. 398:125-131, 1975; Yada et al., J. Biol. Chem. 270:12677-12684, 1995). Ceramidases are disclosed by Tani et al., "Purification and Characterization of a Neutral Ceramidase from Mouse Liver: A Single Protein Catalyzes the Reversible Reaction in Which Ceramide is Both Hydrolyzed and Synthesized", The Journal of Biological Chemistry 275: 3462-3468, 2000; Mao et al., "Cloning and Characterization of a *Saccharomyces cerevisiae* Alkaline Ceramidase with Specificity for Dihydroceramide", The Journal of Biological Chemistry 275:31369-31378, 2000; Zhang et al., "Human Acid Ceramidase Gene: Novel Mutations in Farber Disease", Molecular Genetics and Metabolism 70:301-309, 2000; Mao et al., "Cloning of an Alkaline Ceramidase from *Saccharomyces cerevisiae*: An Enzyme with Reverse (CoA-Independent) Ceramide Synthase Activity", The Journal of Biological Chemistry 275:6876-6884, 2000; Okino et al., "Molecular Cloning, Sequencing, and Expression of the Gene Encoding Alkaline Ceramidase from *Pseudomonas aeruginosa*: Cloning of A Ceramidase Homologue from *Mycobacterium Tuberculosis*", 274:36616-36622, 1999; Kita et al., "Reverse hydrolysis reaction of a recombinant alkaline ceramidade of *Pseudomonas aeruginosa*" Biochimica et Biophysica Acta 1485:111-120, 2000; Li et al., "The Human Acid Ceramidase Genes (ASAH): Structure, Chromosomal Location, Mutation Analysis, and Expression", Genomics, 62:223-231, 1999; Mao et al., "Cloning and Characterization of a Novel Human Alkaline Ceramidase: A Mammalian Enzyme That Hydrolyzes Phytoceramide", The Journal of Biological Chemistry, 276:26577-26588, 2001; Mitsutake et al., "Purification, Characterization, Molecular Cloning, and Subcellular Distribution of Neutral Ceramidase of Rat Kidney", The Journal of Biological Chemistry, 276:26249-26259, 2001; Ito et al., "Ceramidase Gene", PCT/JP00/01802, published as WO00/58448 on Oct. 5, 2000; Okino et al., "Molecular Cloning, Sequencing, and Expression of the Gene Encoding Alkaline Ceramidase from *Pseudomonas aeruginosa*", The Journal of Biological Chemistry, Vol. 274, Dec. 17, 1999, pp. 36616-36622; and Bawab et al., "Molecular Cloning and Characterization of a Human Mitochondrial Ceramidase", The Journal of Biological Chemistry, 275:21508-21513, 2000

Inhibitors of ceramidase include but are not limited to D-erythro-MAPP and L-erythro-MAPP (Bielawska et al., J. Biol. Chem. 271:12646-12654, 1996; Hannun et al., "Inhibitor of Ceramidase", PCT/US96/17769, published as WO97/44019 on Nov. 27, 1997); and N-oleoyl-ethanolamine (NOE; Sugita et al., 1975; Yada et al., J. Biol. Chem. 270:12677-12684, 1995; Meroni et al., "Effect of N-Acetylsphingosine (C2) and the Ceramidase Inhibitor (1S,2R)-D-erythro-2-(N-myristoylamino)-1-phenyl-1-propanol on the Regulation of Sertoli Cell Function", Journal of Andrology, 20:619-625, 1999). As CDase is inhibited by endogenous sphingolipids such as SPH and SM (Hise et al., J. Clin. Invest. 77:768-773, 1986); nontoxic synthetic sphingolipids that inhibit CDase are also used. See also Hannun et al., "Inhibitors of Ceramidase", U.S. Pat. No. 5,851,782, issued Dec. 22, 1998.

Methods for assaying ceramidase activity are disclosed by He et al.; "A Fluorescence-Based High-Performance Liquid Chromatography Assay to Determine Acid Ceramidase Activity", Analytical Biochemistry, 274:264-269, 1999. Pharmaceutical compositions of these and other inhibitors of CDase, especially those that are formulated for rapid cardiac delivery, are used for this form sphingolipid-based cardiovascular therapy.

S-1-P Phosphatase (a.k.a. SPP phosphohydrolase) catalyzes the conversion of S-1-P to sphingosine (Rxn. #2 in FIG. 2) and is described in more detailed in the preceding Example 8. Inhibition of S-1-P phosphatase has the beneficial result of lowering SPH production; however, inhibition of S-1-P phosphatase potentially includes the undesirable effect of inhibiting the degradation of S-1-P. It is thus useful to include one or more stimulators of an enzyme that degrades S-1-P (such as, e.g., S-1-P lyase; see above), in pharmaceutical compositions used for this form sphingolipid-based cardiovascular therapy.

Stimulation of Destruction of SPH

The stimulation of enzymes that catalyze reactions that degrade SPH (i.e., reactions that have SPH as a reactant, e.g., Rxns. #3 and #4 in FIG. 2) is expected to result in the stimulation of degradation of SPH molecules. In general, it is preferable that such reactions do not yield a undesirable, toxic and/or cardiotoxic sphingolipid, especially S-1-P, as a product (e.g., Rxn. #4 in FIG. 2, which is catalyzed by ceramide synthase). SPH kinase may be stimulated to enhance the degradation of SPH but the reaction it catalyzes produces the undesirable sphingolipid S-1-P; accordingly, stimulators of SPH kinase are preferably combined with stimulators of enzymes that degrade S-1-P, e.g., S-1-P lyase (Rxn. # 1 in FIG. 2).

Example 9

Modulation of Ceramide (CER) Metabolism

The concentration of CER is lowered (i) by stimulating reactions that utilize CER as a reactant (i.e., reactions that degrade CER), preferably those reactions that do not yield SPH as a product (e.g., Rxn. # 5 in FIG. 2); and, additionally or alternatively, (ii) by inhibiting chemical reactions that yield CER as a product (i.e., reactions that produce CER), preferably those reactions that do not use SPH as a reactant (e.g., Rxn. #4 in FIG. 2). Such stimulation and/or inhibition is achieved by, for example, (1) increasing the amount of, and/or enhancing the activity of, enzymes that catalyze the catabolism (degradation) of CER and, additionally or alternatively, (2) reducing the amount of, and/or or inhibiting or completely blocking the activity of, enzymes that catalyze the anabolism (production) of CER. However, such CER-producing enzymes do not use SPH as a substrate, as inhibition of such enzymes (e.g., ceramide synthase) is expected to result in an increase in the level of SPH. Because CER is directly converted into the more undesirable, toxic and/or cardiotoxic sphingolipid SPH by enzymes such as ceramidase (Rxn. # 5 in FIG. 2), lowering the concentration of CER has the therapeutic benefit of lowering the production of the more undesirable, toxic and/or cardiotoxic sphingolipid SPH; this effect which results in a lowered production of S-1-P by SPH kinase.

In instances where the goal is to increase the concentration of enzymes that degrade SPH, pharmaceutical formulations of such enzymes are administered to a patient. SPH-degrading enzymes are purified from a variety of mammals, including humans, and other animals; or produced in vitro from cells using recombinant DNA techniques.

Inhibition of Production of CER

The inhibition of enzymes that catalyze reactions that yield CER (i.e., reactions that have CER as a product) is expected to result in the reduction or complete inhibition of the production of CER. Such enzymes include but are not -limited to the following:

Ceramide Synthase (CER synthase), also known as sphingosine N-acyltransferase, catalyzes the acetylation of dihydrosphingosine (Rxn. #10 in FIG. 2) which leads to the production of ceramide.

Inhibitors of CER synthase include the fungal toxin Fumonisin B1 (Merrill et al., J. Lipid Res. 26:215-234A, 1993; Wang et al., Adv. Lipid Res. 26:215-234, 1993; Lee et al., Biochem. J. 334:457-461, 1998; Xu et al., J. Biol. Chem. 273:1652'-16526, 1998; Lochhead et al., Kidney Int. 54:373-381, 1998; Tsunoda et al., J. Biochem. Mol. Toxicol. 12:281-289, 1998); derivatives of fumonisin (Humpf et al., J. Biol. Chem. 273:19060-19064, 1998); *alternaria* toxins (Id. and Mandala et al., J. Antibiot. 48:349-356, 1995); viridiofungins (Merrill et al., J. Lipid Res. 26:215-234A, 1993; astralifungins (Mandala et al., J. Antibiot. 48:349-356, 1995; Furneisen et al., Biochim. Biophys. Acta. 1484:71-82, 2000); and D-erythro-N-myristoyl 2-amino-1-phenylpropanol (Hunnan, Science 274:1855-1859, 1996). Pharmaceutical compositions of these and other inhibitors of CER synthase, especially those that are formulated for rapid cardiac delivery, are used for this form sphingolipid-based cardiovascular therapy.

Ceramide-1-P Phosphatase (CER-1-P phosphatase) catalyzes the production of ceramide from ceramide 1-P (Rxn. #17 in FIG. 2). See Shinghal et al., "Ceramide I-Phosphate Phosphatase Activity in Brain", Journal of Neurochemistry, 61:2279-2285, 1993; Boudker et al., "Detection and Characterization of Ceramide-1-phosphate Phosphatase Activity in Rat Liver Plasma Membrane", The Journal of Biological Chemistry, 268:22150-22155, 1993.

Inhibitors of CER-1-P phosphatase include but are not limited to manganese; cobalt; NaF; propranolol; phenylglyoxal; and n-ethylmaleimide (Fureisen et al., Biochim. Biophys. Acta. 1484:71-82, 2000). Pharmaceutical compositions of these and other inhibitors of CER-1-P phosphatase, especially those that are formulated for rapid cardiac delivery, are used for this form of sphingolipid-based cardiovascular therapy.

Sphingomyelinase (SMase) catalyzes the conversion of sphingomyelin to ceramide (Rxn. #7 in FIG. 2; see also FIG. 1). Various isoforms of SMase have been described. These include nSMases (n for neutral pH isoform), aSMases (a for acidic pH isoform), and alkaline SMases including an SMase isoform found in the gut. Both the acidic and neutral forms of SMase are endogenous to cardiac tissue (Andrieu-Abadie et al., FASEB J. 13:1501-1510, 1999), and a novel form of a high turnover sphingomyelinase localized in the junctional T-tubule membranes (Ghosh et al., Mol. Cellular Biochem. 189:161-168, 1998). The neutral form of SMase is exposed to the extracellular surface of the membrane (Mohan et al., Biochem Biophys Acta 777:339-342, 1984) and would thus be accessible to lipid-insoluble agents. SMases are described in greater detail in Example 13.

It has been demonstrated that the sphingomyelinase inhibitor, L-carnitine, blocks doxorubicin-induced apoptosis coincident with the inhibition of ceramide production (Andrieu-Abadie et al., FASEB J. 13:1501-1510, 1999; Katircioglu, et al., J. Cardiovasc. Surg. 41:45-50, 1999; Gunther, Eur. J. Pharma. 406:123-126, 2000.

Inhibitors of SMase include but are not limited to gentamicin (Ghosh et al., J. Biol. Chem. 262:12550-12556, 1987) and gentamicin derivatives, and other aminoglycosides, as is described in more detail elsewhere herein.

Several inhibitors of SMase have been prepared that are based on the structures of the naturally occurring compounds Scyphostatin and Manumycin. In addition to naturally occurring compounds such as Scyphostatin and Manumycins A-D, several inhibitors have been synthesized in vitro. These include without limitation those described by Arenz et al., "Synthesis and Biochemical Investigation of Scyphostatin Analogues as Inhibitors of Neutral Sphingomyelinase", Bioorganic & Medicinal Chemistry, 9:2901-2904, 2001; Arenz et al., "Synthesis of the First Selective Irreversible Inhibitor of Neutral Sphingomyelinase", Eur. J. Org. Chem., 137-140, 2001; Arenz et al., "Synthese des ersten selektiven irreverilben Inhibitors der neutralen Sphingomyelinase", Angew Chem., 112:1498-1500, 2000; Tanaka et al., "Structural Elucidation of Scyphostatin, an Inhibitor of Membrane-Bound Neutral Sphingomyelinase", J. Am. Chem. Soc. 199: 7871-7872, 1997; Saito et al., "Absolute Configuration of Scyphostatin", Organic Letters, 2:505-506, 2000; Hoye et al., "Synthesis (and Alternative Proof of Configuration) of the Scyphostatin C(1')-C(20') Trienoyl Fragment", Organic Letters, 2:1481-1483, 2000; Izuhara et al., "Studies toward the Total Synthesis of Scyphostatin: First Entry to the Highly Functionalized Cyclohexenone Segment", Organic Letters, 3:1653-1656, 2001; Runcie et al., "A Short and Efficient Route to Novel Scyphostatin Analogues", Organic Letters, 3:3237-3239, 2001; Chau et al., "Synthesis of Simple Aryl Neutral Sphingomyelinase Inhibitors", Asbtr. Pap.—Am. Chem. Soc., 2001; Arenz et al., "Manumycin A and Its Analogues Are Irreversible Inhibitors of Neutral Sphingomyelinase", ChemiBiochem., 2:141-143, 2001; Zeeck et al., "Manumycin derivatives and the use thereof", U.S. Pat. No. 5,079,263, issued Jan. 7, 1992; and Patel et al., "Manumycin Compounds", U.S. Pat. No. 5,444,087, issued Aug. 22, 1995.

Other inhibitors of SMase that may serve as therapeutic agents or lead compounds, or may provide a chemical framework for preparing focused chemical libraries that can be screened for inhibitors of SMase, include but are not limited to L-carnitine (Andrien-Abadie et al., FASEB J. 13:1501-1510, 1999), and related compounds (U.S. Pat. No. 6,284,798); ubiquinol and ubiquinone homologs (Martin et al., J. Bioenerg Biomember 33:143-153, 2001); antioxidants such as ascorbate and alpha-tocoperol (Hernandez et al., Circ. Res. 86:198-204, 2000); glutathione (oxidized form) (Liu et al., J. Biol. Chem. 272:16281-16287, 1997; Liu et al., J. Biol. Chem. 273:11313-11320, 1998; Yoshimura et al., J. Neurochem. 73:675-683, 1999; and Yoshimura et al., "Inhibition of Neutral Sphingomyelinase Activation and Ceramide Formation by Glutathione in Hypoxic PC12 Cell Death", Journal of Neurochemistry, 73:675-683, 1999); Alutenusin, a protein produced by *Penicillium* spp. (Uchida et al., J. Antibiotics 52:572-574, 1999); SR 3357 (2-isopropyl-1-4-[3-N-methyl-N-3,4-dimethoxy-phenethylamino]propyloxy benzenesulfonylindolizine) (Higuchi et al., J. Immunol. 157:297-304, 1996; Lee et al., Biochem J. 334:457-461, 1998); desipramine (Lee et al., Biochem J. 334:457-461, 1998; Xu et al., J. Biol. Chem. 273:16521-16526, 1998); DTT (Yamanaka et al., J. Neurochem. 38:1753-1764, 1982); sphingomyelin methylene analogs (Hakogi et al., Stereocontrolled synthesis of a sphingomyelin methylene analogue as a sphingomyelinase inhibitor, Org Lett 2:2627-2629, 2000); and substituted amino acids (U.S. Pat. No. 6,306,911 B1 to Wachter et al. Published PCT applications WO 99/41265 and WO 00/58491 disclose compounds named KF-1040A, KF-1040B, KF-1040T4A, KF-1040T4B, KF-1040T5A and KF-10407TB, which are stated to be inhibitors of SMase. Other SMase inhibitors are disclosed in published PCT application WO 00/72833 A2. Sphingomyelin derivatives that are inhibitors of SMase are disclosed by Lister et al. (Biochimicha et Biophysica Acta 1256:25-30, 1995); Tazabekova et al. (Bioorg Khim 1987 May; 13:648-653, 1987); and Hakogi et al. (Stereocontrolled synthesis of a sphingomyelin methylene analogue as a sphingomyelinase inhibitor, Org Lett 2:2627-2629, 2000).

Pharmaceutical compositions of these and other inhibitors of SMase, especially those that are formulated for rapid cardiac delivery, are used for this form sphingolipid-based cardiovascular therapy.

Desaturase catalyzes the conversion of dihydroceramide to ceramide (Rxn. #9 in FIG. 2). Dihydroceramidase desaturase are disclosed in Geeraert et al., "Conversion of dihydroceramide into ceramide: involvement of a desaturase", Biochem J., 327:125-132, 1997; Triola et al., "Synthesis of a Cyclopropene Analogue of Ceramide, a Potent Inhibitor of Dihydroceramide Desaturase", Angew. Chem. Int. Ed., 40:1960-1962, 2001; Heinz et al., "Sphingolipid-Desaturase", PCT/DE99/01859, published as WO00/00593 on Jan. 6, 2000; Michel et al., "Characterization of Ceramide Synthesis: A Dihydroceramide Desaturase Introduces The 4,5-TRANS-Double Bond of Sphingosine at the Level of Dihydroceramide", 272:22432-22437, 1997. Inhibitors of desaturase are disclosed in Triola et al., "Synthesis of a Cyclopropene Analogue of Ceramide, a Potent Inhibitor of Dihydroceramide Desaturase", Angew. Chem. Int. Ed., 40:1960-1962, 2001.

Pharmaceutical compositions of inhibitors of desaturase, especially those that are formulated for rapid cardiac delivery, are used for this form sphingolipid-based cardiovascular therapy.

Cerebrosidases catalyze the production of ceramide from glucosylceramide (Rxn. #14 in FIG. 2). Pharmaceutical compositions of inhibitors of one or more cerebrosidases, especially those that are formulated for rapid cardiac delivery, are used for this form of sphingolipid-based cardiovascular therapy.

Stimulation of Destruction of CER

The stimulation of enzymes that catalyze reactions that degrade CER (i.e., reactions that have CER as a reactant) is expected to result in the stimulation of degradation of CER molecules. In general, it is preferable that such reactions do not yield a undesirable, toxic and/or cardiotoxic sphingolipid, such as SPH, as a product (an example of an enzyme of this type is ceramidase). Other enzymes that may be stimulated to enhance the degradation of CER include but are not limited to the following:

Sphingomyelin Synthase catalyzes the conversion of ceramide to sphingomyelin (Rxn. #6 in FIG. 2); see, e.g., Luberto, et al., "Sphingomyelin synthase, a potential regulator of intracellular levels of ceramide and diacylglycerol during SV40 transformation. Does sphingomyelin synthase account for the putative phosphatidylcholine-specific phopholipase C? PubMed, J. Biol Chem, 273:14550-14559, 1998. Inhibitors of SM synthase include sphingomyelin metabolites; Vivekananda et al., "Sphingomyelin metabolites inhibit sphingomyelin synthase and CTP:phosphocholine cytidylyltransferase", Am J. Physiol Lung Cell Mol Physiol, 2281:L91-L107, 2001. CER kinases are disclosed in Bajjalieh et al., "Ceramide Kinase", Methods in Enzymology, 311:207-215, 1999; Kolesnick et al., "Characterization of a Ceramide Kinase Activity from Human Leukemia (HL-60) Cells: Separation From Diacylglycerol Kinase Activity", The Journal of Biological Chemistry, 265:18803-18808, 1990. Pharmaceutical compositions of stimulators of sphinomyelin synthase, especially those that are formulated for rapid cardiac delivery, are used for this form of sphingolipid-based cardiovascular therapy.

Ceramide (CER kinase) catalyzes the conversion of ceramide to ceramide-1-P (Rxn. #16 in FIG. 2). Pharmaceutical compositions of stimulators of CER kinase, especially those that are formulated for rapid cardiac delivery, are used for this form of sphingolipid-based cardiovascular therapy.

Glucosylceramide Synthase catalyzes the conversion of ceramide to glucosylceramide (Rxn. #13 in FIG. 2). For reviews, see Shayman et al., "Glucosylceramide Synthase: Assay and Properties", Methods in Enzymology, 311:42-49, 1999 and Marks et al., "Methods for Studying Glucosylceramide Synthase", Methods in Enzymology, 311:50-59, 1999. Pharmaceutical compositions of stimulators of glucosylceramide synthase, especially those that are formulated for rapid cardiac delivery, are used for this form of sphingolipid-based cardiovascular therapy.

Inhibitors of glucosylceramide synthase are known. See U.S. Pat. No. 6,051,598 to Shayman et al.; Rani et al., "Cell Cycle Arrest Induced by an Inhibitor of Glucosylceramide Synthase", The Journal of Biological Chemistry, 270:2859-2867, 1995; Abe et al., "Use of Sulfobutyl Ether β-Cyclodextrin as a Vehicle for D-threo-1-Phenyl-2-decanoylamino-3-morpholinopropanol-Related Glucosylceramide Synthase Inhibitors", Analytical Biochemistry, 287:344-347, 2000; Oshefski et al., "Glucosylceramide Synthase Inhibition Enhances Vincristine-Induced Cytotoxicity", Int. J. Cancer, 93:131-138, 2001; Abe et al., "Glycosphingolipid depletion in Fabry disease lymphoblasts with potent inhibitors of glucosylceramide synthase", Kidney International, 57:446-454, 2000; Lee et al., "Improved Inhibitors of Glucosylceramide Synthase", The Journal of Biological Chemistry, 274:14662-14669, 1999; Abe et al., "Structural and stereochemical studies of potent inhibitors and glucosylceramide synthase and tumor cell growth", Journal of Lipid Research, 36:611-621, 1995; Shayman et al., "Inhibitors of Glucosylceramide Synthase", Methods in Enzymology, 311:373-387, 1999; Jimbo et al., "Development of a New Inhibitor of Glucosylceramide Synthase", J. Biochem 127:485-491, 2000; and Marks et al., "Methods for Studying Glucosylceramide Synthase", Methods in Enzymology, 311:50-59, 1999.

Enzymes that catalyze the production of galactosylceramide from CER (Rxn. #15 in FIG. 2) are stimulated to enhance the degradation of CER. Pharmaceutical compositions of stimulators of such enzymes, especially those that are formulated for rapid cardiac delivery, are used for this form of sphingolipid-based cardiovascular therapy.

Example 10

Modulation of Metabolic Precursors of CER

The concentration of harmful sphingolipids is lowered by inhibiting reactions that yield metabolic precursors of ceramide (CER), which is a metabolic precursor of SPH and S-1-P. Enzymes that catalyze such reactions include but are not limited to the following.
Inhibition of Production of Metabolic Precursors of CER The concentration of harmful sphingolipids is lowered by inhibiting reactions that yield metabolic precursors of ceramide (CER), which is a metabolic precursor of SPH and S-1-P. Enzymes that catalyze such reactions include but are not limited to the following.

Serine Palmitoyl Transferase catalyzes the production of 3-ketosphinganine (Rxn. #12 in FIG. 2), a precursor in ceramide synthesis. For a review, see Dickson et al., "Serine Palmitoyltransferase", Methods in Enzymology, 311:1-9, 1999.

Inhibitors of serine palmitoyl transferase include but are not limited to viridiofungins (Mandala et al., J. Antibiot. (Tokyo) 50:339-343, 1997; and Mandala et al., "Isolation and Characterization of Novel Inhibitors of Sphingolipid Synthesis: Australifungin, Viridiofungins, Rustmicin, and Khafrefungin, Methods in Enzymology, 311:335-348, 1999), lipoxamycin (Mandala et al., J. Antibiot. (Tokyo) 47:376-379, 1994), and sphingofungins E and F (Horn et al., J. Antibiot. (Tokyo) 45:1692-1696, 1992). Other SPT inhibitors are disclosed by Hanada et al., "Specificity of Inhibitors of Serine Palmitoyltransferase (SPT), a Key Enzyme in Sphingolipid Biosynthesis, in Intact Cells", Biochemical Pharmacology, 59:1211-1216, 2000; Zweerink et al., "Characterization of a Novel, Potent, and Specific Inhibitor of Serine Palmitoyltransferase", The Journal of Biological Chemistry, 267:25032-25038, 1992; and Riley et al., "Fermentation, Partial Purification, and Use of Serine Palmitoyltransferase Inhibitors from Isaria (=Cordyceps) sinclairii, Methods in Enzymology, 311:348-361, 1999.

Pharmaceutical compositions of inhibitors of serine palmitoyl transferase, especially those that are formulated for rapid cardiac delivery, are used for this form of sphingolipid-based cardiovascular therapy.

3-Ketosphiganine Reductase catalyzes the production of sphinganine (dihydrosphingosine) (Rxn. #11 in FIG. 2), a precursor in ceramide synthesis. See Beeler et al., "The *Saccharomyces cerevisiae* TSC10/YBR265ω Gene Encoding 3-Ketosphinganine Reductase Is Identified in a Screen for Temperature-sensitive Suppressors of the CA2+-sensitive csg2Δ Mutant", The Journal of Biological Chemistry, 273:30688-30694, 1998. Pharmaceutical compositions of inhibitors of 3-ketosphiganine reductase, especially those that are formulated for rapid cardiac delivery, are used for this form of sphingolipid-based cardiovascular therapy.

Dihydroceramide Synthase catalyzes the acetylation of dihydrosphingosine (Rxn. #10 in FIG. 2) which leads to the production of dihydroceramide, a direct precursor of ceramide. Without wishing to be bound by any particular theory, dihydroceramide synthase may be the same enzyme as ceramide synthase (Rxn. #4 in FIG. 2).

Inhibitors of ceramide synthase include Fumonisin B1 (a fungal toxin) (Merrill et al., J. Lipid Res. 26:215-234A, 1993; Wang et al., Adv. Lipid Res. 26:215-234, 1993; Tsunoda et al., J. Biochem. Mol. Toxicol. 12:281-289, 1998); derivatives of fumonisin (Humpf et al., J. Biol. Chem. 273:19060-19064, 1998); *alternaria* toxins (Id. and Mandala et al., J. Antibiot. 48:349-356, 1995); viridiofungins (Merrill et al., J. Lipid Res. 26:215-234A, 1993); astralifungins (Mandala et al., J. Antibiot. 48:349-356, 1995; Furneisen et al., Biochim. Biophys. Acta. 1484:71-82, 2000); and D-erythro-N-myristoyl 2-amino-1-phenylpropanol (Hunnan, Science 274:1855-1859, 1996). Pharmaceutical compositions of inhibitors of dihydroceramide synthase, especially those that are formulated for rapid cardiac delivery, are used for this form of sphingolipid-based cardiovascular therapy.
Stimulation of Destruction of Metabolic Precursors of CER The concentration of harmful sphingolipids is lowered by stimulating reactions that degrade metabolic precursors of ceramide (CER), which is a metabolic precursor of SPH and S-1-P. Enzymes that catalyze such reactions include but are not limited to the following.

Sphingomyelin Deacylase (SM deacylase) catalyzes the production of sphingoylphosphorylcholine (SPC) from sphingomyelin (Rxn. #8 in FIG. 2; see also FIG. 1). Pharmaceutical compositions of stimulators of SM deacylase, especially those that are formulated for rapid cardiac delivery, are used for this form of sphingolipid-based cardiovascular therapy.

Example 11

An Inhibitor of Sphingomyelinase Blocks Hypoxia-Induced Production of Sphingosine in a Cellular Model L-carnitine is a known inhibitor of SMase (Andrien-Abadie et al., FASEB J. 13:1501-1510, 1999; see also U.S. Pat. No. 6,284,798). This Example demonstrates that L-carnitine blocks the hypoxia-induced production of sphingosine in a cellular model.

Cardiomyocytes were cultured on plastic dishes that were placed in a humidified modular incubator chamber (ICN Biomedicals, Aurora, Ohio) pressurized to 0.04-0.05 psi by the particular gas mixture used in the treatment. Warm (37oC) Tyrode's solution containing 0.2 mM BSA, ampicillin (50 mg/mL), kanamycin (100 mg/mL) and fungizone (20 μg/mL) was gassed for 15 minutes with 95% N2/5% CO2 prior to cell treatment. The pO2 was monitored by a Micro pO2 System oxygen electrode (Lasar Research Labs, Los Angeles, Calif.) and found to be 4.0 mmHg for the duration of the hypoxia condition. The chamber was maintained at 37oC for the designated times. Control (normoxia) cells were treated the same except for the use of 95% O2/5% CO2 and incubated in a standard incubator. The pO2 of the normoxia treatment was 7.3 mmHg. The pH of control and experimental cell cultures was monitored with a micro pH electrode (Beetrode pH Electrodes, Sarasota, Fla.) and remained constant at pH=7.26+/−0.02 for normoxic cells and 7.15+/−0.03 for hypoxic cells throughout the experiment. Adult cardiomyocytes were cultured under either normoxia or hypoxia conditions for 5 hours.

Figure 4:
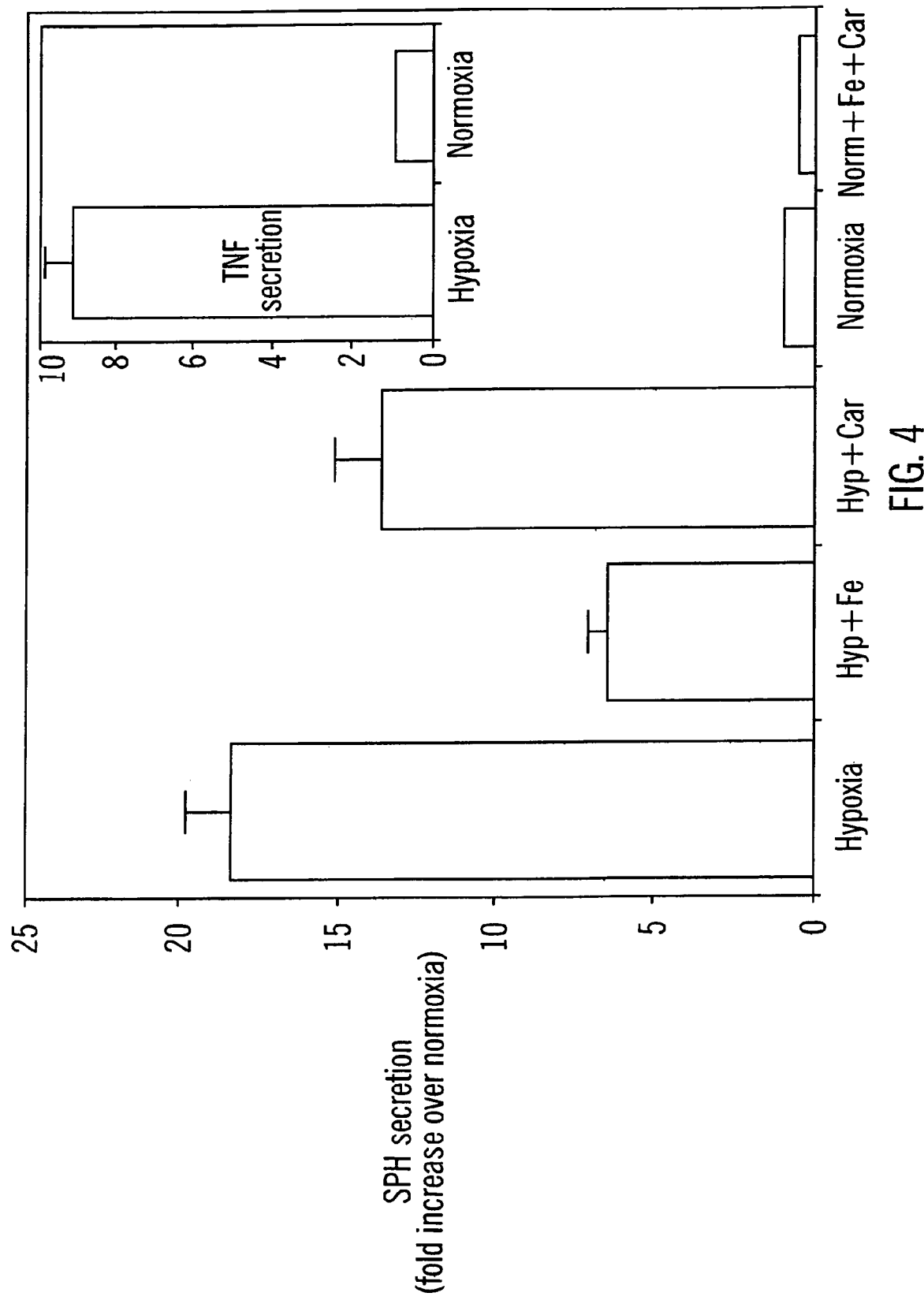
FIG. 4 shows results of experiments that demonstrate that L-carnitine blocks the hypoxia-induced production of sphingosine in a cellular model.

The cell-conditioned Tyrode's solution was collected and the cells were scraped from the culture dish. Both cellular and extracellular sphingolipids were extracted and then quantified by reverse-phase HPLC. The retention times of the key sphingolipids (SPH, SPC, SIP, DHSPH) followed in these experiments are shown in FIG. 4. Hypoxia resulted in a substantial increase in a peak corresponding to D-erythrosphingosine (SPH).

The fold-increases in SPH and TNF-alpha (inset) in response to hypoxia are shown. Cells were pretreated for 30 min with either TNFRII:Fc (0.5 ng/mL) or L-carnitine (20 ng/mL) prior to hypoxia. Data are means +/−SEM from 19 separate experiments. FIG. 4 shows the amount of SPH and TNF-alpha (inset) released into the cell-conditioned media and is expressed in terms of fold increases associated with hypoxia. These data demonstrate that the SPH response (~20-fold increase over normoxia) was more profound than the TNF-alpha response (~10-fold increase over normoxia, inset). Further, FIG. 4 shows that both TNFRII:Fc and the sphingomyelinase inhibitor L-carnitine were capable of significantly (p<0.01) reducing the amount of total SPH.

Example 12

An Inhibitor of Sphingomyelinase Blocks the Effects of Global Ischemia in an Animal Model A rat model of ischemia and reperfusion was used to evaluate the therapeutic potential of a gentamicin, an amino glycoside that inhibits sphingomyelinase.

Reagents

Krebs-Henseleit (KH) Buffer was prepared by combining the following components:

| Chemical | Conc. (mM) | Amount per liter (g) |
|---|---|---|
| $NaHCO_3$ | 25.0 | 2.10 |
| NaCl | 118 | 6.90 |
| KCl | 4.7 | 0.35 |
| $MgSO_4$ (anhy) | 1.2 | 0.145 |
| $NaH_2PO_4$ | 1.2 | 0.145 |
| $CaCl_2$ | 1.2 | 0.175 |
| Glucose | 11 | 1.98 |

The following steps are taken to prepare KH buffer. First, 95% O2/5% CO2 is bubbled through sterile water (Gibco Cat. No. 15230-147), which is concurrently warmed to 37° C. Second, the above ingredients are added and the pH is adjusted to 7.4. Finally, the buffer is sterilized by filtration.

Gentamicin vehicle solution was prepared as follows. A stock solution of 0.1 M Gentamicin was prepared by adding 70 mg of Gentamicin Sulfate (Sigma, G1264) to 1 ml of KH Buffer. KH buffer (150 ml) was combined with 150 μl of the stock solution to yield a 0.1 mM solution.

Protocol

The protocol used was essentially that described by Sakai et al. (A device for recording left ventricular contraction and electrocardiogram in nonworking isolated perfused rat heart, Jpn J Pharmacol 28:223-9, 1978), and Zelinski et al., (Phosphatidylcholine biosynthesis in isolated hamster heart, J Biol Chem. 255:11423-8, 1980) with the exception. in the latter instance, that rat studies were used in the experiments described herein instead of hamster hearts.

In brief, rats were anesthetized and their hearts were excised. The isolated hearts were cannulated and attached to Langendorff perfusion apparatus, and perfused with KH buffer. The hearts were allowed to stabilize for 5-10 min. After stabilization, the hearts should be paceable and drip rate should be between 5 and 10 mls per minute.

A small hole was cut in the left atrium of each animal to expose the mitral valve. A deflated transducer balloon was introduced into the left ventricle through the hole in left atrium. The transducer tube was taped and adjusted so that there was no pressure on the heart. Left ventricular pressure was measured and recorded using the MacLab program. The transducer balloon was filled by adjusting amount of water using a syringe attached to the transducer via a stop-cock so that diastolic pressure was between 0 and 5 mm Hg. The hearts were allowed to stabilize for 10 min. Once stabilized, the hearts should be paceable with a minimum of 100 beats per minute (bpm). The systolic pressure should be at least about 80 mm Hg, resulting in a developed left ventricular pressure of at least about 80 mm Hg.

The flow of KH buffer was switched to Gentamicin vehicle solution using the stop-cock at the top of the canula. The Gentamicin vehicle solution was allowed to recirculate for 30 min., after which time two 1.5 mL aliquots were collected and flash frozen in liquid nitrogen.

Next, all perfusate was turned off for 40 min. in order to begin global ischemia. The set up of the Langendorf apparatus was adjusted so that the peristaltic pump was securely attached and all the air was moved out of the line to begin reperfusion. The flow of KH buffer was turned off after 40 min., and two 1.5 mL aliquots of perfusate dripping from the heart were collected and flash frozen. The heart was then reperfused for 45 min. Perfusate was collected at 2 min. intervals and flash frozen.

After about 45 min., the perfusate was turned off and the ventricular pressure was no longer recorded. The atria were cut off, the pressure transducer was removed, and the ventricles were frozen in a 50 mL conical tube.

Figure 5:
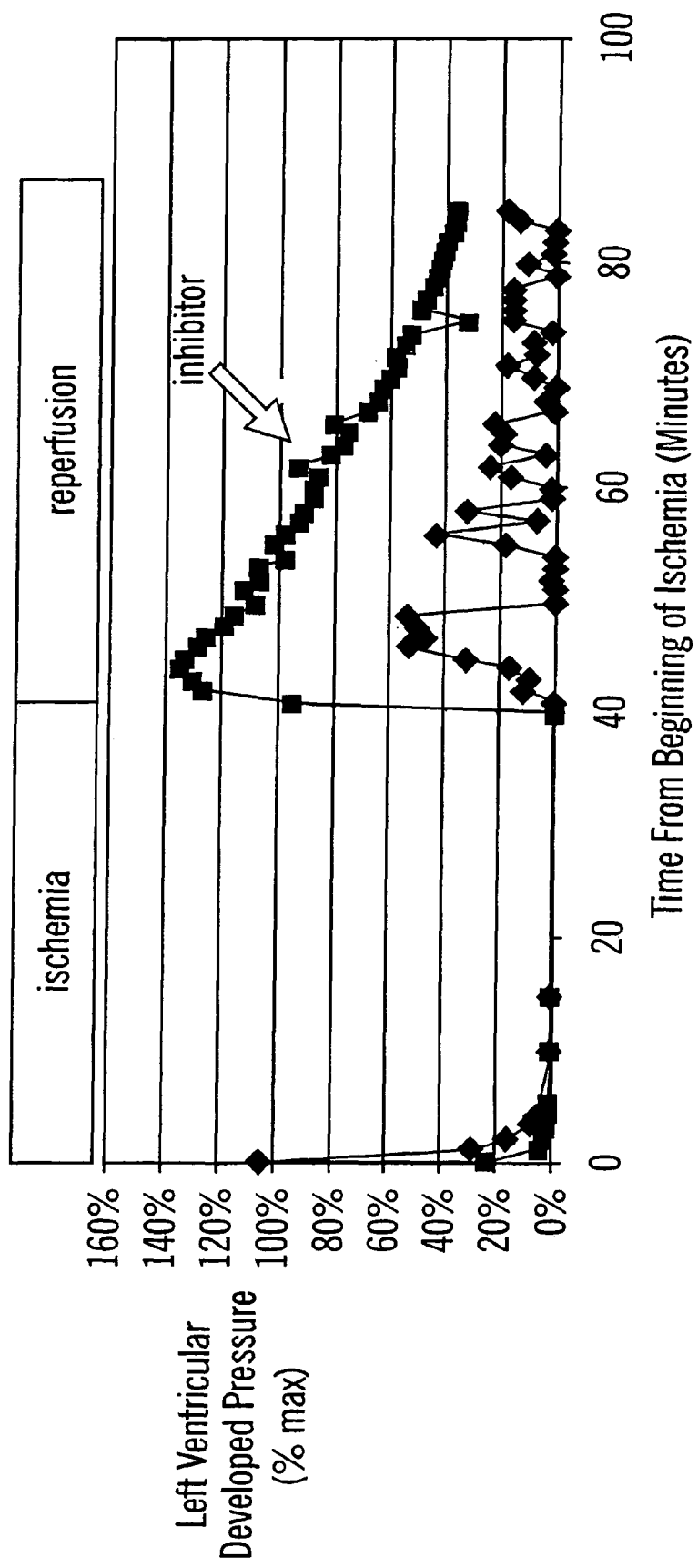
FIG. 5 shows results of experiments in which rat hearts are subject to ischemia with (grey lines) or without (black lines) an inhibitor of sphingomyelinase.

The results, shown in FIG. 5, show that the neutral sphingomyelinase inhibitor gentamicin mitigated ischemia and reperfusion injury in the Langendorff rat heart model of ischemia.

Example 13

HTS Screening for Therapeutic Agents that Inhibit Sphingomyelinase

This Example describes an exemplary screening assay of the invention that is used to screen for and identify compounds useful in the therapeutic methods of the invention. The screening assay of this Example, which is designed to isolate inhibitors of sphingomyelinase (SMase) from a library of compounds based on the structure of aminoglycosides, may be in used high throughput screening (HTS) formats.

This Example describes a high-throughput screening (HTS) scintillation proximity assay (SPA) designed to identify aminoglyosidic inhibitors of sphingomyelinase (SMase). The HTS-SPA of the Example involves high-volume, homogeneous radiometric assays, based upon the principle of scintillation proximity. Although assays of a single plate are described in this Example, it is understood that many such plates would be prepared and tested in high-throughput screening.

Sphingomyelinases

Sphingomyelinase (sphingomyelin choline phosphohydrolase) (SMase) catalyzes the hydrolytic cleavage of sphimgomyelin (SM) via reaction which lead to ceramide and phosphocholine generation (Brady, R. O., Kanfer, J. N., Moek, M. B., and Fredrickson, D. S. 1966. The metabolism of sphingomyelin. II. Evidence of an enzymatic deficiency in Niemann-Pick disease. Proc. Natl. Acad. Sci. USA 55:366). Any sphingomyelinase can be used in the HTS assays, although mammalian SMases, particularly neutral SMases, are of particular interest.

Several different types of mammalian SMases have been identified:

(1) Neutral, membrane-associated, $Mg^{2+}$-stimulated SMases found predominantly in brain and kidney (Spence, M. W. 1993. Sphingomyelinases. Adv. Lipid Res. 26:3-23), which are known to arise from a separate gene from lysosomal SMase (Gatt, S., Dinur, T., and Kopolovic, J. 1978. Niemann Pick disease: presence of the magnesium-dependent sphingomyelinase in brain of the infantile form of the disease. J. Neurochem. 31:547-550). For review of neutral SMases, see Chatterjee, "Neutral Sphingomyelinase", Advances in Lipid Research, 26:25-49, 1993; and Chatterjee, "Neutral sphingomyelinase: past, present and future", Chemistry and Physics of Lipds, 102: 79-96, 1999. At least two structurally different types of mammalian neutral SMase (nS-Mase) have been cloned:

(a) The nSMase described by Stoffel et al., i.e., a cloned human neutral SMase described in Tomiuk et al., Cloned mammalian neutral sphingomyelinase: Functions in sphingolipid signaling? Proc. Natl. Acad. Sci. (U.S.A.) 95: 3638-3643; Hofman et al., Cloning and characterization of the mammalian brain-specific, $Mg^{2+}$-dependent neutral sphingomyelinase Proc. Natl. Acad. Sci. (U.S.A.) 97:5895-5900, 2000; and published PCT application WO 99/07855 to Stofel et al., entitled "Neutral Sphingomyelinase," was filed Aug. 11, 1998 and was published on Feb. 18, 1999.

(b) The nSMase described in U.S. Pat. No. 5,919,687 to Chatterjee, entitled "Recombinant N-SMases and Nucleic Acids Encoding Same", Published PCT application WO 98/28445 to Chatterjee, entitled "Recombinant N-SMases and Nucleic Acids Encoding Same", and Chatterjee, Molecular Cloning, Characterization, and Expression of a Novel Human Neutral Sphingomyelinase, J. Biol. Chem. 274: 37407-37412, 1999). In the latter reference, the nSMase of Chatterjee is stated to be unrelated to the nSMase of Stoffel et al. as the two nSMases have different amino acid sequences (p. 37412, left column, 11, 33-34).

(2) Lysosomal SMases that act optimally at low pH and show no dependence on divalent cations (Kanfer, J. N., Young, O., Shapiro, D., and Brady, R. O. 1966. The metabolism of sphingomyelin. I. Purification and properties of a sphingomyelin-cleaving enzyme from rat liver tissue. J. Biol. Chem. 241:1081; Levade, T., Salvayre, R., and Blazy-Douste, L. 1986. Sphingomyelinases and Niemann-Pick disease. J. Clin. Chem. Biochem. 24:205-220);

(3) Acidic, $Zn^{2+}$-stimulated SMases present in fetal bovine serum and to a lesser degree in newborn human serum (Spence, M. W., Byers, D. M., Palmer, F. B. St. C., and Cook, H. W. 1989. A new $Zn^{2+}$-stimulated sphingomyelinase in fetal bovine serum. J. Biol. Chem. 264:5358-5363), and also secreted by several human cell types during several pathophysiological processes (Schissel, S. L., Shuchman, E. H., Williams, K. J., and Tabas, I. 1996. $Zn^{2+}$-stimulated sphingomyelinase is secreted by many cell types and is a product of the acid sphingomyelinase gene. J. Biol. Chem. 271:18431-18436);

(4) Cytosolic SMases that, like $Mg^{2+}$-dependent neutral SMases, have a neutral pH optimum but no dependence on divalent cations (Okazaki, T., Bielawska, A., Domae, N., Bell, R. M., and Hannun, Y. A. 1994. Characteristics and partial purification of a novel cytosolic magnesium-independent, neutral sphingomyelinase activated in the early signal transduction of 1a,25-dihydroxyvitamin D3-induced HL-60 cell differentiation. J. Biol. Chem. 269:4070-4077).

(5) Placental SMases (Garcia-Ruiz, Human placenta sphingomyelinase, an exogenous acidic pH-optimum sphingomyelinase, induces oxidative stress, glutathione depletion, and apoptosis in rat hepatocytes, Hepatology 32:56-65, 2000).

(6) Brain-specific SMases have been described (Yamanaka et al., J. Neurochem. 38:1753-1764, 1982); Hofmann et al., "Cloning and characterization of the mammalian brain-specific, $Mg^{2+}$-dependent neutral sphingomyelinase", PNAS, 97:5895-5900, 2000; Bernardo et al., "Purification and Characterization of a Magnesium-dependent Neutral Sphingomyelinase from Bovine Brain", The Journal of Biological Chemistry, 275:7641-7647, 2000; Liu et al., "Purification and Characterization of a Membrane Bound Neutral pH Optimum Magnesium-dependent and Phosphatidylserine-stimulated Sphingomyelinase from Rat Brain", The Journal of Biological Chemistry, 273:34472-34479, 1998. A rat brain SMase is commercially available (MDS Panlabs).

SMases from Non-mammalian Species Include:

(1) Bacterial SMases, such as the well-characterized Phospholipase C from *Bacillus cereus* (Ikezawa et al., Studies on sphingomyelinase of *Bacillus cereus*. I. Purification and properties, Biochim Biophys Acta 1978 Feb. 27; 528(2):247-56; Hetland et al., Phospholipase C from *Bacillus cereus* has sphingomyelinase activity, Scand J Clin Lab Invest 1982 February; 42(1):57-61; Gilmore et al., A *Bacillus cereus* cytolytic determinant, cereolysin AB, which comprises the phospholipase C and sphingomyelinase genes: nucleotide sequence and genetic linkage, J Bacteriol 1989 February; 171(2):744-53; Yamada et al., Nucleotide sequence and expression in *Escherichia coli* of the gene coding for sphingomyelinase of *Bacillus cereus*, Eur J Biochem 1988 Aug. 1; 175(2):213-20; Johansen et al., *Bacillus cereus* strain SE-I: nucleotide sequence of the sphingomyelinase C gene, Nucleic Acids Res. 16:103770, 1998; Fujii et al., $Mg^{2+}$ binding and catalytic function of sphingomyelinase from *Bacillus cereus*, J Biochem (Tokyo) 124:1178-1187, 1998; Gavrilenko et al., Nucleotide sequence of phospholipase C and sphingomyelinase genes from *Bacillus cereus* BKM-B164, Bioorg Khim 19:133-138, 1993; Tomita et al., Secondary structure of sphingomyelinase from *Bacillus cereus*, J Biochem (Tokyo) 108:811-815, 1990; and Tamura et al., Mass production of sphingomyelinase of *Bacillus cereus* by a protein-hyperproducing strain, *Bacillus brevis* 47, and its purification, J Biochem (Tokyo) 112:488-491, 1992).

Other bacterial SMases are known and include, by way of non-limiting examples, those from *Helicobacter pylori* (Chan et al., Purification and characterization of neutral sphingomyelinase from *Helicobacter pylori*, Biochemistry 39:4838-4845, 2000; Lin et al., Identification of neutral and acidic sphingomyelinases in *Helicobacter pylori*, FEBS Lett 423:249-253, 1998); *Listeria ivanovii* (Gonzalez-Zorn et al., The smcL gene of *Listeria ivanovii* encodes a sphingomyelinase C that mediates bacterial escape from the phagocytic vacuole, Mol Microbiol 33:510-523, 1999); *Staphylococcus aureus* (Walev et al., Selective killing of human monocytes and cytokine release provoked by sphingomyelinase (beta-toxin) of *Staphylococcus aureus*, Infect Immun 64:2974-2979, 1996); and *Clostridium perfringens* (Saint-Joanis et al., Gene cloning shows the alpha-toxin of *Clostridium perfringens* to contain both sphingomyelinase and lecithinase activities, Mol Gen Genet 1989 November; 219(3):453-60).

(2) Arachnoid SMases, such as the cytotoxic sphingomyelinase D from the brown recluse spider (*Loxosceles reclusa*) (Gates et al., Serum amyloid p component: its role in platelet activation stimulated by sphingomyelinase d purified from the venom of the brown recluse spider (*Loxosceles reclusa*). Toxicon 28: 1303-1315, 1990).

(3) SMase homologs, such as ISC1 (YER019w) of *Saccharomyces cerevisiae* (Sawai et al., Identification of ISC1 (YER019w) as Inositol Phosphosphingolipid Phospholipase C in *Saccharomyces cerevisiae*, J Biol Chem 275:39793-39798, 2000), which may have SMase activity in vitro even though sphingomyelin is not present in cells of the organism from which the SMase homolog is prepared. That is, an SMase homolog may act on substrates other than sphingomyelin in vivo but nevertheless have bona fide SMase activity in vitro.

Other SMases that may be used to practice the invention include without limitation Romiti et al., "Characterization of sphingomyelinase activity released by thrombin-stimulated platelets", Molecular and Cellular Biochemistry, 205:75-81, 200; Sawai et al., "Function of the Cloned Putative Neutral Sphingomyelinase as Lyso-platelet Activating Factor-Phospholipase C", The Journal of Biological Chemistry, Vol. 274, No. 53, Dec. 31, 1999, pp. 38131-38139; Fensome et al., "A Neutral Magnesium-dependent Sphingomyelinase Isoform Associated with Intracellular Membranes and Reversibly Inhibited by Reactive Oxygen Species", The Journal of Biological Chemistry, 275:1128-1136, 2000; Holopainen et al., "Sphingomyelinase Activity Associated with Human Plasma Low Density Lipoprotein", The Journal of Biological Chemistry, 275:16484-16489, 2000; and Hinkovska-Glacheva et al., "Activation of a Plasma Membrane-Associated Neutral Sphingomyelinase and Concomitant Ceramide Accumulation During IgC-Dependent Phagocytosis in Human Polymorphonuclear Leukocytes", Blood, 91:4761-4769, 1998.

Chemical Libraries Based on Aminoglycoside Structures

Figure 6:
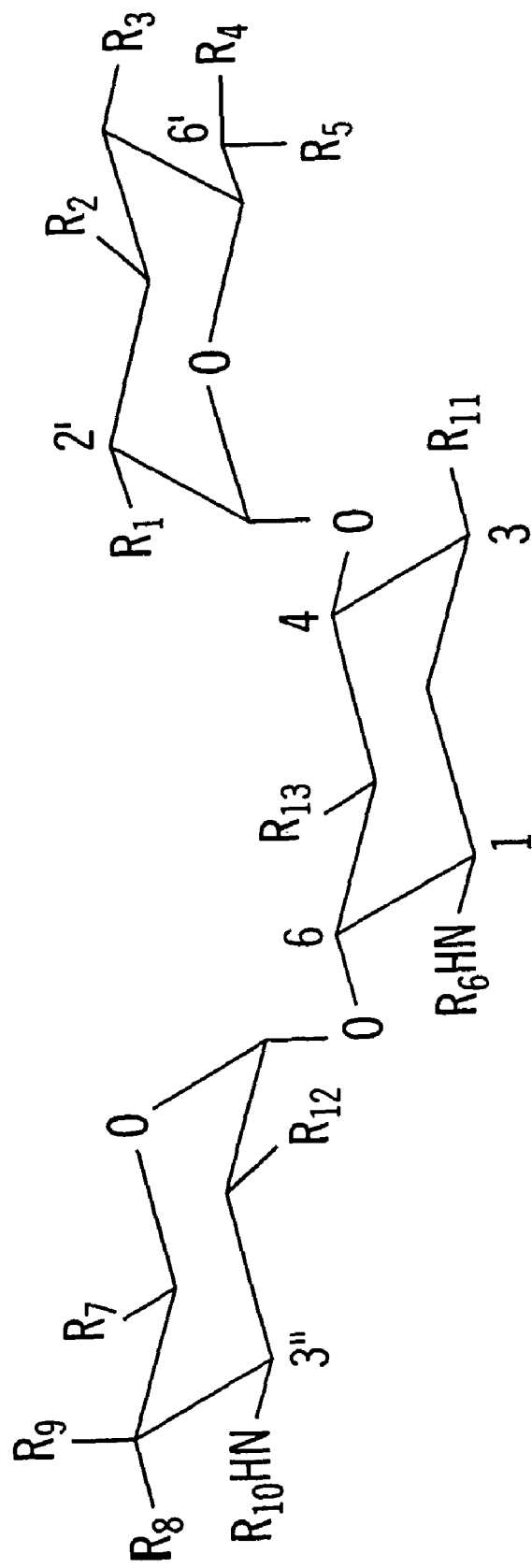
FIG. 6 shows the general chemical structure of aminoglycosides. "R1" through "R13" are substituent groups.

Combinatorial chemical libraries that are used in this screening assay are preferably "biased" in the sense that they are prepared using the basic aminoglycoside structure as a framework to produce aminoglyosidic molecules having a multitude of positions where alternate "R" groups may be incorporated. The structure shown in FIG. 6, which has 13 "R" groups, is used. In the following naturally occurring aminoglycoside antibiotics, the structure shown in FIG. 6 has the following R groups that may be substituted; in all of these compounds, R11 is NH2, and R12 is OH, and R13 is OH.

| Aminoglycoside | R1 | R2 | R3 | R4 | R5 | R6 | R7 | R8 | R9 | R10 |
|---|---|---|---|---|---|---|---|---|---|---|
| Kanamycin A | H | H | H | H | $H_2$ | H | $H_2OH$ | H | H | H |
| Kanamycin B | $H_2$ | H | H | H | $H_2$ | H | $H_2OH$ | H | H | H3 |
| Kanamycin C | $H_2$ | H | H | H | H | H | $H_2OH$ | H | H | H |
| Gentamicin C1 | $H_2$ | H | H | $HCH_3$ | $HCH_3$ | H | H | $H_3$ | H | $CH_3$ |
| Gentamicin C1a | $H_2$ | H | H | $H_2$ | $H_2$ | H | H | $CH_3$ | H | $H_3$ |
| Gentamicin C2 | $H_2$ | H | H | $H_2$ | $H_2$ | H | H | $H_3$ | H | $H_3$ |
| Gentamicin C26 | $H_2$ | H | H | $HCH_3$ | $HCH_3$ | H | H | $H_3$ | H | $H_3$ |
| Gentamicin B | $H_2$ | H | H | $H_2$ | $H_2$ | H | H | $H_3$ | H | $H_3$ |
| Tobramycin | $H_2$ | H | H | H | $H_2$ | H | H | H | H | H |
| Dibekacin | $H_2$ | H | H | H | $H_2$ | H | H | H | H | H |
| Aberkacin | $H_2$ | H | H | H | $H_2$ | OR' | OR' | H | H | H |
| Isepamicin | H | H | H | H | $H_2$ | OR | OR | $H_3$ | H | $H_3$ |

A combinatorial library of aminoglycosides and aminoglycoside derivatives is prepared using methods discussed in Sucheck et al. (Combinatorial synthesis of aminoglycoside libraries, Curr Opin Drug Discov Devel 4:462-70, 2001); Hofstadler et al., (Multiplexed screening of neutral mass-tagged RNA targets against ligand libraries with electrospray ionization FTICR MS: a paradigm for high-throughput affinity screening, Anal Chem 71:3436-40, 1999), and references cited therein.

Pre-Assay Studies

A FlashPlate® microtiter plate (NEN Life Science Products, Boston, Mass.) is used in the assay. The interior of each well of the microtiter plate is permanently coated with a thin layer of polystyrene-based scintillant that produces a signal when the surface of the well is in close proximity to any of a variety of isotopes (e.g., 3H, 125I, 14C and 33P). Because the scintillant is permanently bound to the wells of the plate, a liquid scintillation cocktail does not need to be added to the wells during the assay.

A radiolabeled substrate for SMase is coated or bound onto the surface of wells in a FlashPlate. The radioactive decay associated with the radiolabeled causes a microplate surface scintillation effect detectable on a microplate scintillation counter. Radiolabel that is released from the radiolabeled substrate by the enzymatic activity of SMase does not activate the scintillant. Thus, after SMase is added, the signal from the radiolabel decreases over time. If an inhibitor of SMase is present in a well, the radiolabel is released at a lower rate, and the scintillant-mediated signal thus decreases at a slower rate.

In the present Example, the radiolabelled SMase substrate that is coated onto the surface of wells in a FlashPlate is [3H]sphingomyelin (NEN Life Sciences). Before HTS is begun, studies are done to determine the optimal means and conditions for coating the wells with the substrate. Aliquots of [3H]sphingomyelin, having concentrations ranging from 0.1 to 10 u Ci/ml, are prepared in a constant volume of Tris buffer. The aliquots are added at 0.2 ml/well at room temperature and the signal from the coated microtiter plates is read at regular intervals using a TopCount NXT Microplate Scintillation and Luminescence Counter (Packard BioScience). Two parameters are optimized in these studies. First, the time at which the maximum counts/well is achieved before the signal hits a plateau; typically, this occurs after 10 hours. Second, the range of [3H]sphingomyelin that can be added to the wells and still exhibit a linear increase in signal; typically, 0.2 uCi/well is used.

Next, studies are done to determine the amount of time needed to hydrolyze the maximum amount of substrate at a chosen concentration. A plate is coated using the optimized conditions described above, i.e., 0.2 uCi/well with 10 hours of pre-assay incubation. The SMase being used in the assay is added (0.2 u/ml, diluted in PBS with 1 mg/ml CaCl2 and 1 mg/ml MgCl2). The plate is incubated at room temperature and counts are read at regular time points over a period of 24 hours. The hydrolysis of the substrate occurs rapidly at first before reaching a plateau, typically after about the first 3 hours of incubation.

In these initial studies, and in plates used in HTS, several control wells are used. In one type of control, commercially available (Sigma) SMases are added to control wells to confirm the activity of the assay, including bacterial SMases (from *Staphylococcus aureus* or *Bacillus cereus*) or a human placental SMase. If the target SMase is dependent on a divalent cation, a chelator such as EDTA is added to one or more control wells.

HTS Assays

A target SMase of interest is prepared by recombinant DNA technology. The target SMases in this Example are mammalian neutral SMases. The nSMase described by Chatterjee (U.S. Pat. No. 5,919,687) and the nSMase described by Stoffel et al. (WO 98/28445) are both tested because they have unrelated amino acid sequences, and either or both may be involved in sphingolipid metabolism and/or signaling in cardiovascular tissues.

In the HTS-SPA, many microtiter plates are prepared as described above. In non-control wells, a member of the aminoglycoside chemical library is added to each well, followed by the addition of the target SMase, and the signals from the wells of the plates are read. When large numbers of plates are to be screened, an external plate stacker can be added to the TopCount NXT Microplate Scintillation and Luminescence Counter, which allows for more than 15,000 samples to be loaded and tested unattended. Wells in which the signal from the unhydrolyzed substrate does not decrease, or decreases less rapidly than in a control well comprising the target SMase only, identify members of the library that are candidate inhibitors of the target SMase. The activity of these candidate compounds is confirmed by repeated testing.

The compounds are further characterized in terms of other desirable attributes. For example, the safety and efficacy of the compositions and methods for sphingolipid-based cardiovascular therapy are initially evaluated in cell culture (e.g., cultured cardiomyocytes) and animal models. Non-limiting examples of such animal models include rat and pig models of infarction (Olivetti et al., Cardioscience 6:101-106, 1995; Jacobs et al., J. Mol. Cell Cardiol. 31:1949-1959, 1999; Gunther et al., Eur. J. Pharma. 406:123-126, 2000; and Holmes et al., Circulation 90:411-420, 1994).

Example 14

Modulation of the Sphingomyelin Signaling Pathway

The sphingomyelin signaling pathway (a.k.a. the SM pathway) is a "cascade" of biochemical events in which proteins in the pathway are activated (by enzymatic chemical modification or otherwise) with the end result that sphingosine metabolism is affected. In most instances, activation of the SM pathway leads to increased production of ceramide. For reviews of the molecular biology of the sphingomyelin signaling pathway, see Hannun et al., Adv. Lipid Res. 25:27-41, 1993; Liu et al., Crit. Rev. Clin. Lab. Sci. 36:511-573, 1999; Igarashi, Y., J. Biochem. 122:1080-1087, 1997; and Oral et al., J. Biol. Chem. 272:4836-4842, 1997.

It has suggested that the sphingomyelin signal transduction pathway is activated during cardiac ischemia/hypoxia (Bielawska et al., Am. J. Pathol. 151:1257-1263, 1997; Meldrum, Am. J. Pathol. 274:577-595, 1998; and Cain et al., J. Mol. Cell. Cardiol. 31:931-947, 1999). If so, there must be a factor or process that mediates the ischemia-induced SPH production. The most likely candidate for the mediator is the pro-inflammatory cytokine, tumor necrosis factor alpha (TNFα). In various animal models of ischemia, the myocardium produces TNFα (Squadrito et al., Eur. J. Pharmacol. 237:223-230, 1993; Herrmann et al., European Journal of Clinical Investigation 28:59-66, 1998; Meldrum, Ann. Thorac. Surg. 65:439-443, 1998). Recent evidence demonstrates that the cardiomyocytes themselves produce TNFα and secrete the cytokine into the extracellular fluid (Comstock et al., J. Mol. Cell Cardiol. 30:2761-2775, 1998). Since TNFα receptors are expressed by cardiomyocytes (Krown et al., FEBS Letters 376:24-30, 1995; Torre-Amione et al., Circulation 92:1487-1493, 1995), an autocrine/paracrine role for TNFα has been suggested (Meldrum, Ann. Thorac. Surg. 65:439-443, 1998). Significantly, TNFα induces SPH production and apoptosis in cardiac myocytes (Krown et al., J. Clin. Invest. 98:2854-2865, 1996), presumably by acting by binding to the cardiomyocyte complement of TNFα receptors.

Activation of the sphingomyelin signal transduction cascade is a key early event in the cytotoxic (apoptotic) effects of the cytokine TNFα (Zhang et al., Endo. 136:4157-4160, 1995). TNFα can cause significant apoptosis in cultured rat cardiomyocytes and it has been suggested that TNFα-induced SPH production is responsible for the cell death triggered by TNFα (Krown et al., J. Clin. Invest. 98:2854-2865, 1996).

Inhibitors of Cytokines that Activate the Sphingomyelin Signaling Pathway.

The SM pathway, many steps of which occur intracellularly, is induced by a variety of extracellular stimuli. In sphingolipid-based cardiovascular therapy, such stimuli are at least partially blocked. SM pathway-inducing agents that are desirably interfered with include but are not limited to cytokines. Cytokines of particular interest include but are not limited to pro-inflammatory cytokines, interferons and chemokines. Pro-inflammatory cytokines of particular interest include but are not limited to TNF-alpha; interleukins such as IL-1 beta, IL-2, IL-10, interferons of particular interest include but are not limited to gamma-IFN. Chemokines of particular interest are those involved in the ischemic process including but not limited to interleukin-8 (IL-8), and the monocyte chemotaxic proteins MCP-1 and MCP-2. One non-limiting example of an agent that may be used to modulate the SM pathway (in particular, stroke-induced apoptosis) is the immunosuppressant FK506 (Herr et al., Brain Res. 826:210-219, 1999).

Agents that Block Cytokine-Induced Activation of the SM Pathway

Sphingolipid-based cardiac therapeutic agents that are used to inhibit the actions of cytokines include but are not limited to an antibody directed to a cytokine or to a cytokine receptor; a cytokine receptor fragment that binds a cytokine but is otherwise biologically inactive; and a cytokine analog that binds cytokine receptor but is otherwise biologically inactive.

As one non-limiting example of this aspect of the invention, an antibody directed to a cytokine or a cytokine receptor is used as a therapeutic agent in sphingolipid-based cardiovascular therapy. Such antibodies are generated in an immunoreactive response to a cytokine, a cytokine receptor, or a synthetic polypeptide derived therefrom. A preferred type of antibody is a monoclonal antibody, which is initially isolated from a hybridoma; more preferred is a monoclonal antibody that has been "humanized" via molecular genetic manipulation. Also preferred are fragments, preferably soluble, which are derived from antibodies to a cytokine and retain the ability to bind a cytokine, such as, e.g, single-chain Fv analogs (scFv). The isolation, production, humanization and derivatization of antibodies is described in Ramnarayan et al., Am. Biotechnol. Lab.:26-28, 1995; Gavilondo et al., BioTechniques 29:128-145, 2000; Kling, J., Modern Drug Discovery 2:33-45, 1999; Morrow, K. J. Jr., American Laboratory 32:15-19, 2000; Huston et al., Methods in Enzymology 203:46-88, 1991; Johnson et al., Methods in Enzymology 203:88-98, 1991; Güssow et al., Methods in Enzymology 203:99-121, 1991; and references cited therein.

A preferred antibody that is used as a therapeutic agent in sphingolipid-based cardiovascular therapy is one that blocks the binding of a cytokine to its receptor. Assays for determining the degree of inhibition of binding of a cytokine to its receptor (see, e.g., Murata et al., Anal. Biochem. 282:11-120, 2000) are used in initial assessments of the effectiveness of such antibodies.

As another non-limiting example of this aspect of the invention, a receptor fragment that binds a cytokine but is otherwise biologically inactive is used as a therapeutic agent in sphingolipid-based cardiovascular therapy. For example, therapeutic inhibition of the SM pathway is achieved by blocking the binding of extracellular TNF-alpha to a cellular receptor (TNFR); this in turn prevents the activation of the SM pathway. The binding of TNF-alpha to a TNFR is directly or competitively inhibited. One example of an agent for competitive inhibition of the binding is a soluble TNF-alpha receptor fragment such as TNRFII:Fc. TNFRII:Fc receptor fragment, which is sold as EmbrelR (from Immunex Corporation, Seattle, Wash.). This soluble fusion protein was made from the extracellular binding domain of the TNF type II receptor and an immunoglobulin Fc portion of IgG1. This soluble fusion protein has a very high affinity for TNF (Im et al., J. Biol. Chem 275:14281-14286, 2000).

As another non-limiting example of this aspect of the invention, small molecules that serve as inhibitors and/or antagonists of sphingolipid receptors are used as therapeutic agents in sphingolipid-based cardiovascular therapy. Such molecules include sumarin, which blocks EDG-3 action (Mandala et al., Proc. Natl. Acad. Sci. U.S.A. 97:7859-7864, 2000), and pertussis toxin, which blocks EDG receptors that use Gi (Gonda et al., Biochem. J. 337:67-75, 1999).

In addition to TNF and Fas, other examples of extracellular agents that activate the SM pathway by interacting with their receptors include but are not limited to Fas and the Fas receptor (Brenner et al., J. Biol. Chem. 272:22173-22181, 1997; and nerve growth factor (NGF) and the p75 neutrotrophin receptor (p75NTR) (Dobrowsky et al., Science 265:1596-1599, 1994).

Other Agents Directed to the Sphingomyelin Signaling Pathway

Sphingolipid-based cardiovascular therapy is also achieved through the use of compounds that bind sphingolipid receptors that initiate and stimulate the sphingomyelin signaling pathway. This pathway ultimately results in increased ceramide production. An increased level of ceramide would, in turn, be expected to result in elevated concentrations of undesirable sphingolipids such as, e.g., S-1-P and SPH. Such receptor-binding agents may be, by way on non-limiting example, antibodies or antibody fragments, small (organic) molecules, or sphingolipid derivatives that bind the receptors but do active the SMA signaling pathway. The synthesis of representative sphingolipid derivatives are described in, by way of non-limiting example, PCT published patent application WO 99/12890; U.S. Pat. Nos. 5,663,404 and 6,051,598, and U.S. Pat. Nos. 5,260,288 and 5,391,800.

In other instances, as is explained in detailed elsewhere herein, components of the SM pathway are used to create therapeutic proteins that retain the ability to bind sphingolipids but are otherwise biologically inactive. Moreover, various steps in the SM pathway are specifically inhibited by dominant-negative derivatives of proteins involved in a particular step in the cascade, antisense molecules and constructs, and gene therapeutics.

Example 15

Sphingolipid-Binding Protein Derivatives

Sphingolipid-binding protein derivatives are used for sphingolipid-based cardiovascular therapy in one aspect of the invention. Such protein derivatives retain the ability to bind sphingolipids, even if other functions, biochemical activities and/or characteristics of the protein are altered, compromised or absent in the protein derivative. Protein derivatives may be oligopeptides synthesized in vitro, proteins that have been purified from an animal and chemically or otherwise modified, proteins produced via recombinant DNA technology, or combinations thereof. Non-limiting examples of sphingolipid-binding protein derivatives include enzyme derivatives, and receptor derivatives. A sphingolipid-binding enzyme derivative can be, for example, a noncatalytic derivative of an enzyme involved in sphingolipid metabolism that retains the ability to bind sphingolipids. A sphingolipid binding receptor derivative can be, for example, a soluble derivative of a membrane-bound sphingolipid receptor that binds sphingolipids, e.g., soluble derivatives of a member of the EDG or SCaMPER family of receptors. A "sphingolipid-binding protein derivative" may also be an antibody or antibody derivative; "antibody derivative proteins" are antibody fragments that retain the ability to specifically bind sphingolipids. Such antibody fragments are, by way of non-limiting example, single-chain FV analogs (scFv's), complementarity-determining regions (CDR's), and the like, and fusion proteins comprising such antibody fragments. See Gavilondo et al., BioTechniques 29:128-145, 2000; and Verma et al., Journal of Immunological Methods 216:165-181, 1998.

Such sphingolipid-binding protein derivatives can be, but need not be, derived from an enzyme or receptor from the animal that is intended to be treated. Such derivatives may be prepared from homologous enzymes or receptors from a non-human mammal (e.g., a feline SMase derivative), or from analogous enzymes or receptors from an organism that belongs to a different biological Family, Order, Class or Kingdom (e.g., an arachnid or bacterial SMase).

Sphingolipid-Binding Enzyme Derivatives

Enzymes from which biologically inactive (non-catalytic) sphingolipid-binding derivatives are obtained include but are not limited to the following. Such derivatives of these enzymes bind their substrate, which is a undesirable, toxic and/or cardiotoxic sphingolipid, and thereby lower the actual or available concentration of the sphingolipid, and/or render the sphingolipid biologically inactive with respect to its cardiotoxic effects. Preferably, such derivatives are soluble and may be formulated into a pharmaceutical composition suitable for sphingolipid-based cardiovascular therapy.

S-1-P is bound by enzymes having S-1-P as a substrate, such as, by way of non-limiting example, S-1-P lyase and S-1-P phosphatase. Non-catalytic derivatives of these enzymes bind S-1-P and interfere with its harmful effects.

SPH is bound by enzymes having SPH as a substrate, such as, by way of non-limiting example, SPH Kinase and Ceramide synthase. Non-catalytic derivatives of such enzymes bind SPH and interfere with its harmful effects.

Ceramide is bound by enzymes having ceramide as a substrate, such as, by way of non-limiting example, ceramidase, SM synthase, ceramide kinase, and glucosylceramide synthase. Non-catalytic derivatives of such enzymes bind ceramide and interfere with the harmful effects of its metabolites, such as, in particular, SPH and S-1-P.

Sphingomyelin is bound by enzymes having sphingomyelin as a substrate, such as, by way of non-limiting example, SMase. Non-catalytic derivatives of such enzymes bind sphingomyelin and interfere with the harmful effects of its metabolites such as, e.g., ceramide, SPH and S-1-P.

Sphingolipid-Binding Receptor Derivatives

Receptors from which biologically inactive (e.g., non-signal transducing) sphingolipid-binding derivatives are obtained include but are not limited to the following. Such derivatives of these receptors bind their ligand, which is a cardiotoxic sphingolipid, and thereby lower the actual or available concentration of the sphingolipid, and/or render the sphingolipid biologically inactive with respect to its cardiotoxic effects. Preferably, such derivatives are soluble and may be formulated into a pharmaceutical composition suitable for sphingolipid-based cardiovascular therapy.

EDG Receptors

Receptors that bind S-1-P are used in this aspect of the invention (for a review of some S-1-P-binding receptors, see Spiegel et al., Biochim. Biophys. Acta 1484:107-116, 2000).

EDG-1 was the first identified member of a class of G protein-coupled endothelial-derived receptors (EDG). Such receptors include but are not limited to members of the EDG family of receptors (a.k.a. 1 pA receptors, Chun, Crit. Rev. Neuro. 13:151-168, 1999), and isoforms and homologs thereof such as NRG1 and AGR16.

For reviews, see Goetzl et al., Adv. Exp. Med. Biol. 469: 259-264, 1999; Chun et al., Cell. Biochem. Biophys. 30:213-242, 1999); Sato, "A new role of lipid receptors in vascular and cardiac morphogenesis", The Journal of Clinical Investigation, 6:939-940, 2000.

EDG-1 is described by Lee et al, (Ann. NY Acad. Sci. 845:19-31, 1998). Human EDG-1c genes and proteins are described in published PCT application WO 99/46277 to Bergsma et al. Described in Au-Young, et al., U.S. Pat. No. 5,912,144, issued Jun. 15, 1999, "EDG-I Receptor Homolog"; Bergsma et al., WO 97/46277, published Sep. 16, 1999, "Human EDG-1c Polynucleotides and Polypeptides and Methods of Use"; and Okamoto et al., "EDG1 Is a Functional Sphingosine-1-Phosphate Receptor That Is Linked via a Gi/o to Multiple Signaling Pathways, Including Phospolipase C Activation, Ca2+ Mobilization, Ras-Mitogen-activated Protein Kinase Activation, and Adenylate Cyclase Inhibition", The Journal of Biological Chemistry, 273:27104-27110, 1998.

EDG-3 is described by Okamoto et al. (Biochem. Biophys. Res. Commun. 260:203-208, 1999) and An et al. (FEBS Letts. 417:279-282, 1997). See also An et al., J. Biol. Chem. 275:288-296, 2000; EDG-3 (a.k.a. LP(B4)); Tsui, U.S. Pat. No. 6,130,067, issued Oct. 10, 2000, "Human EDG3SB Gene"; and Siehler et al., "Sphingosine 1-Phosphate Activates Nuclear Factor-KB through Edg Receptors: Activation Through Edg-3 and Edg-5, but not Edg-1, in Human Embryonic Kidney 293 Cells," JBC Papers in Press Published Oct. 22, 2001 as Manuscript M01107220.

EDG-5 human and mammalian genes are described in U.S. Pat. No. 6,057,126 to Munroe et al. and published PCT application WO 99/33972 to Munroe et al. The rat homolog, H218 (a.k.a. ARG16) is described in U.S. Pat. No. 5,585,476 to MacLennan et al. Van Brocklyn et al., J. Biol. Chem. 274: 4626-4632, 1999; and Gonda et al., Biochem. J. 337:67-75, 1999. See also An et al., J. Biol. Chem. 275:288-296, 2000.

EDG-6 is described by Graler et al. (Genomics 53:164-169, 1998) and Yamazaki et al. (Biochem. Biophys. Res. Commun. 268:583-589, 2000).

EDG-8 from rat brain is described by Im et al., (J. Biol. Chem. 275:14281-14286, 2000). Homologs of EDG-8 from other species, including humans, may also be used.

The Mil Receptor (Mil is an abbreviation for "miles apart") binds S-1-P and regulates cell migration during vertebrate heart development. The Mil receptor of Zebrafish is described by Mohler et al. (J. Immunol. 151:1548-1561, 1993). Another S-1-P receptor is NRG1 (nerve growth factor regulated gene-1), the rat version of which has been identified (Glickman et al., Mol. Cel. Neurosci. 14:141-152, 1999).

Receptors that bind SPC are also used in this aspect of the invention. Such receptors include but are not limited to members of the SCaMPER family of receptors (Mao et al., Proc. Natl. Acad. Sci. U.S.A. 93:1993-1996, 1996; Betto et al., Biochem. J. 322:327-333, 1997), and ovarian cancer G-protein-coupled receptor 1; Xu et al., "Sphingosylphopsphoryl-coline is a ligand for ovarian cancer G-protein-coupled receptor 1", Nature Cell Biology, 2:261-267, 2000.

Some evidence suggests that EDG-3 may bind SPC in addition to S-1-P (Okamoto et al., Biochem. Biophys. Res. Commun. 260:203-208, 1999). Derivatives of EDG-3 that bind both S-1-P and SPC are used in one aspect of the invention. Also usable is the receptor described in Ames et al., WO 01/04139 A2, published Jan. 18, 2001, "Polynucleotide and Polypeptide Sequences of Human AXOR29Receptor and Methods of Screening for Agonists and Antagonists of the Interaction Between Human AXOR29Receptor and its Ligands".

Receptors that bind LPA (lysophosphatic acid) are also used in this aspect of the invention. LPA receptors are described by Im et al., "Molecular Cloning and Characterization of a Lysophosphatidic Acid Receptor, Edg-7, Expressed in Prostate", Molecular Pharmacology, 57:753-759, 2000; An et al., "Characterization of a Novel Subtype of Human G Protein-coupled Receptor for Lysophosphotatidic Acid", The Journal of Biological Chemistry, 273:7906-7910, 1998; Fukushima et al., "A single receptor encoded by vzg-1/lpA/edg-2 couples to G proteins and mediates multiple cellular responses to lysophosphatidic acid", Proc. Natl. Acad. Sci., 95:6151-6156, 1998; Chun et al., "U.S. Pat. No. 6,140,060 issued Oct. 31, 2000, "Closed Lysophosphatidic Acid Receptors"; and Kimura et al., "Two Novel *Xenopus* Homologs of Mammalian LPEDG-2 Function as Lysophosphatidic Acid Receptor *Xenopus Oocytes* and Mammalian Cells", JBC Papers in Press Published on-line Feb. 5, 2001 as Manuscript M011588200.

Soluble receptor fragments are derivatives of membrane-bound receptors in which the transmembrane portions of the receptor have been removed. Receptor-derived polypeptides that are soluble, i.e., have lost their transmembrane portion, and which retain their ability to bind the receptor substrate, are soluble receptor fragments that may have therapeutic value as agents that bind undesirable sphingolipids. Studies that have identified portions of Edg receptors that bind to S-1-P are helpful as guides in designing soluble receptor fragments (Parrill et al., Identification of Edg1 Receptor Residues That Recognize Sphingosine 1-Phosphate, The Journal of Biological Chemistry, 275:39379-39384, 2000; and Wang et al., A Single Amino Acid Determines Lysophospholipid Specificity of the S I P1.(EDG1) and LPA1 (EDG2) Phospholipid Growth Factor Receptors, JBC Papers in Press Published on-line Oct. 16, 2001 as Manuscript M107301200.

Sphingolipid-Binding Proteins from Natural Sources

Sphingolipid-binding proteins that may be used in the invention include those isolated from natural sources. A non-limiting example of such a protein is lysenin, a protein that binds sphingomyelin, which has been prepared from the earthworm *Eisenia foetida* (Yamaji et al., J. Biol. Chem. 273:5300-5306, 1998).

Example 16

Cloning of Rat And Human Scamper Genes

The rat and human SCaMPER genes were obtained using a combination of reverse transcription and polymerase chain reactions (RT-PCR) as is known in the art (see, for example, PCR Technology: Principles and Applications for DNA Amplification, H. A. Erlich, ed., 1989).

Tissue was prepared from various human and rat sources as follows. Human heart tissue from an expired heart failure patient was collected, frozen in liquid nitrogen and stored at −70° C. Rat heart and skeletal tissue was freshly obtained from sacrificed adult Sprague-Dawley rats. RNA from these tissues was isolated using the commercially available Qiagen Rneasy Mini Kit according to the manufacturer's protocols (Qiagen, Valencia, Calif.).

PCR amplification of the target sequences was performed using the commercially available Qiagen One-Step RT-PCR kit according to the manufacturer's protocols. Primers sets included:

```
                                            (SEQ ID NO.:1)
    5'-CCAGGATTCATCATATGTTAAAAG-3'  (upper);
    and
                                            (SEQ ID NO.:2)
    5'-ATCAGTGGGTGCATCAGTAGC-3'     (lower)
``` reading frame (ORF) and the 3'-sequence of SCaMPER (designed from GenBank accession number U33628).

Amplification utilized cycling regimens according to the manufacturer's recommendations. Briefly, reactions were optimized using 40 PCR cycles, each cycle consisting of 45 seconds denaturation at 95° C., 45 seconds of annealing at 50° C., and 1 minute of polymerization at 72° C. The resulting PCR products were subcloned into pCR3.1 TOPO or pcDNA3,1-V5/HIS TOPO (Invitrogen, Carlsbad, Calif.) using standard techniques. Sequencing with a T7 primer was performed at the San Diego State University DNA Core Facility (San Diego, Calif.). The resultant SCaMPER sequences are presented as SEQ ID NO.: 3, the open reading frame of the rat SCaMPER gene and SEQ ID NO.: 4, the open reading frame of the human SCaMPER gene.

Rat SCaMPER ORF (SEQ ID NO.:3):

```
001 ATGTTAAAAG TGAGCAGGGT CTCAAGTGAA GGTTTAATAT CACTTTCTAT CACTGAGGCA

061 CCTGATCTTA AGATCAGGGA TCCTAAGATA GAGAAACTCT ACCTTCCAGT TTTTTATTTA

121 AATGCACACA TCTACTTAAA TGCACTCAGT ACTCTCCTGA ACTCTCATTG TGGCGAGAAC

181 TGTTTTCAT  GGTTATGAAC AATTACAGAA TGCCACTTTT CCAGTTTGGA GAAATATATT

241 CATTTATATA AACAGGGTCA GGAACACCAA GAGGCAAGGA GGAGGGGGTG GTGTGAGTGG

301 GAAAGGTGAG ATGAAGCAGT GCTTCCTCTC TTAA
```

Human SCaMPER ORF (SEQ ID NO.:4)

```
ATGTTAAAAGTGAGCAGGGTCTCAAGTGAAGGTTTAATATCACTTTCTAT

CACTGAGGCACCTGATCTTAAGATCAGGGATCCTAAGATAGAGAAACTCT

ACCTTCCAGTTTTTATTTAAATGCACACATCTACTTAAATGCACTCAGTA

CTCTCCTGAACTCTCATTGTGGCGAGAACTGTTTTCATGGTTATGAACAA

TTACAGAATGCCACTTTTCCAGTTTGGAGAAATATATTCATTTATATAAA

CAGGGTCAGGAACATCAAGAGGCAAGGAGGAGGGGGTGGTGTGAGTGGGA

AAGGTGAGATGAAGCAGTGCTTCCTCTCTTAA
```

Example 17

Cloning of Rat Edg-3 Genes

The rat Edg-3 gene was obtained using a combination of reverse transcription and polymerase chain reactions (RT-PCR) as is known in the art (see, for example, PCR Technology: Principles and Applications for DNA Amplification, H. A. Erlich, ed., 1989).

Rat heart, liver and skeletal muscle tissue was freshly obtained from sacrificed rats. RNA from these tissues was isolated using the commercially available Qiagen Rneasy Mini Kit according to the manufacturer's protocols (Qiagen, Valencia, Calif.).

PCR amplification of the target sequences was performed using the commercially available Qiagen One-Step RT-PCR kit according to the manufacturer's protocols. Primers sets included:

```
                                            (SEQ ID NO:5)
    5'-TTATGGCAACCACGCACGCGCAGG-3'  (upper)

(SEQ ID NO.:6)
    5'-AGACCGTCACTTGCAGAGGAC-3'     (lower)
```

Amplification utilized cycling regimens according to the manufacturer's recommendations. Briefly, reactions were started at 50° C. for 30 minutes, followed by 95° C. for 15 minutes; and then optimized using 40 PCR cycles, each cycle consisting of 45 seconds denaturation at 95° C., 45 seconds of annealing at 63±5° C., and 1 minute of polymerization at 72° C. The resulting PCR products were subcloned into pCR3.1 vector using the Invitrogen TA cloning kit (Invitrogen, Carlsbad, Calif.) using standard techniques. Briefly, after RT-PCR, a 1% agarose gel was used to separate the PRC products from unused primers and dNTPs electrophoretically. The approximately 1200 bp fragment was then excised quickly under UV light and the Bio101 Geneclean kit was then used to purify the DNA. The purified DNA was then ligated into the PCR3.1 vector. The ligation mix was then transformed into Invitrogen Top10 chemically competent cells with beat shock. Following a 1 hour incubation shaking at 37° C., the cells were spread on a LB plate containing ampicillin and allowed to grow overnight at 37° C. Several individual colonies were chosen and used to inoculate culture tubes containing 3 mls of LB-ampicillin media. After 8-12 hours of shaking at 37° C., 1.5 mls of the culture was used in the Qiaspin miniprep kit to isolate plasmid DNA. The restriction enzyme EcoRI was used to confirm that the plasmid contained a piece of DNA that was approximately 1200 bp.

Sequencing with a T7 primer was performed at the San Diego State University DNA Core Facility (San Diego, Calif.). The resultant rat Edg-3 sequence are presented as SEQ ID NO.: 7.

Rat Edg-3 Sequence (SEQ ID NO.: 7):

Example 18

Molecular Genetic Approaches to Sphingolipid-Based Cardiovascular Therapy

In addition to traditional approaches to therapeutic agents, approaches based on molecular genetics and recombinant DNA technology are used to produce agents for sphingolipid-based cardiovascular therapy.

Dominant Negative Mutant Proteins

Dominant negative mutant proteins of enzymes that catalyze reactions leading to the production of undesirable, toxic and/or cardiotoxic sphingolipids, or of sphingolipid receptors, are used as agents for sphingolipid-based cardiovascular therapy. Such proteins are delivered to cardiac or other tissues to decrease sphingolipid production and/or to minimize the cardiotoxic effects of circulating sphingolipids. Enzymes of particular interest include ceramidase, sphingomyelinase and SPH kinase. Receptors of particular interest include members of the EDG family of receptors, especially those presently known to bind S-1-P, i.e., EDG-1, EDG-3 and EDG-5.

Dominant negative mutants are prepared in a variety of ways. In general, dominant negative mutants of proteins retain their ability to interact with other molecules but have lost some other function present in the wildtype protein. For example, a dominant negative mutant of a multimeric enzyme

```
0001 ATGGCAACCA CGCACGCGCA GGGGCACCCG CCAGTCTTGG GGAATGATAC TCTCCGGGAA

0061 CATTATGATT ACGTGGGGAA GCTGGCAGGC AGGCTGCGGG ATCCCCCTGA GGGTAGCACC

0121 CTCATCACCA CCATCCTCTT CTTGGTCACC TGTAGCTTCA TCGTCTTGGA GAACCTGATG

0181 GTTTTGATTG CCATCTGGAA AAACAATAAA TTTCATAACC GCATGTACTT TTTCATCGGC

0241 AACTTGGCTC TCTGCGACCT GCTGGCCGGC ATAGCCTACA AGGTCAACAT TCTGATGTCC

0301 GGTAGGAAGA CGTTCAGCCT GTCTCCAACA GTGTGGTTCC TCAGGGAGGG CAGTATGTTC

0361 GTAGCCCTGG GCGCATCCAC ATGCAGCTTA TTGGCCATTG CCATTGAGCG GCACCTGACC

0421 ATGATCAAGA TGAGGCCGTA CGACGCCAAC AAGAAGCACC GCGTGTTCCT TCTGATTGGG

0481 ATGTGCTGGC TAATTGCCTT CTCGCTGGGT GCCCTGCCCA TCCTGGGCTG GAACTGCCTG

0541 GAGAACTTTC CCGACTGCTC TACCATCTTG CCCCTCTACT CCAAGAAATA CATTGCCTTT

0601 CTCATCAGCA TCTTCACAGC CATTCTGGTG ACCATCGTCA TCTTGTACGC GCGCATCTAC

0661 TTCCTGGTCA AGTCCAGCAG CCGCAGGGTG GCCAACCACA ACTCCGAGAG ATCCATGGCC

0721 CTTCTGCGGA CCGTAGTGAT CGTGGTGAGC GTGTTCATCG CCTGTTGGTC CCCCCTTTTC

0781 ATCCTCTTCC TCATCGATGT GGCCTGCAGG GCGAAGGAGT GCTCCATCCT CTTCAAGAGT

0841 CAGTGGTTCA TCATGCTGGC TGTCCTCAAC TCGGCCATGA ACCCTGTCAT CTACACGCTG

0901 GCCAGCAAAG AGATGCGGCG TGCTTTCTTC CGGTTGGTGT GCGGCTGTCT GGTCAAGGGC

0961 AAGGGGACCC AGGCCTCCCC GATGCAGCCT GCTCTTGACC CGAGCAGAAG TAAATCAAGC

1021 TCCAGTAACA ACAGGAGCAG CCACTCTCCA AAGGTCAAGG AAGACCTGCC CCATGTGGCT

1081 ACCTCTTCCT GCGTCACTGA CAAAACGAGG TCGCTTCAGA ATGGGGTCCT CTGCAAGTGA

1141 CGGTCT
``` involved in sphingolipid metabolism would be one that retains the ability to form multimers but has a catalytic domain that has been inactivated by deletion or mutation of amino acid residues in the catalytic domain. Such deletions and mutations are created by site-directed mutagenesis, by random mutagenesis, or by any other suitable procedure.

One non-limiting example of a dominant negative mutant that may be used in the invention of the disclosure is a dominant negative mutant of human SPH kinase. This mutation (Gly82Asp), which was created by site-directed mutagenesis of the presumed catalytic domain of the enzyme, is stated to block the activation of endogenous SPH kinase by TNF-alpha and IL-1-beta (Pitson et al., J. Biol. Chem. 275:33945-33950, 2000).

Antisense

Antisense oligonucleotides against mRNAs of key sphingolipid production enzymes (e.g., sphingomyelinase, ceramidase, sphingosine kinase) are delivered to cardiac and/or other tissues to inhibit or completely block the production and/or harmful effects of undesirable, toxic and/or cardiotoxic sphingolipids. Antisense oligonucleotides are designed to decrease the expression of key sphingolipid binding proteins or receptors such as EDG and SCaMPER are delivered to cardiac and/or other tissues to minimize the cardiotoxic effects of circulating sphingolipids. Ribozymes that degrade such mRNAs are also used. Additionally or alternatively, antisense expression constructs, which transcribe RNA molecules antisense in vivo, may be introduced into an animal, which may be a human, in need thereof.

Gene Therapy

Various forms of gene therapy are used to carry out sphingolipid-based cardiovascular therapy according to the invention. The therapeutic nucleic acid molecule ("gene therapy construct") that is introduced into a patient in need thereof generally comprises nucleic acids having the following genetic elements: (i) an "open reading frame (ORF)," i.e., a protein-encoding nucleotide sequence that is sought to be expressed, and (ii) a "gene therapy vector," which provides the genetic sequences needed for expression of an ORF introduced thereinto, replication of the vector and/or recombination with other nucleic acids. A gene or protein is said to be "expressed" when it is actively creating mRNA molecules having the nucleotide sequence of the ORF of a gene (transcription); and, using these mRNA molecules as blueprints, producing proteins having specific amino acid sequences (translation). It is understood in the art that transcription and translation need not occur contemporaneously. It is also understood in the art that a protein is one type of gene product, but other gene products that may be expressed by gene therapy constructs may be nucleic acids, e.g., antisense transcripts, or structural or enzymatic RNA molecules.

Expression of proteins that influence sphingolipid concentration and/or activity via the administration of gene therapy constructs comprising an ORF that encodes a protein of interest is one type of gene therapy. Such proteins may be expressed at a level that is approximately equal to what is normally found in healthy individuals, "over-expressed" (i.e., expressed at a level that is greater than the amount that is normally found in healthy individuals), or constitutively expressed (i.e., expressed at a constant level).

Another type of gene therapy, in which a genetic deficiency (loss of function of a protein due to mutation) is compensated for by virtue of the in vivo expression of a wildtype protein from a gene therapy construct, is generally called "replacement therapy." This type of gene therapy may be used to treat patients having genetic deficiencies that reduce the amount, activity, or distribution in enzymes involved in sphingolipid metabolism, or in sphingolipid receptors.

In another type of gene therapy, proteins that degrade undesirable sphingolipids, or stimulators thereof, are overexpressed for the immediate and/or long-term treatment of cardiac disorders. In order to achieve gene therapy of this type, gene therapy constructs are designed, by way of non-limiting example, to encode and overexpress an enzyme that degrades an undesirable sphingolipid or metabolite thereof. Such enzymes include, e.g., S-1-P lyase, sphingomyelin synthase, SM deacylase, ceramide synthase, glucosylceramide synthase, ceramide kinase, and S-1-P phosphatase. An indirect way of realize this type of gene therapy involves the administration of gene therapy constructs that encode proteins that are inhibitors or activators of enzymes involved in sphingolipid metabolism or sphingolipid receptors (see Examples 7 to 10).

In another type of gene therapy, proteins that bind undesirable sphingolipids are overexpressed for the immediate and/or long-term treatment of cardiac disorders. In order to achieve gene therapy of this type, gene therapy constructs are designed that encode, by way of non-limiting example, antibodies or antibody derivatives directed to an undesirable sphingolipid (Example 6); naturally occurring proteins, such as lysenin, that bind an undesirable sphingolipid; or polypeptide derivatives of receptors and enzymes that bind undesirable sphingolipids (Example 15).

Another type of gene therapy involves the administration of gene therapy constructs that express a RNA having a nucleotide sequence that is the antisense (hybridizing) of all or a portion of an mRNA that encodes a sphingolipid enzyme that produces, or a receptor that facilitates the cellular uptake of, an undesirable sphingolipid. Binding of the antisense transcript reduces or prevents the expression of the mRNA encoding the enzyme or receptor. Such enzymes include but are not limited to SMase, SPH kinase, ceramidase, cerebrosidase, desaturase, ceramide synthase, ceramide-1-phosphatase, serine palmitoyl transferase, and NADPH-dependent reductase. Such receptors include but are not limited to members of the EDG family of receptors (Example 15).

Another type of gene therapy involves the use of gene therapy constructs that encode and express dominant negative mutants of key sphingolipid production enzymes (e.g., SPH kinase, sphingomyelinase, etc.) or sphingolipid receptors (e.g., the EDG family of receptors). These expression constructs are delivered to cardiac or other tissues in order to decrease sphingolipid production and/or to minimize the effects of circulating undesirable, toxic and/or cardiotoxic sphingolipids.

Gene Therapy Vectors

Gene therapy constructs for the in vivo production of antisense transcripts and dominant negative mutants, and for gene therapy, may be contained in any suitable expression vector known in the art, such as a plasmid, cosmid, or viral vector. Viral vectors such as retroviral vectors, adenovirus vectors, herpes simplex virus vectors, vaccinia virus and the like are particularly useful for the administration of these expression constructs. The choice of vector and route of administering the vector will depend, for example, on the particular target cells, tissues and animal (including a human) that are targeted for drug delivery, and can be determined by those skilled in the art.

Non-limiting examples of vectors for gene therapy include, in general, those that are nonviral (Li et al., Gene Ther. 7:31-34, 2000; episomal (Van Craenenbroeck et al., Eur. J. Biochem. 267:5665-5678, 2000); viral (Walther et al., Drugs 60:249-271, 2000), including, in particular, those derived from retroviruses (Kurian et al., Mol. Pathol. 53:173-176, 2000; Takeuchi et al., Adv. Exp. Med. Biol. 465:23-35, 2000) and other RNA viruses (Hewson, Mol. Med. Today 6:28-35, 2000). Non-limiting examples of particular gene therapy vectors include those derived from adenovirus (see Danthinne et al., Gene Ther. 7:1707-1704, 2000); AAV, adeno-associated virus (Athanasopoulus et al., Int. J. Mol. Med. 6:363-375, 2000; Tal, J. Biomed. Sci. 7:279-291, 2000; Monahan et al., Gene Ther. 7:24-30, 2000); HSV-1, herpes simplex virus (Sean-Esteves et al., Mol. Ther. 2:9-15, 2000; Latchman, Mol. Med. Today 6:28-35, 2000); and lentiviral vectors (Vigna et al., J. Gene Med. 2:308-316, 2000; Buchschacher et al., Blood 95:2499-2504, 2000; Trono, Gene Ther. 7:20-23, 2000).

Gene therapy vectors and constructs may be designed to be targeted to specific cells or tissues (Hallenbeck et al., Adv. Exp. Med. Biol. 465:37-46, 2000). Gene therapy vectors designed to be targeted to myocardial cells and tissues, and strategies for the use thereof, are preferably used in certain modalities of gene therapy. See U.S. Pat. No. 6,121,246; Allen, Ann. Thorac. Surg. 68:1924-1928, 1999; Ponder, Trends Cardiovasc. Med. 9:158-162, 1999; Yla-Herttuala et al., Lancet 355:213-222, 2000; Duckers et al., Med. Clin. North Am. 84:199-213, 2000; Sinnaeve et al., Cardiovasc. Res. 44:498-506, 1999; Hiltunen et al., Vasc. Med. 5:41-48, 2000; Hajjar et al., Circ. Res. 86:616-621, 2000; Stephari et al., Ann. Endocrinol, (Paris) 61:85-90, 2000; O'Brien et al., Mayo Clin. Proc. 75:831-834, 2000; Dedieu et al., Curr. Cardiol. Rep. 2:39-47, 2000.

Example 19

Combination Therapies

The therapeutic compositions and methods of the invention may be used in combination with each other and/or with other agents for cardiovascular therapy, i.e., non-sphingolipid-based therapeutic agents. In such instances, pharmaceutical compositions, medical devices, emergency kits and the like contain two or more of the therapeutic agents of the invention; or at least one of the therapeutic agents of the invention and at least one non-sphingolipid-based therapeutic agent; or two or more of the therapeutic agents of the invention and two or more other therapeutic agents. That is, compositions, devices, methods and the like that are used in combination therapies may be described as those having or using at least one member from two or more of a, b and c, wherein "a" is a first therapeutic agent of the invention; "b" is a second (i.e., other than "a") therapeutic agent of the invention; and "c" is a non-sphingolipid-based therapeutic agent.

In general, any therapeutic agent may be combined with the therapeutic agents of the invention so long as neither agent has a negative impact on the activity of the other agent. Therapeutic agents that may be combined with the therapeutic agents of the invention includes presently known agents for cardiovascular therapy, as well as agents that are discovered or created subsequent to the filing of the present application.

Presently known agents for cardiovascular therapy include but are not limited to alpha and beta adrenergic blocking drugs; parasympathetic drugs; calcium channel blockers; drugs that affect the renin-angiotensin system; diuretic therapy; magnesium, potassium and calcium; digitalis and other inotropic agents; organic nitrates and nitroprusside; antiadrenergic drugs with central action; ganglionic blockers and neuron depletors; nonspecific antihypertensive vasodilators; antiarrhythmic drugs; antiplatelet and other antithrombotic drugs; thrombolytic agents; lipid-lowering drugs; selective dopamine receptor agonists; and prosiacyclin. See Cardiovascular Pharmacotherapeutics Companion Handbook, Wm. H. Frishman and Edmund. H Sonnenblick, McGraw Hill, NY, 1998.

As is noted in the preceding Examples. certain therapeutic agents of the invention are preferably used in combination with a second therapeutic agent designed to ameriolate potential undesired side-effects that may occur as a result of treatment with the first therapeutic agent.

By way of non-limiting example, inhibition of SPH kinase will result in decreased production of the harmful sphingolipid S-1-P, but may lead to an accumulation of SPH, which is also an undesirable sphingolipid, albeit generally less harmful than S-1-P. In order to avoid or mitigate this effect should it occur, additional agents are administered that lower the concentration of available SPH. Such agents include but are not limited to ones that (i) stimulate or are enzymes having SPH as a substrate, with the proviso that such enzymes should not be ones that produce S-1-P; (ii) inhibit enzymes having SPH as a product; (iii) are SPH receptor derivatives, or antibodies to SPH, that bind molecules of SPH, thus sequestering them from locations in the body where they exert their toxic effects; (iii) inhibit the action of inflammatory cytokines and chemokines; (iv) are antisense molecules, or genetic constructs that express antisense transcripts, that act to reduce the expression of a protein that increases concentrations of SPH, e.g., an enzyme that catalyzes reactions that produce SPH; (v) a dominant negative derivative of a protein that increases concentrations of SPH, e.g., an enzyme that catalyzes reactions that produce SPH; and (vi) a gene therapy construct that encodes and expresses a protein that leads to decreased function and/or concentration of SPH including, by way of non-limiting example, a protein that is characterized as being of the type encompassed by the classes defined above in (i), (ii), (iii) and/or (v).

One skilled in the art will readily appreciate that the present invention is well adapted to carry out the objects and obtain the ends and advantages mentioned, as well as those inherent therein. The methods, procedures, treatments, devices, and compositions described herein are presently representative of preferred embodiments, are exemplary, and are not intended as limitations on the scope of the invention. Upon reading this specification, changes therein and other uses will occur to those skilled in the art, each of which is encompassed within the spirit of the invention as defined by the attached claims.

All patents and publications referred to above are herein incorporated by reference to the same extent as if each individual publication was specifically and individually indicated to be incorporated by reference.

The invention illustratively described herein suitably may be practiced in the absence of any element or elements, or limitation or limitations, which is not specifically disclosed herein.

Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art,

I claim:

1. A method for treating a disease or disorder correlated with a sphingolipid or a sphingolipid metabolite, comprising administering to a patient an amount of an antibody or antibody fragment that binds sphingosine-1-phosphate effective to reduce the effective concentration of the sphingosine-1-phosphate, wherein the disease or disorder is selected from the group consisting of cancer, pathologic angiogenesis, and pathologic inflammation.

2. A method according to claim 1 wherein the disease or disorder is cancer.

3. A method according to claim 1 wherein the antibody is a monoclonal antibody.

4. A method according to claim 1 wherein the antibody is a humanized monoclonal antibody.

5. A method according to claim 1 wherein the antibody fragment is an antibody fragment that comprises at least one antigen-binding domain specific for sphingosine-1-phosphate.

6. A method according to claim 1 wherein the disease or disorder is pathologic angiogenesis.

7. A method according to claim 1 wherein the disease or disorder is pathologic inflammation.

* * * * *